US012594242B2

(12) United States Patent
Ying et al.

(10) Patent No.: US 12,594,242 B2
(45) Date of Patent: Apr. 7, 2026

(54) LIPID COMPOUNDS AND LIPID NANOPARTICLE COMPOSITIONS

(71) Applicant: SUZHOU ABOGEN BIOSCIENCES CO., LTD., Jiangsu (CN)

(72) Inventors: Bo Ying, Jiangsu (CN); Xiulian Wang, Jiangsu (CN)

(73) Assignee: SUZHOU ABOGEN BIOSCIENCES CO., LTD., Suzhou (CN)

( * ) Notice: Subject to any disclaimer, the term of this patent is extended or adjusted under 35 U.S.C. 154(b) by 0 days.

(21) Appl. No.: 18/617,058

(22) Filed: Mar. 26, 2024

(65) Prior Publication Data

US 2024/0269074 A1 Aug. 15, 2024

Related U.S. Application Data

(60) Division of application No. 18/163,117, filed on Feb. 1, 2023, now Pat. No. 11,964,052, which is a continuation of application No. PCT/CN2022/094227, filed on May 20, 2022.

(30) Foreign Application Priority Data

May 24, 2021 (WO) ................ PCT/CN2021/095520
Oct. 8, 2021 (WO) ................ PCT/CN2021/122704
Jan. 6, 2022 (CN) ......................... 202210010389.2
Jan. 11, 2022 (WO) ................ PCT/CN2022/071251

(51) Int. Cl.
| | |
|---|---|
| A61K 9/16 | (2006.01) |
| C07C 217/28 | (2006.01) |
| C07C 219/06 | (2006.01) |
| C07C 229/16 | (2006.01) |
| C07C 229/22 | (2006.01) |
| C07C 235/06 | (2006.01) |
| C07D 207/24 | (2006.01) |
| C07D 295/13 | (2006.01) |

(52) U.S. Cl.
CPC .......... *A61K 9/1617* (2013.01); *C07C 217/28* (2013.01); *C07C 219/06* (2013.01); *C07C 229/16* (2013.01); *C07C 229/22* (2013.01); *C07C 235/06* (2013.01); *C07D 207/24* (2013.01); *C07D 295/13* (2013.01); *C07C 2601/04* (2017.05); *C07C 2601/08* (2017.05); *C07C 2601/14* (2017.05); *C07C 2601/18* (2017.05)

(58) Field of Classification Search
CPC .................................................. A61K 9/1617
See application file for complete search history.

(56) References Cited

U.S. PATENT DOCUMENTS

| | | | |
|---|---|---|---|
| 3,341,568 | A | 9/1967 | Ham et al. |
| 5,045,338 | A | 9/1991 | Klemann et al. |
| 5,635,487 | A | 6/1997 | Wolff et al. |
| 5,824,812 | A | 10/1998 | Nantz et al. |
| 5,965,434 | A | 10/1999 | Wolff et al. |
| 6,649,780 | B1 | 11/2003 | Eibl et al. |
| 8,969,353 | B2 | 3/2015 | Mahon et al. |
| 9,254,327 | B2 | 2/2016 | Manoharan et al. |
| 9,315,437 | B2 | 4/2016 | Budzik et al. |
| 9,402,816 | B2 | 8/2016 | Colletti et al. |
| 9,446,132 | B2 | 9/2016 | Stanton et al. |
| 9,926,560 | B2 | 3/2018 | MacLachlan et al. |
| 2010/0178699 | A1 | 7/2010 | Gao et al. |
| 2012/0295832 | A1 | 11/2012 | Constien et al. |
| 2014/0161830 | A1 | 6/2014 | Anderson et al. |
| 2014/0335157 | A1 | 11/2014 | Tange et al. |

FOREIGN PATENT DOCUMENTS

| | | | |
|---|---|---|---|
| AU | 2014259532 | B2 | 11/2014 |
| CA | 2237316 | A1 | 6/1997 |
| CN | 104876831 | A | 9/2015 |
| CN | 108251420 | A | 7/2018 |
| DE | 2357414 | A | 12/1974 |
| EP | 2781507 | B1 | 9/2014 |
| EP | 3275448 | A1 | 1/2018 |
| WO | WO 1991/014178 | A1 | 9/1991 |
| WO | WO 1997/013743 | A1 | 4/1997 |
| WO | WO 2000/003044 | A1 | 6/2000 |
| WO | WO 2002/092554 | A1 | 11/2002 |
| WO | WO 2006/138380 | A2 | 12/2006 |
| WO | WO 2010/053572 | A2 | 5/2010 |
| WO | WO 2010/057150 | A1 | 5/2010 |
| WO | WO 2010/062322 | A2 | 6/2010 |
| WO | WO 2011/000106 | A1 | 1/2011 |
| WO | WO 2011/108955 | A1 | 9/2011 |
| WO | WO 2011/149810 | A1 | 12/2011 |

(Continued)

OTHER PUBLICATIONS

Akita et al., 2013, "A Neutral Envelope-Type Nanoparticle Containing pH-Responsive and SS-Cleavable Lipid-Like Material as a Carrier for Plasmid DNA", Advanced Healthcare Materials 2(8):1120-1125.
Bennett et al., 1995, "A Flexible Approach to Synthetic Lipid Ammonium Salts for Polynucleotide Transfection", Tetrahedron Letters 36(13):2207-2210.
International Search Report and Written Opinion for International Application No. PCT/CN2021/095520, mailed Feb. 22, 2022.

(Continued)

*Primary Examiner* — Brian J Davis
(74) *Attorney, Agent, or Firm* — Jones Day

(57) ABSTRACT

Provided herein are lipid compounds that can be used in combination with other lipid components, such as neutral lipids, cholesterol and polymer conjugated lipids, to form lipid nanoparticles for delivery of therapeutic agents (e.g., nucleic acid molecules) for therapeutic or prophylactic purposes, including vaccination. Also provided herein are lipid nanoparticle compositions comprising said lipid compounds.

20 Claims, No Drawings

Specification includes a Sequence Listing.

(56)     References Cited

FOREIGN PATENT DOCUMENTS

| WO | WO 2014/028487 A1 | 2/2014 |
|----|-------------------|--------|
| WO | WO 2016/004202 A1 | 1/2016 |
| WO | WO 2017/049245 A2 | 3/2017 |
| WO | WO 2017/075531 A1 | 5/2017 |
| WO | WO 2017/099823 A1 | 6/2017 |
| WO | WO 2017/100744 A1 | 6/2017 |
| WO | WO 2018/062413 A1 | 4/2018 |
| WO | WO 2018/064147 A1 | 4/2018 |
| WO | WO 2018/160690 A1 | 9/2018 |
| WO | WO 2019/027999 A1 | 2/2019 |
| WO | WO 2019/090097 A1 | 5/2019 |
| WO | WO 2021/204175 A1 | 10/2021 |
| WO | WO 2021/204179 A1 | 10/2021 |
| WO | WO 2021/226597 A2 | 11/2021 |
| WO | WO 2022/060871 A1 | 3/2022 |
| WO | WO 2022/152109 A2 | 7/2022 |

OTHER PUBLICATIONS

International Search Report and Written Opinion for International Application No. PCT/CN2022/071251, mailed Feb. 8, 2022.

International Search Report and Written Opinion for International Application No. PCT/CN2022/094227, mailed Nov. 11, 2022.

Osanai et al., 1992, "Preparation of Optically Active Double-chained Diammonium Cationic Amphiphiles and Their Surface and Colloidal Properties", J. Jpn. Oil. Chem. Soc. 41(4):293-300.

Schurz et al., 1997, "Analytical measurements of Products of Aniline and Triglycerides in Oil Samples Associated with the Toxic Oil Syndrome", Archives of Toxicology Supplements 19(1):53-64.

Chen et al., 2012, "Rapid Discovery of Potent siRNA-Containing Lipid Nanoparticles Enabled by Controlled Microfluidic Formulation", J. Am. Chem. Soc. 134, 16, 6948-6951.

Database Caplus [online], Chemical Abstracts, Jan. 1, 1974 (Jan. 1, 1974), Yaroshenko et al., "Synthesis of aminopolycarboxylic acid esters", Database accession No. 1974:133388.

Akinc et al., 2008, "A combinatorial library of lipid-like materials for delivery of RNAi therapeutics", Nat Biotechnol 26, 561-569.

LIPID COMPOUNDS AND LIPID NANOPARTICLE COMPOSITIONS

1. CROSS-REFERENCE TO RELATED APPLICATIONS

This application is a divisional application of U.S. Patent Application No. 18/163,117, filed Feb. 1, 2023, which is a continuation application of International Patent Application No. PCT/CN2022/094227, filed on May 20, 2022, which claims priority pursuant to 35 U.S.C. § 365 (b) to International Patent Application No. PCT/CN2021/095520, filed on May 24, 2021, International Patent Application No. PCT/CN2021/122704, filed on Oct. 8, 2021, Chinese Patent Application No. CN202210010389.2, filed on Jan. 6, 2022, and International Patent Application No. PCT/CN2022/071251, filed on Jan. 11, 2022, the entireties of which are incorporated herein by reference.

2. SEQUENCE LISTING

This application contains a computer readable Sequence Listing which has been submitted in XML file format via Patent Center, the entire content of which is incorporated by reference herein in its entirety. The Sequence Listing XML file submitted via Patent Center is entitled "14639-043-999_SequenceListing.xml", was created on Jan. 31, 2023, and is 3,006 bytes in size.

3. FIELD

The present disclosure generally relates to lipid compounds that can be used in combination with other lipid components, such as neutral lipids, cholesterol and polymer conjugated lipids, to form lipid nanoparticles for delivery of therapeutic agents (e.g., nucleic acid molecules, including nucleic acid mimics such as locked nucleic acids (LNAs), peptide nucleic acids (PNAs), and morpholinos), both in vitro and in vivo, for therapeutic or prophylactic purposes, including vaccination. Lipid compounds that can be used in combination with other lipid components, such as neutral lipids, cholesterol and polymer conjugated lipids, to form lipid nanoparticles for delivery of therapeutic agents. There exists a need to develop new lipid compounds (e.g., cationic lipid compounds) that afford efficient delivery of the therapeutic agents, sufficient activity of the therapeutic agents (e.g., expression of mRNA after delivery), optimal pharmacokinetics, and/or other suitable physiological, biological, and/or therapeutic properties.

4. BACKGROUND

Therapeutic nucleic acids have the potential to revolutionize vaccination, gene therapies, protein replacement therapies, and other treatments of genetic diseases. Since the commencement of the first clinical studies on therapeutic nucleic acids in the 2000s, significant progresses have been made through the design of nucleic acid molecules and delivery methods thereof. However, nucleic acid therapeutics still face several challenges, including low cell permeability and high susceptibility to degradation of certain nucleic acids molecules, including RNAs. Thus, there exists a need to develop new nucleic acid molecules, as well as related methods and compositions that facilitate their delivery in vitro or in vivo for therapeutic and/or prophylactic purposes.

5. SUMMARY

In one embodiment, provided herein are lipid compounds, including pharmaceutically acceptable salts, prodrugs or stereoisomers thereof, which can be used alone or in combination with other lipid components such as neutral lipids, charged lipids, steroids (including for example, all sterols) and/or their analogs, and/or polymer conjugated lipids and/or polymers to form lipid nanoparticles for the delivery of therapeutic agents (e.g., nucleic acid molecules, including nucleic acid mimics such as locked nucleic acids (LNAs), peptide nucleic acids (PNAs), and morpholinos). In some instances, the lipid nanoparticles are used to deliver nucleic acids such as antisense and/or messenger RNA. Methods for use of such lipid nanoparticles for treatment of various diseases or conditions, such as those caused by infectious entities and/or insufficiency of a protein, are also provided.

In one embodiment, the lipid compounds provided herein are substituted glyceramine (3-aminopropane-1,2-diol) based lipid compounds.

In one embodiment, provided herein is a compound of Formula (I):

(I)

or a pharmaceutically acceptable salt, prodrug or stereoisomer thereof, wherein $G^1$, $G^2$, $G^3$, $L^1$, $L^2$, $R^0$, $R^4$, $R^5$, and s are as defined herein or elsewhere.

In one embodiment, provided herein is a compound of Formula (II):

(II)

or a pharmaceutically acceptable salt, prodrug or stereoisomer thereof, wherein $G^1$, $G^2$, $G^3$, $L^1$, $L^2$, Y, and $R^3$ are as defined herein or elsewhere.

In one embodiment, provided herein is a compound of Formula (III):

(III)

or a pharmaceutically acceptable salt, prodrug or stereoisomer thereof, wherein $G^3$, $G^4$, $R^0$, $R^1$, $R^2$, and $R^3$ are as defined herein or elsewhere.

In one embodiment, provided herein is a nanoparticle composition comprising a compound provided herein, and a therapeutic or prophylactic agent. In one embodiment, the therapeutic or prophylactic agent comprises at least one mRNA encoding an antigen or a fragment or epitope thereof.

Additional features of the present disclosure will become apparent to those skilled in the art upon consideration of the following detailed description of particular embodiments.

6. DETAILED DESCRIPTION

6.1 General Techniques

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003).

6.2 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

As used herein and unless otherwise specified, the term "lipid" refers to a group of organic compounds that include, but are not limited to, esters of fatty acids and are generally characterized by being poorly soluble in water, but soluble in many nonpolar organic solvents. While lipids generally have poor solubility in water, there are certain categories of lipids (e.g., lipids modified by polar groups, e.g., DMG-PEG2000) that have limited aqueous solubility and can dissolve in water under certain conditions. Known types of lipids include biological molecules such as fatty acids, waxes, sterols, fat-soluble vitamins, monoglycerides, diglycerides, triglycerides, and phospholipids. Lipids can be divided into at least three classes: (1) "simple lipids," which include fats and oils as well as waxes; (2) "compound lipids," which include phospholipids and glycolipids (e.g., DMPE-PEG2000); and (3) "derived lipids" such as steroids. Further, as used herein, lipids also encompass lipidoid compounds. The term "lipidoid compound," also simply "lipidoid", refers to a lipid-like compound (e.g. an amphiphilic compound with lipid-like physical properties).

The term "lipid nanoparticle" or "LNP" refers to a particle having at least one dimension on the order of nanometers (nm) (e.g., 1 to 1,000 nm), which contains one or more types of lipid molecules. The LNP provided herein can further contain at least one non-lipid payload molecule (e.g., one or more nucleic acid molecules). In some embodiments, the LNP comprises a non-lipid payload molecule either partially or completely encapsulated inside a lipid shell. Particularly, in some embodiments, wherein the payload is a negatively charged molecule (e.g., mRNA encoding a viral protein), and the lipid components of the LNP comprise at least one cationic lipid. Without being bound by the theory, it is contemplated that the cationic lipids can interact with the negatively charged payload molecules and facilitates incorporation and/or encapsulation of the payload into the LNP during LNP formation. Other lipids that can form part of a LNP as provided herein include but are not limited to neutral lipids and charged lipids, such as steroids, polymer conjugated lipids, and various zwitterionic lipids. In certain embodiments, a LNP according to the present disclosure comprises one or more lipids of Formula (I), (II), or (III) (and sub-formulas thereof) as described herein.

The term "cationic lipid" refers to a lipid that is either positively charged at any pH value or hydrogen ion activity of its environment, or capable of being positively charged in response to the pH value or hydrogen ion activity of its environment (e.g., the environment of its intended use). Thus, the term "cationic" encompasses both "permanently cationic" and "cationisable." In certain embodiments, the positive charge in a cationic lipid results from the presence of a quaternary nitrogen atom. In certain embodiments, the cationic lipid comprises a zwitterionic lipid that assumes a positive charge in the environment of its intended use (e.g., at physiological pH). In certain embodiments, the cationic lipid is one or more lipids of Formula (I), (II), or (III) (and sub-formulas thereof) as described herein.

The term "polymer conjugated lipid" refers to a molecule comprising both a lipid portion and a polymer portion. An example of a polymer conjugated lipid is a pegylated lipid (PEG-lipid), in which the polymer portion comprises a polyethylene glycol.

The term "neutral lipid" encompasses any lipid molecules existing in uncharged forms or neutral zwitterionic forms at a selected pH value or within a selected pH range. In some embodiments, the selected useful pH value or range corresponds to the pH condition in an environment of the intended uses of the lipids, such as the physiological pH. As non-limiting examples, neutral lipids that can be used in connection with the present disclosure include, but are not limited to, phosphotidylcholines such as 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1-palmitoyl-2-oleoyl-sn-glycero-3-phosphocholine (POPC), 1,2-dioleoyl-sn-glycero-3-phosphocholine (DOPC), phophatidylethanolamines such as 1,2-dioleoyl-sn-glycero-3-phosphoethanolamine (DOPE), 2-((2,3-bis(oleoyloxy) propyl)dimethylammonio)ethyl hydrogen phosphate (DOCP), sphingomyelins (SM), ceramides, steroids such as sterols and their derivatives. Neutral lipids as provided herein may be synthetic or derived (isolated or modified) from a natural source or compound.

The term "charged lipid" encompasses any lipid molecules that exist in either positively charged or negatively charged forms at a selected pH or within a selected pH range. In some embodiments, the selected pH value or range corresponds to the pH condition in an environment of the intended uses of the lipids, such as the physiological pH. As non-limiting examples, neutral lipids that can be used in connection with the present disclosure include, but are not limited to, phosphatidylserines, phosphatidic acids, phosphatidylglycerols, phosphatidylinositols, sterol hemisuccinates, dialkyl trimethylarnmonium-propanes, (e.g., DOTAP, DOTMA), dialkyl dimethylaminopropanes, ethyl phosphocholines, dimethylaminoethane carbamoyl sterols (e.g., DC-Chol), 1,2-dioleoyl-sn-glycero-3-phospho-L-serine sodium salt (DOPS-Na), 1,2-dioleoyl-sn-glycero-3-phospho-(1'-rac-glycerol) sodium salt (DOPG-Na), and 1,2-dioleoyl-sn-glycero-3-phosphate sodium salt (DOPA-Na). Charged lipids as provided herein may be synthetic or derived (isolated or modified) from a natural source or compound.

As used herein, and unless otherwise specified, the term "alkyl" refers to a straight or branched hydrocarbon chain radical consisting solely of carbon and hydrogen atoms, which is saturated. In one embodiment, the alkyl group has, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond. Examples of alkyl groups include, but are not limited to, methyl, ethyl, n-propyl, 1-methylethyl (isopropyl), n-butyl, n-pentyl, 1,1-dimethylethyl (t-butyl), 3-methylhexyl, 2-methylhexyl, and the like. Unless otherwise specified, an alkyl group is optionally substituted.

As used herein, and unless otherwise specified, the term "alkenyl" refers to a straight or branched hydrocarbon chain radical consisting solely of carbon and hydrogen atoms, which contains one or more carbon-carbon double bonds. The term "alkenyl" also embraces radicals having "cis" and "trans" configurations, or alternatively, "E" and "Z" configurations, as appreciated by those of ordinary skill in the art. In one embodiment, the alkenyl group has, for example, from two to twenty-four carbon atoms ($C_2$-$C_{24}$ alkenyl), four to twenty carbon atoms ($C_4$-$C_{20}$ alkenyl), six to sixteen carbon atoms ($C_6$-$C_{16}$ alkenyl), six to nine carbon atoms ($C_6$-$C_9$ alkenyl), two to fifteen carbon atoms ($C_2$-$C_{15}$ alkenyl), two to twelve carbon atoms ($C_2$-$C_{12}$ alkenyl), two to eight carbon atoms ($C_2$-$C_8$ alkenyl) or two to six carbon atoms ($C_2$-$C_6$ alkenyl) and which is attached to the rest of the molecule by a single bond. Examples of alkenyl groups include, but are not limited to, ethenyl, prop-1-enyl, but-1-enyl, pent-1-enyl, penta-1,4-dienyl, and the like. Unless otherwise specified, an alkenyl group is optionally substituted.

As used herein, and unless otherwise specified, the term "alkynyl" refers to a straight or branched hydrocarbon chain radical consisting solely of carbon and hydrogen atoms, which contains one or more carbon-carbon triple bonds. In one embodiment, the alkynyl group has, for example, from two to twenty-four carbon atoms ($C_2$-$C_{24}$ alkynyl), four to twenty carbon atoms ($C_4$-$C_{20}$ alkynyl), six to sixteen carbon atoms ($C_6$-$C_{16}$ alkynyl), six to nine carbon atoms ($C_6$-$C_9$ alkynyl), two to fifteen carbon atoms ($C_2$-$C_{15}$ alkynyl), two to twelve carbon atoms ($C_2$-$C_{12}$ alkynyl), two to eight carbon atoms ($C_2$-$C_8$ alkynyl) or two to six carbon atoms ($C_2$-$C_6$ alkynyl) and which is attached to the rest of the molecule by a single bond. Examples of alkynyl groups include, but are not limited to, ethynyl, propynyl, butynyl, pentynyl, and the like. Unless otherwise specified, an alkynyl group is optionally substituted.

As used herein, and unless otherwise specified, the term "alkylene" or "alkylene chain" refers to a straight or branched multivalent (e.g., divalent or trivalent) hydrocarbon chain linking the rest of the molecule to a radical group (or groups), consisting solely of carbon and hydrogen, which is saturated. In one embodiment, the alkylene has, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene). Examples of alkylene groups include, but are not limited to, methylene, ethylene, propylene, n-butylene, and the like.

The alkylene chain is attached to the rest of the molecule through a single bond and to the radical group through a single bond. The points of attachment of the alkylene chain to the rest of the molecule and to the radical group(s) can be through one carbon or any two (or more) carbons within the chain. Unless otherwise specified, an alkylene chain is optionally substituted.

As used herein, and unless otherwise specified, the term "alkenylene" refers to a straight or branched multivalent (e.g., divalent or trivalent) hydrocarbon chain linking the rest of the molecule to a radical group (or groups), consisting solely of carbon and hydrogen, which contains one or more carbon-carbon double bonds. In one embodiment, the alkenylene has, for example, from two to twenty-four carbon atoms ($C_2$-$C_{24}$ alkenylene), two to fifteen carbon atoms ($C_2$-$C_{15}$ alkenylene), two to twelve carbon atoms ($C_2$-$C_{12}$ alkenylene), two to eight carbon atoms ($C_2$-$C_8$ alkenylene), two to six carbon atoms ($C_2$-$C_6$ alkenylene) or two to four carbon atoms ($C_2$-$C_4$ alkenylene). Examples of alkenylene include, but are not limited to, ethenylene, propenylene, n-butenylene, and the like. The alkenylene is attached to the rest of the molecule through a single or double bond and to the radical group through a single or double bond. The points of attachment of the alkenylene to the rest of the molecule and to the radical group(s) can be through one carbon or any two (or more) carbons within the chain. Unless otherwise specified, an alkenylene is optionally substituted.

As used herein, and unless otherwise specified, the term "cycloalkyl" refers to a non-aromatic monocyclic or polycyclic hydrocarbon radical consisting solely of carbon and hydrogen atoms, and which is saturated. Cycloalkyl group may include fused or bridged ring systems. In one embodiment, the cycloalkyl has, for example, from 3 to 15 ring carbon atoms ($C_3$-$C_{15}$ cycloalkyl), from 3 to 10 ring carbon atoms ($C_3$-$C_{10}$ cycloalkyl), or from 3 to 8 ring carbon atoms ($C_3$-$C_8$ cycloalkyl). The cycloalkyl is attached to the rest of the molecule by a single bond. Examples of monocyclic cycloalkyl radicals include, but are not limited to, cyclopropyl, cyclobutyl, cyclopentyl, cyclohexyl, cycloheptyl, and cyclooctyl. Examples of polycyclic cycloalkyl radicals include, but are not limited to, adamantyl, norbornyl, decalinyl, 7,7-dimethyl-bicyclo[2.2.1]heptanyl, and the like. Unless otherwise specified, a cycloalkyl group is optionally substituted.

As used herein, and unless otherwise specified, the term "cycloalkylene" is a multivalent (e.g., divalent or trivalent) cycloalkyl group. Unless otherwise specified, a cycloalkylene group is optionally substituted.

As used herein, and unless otherwise specified, the term "cycloalkenyl" refers to a non-aromatic monocyclic or polycyclic hydrocarbon radical consisting solely of carbon and hydrogen atoms, and which includes one or more carbon-carbon double bonds. Cycloalkenyl may include fused or bridged ring systems. In one embodiment, the cycloalkenyl has, for example, from 3 to 15 ring carbon atoms ($C_3$-$C_{15}$ cycloalkenyl), from 3 to 10 ring carbon atoms ($C_3$-$C_{10}$ cycloalkenyl), or from 3 to 8 ring carbon atoms ($C_3$-$C_8$ cycloalkenyl). The cycloalkenyl is attached to the rest of the molecule by a single bond. Examples of monocyclic cycloalkenyl radicals include, but are not limited to, cyclopropenyl, cyclobutenyl, cyclopentenyl, cyclohexenyl, cycloheptenyl, cyclooctenyl, and the like. Unless otherwise specified, a cycloalkenyl group is optionally substituted.

As used herein, and unless otherwise specified, the term "cycloalkenylene" is a multivalent (e.g., divalent or trivalent) cycloalkenyl group. Unless otherwise specified, a cycloalkenylene group is optionally substituted.

As used herein, and unless otherwise specified, the term "heterocyclyl" refers to a non-aromatic radical monocyclic or polycyclic moiety that contains one or more (e.g., one, one or two, one to three, or one to four) heteroatoms independently selected from nitrogen, oxygen, phosphorous, and sulfur. The heterocyclyl may be attached to the main structure at any heteroatom or carbon atom. A heterocyclyl group can be a monocyclic, bicyclic, tricyclic, tetracyclic, or other polycyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Saturated heterocycloalkyl groups can be termed "heterocycloalkyl". Partially unsaturated heterocycloalkyl groups can be termed "heterocycloalkenyl" if the heterocyclyl contains at least one double bond, or "heterocycloalkynyl" if the heterocyclyl contains at least one triple bond. In one embodiment, the heterocyclyl has, for example, 3 to 18 ring atoms (3- to 18-membered heterocyclyl), 4 to 18 ring atoms (4- to 18-membered heterocyclyl), 5 to 18 ring atoms (3- to 18-membered heterocyclyl), 4 to 8 ring atoms (4- to 8-membered heterocyclyl), or 5 to 8 ring atoms (5- to 8-membered heterocyclyl). Whenever it appears herein, a numerical range such as "3 to 18" refers to each integer in the given range; e.g., "3 to 18 ring atoms" means that the heterocyclyl group can consist of 3 ring atoms, 4 ring atoms, 5 ring atoms, 6 ring atoms, 7 ring atoms, 8 ring atoms, 9 ring atoms, 10 ring atoms, etc., up to and including 18 ring atoms. Examples of heterocyclyl groups include, but are not limited to, imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl. Unless otherwise specified, a heterocyclyl group is optionally substituted.

As used herein, and unless otherwise specified, the term "heterocyclylene" is a multivalent (e.g., divalent or trivalent) heterocyclyl group. Unless otherwise specified, a heterocyclylene group is optionally substituted.

As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 18 ring carbon atoms ($C_6$-$C_{18}$ aryl), from 6 to 14 ring carbon atoms ($C_6$-$C_{14}$ aryl), or from 6 to 10 ring carbon atoms ($C_6$-$C_{10}$ aryl). Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic, tricyclic, or other multicyclic hydrocarbon rings, where at least one of the rings is aromatic and the others of which may be saturated, partially unsaturated, or aromatic, for example, dihydronaphthyl, indenyl, indanyl, or tetrahydronaphthyl (tetralinyl). Unless otherwise specified, an aryl group is optionally substituted.

As used herein, and unless otherwise specified, the term "arylene" is a multivalent (e.g., divalent or trivalent) aryl group. Unless otherwise specified, an arylene group is optionally substituted.

As used herein, and unless otherwise specified, the term "heteroaryl" refers to a monocyclic aromatic group and/or multicyclic aromatic group that contains at least one aromatic ring, wherein at least one aromatic ring contains one or more (e.g., one, one or two, one to three, or one to four) heteroatoms independently selected from O, S, and N. The heteroaryl may be attached to the main structure at any heteroatom or carbon atom. In certain embodiments, the heteroaryl has from 5 to 20, from 5 to 15, or from 5 to 10 ring atoms. The term "heteroaryl" also refers to bicyclic, tricyclic, or other multicyclic rings, where at least one of the rings is aromatic and the others of which may be saturated, partially unsaturated, or aromatic, wherein at least one aromatic ring contains one or more heteroatoms independently selected from O, S, and N. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. Unless otherwise specified, a heteroaryl group is optionally substituted.

As used herein, and unless otherwise specified, the term "heteroarylene" is a multivalent (e.g., divalent or trivalent) heteroaryl group. Unless otherwise specified, a heteroarylene group is optionally substituted.

When the groups described herein are said to be "substituted," they may be substituted with any appropriate substituent or substituents. Illustrative examples of substituents include, but are not limited to, those found in the exemplary compounds and embodiments provided herein, as well as: a halogen atom such as F, Cl, Br, or I; cyano; oxo (=O); hydroxyl (—OH); alkyl; alkenyl; alkynyl; cycloalkyl; aryl; —(C=O)OR'; —O(C=O)R'; —C(=O)R'; —OR'; —S(O)$_x$R'; —S—SR'; —C(=O)SR'; —SC(=O)R'; —NR'R'; —NR'C(=O)R'; —C(=O)NR'R'; —NR'C(=O) NR'R'; —OC(=O)NR'R'; —NR'C(=O)OR'; —NR'S(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amino group (—NR'R').

As used herein, and unless otherwise specified, the term "optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

As used herein, and unless otherwise specified, the term "prodrug" of a biologically active compound refers to a compound that may be converted under physiological conditions or by solvolysis to the biologically active compound. In one embodiment, the term "prodrug" refers to a metabolic precursor of the biologically active compound that is pharmaceutically acceptable. A prodrug may be inactive when administered to a subject in need thereof, but is converted in vivo to the biologically active compound. Prodrugs are typically rapidly transformed in vivo to yield the parent biologically active compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

In one embodiment, the term "prodrug" is also meant to include any covalently bonded carriers, which release the active compound in vivo when such prodrug is administered to a mammalian subject. Prodrugs of a compound may be prepared by modifying functional groups present in the compound in such a way that the modifications are cleaved, either in routine manipulation or in vivo, to the parent compound. Prodrugs include compounds wherein a hydroxyl, amino or mercapto group is bonded to any group that, when the prodrug of the compound is administered to a mammalian subject, cleaves to form a free hydroxyl, free amino or free mercapto group, respectively.

Examples of prodrugs include, but are not limited to, acetate, formate and benzoate derivatives of alcohol or amide derivatives of amine functional groups in the compounds provided herein.

As used herein, and unless otherwise specified, the term "pharmaceutically acceptable salt" includes both acid and base addition salts.

Examples of pharmaceutically acceptable acid addition salts include, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Examples of pharmaceutically acceptable base addition salt include, but are not limited to, salts prepared from addition of an inorganic base or an organic base to a free acid compound. Salts derived from inorganic bases include, but are not limited to, the sodium, potassium, lithium, ammonium, calcium, magnesium, iron, zinc, copper, manganese, aluminum salts and the like. In one embodiment, the inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. In one embodiment, the organic bases are isopropylamine, diethylamine, ethanolamine, trimethylamine, dicyclohexylamine, choline and caffeine.

A compound provided herein may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Unless otherwise specified, a compound provided herein is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and unless otherwise specified, the term "isomer" refers to different compounds that have the same molecular formula. "Stereoisomers" are isomers that differ only in the way the atoms are arranged in space. "Atropisomers" are stereoisomers from hindered rotation about single bonds. "Enantiomers" are a pair of stereoisomers that are non-superimposable mirror images of each other. A mixture of a pair of enantiomers in any proportion can be known as a "racemic" mixture. "Diastereoisomers" are stereoisomers that have at least two asymmetric atoms, but which are not mirror-images of each other.

"Stereoisomers" can also include E and Z isomers, or a mixture thereof, and cis and trans isomers or a mixture thereof. In certain embodiments, a compound described herein is isolated as either the E or Z isomer. In other embodiments, a compound described herein is a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

It should also be noted a compound described herein can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N) As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound described herein, whether radioactive or not, are intended to be encompassed within the scope of the embodiments provided herein. In some embodiments, there are provided isotopologs of a compound described herein, for example, the isotopologs are deuterium, carbon-13, and/or nitrogen-15 enriched. As used herein, "deuterated", means a compound wherein at least one hydrogen (H) has been replaced by deuterium (indicated by D or $^2$H), that is, the compound is enriched in deuterium in at least one position.

It should be noted that if there is a discrepancy between a depicted structure and a name for that structure, the depicted structure is to be accorded more weight.

As used herein, and unless otherwise specified, the term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "composition" is intended to encompass a product containing the specified ingredients (e.g., a mRNA molecule provided herein) in, optionally, the specified amounts.

The term "polynucleotide" or "nucleic acid," as used interchangeably herein, refers to polymers of nucleotides of any length and includes, e.g., DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. Nucleic acid can be in either single- or double-stranded forms. As used herein and unless otherwise specified, "nucleic acid" also includes nucleic acid mimics such as locked nucleic acids (LNAs), peptide nucleic acids (PNAs), and morpholinos. "Oligonucleotide," as used herein, refers to short synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as an mRNA molecule, can be substantially free of other cellular material, or culture medium when produced by recombinant techniques, or substantially free of chemical precursors or other chemicals when chemically synthesized. In a specific embodiment, one or more nucleic acid molecules encoding an antigen as described herein are isolated or purified. The term embraces nucleic acid sequences that have been removed from their naturally occurring environment, and includes recombinant or cloned DNA or RNA isolates and chemically synthesized analogues or analogues biologically synthesized by heterologous systems. A substantially pure molecule may include isolated forms of the molecule.

The term "encoding nucleic acid" or grammatical equivalents thereof as it is used in reference to nucleic acid molecule encompasses (a) a nucleic acid molecule in its native state or when manipulated by methods well known to those skilled in the art that can be transcribed to produce mRNA which is then translated into a peptide and/or polypeptide, and (b) the mRNA molecule itself. The antisense strand is the complement of such a nucleic acid molecule, and the encoding sequence can be deduced therefrom. The term "coding region" refers to a portion in an encoding nucleic acid sequence that is translated into a peptide or polypeptide. The term "untranslated region" or "UTR" refers to the portion of an encoding nucleic acid that is not translated into a peptide or polypeptide. Depending on the orientation of a UTR with respect to the coding region of a nucleic acid molecule, a UTR is referred to as the 5'-UTR if located to the 5'-end of a coding region, and a UTR is referred to as the 3'-UTR if located to the 3'-end of a coding region.

The term "mRNA" as used herein refers to a message RNA molecule comprising one or more open reading frame (ORF) that can be translated by a cell or an organism provided with the mRNA to produce one or more peptide or protein product. The region containing the one or more ORFs is referred to as the coding region of the mRNA molecule. In certain embodiments, the mRNA molecule further comprises one or more untranslated regions (UTRs).

In certain embodiments, the mRNA is a monocistronic mRNA that comprises only one ORF. In certain embodiments, the monocistronic mRNA encodes a peptide or protein comprising at least one epitope of a selected antigen (e.g., a pathogenic antigen or a tumor associated antigen). In other embodiments, the mRNA is a multicistronic mRNA that comprises two or more ORFs. In certain embodiments, the multiecistronic mRNA encodes two or more peptides or proteins that can be the same or different from each other. In certain embodiments, each peptide or protein encoded by a multicistronic mRNA comprises at least one epitope of a selected antigen. In certain embodiments, different peptide or protein encoded by a multicistronic mRNA each comprises at least one epitope of different antigens. In any of the embodiments described herein, the at least one epitope can be at least 2, at least 3, at least 4, at least 5, at least 6, at least 7, at least 8, at least 9, or at least 10 epitopes of an antigen.

The term "nucleobases" encompasses purines and pyrimidines, including natural compounds adenine, thymine, guanine, cytosine, uracil, inosine, and natural or synthetic analogs or derivatives thereof.

The term "functional nucleotide analog" as used herein refers to a modified version of a canonical nucleotide A, G, C, U or T that (a) retains the base-pairing properties of the corresponding canonical nucleotide, and (b) contains at least one chemical modification to (i) the nucleobase, (ii) the sugar group, (iii) the phosphate group, or (iv) any combinations of (i) to (iii), of the corresponding natural nucleotide. As used herein, base pairing encompasses not only the canonical Watson-Crick adenine-thymine, adenine-uracil, or guanine-cytosine base pairs, but also base pairs formed between canonical nucleotides and functional nucleotide analogs or between a pair of functional nucleotide analogs, wherein the arrangement of hydrogen bond donors and hydrogen bond acceptors permits hydrogen bonding between a modified nucleobase and a canonical nucleobase or between two complementary modified nucleobase structures. For example, a functional analog of guanosine (G) retains the ability to base-pair with cytosine (C) or a functional analog of cytosine. One example of such non-canonical base pairing is the base pairing between the modified nucleotide inosine and adenine, cytosine, or uracil. As described herein, a functional nucleotide analog can be either naturally occurring or non-naturally occurring. Accordingly, a nucleic acid molecule containing a functional nucleotide analog can have at least one modified nucleobase, sugar group and/or internucleoside linkage. Exemplary chemical modifications to the nucleobases, sugar groups, or internucleoside linkages of a nucleic acid molecule are provided herein.

The terms "translational enhancer element," "TEE" and "translational enhancers" as used herein refers to an region in a nucleic acid molecule that functions to promotes translation of a coding sequence of the nucleic acid into a protein or peptide product, such as via cap-dependent or cap-independent translation. A TEE typically locates in the UTR region of a nucleic acid molecule (e.g., mRNA) and enhance the translational level of a coding sequence located either upstream or downstream. For example, a TEE in a 5'-UTR of a nucleic acid molecule can locate between the promoter and the starting codon of the nucleic acid molecule. Various TEE sequences are known in the art (Wellensiek et al. Genome-wide profiling of human cap-independent translation-enhancing elements, *Nature Methods*, 2013 August; 10(8): 747-750; Chappell et al. PNAS Jun. 29, 2004 101 (26) 9590-9594). Some TEEs are known to be conserved across multiple species (Pinek et al. *Nucleic Acids Research*, Volume 41, Issue 16, 1 Sep. 2013, Pages 7625-7634).

As used herein, the term "stem-loop sequence" refers to a single-stranded polynucleotide sequence having at least two regions that are complementary or substantially complementary to each other when read in opposite directions, and thus capable of base-pairing with each other to form at least one double helix and an unpaired loop. The resulting structure is known as a stem-loop structure, a hairpin, or a hairpin loop, which is a secondary structure found in many RNA molecules.

The term "peptide" as used herein refers to a polymer containing between two and fifty (2-50) amino acid residues linked by one or more covalent peptide bond(s). The terms apply to naturally occurring amino acid polymers as well as amino acid polymers in which one or more amino acid residues is a non-naturally occurring amino acid (e.g., an amino acid analog or non-natural amino acid).

The terms "polypeptide" and "protein" are used interchangeably herein to refer to a polymer of greater than fifty

(50) amino acid residues linked by covalent peptide bonds. That is, a description directed to a polypeptide applies equally to a description of a protein, and vice versa. The terms apply to naturally occurring amino acid polymers as well as amino acid polymers in which one or more amino acid residues is a non-naturally occurring amino acid (e.g., an amino acid analog). As used herein, the terms encompass amino acid chains of any length, including full length proteins (e.g., antigens).

The term "antigen" refers to a substance that can be recognized by the immune system of a subject (including by the adaptive immune system), and is capable of triggering an immune response after the subject is contacted with the antigen (including an antigen-specific immune response). In certain embodiments, the antigen is a protein associated with a diseased cell, such as a cell infected by a pathogen or a neoplastic cell (e.g., tumor associated antigen (TAA)).

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, fragments refers to polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950 contiguous amino acid residues of the amino acid sequence of a polypeptide. In a specific embodiment, a fragment of a polypeptide retains at least 1, at least 2, at least 3, or more functions of the polypeptide.

An "epitope" is the site on the surface of an antigen molecule to which a single antibody molecule binds, such as a localized region on the surface of an antigen that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered conformation, such as following activation or binding of another protein or ligand. In certain embodiments, an epitope is a three-dimensional surface feature of a polypeptide. In other embodiments, an epitope is linear feature of a polypeptide. Generally an antigen has several or many different epitopes and may react with many different antibodies.

The term "genetic vaccine" as used herein refers to a therapeutic or prophylactic composition comprising at least one nucleic acid molecule encoding an antigen associated with a target disease (e.g., an infectious disease or a neoplastic disease). Administration of the vaccine to a subject ("vaccination") allows for the production of the encoded peptide or protein, thereby eliciting an immune response against the target disease in the subject. In certain embodiments, the immune response comprises adaptive immune response, such as the production of antibodies against the encoded antigen, and/or activation and proliferations of immune cells capable of specifically eliminating diseased cells expressing the antigen. In certain embodiments, the immune response further comprises innate immune response. According to the present disclosure, a vaccine can be administered to a subject either before or after the onset of clinical symptoms of the target disease. In some embodiments, vaccination of a healthy or asymptomatic subject renders the vaccinated subject immune or less susceptible to the development of the target disease. In some embodiments, vaccination of a subject showing symptoms of the disease improves the condition of, or treats, the disease in the vaccinated subject.

The terms "innate immune response" and "innate immunity" are recognized in the art, and refer to non-specific defense mechanism a body's immune system initiates upon recognition of pathogen-associated molecular patterns, which involves different forms of cellular activities, including cytokine production and cell death through various pathways. As used herein, innate immune responses include, without limitation, increased production of inflammation cytokines (e.g., type I interferon or IL-10 production), activation of the NFκB pathway, increased proliferation, maturation, differentiation and/or survival of immune cells, and in some cases, induction of cell apoptosis. Activation of the innate immunity can be detected using methods known in the art, such as measuring the (NF)-κB activation.

The terms "adaptive immune response" and "adaptive immunity" are recognized in the art, and refer to antigen-specific defense mechanism a body's immune system initiates upon recognition of a specific antigen, which include both humoral response and cell-mediated responses. As used herein, adaptive immune responses include cellular responses that is triggered and/or augmented by a vaccine composition, such as a genetic composition described herein. In some embodiments, the vaccine composition comprises an antigen that is the target of the antigen-specific adaptive immune response. In other embodiments, the vaccine composition, upon administration, allows the production in an immunized subject of an antigen that is the target of the antigen-specific adaptive immune response. Activation of an adaptive immune response can be detected using methods known in the art, such as measuring the antigen-specific antibody production, or the level of antigen-specific cell-mediated cytotoxicity.

The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a polypeptide, a fragment or an epitope thereof. Antibodies also include, but are not limited to, synthetic antibodies, recombinantly produced antibodies, camelized antibodies, intrabodies, anti-idiotypic (anti-Id) antibodies, and functional fragments of any of the above, which refers to a portion of an antibody heavy or light chain polypeptide that retains some or all of the binding activity of the antibody from which the fragment was derived. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site (e.g., one or more CDR[5] of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule.

The term "administer" or "administration" refers to the act of injecting or otherwise physically delivering a substance as it exists outside the body (e.g., a lipid nanoparticle composition as described herein) into a patient, such as by mucosal, intradermal, intravenous, intramuscular delivery, and/or any other method of physical delivery described herein or known in the art. When a disease, disorder, condition, or a symptom thereof, is being treated, administration of the substance typically occurs after the onset of the disease, disorder, condition, or symptoms thereof. When a disease, disorder, condition, or symptoms thereof, are being prevented, administration of the substance typically occurs before the onset of the disease, disorder, condition, or symptoms thereof.

"Chronic" administration refers to administration of the agent(s) in a continuous mode (e.g., for a period of time such as days, weeks, months, or years) as opposed to an acute mode, so as to maintain the initial therapeutic effect (activity) for an extended period of time. "Intermittent" administration is treatment that is not consecutively done without interruption, but rather is cyclic in nature.

The term "targeted delivery" or the verb form "target" as used herein refers to the process that promotes the arrival of a delivered agent (such as a therapeutic payload molecule in a lipid nanoparticle composition as described herein) at a specific organ, tissue, cell and/or intracellular compartment (referred to as the targeted location) more than any other organ, tissue, cell or intracellular compartment (referred to as the non-target location). Targeted delivery can be detected using methods known in the art, for example, by comparing the concentration of the delivered agent in a targeted cell population with the concentration of the delivered agent at a non-target cell population after systemic administration. In certain embodiments, targeted delivery results in at least 2 fold higher concentration at a targeted location as compared to a non-target location.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, infection and neoplasia. In some embodiments, the effective amount is a therapeutically effective amount or a prophylactically effective amount.

The term "therapeutically effective amount" as used herein refers to the amount of an agent (e.g., a vaccine composition) that is sufficient to reduce and/or ameliorate the severity and/or duration of a given disease, disorder, or condition, and/or a symptom related thereto (e.g., an infectious disease such as caused by viral infection, or a neoplastic disease such as cancer). A "therapeutically effective amount" of a substance/molecule/agent of the present disclosure (e.g., the lipid nanoparticle composition as described herein) may vary according to factors such as the disease state, age, sex, and weight of the individual, and the ability of the substance/molecule/agent to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of a lipid nanoparticle composition as described herein or a therapeutic or prophylactic agent contained therein (e.g., a therapeutic mRNA) effective to "treat" a disease, disorder, or condition, in a subject or mammal.

A "prophylactically effective amount" is an amount of a pharmaceutical composition that, when administered to a subject, will have the intended prophylactic effect, e.g., preventing, delaying, or reducing the likelihood of the onset (or reoccurrence) of a disease, disorder, condition, or associated symptom(s) (e.g., an infectious disease such as caused by viral infection, or a neoplastic disease such as cancer). Typically, but not necessarily, since a prophylactic dose is used in subjects prior to or at an earlier stage of a disease, disorder, or condition, a prophylactically effective amount may be less than a therapeutically effective amount. The full therapeutic or prophylactic effect does not necessarily occur by administration of one dose, and may occur only after administration of a series of doses. Thus, a therapeutically or prophylactically effective amount may be administered in one or more administrations.

The terms "prevent," "preventing," and "prevention" refer to reducing the likelihood of the onset (or recurrence) of a disease, disorder, condition, or associated symptom(s) (e.g., an infectious disease such as caused by viral infection, or a neoplastic disease such as cancer).

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as a lipid nanoparticle composition as described herein) to "manage" an infectious or neoplastic disease, one or more symptoms thereof, so as to prevent the progression or worsening of the disease.

The term "prophylactic agent" refers to any agent that can totally or partially inhibit the development, recurrence, onset, or spread of disease and/or symptom related thereto in a subject.

The term "therapeutic agent" refers to any agent that can be used in treating, preventing, or alleviating a disease, disorder, or condition, including in the treatment, prevention, or alleviation of one or more symptoms of a disease, disorder, or condition and/or a symptom related thereto.

The term "therapy" refers to any protocol, method, and/or agent that can be used in the prevention, management, treatment, and/or amelioration of a disease, disorder, or condition. In certain embodiments, the terms "therapies" and "therapy" refer to a biological therapy, supportive therapy, and/or other therapies useful in the prevention, management, treatment, and/or amelioration of a disease, disorder, or condition, known to one of skill in the art such as medical personnel.

As used herein, a "prophylactically effective serum titer" is the serum titer of an antibody in a subject (e.g., a human), that totally or partially inhibits the development, recurrence, onset, or spread of a disease, disorder, or condition, and/or symptom related thereto in the subject.

In certain embodiments, a "therapeutically effective serum titer" is the serum titer of an antibody in a subject (e.g., a human), that reduces the severity, the duration, and/or the symptoms associated with a disease, disorder, or condition, in the subject.

The term "serum titer" refers to an average serum titer in a subject from multiple samples (e.g., at multiple time points) or in a population of at least 10, at least 20, at least 40 subjects, up to about 100, 1000, or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful, uncomfortable, or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, loss of appetite, rashes or swellings at the site of administration, flu-like symptoms such as fever, chills, and fatigue, digestive tract problems, and allergic reactions. Additional undesired effects experienced by patients are numerous and known in the art. Many are described in Physician's Desk Reference (68th ed. 2014).

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal (e.g., a human) having an infectious disease or neoplastic disease. In another embodiment, the subject is a mammal (e.g., a human) at risk of developing an infectious disease or neoplastic disease.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "detectable agent" refers to a substance that can be used to ascertain the existence or presence of a desired molecule, such as an antigen encoded by an mRNA molecule as described herein, in a sample or subject. A detectable agent can be a substance that is capable of being visualized or a substance that is otherwise able to be determined and/or measured (e.g., by quantitation).

"Substantially all" refers to at least about 60%, at least about 65%, at least about 70%, at least about 75%, at least about 80%, at least about 85%, at least about 90%, at least about 95%, at least about 98%, at least about 99%, or about 100%.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 20%, 15%, 10%, 9%, 8%, 7%, 6%, 5%, 4%, 3%, 2%, 1%, 0.5%, 0.05%, or less of a given value or range.

The singular terms "a," "an," and "the" as used herein include the plural reference unless the context clearly indicates otherwise.

All publications, patent applications, accession numbers, and other references cited in this specification are herein incorporated by reference in their entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section and examples are intended to illustrate but not limit the scope of invention described in the claims.

6.3 Lipid Compounds

Unless otherwise specified, the descriptions provided herein apply to all the formulas provided herein (e.g., Formula (I), Formula (II), and Formula (III), including their sub-formulas), to the extent that they are applicable.

In one embodiment, provided herein is a compound of Formula (I):

(I)

or a pharmaceutically acceptable salt, prodrug or stereoisomer thereof, wherein:

$G^1$ and $G^2$ are each independently a bond, $C_2$-$C_{12}$ alkylene, or $C_2$-$C_{12}$ alkenylene;

$L^1$ is —OC(=O)$R^1$, —C(=O)O$R^1$, —OC(=O)O$R^1$, —C(=O)$R^1$, —O$R^1$, —S(O)$_x$$R^1$, —S—S$R^1$, —C(=O)S$R^1$, —SC(=O)$R^1$, —$NR^a$C(=O)$R^1$, —C(=O)$NR^b$$R^c$, —$NR^a$C(=O)$NR^b$$R^c$, —OC(=O)$NR^b$$R^c$, —$NR^a$C(=O)O$R^1$, —SC(=S)$R^1$, —C(=S)S$R^1$, —C(=S)$R^1$, —CH(OH)$R^1$, —P(=O)(O$R^b$)(O$R^c$), —($C_6$-$C_{10}$ arylene)-$R^1$, -(6- to 10-membered heteroarylene)-$R^1$, or $R^1$;

$L^2$ is —OC(=O)$R^2$, —C(=O)O$R^2$, —OC(=O)O$R^2$, —C(=O)$R^2$, —O$R^2$, —S(O)$R^2$, —S—S$R^2$, —C(=O)S$R^2$, —SC(=O)$R^2$, —$NR^a$C(=O)$R^2$, —C(=O)$NR^e$$R^f$, —$NR^d$C(=O)$NR^e$$R^f$, —OC(=O)$NR^e$$R^f$, —$NR^a$C(=O)O$R^2$, —SC(=S)$R^2$, —C(=S)S$R^2$, —C(=S)$R^2$, —CH(OH)$R^2$, —P(=O)(O$R^e$)(O$R^f$), —($C_6$-$C_{10}$ arylene)-$R^2$, -(6- to 10-membered heteroarylene)-$R^2$, or $R^2$;

$R^1$ and $R^2$ are each independently $C_5$-$C_{32}$ alkyl or $C_5$-$C_{32}$ alkenyl;

$R^a$, $R^b$, $R^d$, and $R^e$ are each independently H, $C_1$-$C_{24}$ alkyl, or $C_2$-$C_{24}$ alkenyl;

$R^c$ and $R^f$ are each independently $C_1$-$C_{32}$ alkyl or $C_2$-$C_{32}$ alkenyl;

$R^0$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$G^3$ is $C_2$-$C_{12}$ alkylene or $C_2$-$C_{12}$ alkenylene;

$R^4$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$R^5$ is $C_1$-$C_{12}$ alkyl, $C_3$-$C_8$ cycloalkyl, $C_3$-$C_8$ cycloalkenyl, $C_6$-$C_{10}$ aryl, or 4- to 8-membered heterocycloalkyl;

x is 0, 1, or 2;

s is 0 or 1; and wherein each alkyl, alkenyl, cycloalkyl, cycloalkenyl, heterocycloalkyl, aryl, alkylene, alkenylene, arylene, and heteroarylene, is independently optionally substituted.

In one embodiment, the compound is not

In one embodiment, s is 0. In one embodiment, when s is 0, then $R^4$ is not $C_1$-$C_{12}$ alkyl. In one embodiment, when s is 0, then $R^4$ is $C_3$-$C_8$ cycloalkyl. In one embodiment, s is 1.

In one embodiment, provided herein is a compound of Formula (II):

$$\text{(II)}$$

or a pharmaceutically acceptable salt, prodrug or stereoisomer thereof, wherein:

$G^1$ and $G^2$ are each independently a bond, $C_2$-$C_{12}$ alkylene, or $C_2$-$C_{12}$ alkenylene;

$L^1$ is —OC(=O)$R^1$, —C(=O)O$R^1$, —OC(=O)O$R^1$, —C(=O)$R^1$, —O$R^1$, —S(O)$_x$$R^1$, —S—S$R^1$, —C(=O)S$R^1$, —SC(=O)$R^1$, —NR$^a$C(=O)$R^1$, —C(=O)NR$^b$R$^b$, —NR$^a$C(=O)NR$^b$R$^c$, —OC(=O)NR$^b$R$^c$, —NR$^a$C(=O)O$R^1$, —SC(=S)$R^1$, —C(=S)S$R^1$, —C(=S)$R^1$, —CH(OH)$R^1$, —P(=O)(OR$^b$)(OR$^c$), —($C_6$-$C_{10}$ arylene)-$R^1$, -(6- to 10-membered heteroarylene)-$R^1$, or $R^1$;

$L^2$ is —OC(=O)$R^2$, —C(=O)O$R^2$, —OC(=O)O$R^2$, —C(=O)$R^2$, —O$R^2$, —S(O)$_x$$R^2$, —S—S$R^2$, —C(=O)S$R^2$, —SC(=O)$R^2$, —NR$^d$C(=O)$R^2$, —C(=O)NR$^e$R$^f$, —NR$^d$C(=O)NR$^e$R$^f$, —OC(=O)NR$^e$R$^f$, —NR$^d$C(=O)O$R^2$, —SC(=S)$R^2$, —C(=S)S$R^2$, —C(=S)$R^2$, —CH(OH)$R^2$, —P(=O)(OR$^e$)(OR$^f$), —($C_6$-$C_{10}$ arylene)-$R^2$, -(6- to 10-membered heteroarylene)-$R^2$, or $R^2$;

$R^1$ and $R^2$ are each independently $C_5$-$C_{32}$ alkyl or $C_5$-$C_{32}$ alkenyl;

Y is H, $C_1$-$C_{14}$ alkyl, or —C(=O)($C_1$-$C_{14}$ alkyl);

$R^a$, $R^b$, $R^d$, and $R^c$ are each independently H, $C_1$-$C_{24}$ alkyl, or $C_2$-$C_{24}$ alkenyl;

$R^c$ and $R^f$ are each independently $C_1$-$C_{32}$ alkyl or $C_2$-$C_{32}$ alkenyl;

$G^3$ is $C_2$-$C_{12}$ alkylene or $C_2$-$C_{12}$ alkenylene;

$R^3$ is —N($R^4$)$R^5$ or —OR$^6$;

$R^4$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$R^5$ is $C_1$-$C_{12}$ alkyl, $C_3$-$C_8$ cycloalkyl, $C_3$-$C_8$ cycloalkenyl, $C_6$-$C_{10}$ aryl, or 4- to 8-membered heterocycloalkyl; or $R^4$, $R^5$, together with the nitrogen to which they are attached form a cyclic moiety;

$R^6$ is hydrogen, $C_1$-$C_{12}$ alkyl, $C_3$-$C_8$ cycloalkyl, $C_3$-$C_8$ cycloalkenyl, or $C_6$-$C_{10}$ aryl;

x is 0, 1, or 2; and wherein each alkyl, alkenyl, cycloalkyl, cycloalkenyl, heterocycloalkyl, aryl, alkylene, alkenylene, arylene, heteroarylene, and cyclic moiety is independently optionally substituted.

In one embodiment, Y is H.

In one embodiment, Y is $C_1$-$C_{14}$ alkyl. In one embodiment, Y is $C_4$-$C_{14}$ alkyl. In one embodiment, Y is $C_6$-$C_{12}$ alkyl. In one embodiment, Y is n-hexyl. In one embodiment, Y is n-octyl. In one embodiment, Y is n-decyl. In one embodiment, Y is n-dodecyl.

In one embodiment, Y is —C(=O)($C_1$-$C_{14}$ alkyl). In one embodiment, Y is —C(=O)($C_1$-$C_5$ alkyl). In one embodiment, Y is acetyl. In one embodiment, Y is propionyl. In one embodiment, Y is —C(=O)(n-pentyl).

In one embodiment, provided herein is a compound of Formula (III):

$$\text{(III)}$$

or a pharmaceutically acceptable salt, prodrug or stereoisomer thereof, wherein:

$R^1$ and $R^2$ are each independently $C_5$-$C_{32}$ alkyl or $C_5$-$C_{32}$ alkenyl;

$R^0$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$G^3$ is $C_2$-$C_{12}$ alkylene or $C_2$-$C_{12}$ alkenylene;

$G^4$ is $C_2$-$C_{12}$ alkylene or $C_2$-$C_{12}$ alkenylene;

$R^3$ is —$N(R^4)R^5$ or —$OR^6$;

$R^4$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$R^5$ is $C_1$-$C_{12}$ alkyl, $C_3$-$C_8$ cycloalkyl, $C_3$-$C_8$ cycloalkenyl, $C_6$-$C_{10}$ aryl, or 4- to 8-membered heterocycloalkyl; or $R^4$, $R^5$, together with the nitrogen to which they are attached form a cyclic moiety;

$R^6$ is hydrogen, $C_1$-$C_{12}$ alkyl, $C_3$-$C_8$ cycloalkyl, $C_3$-$C_8$ cycloalkenyl, or $C_6$-$C_{10}$ aryl; and wherein each alkyl, alkenyl, cycloalkyl, cycloalkenyl, heterocycloalkyl, aryl, alkylene, alkenylene, and cyclic moiety is independently optionally substituted.

In one embodiment, $G^4$ is $C_2$-$C_{12}$ alkylene. In one embodiment, $G^4$ is $C_2$-$C_8$ alkylene. In one embodiment, $G^4$ is $C_2$-$C_6$ alkylene. In one embodiment, $G^4$ is $C_2$-$C_4$ alkylene. In one embodiment, $G^4$ is $C_2$ alkylene. In one embodiment, $G^4$ is $C_4$ alkylene.

In one embodiment, $G^4$ is $C_2$-$C_{12}$ alkenylene. In one embodiment, $G^4$ is $C_2$-$C_8$ alkenylene. In one embodiment, $G^4$ is $C_2$-$C_6$ alkenylene. In one embodiment, $G^4$ is $C_2$-$C_4$ alkenylene.

In one embodiment, $G^4$ is unsubstituted. In one embodiment, $G^4$ is substituted.

In one embodiment, $G^3$ is $C_2$-$C_{12}$ alkylene. In one embodiment, $G^3$ is $C_2$-$C_8$ alkylene. In one embodiment, $G^3$ is $C_2$-$C_6$ alkylene. In one embodiment, $G^3$ is $C_2$-$C_4$ alkylene. In one embodiment, $G^3$ is $C_2$ alkylene. In one embodiment, $G^3$ is $C_4$ alkylene.

In one embodiment, $G^3$ is $C_2$-$C_{12}$ alkenylene. In one embodiment, $G^3$ is $C_2$-$C_8$ alkenylene. In one embodiment, $G^3$ is $C_2$-$C_6$ alkenylene. In one embodiment, $G^3$ is $C_2$-$C_4$ alkenylene.

In one embodiment, $G^3$ is unsubstituted. In one embodiment, $G^3$ is substituted. In one embodiment, $G^3$ is substituted with one or more oxo. In one embodiment, $G^3$ is —($C_1$-$C_{11}$ alkylene)-C(=O)—. In one embodiment, $G^3$ is —($C_1$-$C_7$ alkylene)-C(=O)—. In one embodiment, $G^3$ is —($C_1$-$C_5$ alkylene)-C(=O)—. In one embodiment, $G^3$ is —($C_1$-$C_3$ alkylene)-C(=O)—. In one embodiment, $G^3$ is —$CH_2$—C(=O)—. In one embodiment, $G^3$ is —$CH_2$—$CH_2$—$CH_2$—C(=O)—. In one embodiment, the —C(=O)— is connected to the nitrogen atom, and the alkylene is connected to —$N(R^4)R^5$ or —$OR^6$.

In one embodiment, $R^3$ is —$OR^6$.

In one embodiment, $R^6$ is hydrogen (i.e., $R^3$ is —OH). In one embodiment, $R^6$ is $C_1$-$C_{12}$ alkyl. In one embodiment, $R^6$ is $C_1$-$C_8$ alkyl. In one embodiment, $R^6$ is $C_1$-$C_6$ alkyl. In one embodiment, $R^6$ is $C_1$-$C_4$ alkyl. In one embodiment, $R^6$ is methyl. In one embodiment, $R^6$ is ethyl. In one embodiment, $R^6$ is $C_3$-$C_8$ cycloalkyl. In one embodiment, $R^6$ is $C_3$-$C_8$ cycloalkenyl. In one embodiment, $R^6$ is $C_6$-$C_{10}$ aryl. In one embodiment, $R^6$ is phenyl. In one embodiment, $R^6$ is unsubstituted. In one embodiment, $R^6$ is substituted.

In one embodiment, $R^3$ is —$N(R^4)R^5$. $R^4$ and $R^5$ are described herein or elsewhere.

In one embodiment, the compound is a compound of Formula (IV):

(IV)

or a pharmaceutically acceptable salt, prodrug or stereoisomer thereof.

In one embodiment, the compound is a compound of Formula (V):

(V)

wherein t is an integer from 2 to 12, or a pharmaceutically acceptable salt, prodrug or stereoisomer thereof.

In one embodiment, the compound is a compound of Formula (VI):

(VI)

wherein t is an integer from 2 to 12, or a pharmaceutically acceptable salt, prodrug or stereoisomer thereof.

In one embodiment, the compound is a compound of Formula (VII):

(VII)

wherein t is an integer from 2 to 12, and u is an integer from 2 to 12, or a pharmaceutically acceptable salt, prodrug or stereoisomer thereof.

In one embodiment, t is an integer from 2 to 12. In one embodiment, t is an integer from 1 to 10. In one embodiment, t is an integer from 1 to 8. In one embodiment, t is an integer from 1 to 6. In one embodiment, t is an integer from 1 to 4. In one embodiment, t is an integer from 1 to 3. In one embodiment, t is an integer from 1 to 2. In one embodiment, t is 1. In one embodiment, t is 2. In one embodiment, t is 3. In one embodiment, t is 4. In one embodiment, t is 5. In one embodiment, t is 6. In one embodiment, t is 7.

In one embodiment, u is an integer from 2 to 12. In one embodiment, u is an integer from 1 to 10. In one embodiment, u is an integer from 1 to 8. In one embodiment, u is an integer from 1 to 6. In one embodiment, u is an integer from 1 to 4. In one embodiment, u is an integer from 1 to 3. In one embodiment, u is an integer from 1 to 2. In one embodiment, u is 1. In one embodiment, u is 2. In one embodiment, u is 3. In one embodiment, u is 4. In one embodiment, u is 5. In one embodiment, u is 6. In one embodiment, u is 7.

In one embodiment, t is 2 and u is 4.

In one embodiment, $R^0$ is $C_1$-$C_{12}$ alkyl. In one embodiment, $R^0$ is $C_1$-$C_{10}$ alkyl. In one embodiment, $R^0$ is $C_1$-$C_8$ alkyl. In one embodiment, $R^0$ is $C_1$-$C_6$ alkyl. In one embodiment, $R^0$ is $C_1$-$C_4$ alkyl. In one embodiment, $R^0$ is $C_1$-$C_2$ alkyl. In one embodiment, $R^0$ is methyl. In one embodiment, $R^0$ is ethyl. In one embodiment, $R^0$ is propyl. In one embodiment, $R^0$ is n-butyl. In one embodiment, $R^0$ is n-pentyl. In one embodiment, $R^0$ is n-hexyl. In one embodiment, $R^0$ is n-octyl. In one embodiment, $R^0$ is n-nonyl.

In one embodiment, $R^0$ is $C_2$-$C_{12}$ alkenyl. In one embodiment, $R^0$ is $C_2$-$C_8$ alkenyl. In one embodiment, $R^0$ is $C_2$-$C_6$ alkenyl. In one embodiment, $R^0$ is $C_2$-$C_4$ alkenyl. In one embodiment, the alkenyl is straight alkenyl. In one embodiment, the alkenyl is branched alkenyl. In one embodiment, $R^0$ is ethenyl. In one embodiment, $R^0$ is allyl.

In one embodiment, $R^0$ is $C_3$-$C_8$ cycloalkyl. In one embodiment, $R^0$ is cyclopropyl. In one embodiment, $R^0$ is cyclobutyl. In one embodiment, $R^0$ is cyclopentyl. In one embodiment, $R^0$ is cyclohexyl. In one embodiment, $R^0$ is cycloheptyl. In one embodiment, $R^0$ is cyclooctyl.

In one embodiment, $R^0$ is $C_3$-$C_8$ cycloalkenyl. In one embodiment, $R^0$ is cyclopropenyl. In one embodiment, $R^0$ is cyclobutenyl. In one embodiment, $R^0$ is cyclopentenyl. In one embodiment, $R^0$ is cyclohexenyl. In one embodiment, $R^0$ is cycloheptenyl. In one embodiment, $R^0$ is cyclooctenyl.

In one embodiment, $R^0$ is $C_6$-$C_{10}$ aryl. In one embodiment, $R^0$ is phenyl.

In one embodiment, $R^0$ is 4- to 8-membered heterocyclyl. In one embodiment, $R^0$ is 4- to 8-membered heterocycloalkyl. In one embodiment, $R^0$ is oxetanyl. In one embodiment, $R^0$ is tetrahydrofuranyl. In one embodiment, $R^0$ is tetrahydropyranyl. In one embodiment, $R^0$ is tetrahydrothiopyranyl. In one embodiment, $R^0$ is N-methylpiperidinyl.

In one embodiment, $R^0$ is unsubstituted. In one embodiment, $R^0$ is substituted.

In one embodiment, $R^4$ is $C_1$-$C_{12}$ alkyl. In one embodiment, $R^4$ is $C_1$-$C_8$ alkyl. In one embodiment, $R^4$ is $C_1$-$C_6$ alkyl. In one embodiment, $R^4$ is $C_1$-$C_4$ alkyl. In one embodiment, $R^4$ is methyl. In one embodiment, $R^4$ is ethyl. In one embodiment, $R^4$ is n-propyl. In one embodiment, $R^4$ is n-butyl. In one embodiment, $R^4$ is n-pentyl. In one embodiment, $R^4$ is n-hexyl. In one embodiment, $R^4$ is n-octyl. In one embodiment, $R^4$ is n-nonyl.

In one embodiment, $R^4$ is $C_2$-$C_{12}$ alkenyl. In one embodiment, $R^4$ is $C_2$-$C_8$ alkenyl. In one embodiment, $R^4$ is $C_2$-$C_6$ alkenyl. In one embodiment, $R^4$ is $C_2$-$C_4$ alkenyl. In one embodiment, the alkenyl is straight alkenyl. In one embodiment, the alkenyl is branched alkenyl. In one embodiment, $R^4$ is ethenyl. In one embodiment, $R^4$ is allyl.

In one embodiment, $R^4$ is $C_3$-$C_8$ cycloalkyl. In one embodiment, $R^4$ is cyclopropyl. In one embodiment, $R^4$ is cyclobutyl. In one embodiment, $R^4$ is cyclopentyl. In one embodiment, $R^4$ is cyclohexyl. In one embodiment, $R^4$ is cycloheptyl. In one embodiment, $R^4$ is cyclooctyl.

In one embodiment, $R^4$ is $C_3$-$C_8$ cycloalkenyl. In one embodiment, $R^4$ is cyclopropenyl. In one embodiment, $R^4$ is cyclobutenyl. In one embodiment, $R^4$ is cyclopentenyl. In one embodiment, $R^4$ is cyclohexenyl. In one embodiment, $R^4$ is cycloheptenyl. In one embodiment, $R^4$ is cyclooctenyl.

In one embodiment, $R^4$ is $C_6$-$C_{10}$ aryl. In one embodiment, $R^4$ is phenyl.

In one embodiment, $R^4$ is 4- to 8-membered heterocyclyl. In one embodiment, $R^4$ is 4- to 8-membered heterocycloalkyl. In one embodiment, $R^4$ is oxetanyl. In one embodiment, $R^4$ is tetrahydrofuranyl. In one embodiment, $R^4$ is tetrahydropyranyl. In one embodiment, $R^4$ is tetrahydrothiopyranyl. In one embodiment, $R^4$ is N-methylpiperidinyl.

In one embodiment, $R^4$ is unsubstituted.

In one embodiment, $R^4$ is substituted with one or more substituents selected from the group consisting of oxo, —OR', —NR$^g$C(═O)R$^h$, —C(═O)NR$^g$R$^h$, —C(═O)R$^h$, —OC(═O)R$^h$, —C(═O)OR$^h$ and —O—R$^i$—OH, wherein:
R$^g$ is at each occurrence independently H or $C_1$-$C_6$ alkyl;
R$^h$ is at each occurrence independently $C_1$-$C_6$ alkyl; and
R$^i$ is at each occurrence independently $C_1$-$C_6$ alkylene.

In one embodiment, $R^4$ is substituted with one or more hydroxyl. In one embodiment, $R^4$ is substituted with one hydroxyl.

In one embodiment, $R^4$ is substituted with one or more hydroxyl and one or more oxo. In one embodiment, $R^4$ is substituted with one hydroxyl and one oxo.

In one embodiment, $R^5$ is $C_1$-$C_{12}$ alkyl. In one embodiment, $R^5$ is $C_1$-$C_{10}$ alkyl. In one embodiment, $R^5$ is $C_1$-$C_8$ alkyl. In one embodiment, $R^5$ is $C_1$-$C_6$ alkyl. In one embodiment, $R^5$ is $C_1$-$C_4$ alkyl. In one embodiment, $R^5$ is $C_1$-$C_2$ alkyl. In one embodiment, $R^5$ is methyl. In one embodiment, $R^5$ is ethyl. In one embodiment, $R^5$ is propyl. In one embodiment, $R^5$ is n-butyl. In one embodiment, $R^5$ is n-hexyl. In one embodiment, $R^5$ is n-octyl. In one embodiment, $R^5$ is n-nonyl.

In one embodiment, $R^5$ is $C_3$-$C_8$ cycloalkyl. In one embodiment, $R^5$ is cyclopropyl. In one embodiment, $R^5$ is cyclobutyl. In one embodiment, $R^5$ is cyclopentyl. In one embodiment, $R^5$ is cyclohexyl. In one embodiment, $R^5$ is cycloheptyl. In one embodiment, $R^5$ is cyclooctyl.

In one embodiment, $R^5$ is $C_3$-$C_8$ cycloalkenyl. In one embodiment, $R^5$ is cyclopropenyl. In one embodiment, $R^5$ is cyclobutenyl. In one embodiment, $R^5$ is cyclopentenyl. In one embodiment, $R^5$ is cyclohexenyl. In one embodiment, $R^5$ is cycloheptenyl. In one embodiment, $R^5$ is cyclooctenyl.

In one embodiment, $R^5$ is $C_6$-$C_{10}$ aryl. In one embodiment, $R^5$ is phenyl.

In one embodiment, the $R^5$ is 4- to 8-membered heterocyclyl. In one embodiment, the $R^5$ is 4- to 8-membered heterocycloalkyl. In one embodiment, the $R^5$ is oxetanyl. In one embodiment, the $R^5$ is tetrahydrofuranyl. In one embodiment, the $R^5$ is tetrahydropyranyl. In one embodiment, the $R^5$ is tetrahydrothiopyranyl.

In one embodiment, $R^4$, $R^5$, together with the nitrogen to which they are attached form a cyclic moiety.

In one embodiment, the cyclic moiety (formed by $R^4$ and $R^5$ together with the nitrogen to which they are attached) is heterocyclyl. In one embodiment, the cyclic moiety is heterocycloalkyl. In one embodiment, the cyclic moiety is 4- to 8-membered heterocycloalkyl. In one embodiment, the cyclic moiety is 4-membered heterocycloalkyl. In one embodiment, the cyclic moiety is 5-membered heterocycloalkyl. In one embodiment, the cyclic moiety is 6-membered heterocycloalkyl. In one embodiment, the cyclic moiety is 7-membered heterocycloalkyl. In one embodiment, the cyclic moiety is 8-membered heterocycloalkyl.

In one embodiment, the cyclic moiety (formed by $R^4$ and $R^5$ together with the nitrogen to which they are attached) is azetidin-1-yl. In one embodiment, the cyclic moiety is pyrrolidin-1-yl. In one embodiment, the cyclic moiety is piperidin-1-yl. In one embodiment, the cyclic moiety is azepan-1-yl. In one embodiment, the cyclic moiety is azo-can-1-yl. In one embodiment, the cyclic moiety is morpholi-nyl. In one embodiment, the cyclic moiety is piperazin-1-yl. The point of attachment in these groups is to $G^3$.

As described herein and unless otherwise specified, the substitution patterns for $R^5$ also applies to the cyclic moiety formed by $R^4$ and $R^5$ together with the nitrogen to which they are attached.

In one embodiment, $R^5$ is unsubstituted.

In one embodiment, $R^5$ is substituted with one or more substituents selected from the group consisting of oxo, —OR', —NR$^g$C(=O)R$^h$, —C(=O)NR$^g$R$^h$, —C(=O)R$^h$, —OC(=O)R$^h$, —C(=O)OR$^h$ and —O—R$^i$—OH, wherein:

$R^g$ is at each occurrence independently H or $C_1$-$C_6$ alkyl;

$R^h$ is at each occurrence independently $C_1$-$C_6$ alkyl; and $R^i$ is at each occurrence independently $C_1$-$C_6$ alkylene.

In one embodiment, $R^5$ is substituted with one or more hydroxyl. In one embodiment, $R^5$ is substituted with one hydroxyl.

In one embodiment, $R^5$ is substituted with one or more hydroxyl and one or more oxo. In one embodiment, $R^5$ is substituted with one hydroxyl and one oxo. In one embodiment, $R^5$ is —CH$_2$CH$_2$OH.

In one embodiment, $R^5$ is —(CH$_2$)$_p$Q, —(CH$_2$)$_p$CHQR, —CHQR, or —CQ(R)$_2$, wherein Q is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, 5- to 10-membered heteroaryl, —OR, —O(CH$_2$)$_p$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$^{22}$, —O(CH$_2$)$_p$OR, —N(R)C(=NR$^{23}$)N(R)$_2$, —N(R)C(=CHR$^{23}$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$^{23}$)N(R)$_2$, —N(OR)C(=CHR$^{23}$)N(R)$_2$, —C(=NR$^{23}$)N(R)$_2$, —C(=NR$^{23}$)R, —C(O)N(R)OR, or —C(R)N(R)$_2$C(O)OR, and each p is independently 1, 2, 3, 4, or 5;

$R^{22}$ is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered heteroaryl;

$R^{23}$ is H, —CN, —NO$_2$, $C_1$-$C_6$ alkyl, —OR, —S(O)$_2$R, —S(O)$_2$N(R)$_2$, $C_2$-$C_6$ alkenyl, $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered het-eroaryl;

each R is independently H, $C_1$-$C_3$ alkyl, or $C_2$-$C_3$ alkenyl; or two R in a N(R)$_2$ moiety together with the nitrogen to which they are attached form a cyclic moiety; and each X is independently F, Cl, Br, or I.

In one embodiment, $G^1$ is a bond. In one embodiment, $G^1$ is $C_2$-$C_{12}$ alkylene. In one embodiment, $G^1$ is $C_4$-$C_8$ alkylene. In one embodiment, $G^1$ is $C_5$-$C_7$ alkylene. In one embodiment, $G^1$ is $C_5$ alkylene. In one embodiment, $G^1$ is $C_7$ alkylene. In one embodiment, $G^1$ is $C_2$-$C_{12}$ alkenylene. In one embodiment, $G^1$ is $C_4$-$C_8$ alkenylene. In one embodi-ment, $G^1$ is $C_5$-$C_7$ alkenylene. In one embodiment, $G^1$ is $C_5$ alkenylene. In one embodiment, $G^1$ is $C_7$ alkenylene.

In one embodiment, $G^2$ is a bond. In one embodiment, $G^2$ is $C_2$-$C_{12}$ alkylene. In one embodiment, $G^2$ is $C_4$-$C_8$ alkylene. In one embodiment, $G^2$ is $C_5$-$C_7$ alkylene. In one embodiment, $G^2$ is $C_5$ alkylene. In one embodiment, $G^2$ is $C_7$ alkylene. In one embodiment, $G^2$ is $C_2$-$C_{12}$ alkenylene. In one embodiment, $G^2$ is $C_4$-$C_8$ alkenylene. In one embodi-ment, $G^2$ is $C_5$-$C_7$ alkenylene. In one embodiment, $G^2$ is $C_5$ alkenylene. In one embodiment, $G^2$ is $C_7$ alkenylene.

In one embodiment, $G^1$ and $G^2$ are each independently $C_2$-$C_{12}$ alkylene. In one embodiment, $G^1$ and $G^2$ are each independently $C_2$ alkylene. In one embodiment, $G^1$ and $G^2$ are each independently $C_5$ alkylene. In one embodiment, $G^1$ and $G^2$ are each independently $C_7$ alkylene.

In one embodiment, $G^1$ is unsubstituted. In one embodi-ment, $G^1$ is substituted. In one embodiment, $G^2$ is unsubsti-tuted. In one embodiment, $G^2$ is substituted.

In one embodiment, $L^1$ is —OC(=O)R$^1$, —C(=O)OR$^1$, —OC(=O)OR$^1$, —C(=O)R$^1$, —OR', —S(O)$_x$R$^1$, —S—SR$^1$, —C(=O)SR$^1$, —SC(=O)R$^1$, —NR$^a$C(=O)R$^1$, —C(=O)NR$^b$R$^c$, —NR$^a$C(=O)NR$^b$R$^c$, —OC(=O)NR$^b$R$^c$, —NR$^a$C(=O)OR$^1$, —SC(=S)R$^1$, —C(=S)SR$^1$, —C(=S)R$^1$, —CH(OH)R$^1$, or —P(=O)(OR)(OR$^c$). In one embodiment, $L^1$ is —(C$_6$-C$_{10}$ arylene)-R$^1$. In one embodi-ment, $L^1$ is -(6- to 10-membered heteroarylene)-R$^1$. In one embodiment, $L^1$ is R$^1$.

In one embodiment, $L^1$ is —C(=O)R$^1$, —OC(=O)R$^1$, —C(=O)OR$^1$, —C(=O)SR$^1$, —SC(=O)R$^1$, —NR$^a$C(=O)R$^1$, or —C(=O)NR$^b$R$^c$. In one embodiment, $L^1$ is —OC(=O)R$^1$, —C(=O)OR$^1$, —NR$^a$C(=O)R$^1$, or —C(=O)NR$^b$R$^c$. In one embodiment, $L^1$ is —C(=O)R$^1$. In one embodiment, $L^1$ is —OC(=O)R$^1$. In one embodiment, $L^1$ is —C(=O)OR$^1$. In one embodiment, $L^1$ is —NR$^a$C(=O)R$^1$. In one embodiment, $L^1$ is —C(=O)NR$^b$R$^c$. In one embodiment, $L^1$ is —NR$^a$C(=O)NR$^b$R$^c$. In one embodi-ment, $L^1$ is —OC(=O)NR$^b$R$^c$. In one embodiment, $L^1$ is —NR$^a$C(=O)OR$^1$.

In one embodiment, $L^2$ is —OC(=O)R$^2$, —C(=O)OR$^2$, —OC(=O)OR$^2$, —C(=O)R$^2$, —OR$^2$, —S(O)$_x$R$^2$, —S—SR$^2$, —C(=O)SR$^2$, —SC(=O)R$^2$, —NR$^a$C(=O)R$^2$, —C(=O)NR$^e$R$^f$, —NR$^d$C(=O)NR$^e$R$^f$, —OC(=O)NR$^e$R$^f$, —NR$^a$C(=O)OR$^2$, —SC(=S)R$^2$, —C(=S)SR$^2$, —C(=S)R$^2$, —CH(OH)R$^2$, or —P(=O)(OR$^e$)(OR$^f$). In one embodi-ment, $L^2$ is —(C$_6$-C$_{10}$ arylene)-R$^2$. In one embodiment, $L^2$ is -(6- to 10-membered heteroarylene)-R$^2$. In one embodi-ment, $L^2$ is R$^2$.

In one embodiment, $L^2$ is —C(=O)R$^2$, —OC(=O)R$^2$, —C(=O)OR$^2$, —C(=O)SR$^2$, —SC(=O)R$^2$, —NR$^a$C(=O)R$^2$, or —C(=O)NR$^e$R$^f$. In one embodiment, $L^2$ is —OC(=O)R$^2$, —C(=O)OR$^2$, —NR$^a$C(=O)R$^2$, or —C(=O)NR$^e$R$^f$. In one embodiment, $L^2$ is —C(=O)R$^2$. In one embodiment, $L^2$ is —OC(=O)R$^2$. In one embodiment, $L^2$ is —C(=O)OR$^2$. In one embodiment, $L^2$ is —NR$^a$C(=O)R$^2$. In one embodiment, $L^2$ is —C(=O)NR$^e$R$^f$. In one embodiment, $L^2$ is —NR$^d$C(=O)NR$^e$R$^f$. In one embodi-ment, $L^2$ is —OC(=O)NR$^e$R$^f$. In one embodiment, $L^2$ is —NR$^a$C(=O)OR$^2$.

In one embodiment, $L^1$ is —OC(=O)R$^1$, —NR$^a$C(=O)R$^1$, —C(=O)OR$^1$, or —C(=O)NR$^b$R$^c$ and $L^2$ is —OC(=O)R$^2$, —NR$^a$C(=O)R$^2$, —C(=O)OR$^2$, or —C(=O)NR$^e$R$^f$. In one embodiment, $L^1$ is —OC(=O)R$^1$, —C(=O)OR$^1$, or —C(=O)NR$^b$R$^c$ and $L^2$ is —OC(=O)R$^2$, —C(=O)OR$^2$, or —C(=O)NR$^e$R$^f$. In one embodiment, $L^1$ is —OC(=O)R$^1$ and $L^2$ is —OC(=O)R$^2$. In one embodi-ment, $L^1$ is —OC(=O)R$^1$ and $L^2$ is —NR$^a$C(=O)R$^2$. In one embodiment, $L^1$ is —NR$^a$C(=O)R$^1$ and $L^2$ is —NR$^a$C(=O)R$^2$. In one embodiment, $L^1$ is —C(=O)OR$^1$ and $L^2$ is —C(=O)OR$^2$. In one embodiment, $L^1$ is —C(=O)OR' and $L^2$ is —C(=O)NR$^e$R$^f$. In one embodiment, $L^1$ is —C(=O)NR$^b$R$^c$ and $L^2$ is —C(=O)NR$^e$R$^f$.

In one embodiment, $L^1$ is —NR$^a$C(=O)NR$^b$R$^c$ and $L^2$ is —NR$^d$C(=O)NR$^e$R$^f$. In one embodiment, $L^1$ is —OC(=O)NR$^b$R$^c$ and $L^2$ is —OC(=O)NR$^e$R$^f$. In one embodiment, $L^1$ is —NR$^a$C(=O)OR$^1$ and $L^2$ is —NR$^a$C(=O)OR$^2$.

In one embodiment, $L^1$ is —OC(=O)$R^1$, —C(=O)OR', —C(=O)$R^1$, —C(=O)NR$^b$R$^c$, or $R^1$; and $L^2$ is —OC(=O)$R^2$, —C(=O)OR$^2$, —C(=O)$R^2$, —C(=O)NR$^e$R$^f$, or $R^2$.

In one embodiment, -$G^1$-$L^1$ is $R^1$, and -$G^2$-$L^2$ is $R^2$. In one embodiment, -$G^1$-$L^1$ is $R^1$, and -$G^2$-$L^2$ is —C(=O)$R^2$. In one embodiment, -$G^1$-$L^1$ is $R^1$, and -$G^2$-$L^2$ is —($C_2$-$C_{12}$ alkylene)-C(=O)O$R^2$. In one embodiment, -$G^1$-$L^1$ is $R^1$, and -$G^2$-$L^2$ is —($C_2$-$C_{12}$ alkylene)-C(=O)NR$^e$R$^f$.

In one embodiment, -$G^1$-$L^1$ is —C(=O)$R^1$, and -$G^2$-$L^2$ is $R^2$. In one embodiment, -$G^1$-$L^1$ is —C(=O)$R^1$, and -$G^2$-$L^2$ is —C(=O)$R^2$. In one embodiment, -$G^1$-$L^1$ is —C(=O)$R^1$, and -$G^2$-$L^2$ is —($C_2$-$C_{12}$ alkylene)-C(=O)O$R^2$. In one embodiment, -$G^1$-$L^1$ is —C(=O)$R^1$, and -$G^2$-$L^2$ is —($C_2$-$C_{12}$ alkylene)-C(=O)NR$^e$R$^f$.

In one embodiment, -$G^1$-$L^1$ is —($C_2$-$C_{12}$ alkylene)-C(=O)O$R^1$, and -$G^2$-$L^2$ is $R^2$. In one embodiment, -$G^1$-$L^1$ is —($C_2$-$C_{12}$ alkylene)-C(=O)O$R^1$, and -$G^2$-$L^2$ is —C(=O)$R^2$. In one embodiment, -$G^1$-$L^1$ is —($C_2$-$C_{12}$ alkylene)-C(=O)O$R^1$, and -$G^2$-$L^2$ is —($C_2$-$C_{12}$ alkylene)-C(=O)O$R^2$. In one embodiment, -$G^1$-$L^1$ is —($C_2$-$C_{12}$ alkylene)-C(=O)O$R^1$, and -$G^2$-$L^2$ is —($C_2$-$C_{12}$ alkylene)-C(=O)NR$^e$R$^f$.

In one embodiment, -$G^1$-$L^1$ is —($C_2$-$C_{12}$ alkylene)-C(=O)NR$^b$R$^c$, and -$G^2$-$L^2$ is $R^2$. In one embodiment, -$G^1$-$L^1$ is —($C_2$-$C_{12}$ alkylene)-C(=O)NR$^b$R$^c$, and -$G^2$-$L^2$ is —C(=O)$R^2$. In one embodiment, -$G^1$-$L^1$ is —($C_2$-$C_{12}$ alkylene)-C(=O)NR$^b$R$^c$, and -$G^2$-$L^2$ is —($C_2$-$C_{12}$ alkylene)-C(=O)O$R^2$. In one embodiment, -$G^1$-$L^1$ is —($C_2$-$C_{12}$ alkylene)-C(=O)NR$^b$R$^c$, and -$G^2$-$L^2$ is —($C_2$-$C_{12}$ alkylene)-C(=O)NR$^e$R$^f$.

In one embodiment of Formula (I) (or a sub-formula thereof), either -$G^1$-$L^1$ is not $R^1$, or -$G^2$-$L^2$ is not $R^2$, or -$G^1$-$L^1$ is not $R^1$ and -$G^2$-$L^2$ is not $R^2$. In one embodiment of Formula (IV) (or a sub-formula thereof), either -$G^1$-$L^1$ is not $R^1$, or -$G^2$-$L^2$ is not $R^2$, or -$G^1$-$L^1$ is not $R^1$ and -$G^2$-$L^2$ is not $R^2$.

In one embodiment, the compound is a compound of Formula (IV-A), (IV-B), (IV-C), (IV-D), (IV-E), (IV-F), (IV-G), or (IV-H):

(IV-A)

(IV-B)

(IV-C)

(IV-D)

-continued (IV-E)

(IV-F)

(IV-G)

(IV-H)

wherein y and z are each independently an integer from 2 to 12, t is an integer from 2 to 12, or a pharmaceutically acceptable salt, prodrug or stereoisomer thereof.

In one embodiment, the compound is a compound of Formula (V-A), (V-B), (V-C), (V-D), (V-E), (V-F), (V-G), or (V-H):

(V-A)

(V-B)

(V-C)

-continued (V-D)

(V-E)

(V-F)

(V-G)

(V-H)

wherein y and z are each independently an integer from 2 to 12, and t is an integer from 2 to 12, or a pharmaceutically acceptable salt, prodrug or stereoisomer thereof.

In one embodiment, the compound is a compound of Formula (VI-A), (VI-B), (VI-C), or (VI-D):

(VI-A)

(VI-B)

-continued (VI-C)

(VI-D)

wherein z is an integer from 2 to 12, and t is an integer from 2 to 12, or a pharmaceutically acceptable salt, prodrug or stereoisomer thereof.

In one embodiment, y is an integer from 2 to 12. In one embodiment, y is an integer from 1 to 10. In one embodiment, y is an integer from 1 to 8. In one embodiment, y is an integer from 1 to 6. In one embodiment, y is an integer from 1 to 4. In one embodiment, y is an integer from 1 to 3. In one embodiment, y is an integer from 1 to 2. In one embodiment, y is 1. In one embodiment, y is 2. In one embodiment, y is 3. In one embodiment, y is 4. In one embodiment, y is 5. In one embodiment, y is 6. In one embodiment, y is 7.

In one embodiment, z is an integer from 2 to 12. In one embodiment, z is an integer from 1 to 10. In one embodiment, z is an integer from 1 to 8. In one embodiment, z is an integer from 1 to 6. In one embodiment, z is an integer from 1 to 4. In one embodiment, z is an integer from 1 to 3. In one embodiment, z is an integer from 1 to 2. In one embodiment, z is 1. In one embodiment, z is 2. In one embodiment, z is 3. In one embodiment, z is 4. In one embodiment, z is 5. In one embodiment, z is 6. In one embodiment, z is 7.

In one embodiment, y and z are different. In one embodiment, y and z are the same. In one embodiment, y and z are the same and are selected from 2, 3, 4, 5, 6, 7, 8, and 9. In one embodiment, y is 2 and z is 2. In one embodiment, y is 5 and z is 5.

In one embodiment, $R^1$ is straight $C_5$-$C_{32}$ alkyl. In one embodiment, $R^1$ is straight $C_6$-$C_{32}$ alkyl. In one embodiment, $R^1$ is straight $C_6$-$C_{24}$ alkyl. In one embodiment, $R^1$ is straight $C_7$-$C_{15}$ alkyl. In one embodiment, $R^1$ is straight $C_7$ alkyl. In one embodiment, $R^1$ is straight $C_8$ alkyl. In one embodiment, $R^1$ is straight $C_9$ alkyl. In one embodiment, $R^1$ is straight $C_{10}$ alkyl. In one embodiment, $R^1$ is straight $C_{11}$ alkyl. In one embodiment, $R^1$ is straight $C_{12}$ alkyl. In one embodiment, $R^1$ is straight $C_{13}$ alkyl. In one embodiment, $R^1$ is straight $C_{14}$ alkyl. In one embodiment, $R^1$ is straight $C_{15}$ alkyl.

In one embodiment, $R^1$ is straight $C_5$-$C_{32}$ alkenyl. In one embodiment, $R^1$ is straight $C_6$-$C_{32}$ alkenyl. In one embodiment, $R^1$ is straight $C_6$-$C_{24}$ alkenyl. In one embodiment, $R^1$ is straight $C_7$-$C_{17}$ alkenyl. In one embodiment, $R^1$ is straight $C_7$ alkenyl. In one embodiment, $R^1$ is straight $C_8$ alkenyl. In one embodiment, $R^1$ is straight $C_9$ alkenyl. In one embodiment, $R^1$ is straight $C_{10}$ alkenyl. In one embodiment, $R^1$ is straight $C_{11}$ alkenyl. In one embodiment, $R^1$ is straight $C_{12}$ alkenyl. In one embodiment, $R^1$ is straight $C_{13}$ alkenyl. In one embodiment, $R^1$ is straight $C_{14}$ alkenyl. In one embodiment, $R^1$ is straight $C_{15}$ alkenyl. In one embodiment, $R^1$ is straight $C_{16}$ alkenyl. In one embodiment, $R^1$ is straight $C_{17}$ alkenyl.

In one embodiment, $R^1$ is branched $C_5$-$C_{32}$ alkyl. In one embodiment, $R^1$ is branched $C_6$-$C_{32}$ alkyl. In one embodiment, $R^1$ is branched $C_6$-$C_{24}$ alkyl. In one embodiment, $R^1$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^1$ is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment, $R^1$ is branched $C_5$-$C_{32}$ alkenyl. In one embodiment, $R^1$ is branched $C_6$-$C_{32}$ alkenyl. In one embodiment, $R^1$ is branched $C_6$-$C_{24}$ alkenyl. In one embodiment, $R^1$ is —$R^7$—$CH(R^8)(R^9)$, wherein $R^7$ is $C_0$-$C_5$ alkylene, and $R^7$ and $R^9$ are independently $C_2$-$C_{10}$ alkenyl. In one embodiment, $R^1$ is —$R^7$—$CH(R^8)(R^9)$, wherein $R^7$ is $C_0$-$C_1$ alkylene, and $R^7$ and $R^9$ are independently $C_6$-$C_{10}$ alkenyl.

In one embodiment, $R^2$ is straight $C_5$-$C_{32}$ alkyl. In one embodiment, $R^2$ is straight $C_6$-$C_{32}$ alkyl. In one embodiment, $R^2$ is straight $C_6$-$C_{24}$ alkyl. In one embodiment, $R^2$ is straight $C_7$-$C_{15}$ alkyl. In one embodiment, $R^2$ is straight $C_7$ alkyl. In one embodiment, $R^2$ is straight $C_8$ alkyl. In one embodiment, $R^2$ is straight $C_9$ alkyl. In one embodiment, $R^2$ is straight $C_{10}$ alkyl. In one embodiment, $R^2$ is straight $C_{11}$ alkyl. In one embodiment, $R^2$ is straight $C_{12}$ alkyl. In one embodiment, $R^2$ is straight $C_{13}$ alkyl. In one embodiment, $R^2$ is straight $C_{14}$ alkyl. In one embodiment, $R^2$ is straight $C_{15}$ alkyl.

In one embodiment, $R^2$ is straight $C_5$-$C_{32}$ alkenyl. In one embodiment, $R^2$ is straight $C_6$-$C_{32}$ alkenyl. In one embodiment, $R^2$ is straight $C_6$-$C_{24}$ alkenyl. In one embodiment, $R^2$ is straight $C_7$-$C_{17}$ alkenyl. In one embodiment, $R^2$ is straight $C_7$ alkenyl. In one embodiment, $R^2$ is straight $C_8$ alkenyl. In one embodiment, $R^2$ is straight $C_9$ alkenyl. In one embodiment, $R^2$ is straight $C_{10}$ alkenyl. In one embodiment, $R^2$ is straight $C_{11}$ alkenyl. In one embodiment, $R^2$ is straight $C_{12}$ alkenyl. In one embodiment, $R^2$ is straight $C_{13}$ alkenyl. In one embodiment, $R^2$ is straight $C_{14}$ alkenyl. In one embodiment, $R^2$ is straight $C_{15}$ alkenyl. In one embodiment, $R^2$ is straight $C_{16}$ alkenyl. In one embodiment, $R^2$ is straight $C_{17}$ alkenyl.

In one embodiment, $R^2$ is branched $C_5$-$C_{32}$ alkyl. In one embodiment, $R^2$ is branched $C_6$-$C_{32}$ alkyl. In one embodiment, $R^2$ is branched $C_6$-$C_{24}$ alkyl. In one embodiment, $R^2$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^2$ is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment, $R^2$ is branched $C_5$-$C_{32}$ alkenyl. In one embodiment, $R^2$ is branched $C_6$-$C_{32}$ alkenyl. In one embodiment, $R^2$ is branched $C_6$-$C_{24}$ alkenyl. In one embodiment, $R^2$ is —$R^7$—$CH(R^8)(R^9)$, wherein $R^7$ is $C_0$-$C_5$ alkylene, and $R^7$ and $R^9$ are independently $C_2$-$C_{10}$ alkenyl. In one embodiment, $R^2$ is —$R^7$—$CH(R^8)(R^9)$, wherein $R^7$ is $C_0$-$C_1$ alkylene, and $R^7$ and $R^9$ are independently $C_6$-$C_{10}$ alkenyl.

In one embodiment, R is straight $C_5$-$C_{32}$ alkyl. In one embodiment, $R^c$ is straight $C_6$-$C_{32}$ alkyl. In one embodiment, $R^c$ is straight $C_6$-$C_{24}$ alkyl. In one embodiment, $R^c$ is straight $C_7$-$C_{15}$ alkyl. In one embodiment, $R^c$ is straight $C_7$ alkyl. In one embodiment, $R^c$ is straight $C_8$ alkyl. In one embodiment, $R^c$ is straight $C_9$ alkyl. In one embodiment, $R^c$ is straight $C_{10}$ alkyl. In one embodiment, $R^c$ is straight $C_{11}$ alkyl. In one embodiment, $R^c$ is straight $C_{12}$ alkyl. In one embodiment, $R^c$ is straight $C_{13}$ alkyl. In one embodiment, $R^c$ is straight $C_{14}$ alkyl. In one embodiment, $R^c$ is straight $C_{15}$ alkyl.

In one embodiment, $R^c$ is straight $C_5$-$C_{32}$ alkenyl. In one embodiment, $R^c$ is straight $C_6$-$C_{32}$ alkenyl. In one embodiment, $R^c$ is straight $C_6$-$C_{24}$ alkenyl. In one embodiment, $R^c$ is straight $C_7$-$C_{17}$ alkenyl. In one embodiment, $R^c$ is straight $C_7$ alkenyl. In one embodiment, $R^c$ is straight $C_8$ alkenyl. In one embodiment, $R^c$ is straight $C_9$ alkenyl. In one embodiment, $R^c$ is straight $C_{10}$ alkenyl. In one embodiment, $R^c$ is straight $C_{11}$ alkenyl. In one embodiment, $R^c$ is straight $C_{12}$ alkenyl. In one embodiment, $R^c$ is straight $C_{13}$ alkenyl. In one embodiment, $R^c$ is straight $C_{14}$ alkenyl. In one embodiment, $R^c$ is straight $C_{15}$ alkenyl. In one embodiment, $R^c$ is straight $C_{16}$ alkenyl. In one embodiment, $R^c$ is straight $C_{17}$ alkenyl.

In one embodiment, $R^c$ is branched $C_5$-$C_{32}$ alkyl. In one embodiment, $R^c$ is branched $C_6$-$C_{32}$ alkyl. In one embodiment, $R^c$ is branched $C_6$-$C_{24}$ alkyl. In one embodiment, $R^c$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, R is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment, $R^c$ is branched $C_5$-$C_{32}$ alkenyl. In one embodiment, $R^c$ is branched $C_6$-$C_{32}$ alkenyl. In one embodiment, $R^c$ is branched $C_6$-$C_{24}$ alkenyl. In one embodiment, $R^c$ is —$R^7$—$CH(R^8)(R^9)$, wherein $R^7$ is $C_0$-$C_5$ alkylene, and $R^7$ and $R^9$ are independently $C_2$-$C_{10}$ alkenyl. In one embodiment, $R^c$ is —R—$CH(R^8)(R^9)$, wherein $R^7$ is $C_0$-$C_1$ alkylene, and $R^7$ and $R^9$ are independently $C_6$-$C_{10}$ alkenyl.

In one embodiment, $R^f$ is straight $C_5$-$C_{32}$ alkyl. In one embodiment, $R^f$ is straight $C_6$-$C_{32}$ alkyl. In one embodiment, $R^f$ is straight $C_6$-$C_{24}$ alkyl. In one embodiment, $R^f$ is straight $C_7$-$C_{15}$ alkyl. In one embodiment, $R^f$ is straight $C_7$ alkyl. In one embodiment, $R^f$ is straight $C_8$ alkyl. In one embodiment, $R^f$ is straight $C_9$ alkyl. In one embodiment, $R^f$ is straight $C_{10}$ alkyl. In one embodiment, $R^f$ is straight $C_{11}$ alkyl. In one embodiment, $R^f$ is straight $C_{12}$ alkyl. In one embodiment, R is straight $C_{13}$ alkyl. In one embodiment, $R^f$ is straight $C_{14}$ alkyl. In one embodiment, $R^f$ is straight $C_{15}$ alkyl.

In one embodiment, $R^f$ is straight $C_5$-$C_{32}$ alkenyl. In one embodiment, $R^f$ is straight $C_6$-$C_{32}$ alkenyl. In one embodiment, $R^f$ is straight $C_6$-$C_{24}$ alkenyl. In one embodiment, $R^f$ is straight $C_7$-$C_{17}$ alkenyl. In one embodiment, $R^f$ is straight $C_7$ alkenyl. In one embodiment, $R^f$ is straight $C_8$ alkenyl. In one embodiment, $R^f$ is straight $C_9$ alkenyl. In one embodiment, $R^f$ is straight $C_{10}$ alkenyl. In one embodiment, $R^f$ is straight $C_{11}$ alkenyl. In one embodiment, $R^f$ is straight $C_{12}$ alkenyl. In one embodiment, $R^f$ is straight $C_{13}$ alkenyl. In one embodiment, $R^f$ is straight $C_{14}$ alkenyl. In one embodiment, $R^f$ is straight $C_{15}$ alkenyl. In one embodiment, $R^f$ is straight $C_{16}$ alkenyl. In one embodiment, $R^f$ is straight $C_{17}$ alkenyl.

In one embodiment, $R^f$ is branched $C_5$-$C_{32}$ alkyl. In one embodiment, $R^f$ is branched $C_6$-$C_{32}$ alkyl. In one embodiment, $R^f$ is branched $C_6$-$C_{24}$ alkyl. In one embodiment, $R^f$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^f$ is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment, $R^f$ is branched $C_5$-$C_{32}$ alkenyl. In one embodiment, $R^f$ is branched $C_6$-$C_{32}$ alkenyl. In one embodiment, $R^f$ is branched $C_6$-$C_{24}$ alkenyl. In one embodiment, $R^f$ is —$R^7$—$CH(R^8)(R^9)$, wherein $R^7$ is $C_0$-$C_5$ alkylene, and $R^7$ and $R^9$ are independently $C_2$-$C_{10}$ alkenyl. In one embodiment, $R^f$ is —$R^7$—$CH(R^8)(R^9)$, wherein $R^7$ is $C_0$-$C_1$ alkylene, and $R^7$ and $R^9$ are independently $C_6$-$C_{10}$ alkenyl.

In one embodiment, $R^1$, $R^2$, $R^c$, and $R^f$ are each independently straight $C_6$-$C_{18}$ alkyl, straight $C_6$-$C_{18}$ alkenyl, or —$R^7$—$CH(R^8)(R^9)$, wherein $R^7$ is $C_0$-$C_5$ alkylene, and $R^7$ and $R^9$ are independently $C_2$-$C_{10}$ alkyl or $C_2$-$C_{10}$ alkenyl.

In one embodiment, $R^1$, $R^2$, $R^c$, and $R^f$ are each independently straight $C_7$-$C_{15}$ alkyl, straight $C_7$-$C_{15}$ alkenyl, or —$R^7$—$CH(R^8)(R^9)$, wherein $R^7$ is $C_0$-$C_1$ alkylene, and $R^7$ and $R^9$ are independently $C_4$-$C_8$ alkyl or $C_6$-$C_{10}$ alkenyl.

In one embodiment, $R^1$, $R^2$, $R^c$, and $R^f$ are each independently branched $C_6$-$C_{24}$ alkyl or branched $C_6$-$C_{24}$ alkenyl. In one embodiment, $R^c$ and $R^f$ are each independently —$R^7$—$CH(R^8)(R^9)$, wherein $R^7$ is $C_1$-$C_5$ alkylene, and $R^7$ and $R^9$ are independently $C_2$-$C_{10}$ alkyl or $C_2$-$C_{10}$ alkenyl.

In one embodiment of Formula (I) (or a sub-formula thereof), $R^1$ is straight $C_5$-$C_{32}$ alkyl, and $R^2$ is straight $C_5$-$C_{32}$ alkyl. In one embodiment, $R^1$ is straight $C_7$-$C_{15}$ alkyl, and $R^2$ is straight $C_7$-$C_{15}$ alkyl.

In one embodiment of Formula (I) (or a sub-formula thereof), $R^1$ is branched $C_5$-$C_{32}$ alkyl, and $R^2$ is branched $C_5$-$C_{32}$ alkyl. In one embodiment, $R^1$ is —$R^7$—$CH(R^8)(R^9)$, wherein $R^7$ is $C_0$-$C_5$ alkylene, and $R^7$ and $R^9$ are independently $C_2$-$C_{10}$ alkyl, and $R^2$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^1$ is —$R^7$—$CH(R^8)(R^9)$, wherein $R^7$ is $C_0$-$C_1$ alkylene, and $R^7$ and $R^9$ are independently $C_4$-$C_8$ alkyl, and $R^2$ is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment of Formula (II) (or a sub-formula thereof), $R^1$ is straight $C_5$-$C_{32}$ alkyl, and $R^2$ is branched $C_5$-$C_{32}$ alkyl. In one embodiment, $R^1$ is straight $C_7$-$C_{15}$ alkyl, and $R^2$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^1$ is straight $C_7$-$C_{15}$ alkyl, and $R^2$ is —$R$—$CH(R^8)(R^9)$, wherein $R^7$ is $C_0$-$C_1$ alkylene, and $R^7$ and $R^9$ are independently $C_4$-$C_8$ alkyl.

In one embodiment of Formula (III) (or a sub-formula thereof), $R^1$ is branched $C_5$-$C_{32}$ alkyl, and $R^2$ is branched $C_5$-$C_{32}$ alkyl. In one embodiment, $R^1$ is —$R$—$CH(R^8)(R^9)$, wherein $R^7$ is $C_0$-$C_5$ alkylene, and $R^7$ and $R^9$ are independently $C_2$-$C_{10}$ alkyl, and $R^2$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^1$ is —$R^7$—$CH(R^8)(R^9)$, wherein $R^7$ is $C_0$-$C_1$ alkylene, and $R^7$ and $R^9$ are independently $C_4$-$C_8$ alkyl, and $R^2$ is —$R^7$—$CH(R^8)(R^9)$, wherein $R^7$ is $C_0$-$C_1$ alkylene, and $R^7$ and $R^9$ are independently $C_4$-$C_8$ alkyl.

In one embodiment of Formula (III) (or a sub-formula thereof), $R^1$ is straight $C_5$-$C_{32}$ alkyl, and $R^2$ is branched $C_5$-$C_{32}$ alkyl. In one embodiment, $R^1$ is straight $C_7$-$C_{15}$ alkyl, and $R^2$ is —$R^7$—$CH(R^8)(R^9)$, wherein $R^7$ is $C_0$-$C_5$ alkylene, and $R^7$ and $R^9$ are independently $C_2$-$C_{10}$ alkyl. In one embodiment, $R^1$ is straight $C_7$-$C_{15}$ alkyl, and $R^2$ is —$R$—$CH(R^8)(R^9)$, wherein $R^7$ is $C_0$-$C_1$ alkylene, and $R^7$ and $R^9$ are independently $C_4$-$C_8$ alkyl.

In one embodiment, $R^1$, $R^2$, $R^c$, and $R^f$ are each independently one of the following structures:

36

-continued

-continued

, or

.

In one embodiment, $R^1$, $R^2$, $R^c$, and $R^f$ are each independently optionally substituted. In one embodiment, $R^1$ is unsubstituted. In one embodiment, $R^1$ is substituted. In one embodiment, $R^2$ is unsubstituted. In one embodiment, $R^2$ is substituted. In one embodiment, $R^c$ is unsubstituted. In one embodiment, $R^c$ is substituted. In one embodiment, $R^f$ is unsubstituted. In one embodiment, $R^f$ is substituted.

In one embodiment, $R^a$ and $R^d$ are each independently H. In one embodiment, $R^a$, $R^b$, $R^d$, and $R^e$ are each independently H. In one embodiment, $R^a$ and $R^d$ are each independently $C_1$-$C_{24}$ alkyl. In one embodiment, $R^a$ and $R^d$ are each independently $C_1$-$C_{18}$ alkyl. In one embodiment, $R^a$ and $R^d$ are each independently $C_1$-$C_{12}$ alkyl. In one embodiment, $R^a$ and $R^d$ are each independently $C_1$-$C_6$ alkyl. In one embodiment, $R^a$, $R^b$, $R^c$, and $R^e$ are each independently unsubstituted or substituted.

In one embodiment, $R^b$, $R^c$, $R^e$, and $R^f$ are each independently n-hexyl or n-octyl.

In one embodiment, the compound is a compound in Table 1, or a pharmaceutically acceptable salt, prodrug or stereoisomer thereof.

TABLE 1

Compound 1

Compound 2

Compound 3

Compound 4

Compound 5

Compound 6

TABLE 1-continued

Compound 7

Compound 8

Compound 9

Compound 10

Compound 11

TABLE 1-continued

Compound 13

Compound 14

Compound 15

Compound 16

Compound 17

TABLE 1-continued

Compound 18

Compound 19

Compound 20

Compound 21

Compound 22

TABLE 1-continued

Compound 23

Compound 24

Compound 25

Compound 26

Compound 27

TABLE 1-continued

Compound 28

Compound 29

Compound 30

Compound 31

Compound 32

TABLE 1-continued

Compound 33

Compound 34

Compound 35

Compound 36

Compound 37

TABLE 1-continued

Compound 38

Compound 39

Compound 40

Compound 41

Compound 42

Compound 43

Compound 44

TABLE 1-continued

Compound 45

Compound 46

Compound 47

Compound 48

Compound 49

Compound 50

TABLE 1-continued

Compound 51

Compound 52

Compound 53

Compound 55

Compound 56

TABLE 1-continued

Compound 57

Compound 58

Compound 59

Compound 60

Compound 61

TABLE 1-continued

Compound 62

Compound 63

Compound 64

Compound 65

Compound 66

TABLE 1-continued

Compound 67

Compound 68

Compound 69

Compound 70

Compound 71

TABLE 1-continued

Compound 72

Compound 73

Compound 74

Compound 76

Compound 77

TABLE 1-continued

Compound 78

Compound 79

Compound 80

Compound 81

Compound 82

TABLE 1-continued

Compound 83

Compound 84

Compound 85

Compound 86

Compound 87

TABLE 1-continued

Compound 88

Compound 89

Compound 90

Compound 91

Compound 92

TABLE 1-continued

Compound 93

Compound 94

Compound 95

Compound 96

Compound 97

TABLE 1-continued

Compound 98

Compound 99

Compound 100

Compound 101

Compound 104

TABLE 1-continued

Compound 105

Compound 106

Compound 107

Compound 108

Compound 109

TABLE 1-continued

Compound 110

Compound 111

Compound 112

Compound 113

Compound 114

TABLE 1-continued

Compound 115

Compound 116

Compound 117

Compound 118

Compound 119

TABLE 1-continued

Compound 120

Compound 121

Compound 122

Compound 123

Compound 124

Compound 125

TABLE 1-continued

Compound 126

Compound 127

Compound 128

Compound 129

Compound 130

Compound 131

TABLE 1-continued

Compound 132

Compound 133

Compound 134

Compound 135

Compound 136

Compound 137

TABLE 1-continued

Compound 138

Compound 139

Compound 140

Compound 141

Compound 142

Compound 143

TABLE 1-continued

Compound 144

In one embodiment, the compound is a compound in Table 2, or a pharmaceutically acceptable salt, prodrug or stereoisomer thereof.

TABLE 2

TABLE 2-continued

TABLE 2-continued

TABLE 2-continued

Certain compounds of Formula (III) are described in International Patent Application No. PCT/CN2021/122704, filed on Oct. 8, 2021, and International Patent Application No. PCT/CN2022/071251, filed on Jan. 11, 2022, the entireties of which are incorporated herein by reference.

In one embodiment, the compound is a compound in Table 3, or a pharmaceutically acceptable salt, prodrug or stereoisomer thereof.

TABLE 3

Compound 145

Compound 146

Compound 147

Compound 148

Compound 149

TABLE 3-continued

Compound 150

Compound 151

Compound 152

Compound 153

Compound 154

TABLE 3-continued

Compound 155

Compound 156

Compound 157

Compound 158

Compound 159

TABLE 3-continued

Compound 160

Compound 161

Compound 162

Compound 163

Compound 164

In one embodiment, provided herein is a compound of Formula (XI), (XII), (XIII), (XIV), or (XV):

(XI)

(XII)

(XIII)

(XIV)

(XV)

(XVI)

or (XVII)

or a pharmaceutically acceptable salt, prodrug or stereoisomer thereof, wherein $G^1$, $G^2$, $G^3$, $L^1$, $L^2$, $R^0$, s, and t are as defined herein or elsewhere, and wherein Z is —OH, halogen, or a leaving group (e.g., —OMs or —OTs).

In one embodiment, Z is —OH. In one embodiment, Z is halogen. In one embodiment, Z is —Cl. In one embodiment, Z is —OMs.

In one embodiment, a compound of Formula (XI), (XII), (XIII), (XIV), (XV), (XVI), or (XVII) is an intermediate used in a process of preparing a compound of Formula (I), (II), (IV), (V), (VI), or (VII), e.g., as exemplified in the examples provided herein, respectively.

In one embodiment, a compound of Formula (XI), (XII), (XIII), (XIV), (XV), (XVI), or (XVII) itself is a lipid compound, and is used in a lipid nanoparticle or a method provided herein.

It is understood that any embodiment of the compounds provided herein, as set forth above, and any specific substituent and/or variable in the compound provided herein, as set forth above, may be independently combined with other embodiments and/or substituents and/or variables of the compounds to form embodiments not specifically set forth above. In addition, in the event that a list of substituents and/or variables is listed for any particular group or variable, it is understood that each individual substituent and/or variable may be deleted from the particular embodiment and/or claim and that the remaining list of substituents and/or variables will be considered to be within the scope of embodiments provided herein.

It is understood that in the present description, combinations of substituents and/or variables of the depicted formulae are permissible only if such contributions result in stable compounds.

6.4 Nanoparticle Compositions

In one aspect, described herein are nanoparticle compositions comprising a lipid compound described herein. In particular embodiments, the nanoparticle composition comprises a compound according to Formulae (I), (II), or (III) (and sub-formulas thereof) as described herein.

In some embodiments, the largest dimension of a nanoparticle composition provided herein is 1 μm or shorter (e.g., 1 μm, ≤900 nm, ≤800 nm, ≤700 nm, ≤600 nm, ≤500 nm, ≤400 nm, 300 nm, ≤200 nm, ≤175 nm, ≤150 nm, ≤125 nm, ≤100 nm, ≤75 nm, ≤50 nm, or shorter), such as when measured by dynamic light scattering (DLS), transmission electron microscopy, scanning electron microscopy, or another method. In one embodiment, the lipid nanoparticle provided herein has at least one dimension that is in the range of from about 40 to about 200 nm. In one embodiment, the at least one dimension is in the range of from about 40 to about 100 nm.

Nanoparticle compositions that can be used in connection with the present disclosure include, for example, lipid nanoparticles (LNPs), nano liproprotein particles, liposomes, lipid vesicles, and lipoplexes. In some embodiments, nanoparticle compositions are vesicles including one or more lipid bilayers. In some embodiments, a nanoparticle composition includes two or more concentric bilayers separated by aqueous compartments. Lipid bilayers may be functionalized and/or crosslinked to one another. Lipid bilayers may include one or more ligands, proteins, or channels.

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvem Instruments Ltd, Malvem, and Worcestershire, UK) may also be used to measure multiple characteristics of a nanoparticle composition, such as particle size, polydispersity index, and zeta potential.

Dh (size): The mean size of a nanoparticle composition may be between 10s of nm and 100s of nm. For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition may be from about 70 nm to about 100 nm. In some embodiments, the mean size may be about 80 nm. In other embodiments, the mean size may be about 100 nm.

PDI: A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20.

Encapsulation Efficiency: The efficiency of encapsulation of a therapeutic and/or prophylactic agent describes the amount of therapeutic and/or prophylactic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic and/or prophylactic agent in a solution containing the nanoparticle composition before and after breaking up the nanoparticle composition with one or more organic solvents or detergents. Fluorescence may be used to measure the amount of free therapeutic and/or prophylactic agent (e.g., RNA) in a solution. For the nanoparticle compositions described herein, the encapsulation efficiency of a therapeutic and/or prophylactic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

Apparent pKa: The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In another embodiment, the self-replicating RNA may be formulated in a liposome. As a non-limiting example, the self-replicating RNA may be formulated in liposomes as described in International Publication No. WO20120067378, herein incorporated by reference in its entirety. In one aspect, the liposomes may comprise lipids which have a pKa value which may be advantageous for delivery of mRNA. In another aspect, the liposomes may have an essentially neutral Surface charge at physiological pH and may therefore be effective for immunization (see e.g., the liposomes described in International Publication No. WO20120067378, herein incorporated by reference in its entirety).

In some embodiments, nanoparticle compositions as described comprise a lipid component including at least one lipid, such as a compound according to one of Formulae (I), (II), or (III) (and sub-formulas thereof) as described herein. For example, in some embodiments, a nanoparticle composition may include a lipid component including one of compounds provided herein. Nanoparticle compositions may also include one or more other lipid or non-lipid components as described below.

In one embodiment, a nanoparticle composition comprising a compound provided herein and an mRNA shows improved expression level of the mRNA (e.g., as compared to standard cationic lipid compounds known in the art, e.g., MC3). 6.4.1 Cationic/Ionizable Lipids As described herein, in some embodiments, a nanoparticle composition provided herein comprises one or more charged or ionizable lipids in addition to a lipid according Formulae (I), (II), or (III) (and sub-formulas thereof). Without being bound by the theory, it is contemplated that certain charged or zwitterionic lipid components of a nanoparticle composition resembles the lipid component in the cell membrane, thereby can improve cellular uptake of the nanoparticle. Exemplary charged or ionizable lipids that can form part of the present nanoparticle composition include but are not limited to 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLinDMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3p)-cholest-5-en-3-yloxy]octyl}oxy)-N,N-dimethyl-3 [(9Z,12Z)-octadeca-9,12-dien-1-yloxy]propan-1-amine (Octyl-CLinDMA), (2R)-2-({8-[(3f)-cholest-5-en-3-yloxy]

octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,-12Z)-octadeca-9,12-dien-1-yloxy]propan-1-amine (Octyl-CLinDMA (2S)), (12Z,15Z)—N,N-dimethyl-2-non-ylhenicosa-12,15-den-1-amine, N,N-dimethyl-1-{(1S,2R)-2-octylcyclopropyl}heptadecan-8-amine. Additional exemplary charged or ionizable lipids that can form part of the present nanoparticle composition include the lipids (e.g., lipid 5) described in Sabnis et al. "A Novel Amino Lipid Series for mRNA Delivery: Improved Endosomal Escape and Sustained Pharmacology and Safety in Non-human Primates", Molecular Therapy Vol. 26 No 6, 2018, the entirety of which is incorporated herein by reference.

In some embodiments, suitable cationic lipids include N-[1-(2,3-dioleyloxy)propyl]-N,N,N-trimethylammonium chloride (DOTMA); N-[1-(2,3-dioleoyloxy)propyl]-N,N,N-trimethylammonium chloride (DOTAP); 1,2-dioleoyl-sn-glycero-3-ethylphosphocholine (DOEPC); 1,2-dilauroyl-sn-glycero-3-ethylphosphocholine (DLEPC); 1,2-dimyristoyl-sn-glycero-3-ethylphosphocholine (DMEPC); 1,2-dimyristoleoyl-sn-glycero-3-ethylphosphocholine (14:1); N1-[2-((1S)-1-[(3-aminopropyl)amino]-4-[di(3-amino-pro-pyl)amino]butylcarboxamido)ethyl]-3,4-di[oleyloxy]-benz-amide (MVL5); dioctadecylamido-glycylspermine (DOGS); 3b-[N—(N',N'-dimethylaminoethyl)carbamoyl]cholesterol (DC-Chol); dioctadecyldimethylammonium bromide (DDAB); SAINT-2, N-methyl-4-(dioleyl)methylpyri-dinium; 1,2-dimyristyloxypropyl-3-dimethylhydroxyethyl-ammonium bromide (DMRIE); 1,2-dioleoyl-3-dimethyl-hy-droxyethyl ammonium bromide (DORIE); 1,2-dioleoyloxypropyl-3-dimethylhydroxyethyl ammonium chloride (DORI); di-alkylated amino acid (DILA$^2$) (e.g., C18:1-norArg-C16); dioleyldimethylammonium chloride (DODAC); 1-palmitoyl-2-oleoyl-sn-glycero-3-ethylphos-phocholine (POEPC); 1,2-dimyristoleoyl-sn-glycero-3-eth-ylphosphocholine (MOEPC); (R)-5-(dimethylamino)pen-tane-1,2-diyl dioleate hydrochloride (DODAPen-Cl); (R)-5-guanidinopentane-1,2-diyl dioleate hydrochloride (DOPen-G); and (R)—N,N,N-trimethyl-4,5-bis(oleoyloxy)pentan-1-aminium chloride (DOTAPen). Also suitable are cationic lipids with headgroups that are charged at physiological pH, such as primary amines (e.g., DODAG N',N'-dioctadecyl-N-4,8-diaza-10-aminodecanoylglycine amide) and guani-dinium head groups (e.g., bis-guanidinium-spermidine-cho-lesterol (BGSC), bis-guanidiniumtren-cholesterol (BGTC), PONA, and (R)-5-guanidinopentane-1,2-diyl dioleate hydrochloride (DOPen-G)). Yet another suitable cationic lipid is (R)-5-(dimethylamino)pentane-1,2-diyl dioleate hydrochloride (DODAPen-Cl). In certain embodiments, the cationic lipid is a particular enantiomer or the racemic form, and includes the various salt forms of a cationic lipid as above (e.g., chloride or sulfate). For example, in some embodiments, the cationic lipid is N-[1-(2,3-dioleoyloxy)propyl]-N,N,N-trimethylammonium chloride (DOTAP-Cl) or N-[1-(2,3-dioleoyloxy)propyl]-N,N,N-trimethylammo-nium sulfate (DOTAP-Sulfate). In some embodiments, the cationic lipid is an ionizable cationic lipid such as, e.g., dioctadecyldimethylammonium bromide (DDAB); 1,2-dili-noleyloxy-3-dimethylaminopropane (DLinDMA); 2,2-dili-noleyl-4-(2dimethylaminoethyl)-[1,3]-dioxolane (DLin-KC2-DMA); heptatriaconta-6,9,28,31-tetraen-19-yl 4-(dimethylamino)butanoate (DLin-MC3-DMA); 1,2-dio-leoyloxy-3-dimethylaminopropane (DODAP); 1,2-dioley-loxy-3-dimethylaminopropane (DODMA); and mor-pholinocholesterol (Mo-CHOL). In certain embodiments, a lipid nanoparticle includes a combination or two or more cationic lipids (e.g., two or more cationic lipids as above).

Additionally, in some embodiments, the charged or ion-izable lipid that can form part of the present nanoparticle composition is a lipid including a cyclic amine group. Additional cationic lipids that are suitable for the formula-tions and methods disclosed herein include those described in WO2015199952, WO2016176330, and WO2015011633, the entire contents of each of which are hereby incorporated by reference in their entireties.

6.4.2 Polymer Conjugated Lipids

In some embodiments, the lipid component of a nanopar-ticle composition can include one or more polymer conju-gated lipids, such as PEGylated lipids (PEG lipids). Without being bound by the theory, it is contemplated that a polymer conjugated lipid component in a nanoparticle composition can improve of colloidal stability and/or reduce protein absorption of the nanoparticles. Exemplary cationic lipids that can be used in connection with the present disclosure include but are not limited to PEG-modified phosphatidy-lethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, PEG-DSPE, Ceramide-PEG2000, or Chol-PEG2000.

In one embodiment, the polymer conjugated lipid is a pegylated lipid. For example, some embodiments include a pegylated diacylglycerol (PEG-DAG) such as 1-(monomethoxy-polyethyleneglycol)-2,3-dimyristoylglyc-erol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O—(ω-methoxy(polyethoxy)ethyl)butanedioate (PEG-S-DMG), a pegylated ceramide (PEG-cer), or a PEG dialkoxypropyl-carbamate such as ω-methoxy(polyethoxy)ethyl-N-(2,3-di (tetradecanoxy)propyl)carbamate or 2,3-di(tetradecanoxy) propyl-N—(ω-methoxy(polyethoxy)ethyl)carbamate.

In one embodiment, the polymer conjugated lipid is present in a concentration ranging from 1.0 to 2.5 molar percent. In one embodiment, the polymer conjugated lipid is present in a concentration of about 1.7 molar percent. In one embodiment, the polymer conjugated lipid is present in a concentration of about 1.5 molar percent.

In one embodiment, the molar ratio of cationic lipid to the polymer conjugated lipid ranges from about 35:1 to about 25:1. In one embodiment, the molar ratio of cationic lipid to polymer conjugated lipid ranges from about 100:1 to about 20:1.

In one embodiment, the pegylated lipid has the following Formula:

or a pharmaceutically acceptable salt, tautomer or stereoi-somer thereof, wherein:

R$^{12}$ and R$^3$ are each independently a straight or branched, saturated or unsaturated alkyl chain containing from 10 to 30 carbon atoms, wherein the alkyl chain is option-ally interrupted by one or more ester bonds; and w has a mean value ranging from 30 to 60.

In one embodiment, $R^{12}$ and $R^3$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In one embodiment, the pegylated lipid has the following Formula:

wherein the average w is about 49.

6.4.3 Structural Lipids

In some embodiments, the lipid component of a nanoparticle composition can include one or more structural lipids. Without being bound by the theory, it is contemplated that structural lipids can stabilize the amphiphilic structure of a nanoparticle, such as but not limited to the lipid bilayer structure of a nanoparticle. Exemplary structural lipids that can be used in connection with the present disclosure include but are not limited to cholesterol, fecosterol, sitosterol, ergosterol, campesterol, stigmasterol, brassicasterol, tomatidine, tomatine, ursolic acid, alpha-tocopherol, and mixtures thereof. In certain embodiments, the structural lipid is cholesterol. In some embodiments, the structural lipid includes cholesterol and a corticosteroid (such as prednisolone, dexamethasone, prednisone, and hydrocortisone), or a combination thereof.

In one embodiment, the lipid nanoparticles provided herein comprise a steroid or steroid analogue. In one embodiment, the steroid or steroid analogue is cholesterol. In one embodiment, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent.

In one embodiment, the molar ratio of cationic lipid to the steroid ranges from 1.0:0.9 to 1.0:1.2, or from 1.0:1.0 to 1.0:1.2. In one embodiment, the molar ratio of cationic lipid to cholesterol ranges from about 5:1 to 1:1. In one embodiment, the steroid is present in a concentration ranging from 32 to 40 mol percent of the steroid.

6.4.4 Phospholipids

In some embodiments, the lipid component of a nanoparticle composition can include one or more phospholipids, such as one or more (poly)unsaturated lipids. Without being bound by the theory, it is contemplated that phospholipids may assemble into one or more lipid bilayers structures. Exemplary phospholipids that can form part of the present nanoparticle composition include but are not limited to 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In certain embodiments, a nanoparticle composition includes DSPC. In certain embodiments, a nanoparticle composition includes DOPE. In some embodiments, a nanoparticle composition includes both DSPC and DOPE.

Additional exemplary neutral lipids include, for example, dipalmitoylphosphatidylglycerol (DPPG), palmitoyloleoyl-phosphatidylethanolamine (POPE) and dioleoyl-phosphatidylethanolamine 4-(N-maleimidomethyl)-cyclohexane-lcarboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC). In one embodiment, the neutral lipid is selected from DSPC, DPPC, DMPC, DOPC, POPC, DOPE and SM.

In one embodiment, the neutral lipid is phosphatidylcholine (PC), phosphatidylethanolamine (PE) phosphatidylserine (PS), phosphatidic acid (PA), or phosphatidylglycerol (PG).

Additionally phospholipids that can form part of the present nanoparticle composition also include those described in WO2017/112865, the entire content of which is hereby incorporated by reference in its entirety.

6.4.5 Therapeutic Payload

According to the present disclosure, nanoparticle compositions as described herein can further comprise one or more therapeutic and/or prophylactic agents. These therapeutic and/or prophylactic agents are sometimes referred to as a "therapeutic payload" or "payload" in the present disclosure. In some embodiments, the therapeutic payload can be administered in vivo or in vitro using the nanoparticles as a delivery vehicle.

In some embodiments, the nanoparticle composition comprises, as the therapeutic payload, a small molecule compound (e.g., a small molecule drug) such as antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracyclines, alkylating agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetalol), antihypertensive agents (e.g., clonidine and hydralazine), anti-depressants (e.g., imipramine, amitriptyline, and doxepin), anti-convulsants (e.g., phenytoin), antihistamines (e.g., diphenhydramine, chlorpheniramine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

In some embodiments, the therapeutic payload comprises a cytotoxin, a radioactive ion, a chemotherapeutic, a vaccine, a compound that elicits an immune response, and/or another therapeutic and/or prophylactic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol, rachelmycin (CC-1065), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium.

In other embodiments, the therapeutic payload of the present nanoparticle composition can include, but is not limited to, therapeutic and/or prophylactic agents such as antimetabolites (e.g., methotrexate, 6-mercaptopurine, 6-thioguanine, cytarabine, 5-fluorouracil, dacarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the nanoparticle composition comprises, as the therapeutic payload, a biological molecule such as peptides and polypeptides. The biological molecules forming part of the present nanoparticle composition can be either of a natural source or synthetic. For example, in some embodiments, the therapeutic payload of the present nanoparticle composition can include, but is not limited to gentamycin, amikacin, insulin, erythropoietin (EPO), granulocyte-colony stimulating factor (G-CSF), granulocyte-macrophage colony stimulating factor (GM-CSF), Factor VIR, luteinizing hormone-releasing hormone (LHRH) analogs, interferons, heparin, Hepatitis B surface antigen, typhoid vaccine, cholera vaccine, and peptides and polypeptides.

6.4.5.1 Nucleic Acids

In some embodiments, the present nanoparticle composition comprises one or more nucleic acid molecules (e.g., DNA or RNA molecules) as the therapeutic payload. Exemplary forms of nucleic acid molecules that can be included in the present nanoparticle composition as therapeutic payload include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In certain embodiments, the therapeutic payload comprises an RNA. RNA molecules that can be included in the present nanoparticle composition as the therapeutic payload include, but are not limited to, shortmers, agomirs, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and other forms of RNA molecules known in the art. In particular embodiments, the RNA is an mRNA.

In other embodiments, the nanoparticle composition comprises a siRNA molecule as the therapeutic payload. Particularly, in some embodiments, the siRNA molecule is capable of selectively interfering with and downregulate the expression of a gene of interest. For example, in some embodiments, the siRNA payload selectively silence a gene associated with a particular disease, disorder, or condition upon administration to a subject in need thereof of a nanoparticle composition including the siRNA. In some embodiments, the siRNA molecule comprises a sequence that is complementary to an mRNA sequence encoding a protein product of interest. In some embodiments, the siRNA molecule is an immunomodulatory siRNA.

In some embodiments, the nanoparticle composition comprises a shRNA molecule or a vector encoding the shRNA molecule as the therapeutic payload. Particularly, in some embodiments, the therapeutic payload, upon administering to a target cell, produces shRNA inside the target cell. Constructs and mechanisms relating to shRNA are well known in the relevant arts.

In some embodiments, the nanoparticle composition comprises an mRNA molecule as the therapeutic payload. Particularly, in some embodiments, the mRNA molecule encodes a polypeptide of interest, including any naturally or non-naturally occurring or otherwise modified polypeptide. A polypeptide encoded by an mRNA may be of any size and may have any secondary structure or activity. In some embodiments, the polypeptide encoded by an mRNA payload can have a therapeutic effect when expressed in a cell.

In some embodiment, a nucleic acid molecule of the present disclosure comprises an mRNA molecule. In specific embodiments, the nucleic acid molecule comprises at least one coding region encoding a peptide or polypeptide of interest (e.g., an open reading frame (ORF)). In some embodiments, the nucleic acid molecule further comprises at least one untranslated region (UTR). In particular embodiments, the untranslated region (UTR) is located upstream (to the 5'-end) of the coding region, and is referred to herein as the 5'-UTR. In particular embodiments, the untranslated region (UTR) is located downstream (to the 3'-end) of the coding region, and is referred to herein as the 3'-UTR. In particular embodiments, the nucleic acid molecule comprises both a 5'-UTR and a 3'-UTR. In some embodiments, the 5'-UTR comprises a 5'-Cap structure. In some embodiments, the nucleic acid molecule comprises a Kozak sequence (e.g., in the 5'-UTR). In some embodiments, the nucleic acid molecule comprises a poly-A region (e.g., in the 3'-UTR). In some embodiments, the nucleic acid molecule comprises a polyadenylation signal (e.g., in the 3'-UTR). In some embodiments, the nucleic acid molecule comprises stabilizing region (e.g., in the 3'-UTR). In some embodiments, the nucleic acid molecule comprises a secondary structure. In some embodiments, the secondary structure is a stem-loop. In some embodiments, the nucleic acid molecule comprises a stem-loop sequence (e.g., in the 5'-UTR and/or the 3'-UTR). In some embodiments, the nucleic acid molecule comprises one or more intronic regions capable of being excised during splicing. In a specific embodiment, the nucleic acid molecule comprises one or more region selected from a 5'-UTR, and a coding region. In a specific embodiment, the nucleic acid molecule comprises one or more region selected from a coding region and a 3'-UTR. In a specific embodiment, the nucleic acid molecule comprises one or more region selected from a 5'-UTR, a coding region, and a 3'-UTR.

Coding Region

In some embodiments, the nucleic acid molecule of the present disclosure comprises at least one coding region. In some embodiments, the coding region is an open reading frame (ORF) that encodes for a single peptide or protein. In some embodiments, the coding region comprises at least two ORFs, each encoding a peptide or protein. In those embodiments where the coding region comprises more than one ORFs, the encoded peptides and/or proteins can be the same as or different from each other. In some embodiments, the multiple ORFs in a coding region are separated by non-coding sequences. In specific embodiments, a non-coding sequence separating two ORFs comprises an internal ribosome entry sites (IRES).

Without being bound by the theory, it is contemplated that an internal ribosome entry sites (IRES) can act as the sole ribosome binding site, or serve as one of multiple ribosome binding sites of an mRNA. An mRNA molecule containing more than one functional ribosome binding site can encode several peptides or polypeptides that are translated independently by the ribosomes (e.g., multicistronic mRNA). Accordingly, in some embodiments, the nucleic acid molecule of the present disclosure (e.g., mRNA) comprises one or more internal ribosome entry sites (IRES). Examples of IRES sequences that can be used in connection with the present disclosure include, without limitation, those from picomaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

In various embodiments, the nucleic acid molecule of the present disclose encodes for at least 1, 2, 3, 4, 5, 6, 7, 8, 9, 10 or more than 10 peptides or proteins. Peptides and proteins encoded by a nucleic acid molecule can be the same or different. In some embodiments, the nucleic acid molecule of the present disclosure encodes a dipeptide (e.g., camosine and anserine). In some embodiments, the nucleic acid molecule encodes a tripeptide. In some embodiments, the nucleic acid molecule encodes a tetrapeptide. In some embodiments, the nucleic acid molecule encodes a penta-peptide. In some embodiments, the nucleic acid molecule encodes a hexapeptide. In some embodiments, the nucleic acid molecule encodes a heptapeptide. In some embodiments, the nucleic acid molecule encodes an octapeptide. In some embodiments, the nucleic acid molecule encodes a nonapeptide. In some embodiments, the nucleic acid molecule encodes a decapeptide. In some embodiments, the nucleic acid molecule encodes a peptide or polypeptide that has at least about 15 amino acids. In some embodiments, the nucleic acid molecule encodes a peptide or polypeptide that has at least about 50 amino acids. In some embodiments, the nucleic acid molecule encodes a peptide or polypeptide that has at least about 100 amino acids. In some embodiments, the nucleic acid molecule encodes a peptide or polypeptide that has at least about 150 amino acids. In some embodiments, the nucleic acid molecule encodes a peptide or polypeptide that has at least about 300 amino acids. In some embodiments, the nucleic acid molecule encodes a peptide or polypeptide that has at least about 500 amino acids. In some embodiments, the nucleic acid molecule encodes a peptide or polypeptide that has at least about 1000 amino acids.

In some embodiments, the nucleic acid molecule of the present disclosure is at least about 30 nucleotides (nt) in length. In some embodiments, the nucleic acid molecule is at least about 35 nt in length. In some embodiments, the nucleic acid molecule is at least about 40 nt in length. In some embodiments, the nucleic acid molecule is at least about 45 nt in length. In some embodiments the nucleic acid molecule is at least about 50 nt in length. In some embodiments, the nucleic acid molecule is at least about 55 nt in length. In some embodiments, the nucleic acid molecule is at least about 60 nt in length. In some embodiments, the nucleic acid molecule is at least about 65 nt in length. In some embodiments, the nucleic acid molecule is at least about 70 nt in length. In some embodiments, the nucleic acid molecule is at least about 75 nt in length. In some embodiments, the nucleic acid molecule is at least about 80 nt in length. In some embodiments the nucleic acid molecule is at least about 85 nt in length. In some embodiments, the nucleic acid molecule is at least about 90 nt in length. In some embodiments, the nucleic acid molecule is at least about 95 nt in length. In some embodiments, the nucleic acid molecule is at least about 100 nt in length. In some embodiments, the nucleic acid molecule is at least about 120 nt in length. In some embodiments, the nucleic acid molecule is at least about 140 nt in length. In some embodiments, the nucleic acid molecule is at least about 160 nt in length. In some embodiments, the nucleic acid molecule is at least about 180 nt in length. In some embodiments, the nucleic acid molecule is at least about 200 nt in length. In some embodiments, the nucleic acid molecule is at least about 250 nt in length. In some embodiments, the nucleic acid molecule is at least about 300 nt in length. In some embodiments, the nucleic acid molecule is at least about 400 nt in length. In some embodiments, the nucleic acid molecule is at least about 500 nt in length. In some embodiments, the nucleic acid molecule is at least about 600 nt in length. In some embodiments, the nucleic acid molecule is at least about 700 nt in length. In some embodiments, the nucleic acid molecule is at least about 800 nt in length. In some embodiments, the nucleic acid molecule is at least about 900 nt in length. In some embodiments, the nucleic acid molecule is at least about 1000 nt in length. In some embodiments, the nucleic acid molecule is at least about 1100 nt in length. In some embodiments, the nucleic acid molecule is at least about 1200 nt in length. In some embodiments, the nucleic acid molecule is at least about 1300 nt in length. In some embodiments, the nucleic acid molecule is at least about 1400 nt in length. In some embodiments, the nucleic acid molecule is at least about 1500 nt in length. In some embodiments, the nucleic acid molecule is at least about 1600 nt in length. In some embodiments, the nucleic acid molecule is at least about 1700 nt in length. In some embodiments, the nucleic acid molecule is at least about 1800 nt in length. In some embodiments, the nucleic acid molecule is at least about 1900 nt in length. In some embodiments, the nucleic acid molecule is at least about 2000 nt in length. In some embodiments, the nucleic acid molecule is at least about 2500 nt in length. In some embodiments, the nucleic acid molecule is at least about 3000 nt in length. In some embodiments, the nucleic acid molecule is at least about 3500 nt in length. In some embodiments, the nucleic acid molecule is at least about 4000 nt in length. In some embodiments, the nucleic acid molecule is at least about 4500 nt in length. In some embodiments, the nucleic acid molecule is at least about 5000 nt in length.

In specific embodiments, the therapeutic payload comprises a vaccine composition (e.g., a genetic vaccine) as described herein. In some embodiments, the therapeutic payload comprises a compound capable of eliciting immunity against one or more target conditions or disease. In some embodiments, the target condition is related to or caused by infection by a pathogen, such as a coronavirus (e.g. 2019-nCoV), influenza, measles, human papillomavirus (HPV), rabies, meningitis, whooping cough, tetanus, plague, hepatitis, and tuberculosis. In some embodiments, the therapeutic payload comprises a nucleic acid sequence (e.g., mRNA) encoding a pathogenic protein characteristic for the pathogen, or an antigenic fragment or epitope thereof. The vaccine, upon administration to a vaccinated subject, allows for expression of the encoded pathogenic protein (or the antigenic fragment or epitope thereof), thereby eliciting immunity in the subject against the pathogen.

In some embodiments, the target condition is related to or caused by neoplastic growth of cells, such as a cancer. In some embodiments, the therapeutic payload comprises a nucleic acid sequence (e.g., mRNA) encoding a tumor associated antigen (TAA) characteristic for the cancer, or an antigenic fragment or epitope thereof. The vaccine, upon administration to a vaccinated subject, allows for expression of the encoded TAA (or the antigenic fragment or epitope thereof), thereby eliciting immunity in the subject against the neoplastic cells expressing the TAA.

5'-Cap Structure

Without being bound by the theory, it is contemplated that, a 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The 5'-cap structure further assists the removal of 5'-proximal introns removal during mRNA splicing. Accordingly, in some embodiments, the nucleic acid molecules of the present disclosure comprise a 5'-cap structure.

Nucleic acid molecules may be 5'-end capped by the endogenous transcription machinery of a cell to generate a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a nucleic acid molecule, such as an mRNA molecule, for degradation.

In some embodiments, the nucleic acid molecules of the present disclosure comprise one or more alterations to the natural 5'-cap structure generated by the endogenous process. Without being bound by the theory, a modification on the 5'-cap may increase the stability of polynucleotide, increase the half-life of the polynucleotide, and could increase the polynucleotide translational efficiency.

Exemplary alterations to the natural 5'-Cap structure include generation of a non-hydrolyzable cap structure preventing decapping and thus increasing polynucleotide half-life. In some embodiments, because cap structure hydrolysis requires cleavage of 5'-ppp-5' phosphorodiester linkages, in some embodiments, modified nucleotides may be used during the capping reaction. For example, in some embodiments, a Vaccinia Capping Enzyme from New England Biolabs (Ipswich, Mass.) may be used with $\alpha$-thio-guanosine nucleotides according to the manufacturer's instructions to create a phosphorothioate linkage in the 5'-ppp-5' cap. Additional modified guanosine nucleotides may be used, such as $\alpha$-methyl-phosphonate and seleno-phosphate nucleotides.

Additional exemplary alterations to the natural 5'-Cap structure also include modification at the 2'- and/or 3'-position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

Additional exemplary alterations to the natural 5'-cap structure include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule. Additional exemplary 5'-Cap structures that can be used in connection with the present disclosure further include those described in International Patent Publication Nos. WO2008127688, WO 2008016473, and WO 2011015347, the entire contents of each of which are incorporated herein by reference.

In various embodiments, 5'-terminal caps can include cap analogs. Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7G$-3'mppp-G, which may equivalently be designated 3' O-Me-m7G(5')ppp (5')G). The 3'-O atom of the other, unaltered, guanosine becomes linked to the 5'-terminal nucleotide of the capped polynucleotide (e.g., an mRNA). The N7- and 3'-O-methylated guanosine provides the terminal moiety of the capped polynucleotide (e.g., mRNA). Another exemplary cap structure is mCAP, which is similar to ARCA but has a 2'-O-methyl group on guanosine (i.e., N7,2'-O-dimethyl-guanosine-5'-triphosphate-5'-guanosine, $m_7$Gm-ppp-G).

In some embodiments, a cap analog can be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the entire content of which is herein incorporated by reference in its entirety.

In some embodiments, a cap analog can be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxy-ethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the entire content of which is herein incorporated by reference). In other embodiments, a cap analog useful in connection with the nucleic acid molecules of the present disclosure is a 4-chloro/bromophenoxyethyl analog.

In various embodiments, a cap analog can include a guanosine analog. Useful guanosine analogs include but are not limited to inosine, N1-methyl-guanosine, 2'-fluoro-guanosine, 7-deaza-guanosine, 8-oxo-guanosine, 2-amino-guanosine, LNA-guanosine, and 2-azido-guanosine.

Without being bound by the theory, it is contemplated that while cap analogs allow for the concomitant capping of a polynucleotide in an in vitro transcription reaction, up to 20% of transcripts remain uncapped. This, as well as the structural differences of a cap analog from the natural 5'-cap structures of polynucleotides produced by the endogenous transcription machinery of a cell, may lead to reduced translational competency and reduced cellular stability.

Accordingly, in some embodiments, a nucleic acid molecule of the present disclosure can also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in connection with the nucleic acid molecules of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). For example, in some embodiments, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5'cap analog structures known in the art. Other exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2') Up (Cap 4).

Without being bound by the theory, it is contemplated that the nucleic acid molecules of the present disclosure can be capped post-transcriptionally, and because this process is more efficient, nearly 100% of the nucleic acid molecules may be capped.

Untranslated Regions (UTRs)

In some embodiments, the nucleic acid molecules of the present disclosure comprise one or more untranslated regions (UTRs). In some embodiments, an UTR is positioned upstream to a coding region in the nucleic acid molecule, and is termed 5'-UTR. In some embodiments, an UTR is positioned downstream to a coding region in the nucleic acid molecule, and is termed 3'-UTR. The sequence of an UTR can be homologous or heterologous to the sequence of the coding region found in a nucleic acid molecule. Multiple UTRs can be included in a nucleic acid molecule and can be of the same or different sequences, and/or genetic origin. According to the present disclosure, any portion of UTRs in a nucleic acid molecule (including none) can be codon optimized and any may independently contain one or more different structural or chemical modification, before and/or after codon optimization.

In some embodiments, a nucleic acid molecule of the present disclosure (e.g., mRNA) comprises UTRs and coding regions that are homologous with respect to each other. In other embodiments, a nucleic acid molecule of the present disclosure (e.g., mRNA) comprises UTRs and coding regions that are heterogeneous with respect to each other. In some embodiments, to monitor the activity of a UTR sequence, a nucleic acid molecule comprising the UTR and a coding sequence of a detectable probe can be administered in vitro (e.g., cell or tissue culture) or in vivo (e.g., to a subject), and an effect of the UTR sequence (e.g., modulation on the expression level, cellular localization of the encoded product, or half-life of the encoded product) can be measured using methods known in the art.

In some embodiments, the UTR of a nucleic acid molecule of the present disclosure (e.g., mRNA) comprises at least one translation enhancer element (TEE) that functions to increase the amount of polypeptide or protein produced from the nucleic acid molecule. In some embodiments, the TEE is located in the 5'-UTR of the nucleic acid molecule. In other embodiments, the TEE is located at the 3'-UTR of the nucleic acid molecule. In yet other embodiments, at least two TEE are located at the 5'-UTR and 3'-UTR of the nucleic acid molecule respectively. In some embodiments, a nucleic acid molecule of the present disclosure (e.g., mRNA) can comprise one or more copies of a TEE sequence or comprise more than one different TEE sequences. In some embodiments, different TEE sequences that are present in a nucleic acid molecule of the present disclosure can be homologues or heterologous with respect to one another.

Various TEE sequences that are known in the art and can be used in connection with the present disclosure. For example, in some embodiments, the TEE can be an internal ribosome entry site (IRES), HCV-IRES or an IRES element. Chappell et al. *Proc. Natl. Acad. Sci. USA* 101:9590-9594, 2004; Zhou et al. *Proc. Natl. Acad. Sci.* 102:6273-6278, 2005. Additional internal ribosome entry site (IRES) that can be used in connection with the present disclosure include but are not limited to those described in U.S. Pat. No. 7,468,275, U.S. Patent Publication No. 2007/0048776 and U.S. Patent Publication No. 2011/0124100 and International Patent Publication No. WO2007/025008 and International Patent Publication No. WO2001/055369, the content of each of which is enclosed herein by reference in its entirety. In some embodiments, the TEE can be those described in Supplemental Table 1 and in Supplemental Table 2 of Wellensiek et al Genome-wide profiling of human cap-independent translation-enhancing elements, *Nature Methods,* 2013 August; 10(8): 747-750; the content of which is incorporated by reference in its entirety.

Additional exemplary TEEs that can be used in connection with the present disclosure include but are not limited to the TEE sequences disclosed in U.S. Pat. Nos. 6,310,197, 6,849,405, 7,456,273, 7,183,395, U.S. Patent Publication No. 2009/0226470, U.S. Patent Publication No. 2013/0177581, U.S. Patent Publication No. 2007/0048776, U.S. Patent Publication No. 2011/0124100, U.S. Patent Publication No. 2009/0093049, International Patent Publication No. WO2009/075886, International Patent Publication No. WO2012/009644, and International Patent Publication No. WO1999/024595, International Patent Publication No.

WO2007/025008, International Patent Publication No. WO2001/055371, European Patent No. 2610341, European Patent No. 2610340, the content of each of which is enclosed herein by reference in its entirety.

In various embodiments, a nucleic acid molecule of the present disclosure (e.g., mRNA) comprises at least one UTR that comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In some embodiments, the TEE sequences in the UTR of a nucleic acid molecule are copies of the same TEE sequence. In other embodiments, at least two TEE sequences in the UTR of a nucleic acid molecule are of different TEE sequences. In some embodiments, multiple different TEE sequences are arranged in one or more repeating patterns in the UTR region of a nucleic acid molecule. For illustrating purpose only, a repeating pattern can be, for example, ABABAB, AABBAAB-BAABB, ABCABCABC, or the like, where in these exemplary patterns, each capitalized letter (A, B, or C) represents a different TEE sequence. In some embodiments, at least two TEE sequences are consecutive with one another (i.e., no spacer sequence in between) in a UTR of a nucleic acid molecule. In other embodiments, at least two TEE sequences are separated by a spacer sequence. In some embodiments, a UTR can comprise a TEE sequence-spacer sequence module that is repeated at least once, at least twice, at least 3 times, at least 4 times, at least 5 times, at least 6 times, at least 7 times, at least 8 times, at least 9 times, or more than 9 times in the UTR. In any of the embodiments described in this paragraph, the UTR can be a 5'-UTR, a 3'-UTR or both 5'-UTR and 3'-UTR of a nucleic acid molecule.

In some embodiments, the UTR of a nucleic acid molecule of the present disclosure (e.g., mRNA) comprises at least one translation suppressing element that functions to decrease the amount of polypeptide or protein produced from the nucleic acid molecule. In some embodiments, the UTR of the nucleic acid molecule comprises one or more miR sequences or fragment thereof (e.g., miR seed sequences) that are recognized by one or more microRNA. In some embodiments, the UTR of the nucleic acid molecule comprises one or more stem-loop structure that downregulates translational activity of the nucleic acid molecule. Other mechanisms for suppressing translational activities associated with a nucleic acid molecules are known in the art. In any of the embodiments described in this paragraph, the UTR can be a 5'-UTR, a 3'-UTR or both 5'-UTR and 3'-UTR of a nucleic acid molecule.

The Polyadenylation (Poly-A) Regions

During natural RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long. Without being bound by the theory, it is contemplated that a poly-A region can confer various advantages to the nucleic acid molecule of the present disclosure.

Accordingly, in some embodiments, a nucleic acid molecule of the present disclosure (e.g., an mRNA) comprises a polyadenylation signal. In some embodiments, a nucleic acid molecule of the present disclosure (e.g., an mRNA)

comprises one or more polyadenylation (poly-A) regions. In some embodiments, a poly-A region is composed entirely of adenine nucleotides or functional analogs thereof. In some embodiments, the nucleic acid molecule comprises at least one poly-A region at its 3'-end. In some embodiments, the nucleic acid molecule comprises at least one poly-A region at its 5'-end. In some embodiments, the nucleic acid molecule comprises at least one poly-A region at its 5'-end and at least one poly-A region at its 3'-end.

According to the present disclosure, the poly-A region can have varied lengths in different embodiments. Particularly, in some embodiments, the poly-A region of a nucleic acid molecule of the present disclosure is at least 30 nucleotides in length. In some embodiments, the poly-A region of a nucleic acid molecule of the present disclosure is at least 35 nucleotides in length. In some embodiments, the poly-A region of a nucleic acid molecule of the present disclosure is at least 40 nucleotides in length. In some embodiments, the poly-A region of a nucleic acid molecule of the present disclosure is at least 45 nucleotides in length. In some embodiments, the poly-A region of a nucleic acid molecule of the present disclosure is at least 50 nucleotides in length. In some embodiments, the poly-A region of a nucleic acid molecule of the present disclosure is at least 55 nucleotides in length. In some embodiments, the poly-A region of a nucleic acid molecule of the present disclosure is at least 60 nucleotides in length. In some embodiments, the poly-A region of a nucleic acid molecule of the present disclosure is at least 65 nucleotides in length. In some embodiments, the poly-A region of a nucleic acid molecule of the present disclosure is at least 70 nucleotides in length. In some embodiments, the poly-A region of a nucleic acid molecule of the present disclosure is at least 75 nucleotides in length. In some embodiments, the poly-A region of a nucleic acid molecule of the present disclosure is at least 80 nucleotides in length. In some embodiments, the poly-A region of a nucleic acid molecule of the present disclosure is at least 85 nucleotides in length. In some embodiments, the poly-A region of a nucleic acid molecule of the present disclosure is at least 90 nucleotides in length. In some embodiments, the poly-A region of a nucleic acid molecule of the present disclosure is at least 95 nucleotides in length. In some embodiments, the poly-A region of a nucleic acid molecule of the present disclosure is at least 100 nucleotides in length. In some embodiments, the poly-A region of a nucleic acid molecule of the present disclosure is at least 110 nucleotides in length. In some embodiments, the poly-A region of a nucleic acid molecule of the present disclosure is at least 120 nucleotides in length. In some embodiments, the poly-A region of a nucleic acid molecule of the present disclosure is at least 130 nucleotides in length. In some embodiments, the poly-A region of a nucleic acid molecule of the present disclosure is at least 140 nucleotides in length. In some embodiments, the poly-A region of a nucleic acid molecule of the present disclosure is at least 150 nucleotides in length. In some embodiments, the poly-A region of a nucleic acid molecule of the present disclosure is at least 160 nucleotides in length. In some embodiments, the poly-A region of a nucleic acid molecule of the present disclosure is at least 170 nucleotides in length. In some embodiments, the poly-A region of a nucleic acid molecule of the present disclosure is at least 180 nucleotides in length. In some embodiments, the poly-A region of a nucleic acid molecule of the present disclosure is at least 190 nucleotides in length. In some embodiments, the poly-A region of a nucleic acid molecule of the present disclosure is at least 200 nucleotides in length. In some embodiments, the poly-A region of a nucleic acid molecule of the present disclosure is at least 225 nucleotides in length. In some embodiments, the poly-A region of a nucleic acid molecule of the present disclosure is at least 250 nucleotides in length. In some embodiments, the poly-A region of a nucleic acid molecule of the present disclosure is at least 275 nucleotides in length. In some embodiments, the poly-A region of a nucleic acid molecule of the present disclosure is at least 300 nucleotides in length. In some embodiments, the poly-A region of a nucleic acid molecule of the present disclosure is at least 350 nucleotides in length. In some embodiments, the poly-A region of a nucleic acid molecule of the present disclosure is at least 400 nucleotides in length. In some embodiments, the poly-A region of a nucleic acid molecule of the present disclosure is at least 450 nucleotides in length. In some embodiments, the poly-A region of a nucleic acid molecule of the present disclosure is at least 500 nucleotides in length. In some embodiments, the poly-A region of a nucleic acid molecule of the present disclosure is at least 600 nucleotides in length. In some embodiments, the poly-A region of a nucleic acid molecule of the present disclosure is at least 700 nucleotides in length. In some embodiments, the poly-A region of a nucleic acid molecule of the present disclosure is at least 800 nucleotides in length. In some embodiments, the poly-A region of a nucleic acid molecule of the present disclosure is at least 900 nucleotides in length. In some embodiments, the poly-A region of a nucleic acid molecule of the present disclosure is at least 1000 nucleotides in length. In some embodiments, the poly-A region of a nucleic acid molecule of the present disclosure is at least 1100 nucleotides in length. In some embodiments, the poly-A region of a nucleic acid molecule of the present disclosure is at least 1200 nucleotides in length. In some embodiments, the poly-A region of a nucleic acid molecule of the present disclosure is at least 1300 nucleotides in length. In some embodiments, the poly-A region of a nucleic acid molecule of the present disclosure is at least 1400 nucleotides in length. In some embodiments, the poly-A region of a nucleic acid molecule of the present disclosure is at least 1500 nucleotides in length. In some embodiments, the poly-A region of a nucleic acid molecule of the present disclosure is at least 1600 nucleotides in length. In some embodiments, the poly-A region of a nucleic acid molecule of the present disclosure is at least 1700 nucleotides in length. In some embodiments, the poly-A region of a nucleic acid molecule of the present disclosure is at least 1800 nucleotides in length. In some embodiments, the poly-A region of a nucleic acid molecule of the present disclosure is at least 1900 nucleotides in length. In some embodiments, the poly-A region of a nucleic acid molecule of the present disclosure is at least 2000 nucleotides in length. In some embodiments, the poly-A region of a nucleic acid molecule of the present disclosure is at least 2250 nucleotides in length. In some embodiments, the poly-A region of a nucleic acid molecule of the present disclosure is at least 2500 nucleotides in length. In some embodiments, the poly-A region of a nucleic acid molecule of the present disclosure is at least 2750 nucleotides in length. In some embodiments, the poly-A region of a nucleic acid molecule of the present disclosure is at least 3000 nucleotides in length.

In some embodiments, length of a poly-A region in a nucleic acid molecule can be selected based on the overall length of the nucleic acid molecule, or a portion thereof (such as the length of the coding region or the length of an open reading frame of the nucleic acid molecule, etc.). For example, in some embodiments, the poly-A region accounts for about 5%, 10%, 15%, 20%, 25%, 30%, 35%, 40%, 45%, 50%, 55%, 60%, 65%, 70%, 75%, 80%, 85%, 90%, 95% or more of the total length of nucleic acid molecule containing the poly-A region.

Without being bound by the theory, it is contemplated that certain RNA-binding proteins can bind to the poly-A region located at the 3'-end of an mRNA molecule. These poly-A binding proteins (PABP) can modulate mRNA expression, such as interacting with translation initiation machinery in a cell and/or protecting the 3'-poly-A tails from degradation. Accordingly, in some embodiments, in some embodiments, the nucleic acid molecule of the present disclosure (e.g., mRNA) comprises at least one binding site for poly-A binding protein (PABP). In other embodiments, the nucleic acid molecule is conjugated or complex with a PABP before loaded into a delivery vehicle (e.g., lipid nanoparticles).

In some embodiments, the nucleic acid molecule of the present disclosure (e.g., mRNA) comprises a poly-A-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet structure results in protein production equivalent to at least 75% of that seen using a poly-A region of 120 nucleotides alone.

In some embodiments, the nucleic acid molecule of the present disclosure (e.g., mRNA) may include a poly-A region and may be stabilized by the addition of a 3'-stabilizing region. In some embodiments, the 3'-stabilizing region which may be used to stabilize a nucleic acid molecule (e.g., mRNA) including the poly-A or poly-A-G Quartet structures as described in International Patent Publication No. WO2013/103659, the content of which is incorporated herein by reference in its entirety.

In other embodiments, the 3'-stabilizing region which may be used in connection with the nucleic acid molecules of the present disclosure include a chain termination nucleoside such as but is not limited to 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside, 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Secondary Structure

Without being bound by the theory, it is contemplated that a stem-loop structure can direct RNA folding, protect structural stability of a nucleic acid molecule (e.g., mRNA), provide recognition sites for RNA binding proteins, and serve as a substrate for enzymatic reactions. For example, the incorporation of a miR sequence and/or a TEE sequence changes the shape of the stem loop region which may increase and/or decrease translation (Kedde et al. A *Pumilio*-induced RNA structure switch in p27-3'UTR controls miR-221 and miR-222 accessibility. *Nat Cell Biol.*, 2010 October; 12(10):1014-20, the content of which is herein incorporated by reference in its entirety).

Accordingly, in some embodiments, the nucleic acid molecules as described herein (e.g., mRNA) or a portion thereof may assume a stem-loop structure, such as but is not limited to a histone stem loop. In some embodiments, the stem-loop structure is formed from a stem-loop sequence that is about 25 or about 26 nucleotides in length such as, but not limited to, those as described in International Patent Publication No. WO2013/103659, the content of which is incorporated herein by reference in its entirety. Additional examples of stem-loop sequences include those described in International Patent Publication No. WO2012/019780 and International Patent Publication No. WO201502667, the contents of which are incorporated herein by reference. In some embodiments, the step-loop sequence comprises a TEE as described herein. In some embodiments, the step-loop sequence comprises a miR sequence as described herein. In specific embodiments, the stem loop sequence may include a miR-122 seed sequence. In specific embodiments, the nucleic acid molecule comprises the stem-loop sequence CAAAGGCTCTTTTCAGAGCCACCA (SEQ ID NO:1). In other embodiments, the nucleic acid molecule comprises the stem-loop sequence CAAAGGCUC-UUUUCAGAGCCACCA (SEQ ID NO:2).

In some embodiments, the nucleic acid molecule of the present disclosure (e.g., mRNA) comprises a stem-loop sequence located upstream (to the 5'-end) of the coding region in a nucleic acid molecule. In some embodiments, the stem-loop sequence is located within the 5'-UTR of the nucleic acid molecule. In some embodiments, the nucleic acid molecule of the present disclosure (e.g., mRNA) comprises a stem-loop sequence located downstream (to the 3'-end) of the coding region in a nucleic acid molecule. In some embodiments, the stem-loop sequence is located within the 3'-UTR of the nucleic acid molecule. In some cases, a nucleic acid molecule can contain more than one stem-loop sequences. In some embodiment, the nucleic acid molecule comprises at least one stem-loop sequence in the 5'-UTR, and at least one stem-loop sequence in the 3'-UTR.

In some embodiments, a nucleic acid molecule comprising a stem-loop structure further comprises a stabilization region. In some embodiment, the stabilization region comprises at least one chain terminating nucleoside that functions to slow down degradation and thus increases the half-life of the nucleic acid molecule. Exemplary chain terminating nucleoside that can be used in connection with the present disclosure include but are not limited to 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside, 3'-deoxynucleoside, 2',3'-dideoxynucleoside 3'-O-methylnucleosides, 3'-O-ethylnucleosides, 3'-arabinosides, and other alternative nucleosides known in the art and/or described herein. In other embodiments, a stem-loop structure may be stabilized by an alteration to the 3'-region of the polynucleotide that can prevent and/or inhibit the addition of oligio (U) (International Patent Publication No. WO2013/103659, incorporated herein by reference in its entirety).

In some embodiments, a nucleic acid molecule of the present disclosure comprises at least one stem-loop sequence and a poly-A region or polyadenylation signal. Non-limiting examples of polynucleotide sequences comprising at least one stem-loop sequence and a poly-A region or a polyadenylation signal include those described in International Patent Publication No. WO2013/120497, International Patent Publication No. WO2013/120629, International Patent Publication No. WO2013/120500, International Patent Publication No. WO2013/120627, International Patent Publication No. WO2013/120498, International Patent Publication No. WO2013/120626, International Patent Publication No. WO2013/120499 and International Patent Publication No. WO2013/120628, the content of each of which is incorporated herein by reference in its entirety.

In some embodiments, the nucleic acid molecule comprising a stem-loop sequence and a poly-A region or a polyadenylation signal can encode for a pathogen antigen or fragment thereof such as the polynucleotide sequences described in International Patent Publication No. WO2013/120499 and International Patent Publication No. WO2013/120628, the content of each of which is incorporated herein by reference in its entirety.

In some embodiments, the nucleic acid molecule comprising a stem-loop sequence and a poly-A region or a polyadenylation signal can encode for a therapeutic protein such as the polynucleotide sequences described in International Patent Publication No. WO2013/120497 and International Patent Publication No. WO2013/120629, the content of each of which is incorporated herein by reference in its entirety.

In some embodiments, the nucleic acid molecule comprising a stem-loop sequence and a poly-A region or a polyadenylation signal can encode for a tumor antigen or fragment thereof such as the polynucleotide sequences described in International Patent Publication No. WO2013/120500 and International Patent Publication No. WO2013/120627, the content of each of which is incorporated herein by reference in its entirety.

In some embodiments, the nucleic acid molecule comprising a stem-loop sequence and a poly-A region or a polyadenylation signal can code for an allergenic antigen or an autoimmune self-antigen such as the polynucleotide sequences described in International Patent Publication No. WO2013/120498 and International Patent Publication No. WO2013/120626, the content of each of which is incorporated herein by reference in its entirety.

Functional Nucleotide Analogs

In some embodiments, a payload nucleic acid molecule described herein contains only canonical nucleotides selected from A (adenosine), G (guanosine), C (cytosine), U (uridine), and T (thymidine). Without being bound by the theory, it is contemplated that certain functional nucleotide analogs can confer useful properties to a nucleic acid molecule. Examples of such as useful properties in the context of the present disclosure include but are not limited to increased stability of the nucleic acid molecule, reduced immunogenicity of the nucleic acid molecule in inducing innate immune responses, enhanced production of protein encoded by the nucleic acid molecule, increased intracellular delivery and/or retention of the nucleic acid molecule, and/or reduced cellular toxicity of the nucleic acid molecule, etc.

Accordingly, in some embodiments, a payload nucleic acid molecule comprises at least one functional nucleotide analog as described herein. In some embodiments, the functional nucleotide analog contains at least one chemical modification to the nucleobase, the sugar group and/or the phosphate group. Accordingly, a payload nucleic acid molecule comprising at least one functional nucleotide analog contains at least one chemical modification to the nucleobases, the sugar groups, and/or the internucleoside linkage. Exemplary chemical modifications to the nucleobases, sugar groups, or internucleoside linkages of a nucleic acid molecule are provided herein.

As described herein, ranging from 0% to 100% of all nucleotides in a payload nucleic acid molecule can be functional nucleotide analogs as described herein. For example, in various embodiments, from about 1% to about 20%, from about 1% to about 25%, from about 1% to about 50%, from about 10% to about 60%, from about 10% to about 70%, from about 10% to about 80%, from about 1% to about 90%, from about 1% to about 95%, from about 10% to about 20%, from about 10% to about 25%, from about 10% to about 50%, from about 10% to about 60%, from about 10% to about 70%, from about 10% to about 80%, from about 10% to about 90%, from about 10% to about 95%, from about 10% to about 100%, from about 20% to about 25%, from about 20% to about 50%, from about 20% to about 60%, from about 20% to about 70%, from about 20% to about 80%, from about 20% to about 90%, from about 20% to about 95%, from about 20% to about 100%, from about 50% to about 60%, from about 50% to about 70%, from about 50% to about 80%, from about 50% to about 90%, from about 50% to about 95%, from about 50% to about 100%, from about 70% to about 80%, from about 70% to about 90%, from about 70% to about 95%, from about 70% to about 100%, from about 80% to about 90%, from about 80% to about 95%, from about 80% to about 100%, from about 90% to about 95%, from about 90% to about 100%, or from about 95% to about 100% of all nucleotides in a nucleic acid molecule are functional nucleotide analogs described herein. In any of these embodiments, a functional nucleotide analog can be present at any position (s) of a nucleic acid molecule, including the 5'-terminus, 3'-terminus, and/or one or more internal positions. In some embodiments, a single nucleic acid molecule can contain different sugar modifications, different nucleobase modifications, and/or different types internucleoside linkages (e.g., backbone structures).

As described herein, ranging from 0% to 100% of all nucleotides of a kind (e.g., all purine-containing nucleotides as a kind, or all pyrimidine-containing nucleotides as a kind, or all A, G, C, T or U as a kind) in a payload nucleic acid molecule can be functional nucleotide analogs as described herein. For example, in various embodiments, from about 1% to about 20%, from about 1% to about 25%, from about 1b % to about 50%, from about 1b % to about 60%, from about 1b % to about 70%, from about 1% to about 80%, from about 1% to about 90%, from about 1% to about 95%, from about 10% to about 20%, from about 10% to about 25%, from about 10% to about 50%, from about 10% to about 60%, from about 10% to about 70%, from about 10% to about 80%, from about 10% to about 90%, from about 10% to about 95%, from about 10% to about 100%, from about 20% to about 25%, from about 20% to about 50%, from about 20% to about 60%, from about 20% to about 70%, from about 20% to about 80%, from about 20% to about 90%, from about 20% to about 95%, from about 20% to about 100%, from about 50% to about 60%, from about 50% to about 70%, from about 50% to about 80%, from about 50% to about 90%, from about 50% to about 95%, from about 50% to about 100%, from about 70% to about 80%, from about 70% to about 90%, from about 70% to about 95%, from about 70% to about 100%, from about 80% to about 90%, from about 80% to about 95%, from about 80% to about 100%, from about 90% to about 95%, from about 90% to about 100%, or from about 95% to about 100% of a kind of nucleotides in a nucleic acid molecule are functional nucleotide analogs described herein. In any of these embodiments, a functional nucleotide analog can be present at any position(s) of a nucleic acid molecule, including the 5'-terminus, 3'-terminus, and/or one or more internal positions. In some embodiments, a single nucleic acid molecule can contain different sugar modifications, different nucleobase modifications, and/or different types internucleoside linkages (e.g., backbone structures).

Modification to Nucleobases

In some embodiments, a functional nucleotide analog contains a non-canonical nucleobase. In some embodiments, canonical nucleobases (e.g., adenine, guanine, uracil, thymine, and cytosine) in a nucleotide can be modified or replaced to provide one or more functional analogs of the nucleotide. Exemplary modification to nucleobases include but are not limited to one or more substitutions or modifications including but not limited to alkyl, aryl, halo, oxo, hydroxyl, alkyloxy, and/or thio substitutions; one or more fused or open rings, oxidation, and/or reduction.

In some embodiments, the non-canonical nucleobase is a modified uracil. Exemplary nucleobases and nucleosides having an modified uracil include pseudouridine ($\psi$), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxy-hydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s2U$), 5-methylaminomethyl-uracil ($mnm^5U$), 5-methylaminomethyl-2-thio-uracil ($mnm^5s2U$), 5-methylaminomethyl-2-seleno-uracil ($mnm^5se^2U$), 5-carbamoylmethyl-uracil ($nCm^5U$), 5-carboxymethylaminomethyl-uracil ($cmnm^5U$), 5-carboxymethylaminomethyl-2-thio-uracil ($cmnm^5s2U$), 5-propynyl-uracil, 1-propynyl-pseudouracil, 5-taurinomethyl-uracil ($\tau m^5U$), 1-taurinomethyl-pseudouridine, 5-taurinomethyl-2-thio-uracil($\tau m^5s^2U$), 1-taurinomethyl-4-thio-pseudouridine, 5-methyl-uracil ($m^5U$, i.e., having the nucleobase deoxythymine), 1-methyl-pseudouridine ($m^1\psi$), 1-ethyl-pseudouridine ($Et^1\psi$), 5-methyl-2-thio-uracil ($m^5s2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil ($acp^3U$), 1-methyl-3-(3-amino-3-carboxypropyl)pseudouridine ($acp^3V$), 5-(isopentenylaminomethyl)uracil ($m^5U$), 5-(isopentenylaminomethyl)-2-thio-uracil ($m^5s2U$), 5,2'-O-dimethyl-uridine ($m^5Um$), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($nCm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the non-canonical nucleobase is a modified cytosine. Exemplary nucleobases and nucleosides having a modified cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm⁵C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the non-canonical nucleobase is a modified adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonyl-carbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the non-canonical nucleobase is a modified guanine. Exemplary nucleobases and nucleosides having a modified guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQO), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

In some embodiments, the non-canonical nucleobase of a functional nucleotide analog can be independently a purine, a pyrimidine, a purine or pyrimidine analog. For example, in some embodiments, the non-canonical nucleobase can be modified adenine, cytosine, guanine, uracil, or hypoxanthine. In other embodiments, the non-canonical nucleobase can also include, for example, naturally-occurring and synthetic derivatives of abase, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d] pyrimidines, pyrazin-2-ones, 1,2,4-triazine, pyridazine; or 1,3,5 triazine.

Modification to the Sugar

In some embodiments, a functional nucleotide analog contains a non-canonical sugar group. In various embodiments, the non-canonical sugar group can be a 5-carbon or 6-carbon sugar (such as pentose, ribose, arabinose, xylose, glucose, galactose, or a deoxy derivative thereof) with one or more substitutions, such as a halo group, a hydroxy group, a thiol group, an alkyl group, an alkoxy group, an alkenyloxy group, an alkynyloxy group, an cycloalkyl group, an aminoalkoxy group, an alkoxyalkoxy group, an hydroxyalkoxy group, an amino group, an azido group, an aryl group, an aminoalkyl group, an aminoalkenyl group, an aminoalkynyl group, etc.

Generally, RNA molecules contains the ribose sugar group, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a nucleic acid molecule can include nucleotides containing, e.g., arabinose or L-ribose, as the sugar. In some embodiments, the nucleic acid molecule includes at least one nucleoside wherein the sugar is L-ribose, 2'-O-methyl-ribose, 2'-fluoro-ribose, arabinose, hexitol, an LNA, or a PNA.

Modifications to the Internucleoside Linkage

In some embodiments, the payload nucleic acid molecule of the present disclosure can contain one or more modified internucleoside linkage (e.g., phosphate backbone). Backbone phosphate groups can be altered by replacing one or more of the oxygen atoms with a different substituent.

In some embodiments, the functional nucleotide analogs can include the replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha ($\alpha$), beta ($\beta$) or gamma ($\gamma$) position) can be replaced with a sulfur (thio) and a methoxy. The replacement of one or more of the oxygen atoms at the position of the phosphate moiety (e.g., $\alpha$-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Additional examples of nucleic acid molecules (e.g., mRNA), compositions, formulations and/or methods associated therewith that can be used in connection with the present disclosure further include those described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, the content of each of which is incorporated herein in its entirety.

6.5 Formulation

According to the present disclosure, nanoparticle compositions described herein can include at least one lipid component and one or more additional components, such as a therapeutic and/or prophylactic agent. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to one of formulae (I), (II), or (III) (and sub-formulas thereof) described herein, a phospholipid (such as an unsaturated lipid, e.g., DOPE or DSPC), a PEG lipid, and a structural lipid. The elements of the lipid component may be provided in specific fractions.

In one embodiment, provided herein is a nanoparticle compositions comprising a cationic or ionizable lipid compound provided herein, a therapeutic agent, and one or more excipients. In one embodiment, cationic or ionizable lipid compound comprises a compound according to one of Formulae (I), (II), or (III) (and sub-formulas thereof) as described herein, and optionally one or more additional ionizable lipid compounds. In one embodiment, the one or more excipients are selected from neutral lipids, steroids, and polymer conjugated lipids. In one embodiment, the therapeutic agent is encapsulated within or associated with the lipid nanoparticle.

In one embodiment, provided herein is a nanoparticle composition (lipid nanoparticle) comprising:

i) between 40 and 50 mol percent of a cationic lipid;
ii) a neutral lipid;
iii) a steroid;
iv) a polymer conjugated lipid; and
v) a therapeutic agent.

As used herein, "mol percent" refers to a component's molar percentage relative to total mols of all lipid components in the LNP (i.e., total mols of cationic lipid(s), the neutral lipid, the steroid and the polymer conjugated lipid).

In one embodiment, the lipid nanoparticle comprises from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, or from 47.2 to 47.8 mol percent of the cationic lipid. In one embodiment, the lipid nanoparticle comprises about 47.0, 47.1, 47.2, 47.3, 47.4, 47.5, 47.6, 47.7, 47.8, 47.9 or 48.0 mol percent of the cationic lipid.

In one embodiment, the neutral lipid is present in a concentration ranging from 5 to 15 mol percent, 7 to 13 mol percent, or 9 to 11 mol percent. In one embodiment, the neutral lipid is present in a concentration of about 9.5, 10 or 10.5 mol percent. In one embodiment, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In one embodiment, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent. In one embodiment, the molar ratio of cationic lipid to the steroid ranges from 1.0:0.9 to 1.0:1.2, or from 1.0:1.0 to 1.0:1.2. In one embodiment, the steroid is cholesterol.

In one embodiment, the therapeutic agent to lipid ratio in the LNP (i.e., N/P, were N represents the moles of cationic lipid and P represents the moles of phosphate present as part of the nucleic acid backbone) range from 2:1 to 30:1, for example 3:1 to 22:1. In one embodiment, N/P ranges from 6:1 to 20:1 or 2:1 to 12:1. Exemplary N/P ranges include about 3:1. About 6:1, about 12:1 and about 22:1.

In one embodiment, provided herein is a lipid nanoparticle comprising:

i) a cationic lipid having an effective pKa greater than 6.0;

ii) from 5 to 15 mol percent of a neutral lipid;

iii) from 1 to 15 mol percent of an anionic lipid;

iv) from 30 to 45 mol percent of a steroid;

v) a polymer conjugated lipid; and vi) a therapeutic agent, or a pharmaceutically acceptable salt or prodrug thereof, wherein the mol percent is determined based on total mol of lipid present in the lipid nanoparticle.

In one embodiment, the cationic lipid can be any of a number of lipid species which carry a net positive charge at a selected pH, such as physiological pH. Exemplary cationic lipids are described herein below. In one embodiment, the cationic lipid has a pKa greater than 6.25. In one embodiment, the cationic lipid has a pKa greater than 6.5. In one embodiment, the cationic lipid has a pKa greater than 6.1, greater than 6.2, greater than 6.3, greater than 6.35, greater than 6.4, greater than 6.45, greater than 6.55, greater than 6.6, greater than 6.65, or greater than 6.7.

In one embodiment, the lipid nanoparticle comprises from 40 to 45 mol percent of the cationic lipid. In one embodiment, the lipid nanoparticle comprises from 45 to 50 mole percent of the cationic lipid.

In one embodiment, the molar ratio of the cationic lipid to the neutral lipid ranges from about 2:1 to about 8:1. In one embodiment, the lipid nanoparticle comprises from 5 to 10 mol percent of the neutral lipid.

Exemplary anionic lipids include, but are not limited to, phosphatidylglycerol, dioleoylphosphatidylglycerol (DOPG), dipalmitoylphosphatidylglycerol (DPPG) or 1,2-distearoyl-sn-glycero-3-phospho-(1'-rac-glycerol) (DSPG).

In one embodiment, the lipid nanoparticle comprises from 1 to 10 mole percent of the anionic lipid. In one embodiment, the lipid nanoparticle comprises from 1 to 5 mole percent of the anionic lipid. In one embodiment, the lipid nanoparticle comprises from 1 to 9 mole percent, from 1 to 8 mole percent, from 1 to 7 mole percent, or from 1 to 6 mole percent of the anionic lipid. In one embodiment, the mol ratio of anionic lipid to neutral lipid ranges from 1:1 to 1:10.

In one embodiment, the steroid cholesterol. In one embodiment, the molar ratio of the cationic lipid to cholesterol ranges from about 5:1 to 1:1. In one embodiment, the lipid nanoparticle comprises from 32 to 40 mol percent of the steroid.

In one embodiment, the sum of the mol percent of neutral lipid and mol percent of anionic lipid ranges from 5 to 15 mol percent. In one embodiment, wherein the sum of the mol percent of neutral lipid and mol percent of anionic lipid ranges from 7 to 12 mol percent.

In one embodiment, the mol ratio of anionic lipid to neutral lipid ranges from 1:1 to 1:10. In one embodiment, the sum of the mol percent of neutral lipid and mol percent steroid ranges from 35 to 45 mol percent.

In one embodiment, the lipid nanoparticle comprises:

i) from 45 to 55 mol percent of the cationic lipid;

ii) from 5 to 10 mol percent of the neutral lipid;

iii) from 1 to 5 mol percent of the anionic lipid; and iv) from 32 to 40 mol percent of the steroid.

In one embodiment, the lipid nanoparticle comprises from 1.0 to 2.5 mol percent of the conjugated lipid. In one embodiment, the polymer conjugated lipid is present in a concentration of about 1.5 mol percent.

In one embodiment, the neutral lipid is present in a concentration ranging from 5 to 15 mol percent, 7 to 13 mol percent, or 9 to 11 mol percent. In one embodiment, the neutral lipid is present in a concentration of about 9.5, 10 or 10.5 mol percent. In one embodiment, the molar ratio of the cationic lipid to the neutral lipid ranges from about 4.1:1.0 to about 4.9:1.0, from about 4.5:1.0 to about 4.8:1.0, or from about 4.7:1.0 to 4.8:1.0.

In one embodiment, the steroid is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In one embodiment, the steroid is present in a concentration of 40, 41, 42, 43, 44, 45, or 46 molar percent. In certain embodiments, the molar ratio of cationic lipid to the steroid ranges from 1.0:0.9 to 1.0:1.2, or from 1.0:1.0 to 1.0:1.2.

In one embodiment, the molar ratio of cationic lipid to steroid ranges from 5:1 to 1:1.

In one embodiment, the lipid nanoparticle comprises from 1.0 to 2.5 mol percent of the conjugated lipid. In one embodiment, the polymer conjugated lipid is present in a concentration of about 1.5 mol percent.

In one embodiment, the molar ratio of cationic lipid to polymer conjugated lipid ranges from about 100:1 to about 20:1. In one embodiment, the molar ratio of cationic lipid to the polymer conjugated lipid ranges from about 35:1 to about 25:1.

In one embodiment, the lipid nanoparticle has a mean diameter ranging from 50 nm to 100 nm, or from 60 nm to 85 nm.

In one embodiment, the composition comprises a cationic lipid provided herein, DSPC, cholesterol, and PEG-lipid, and mRNA. In one embodiment, the a cationic lipid provided herein, DSPC, cholesterol, and PEG-lipid are at a molar ratio of about 50:10:38.5:1.5.

Nanoparticle compositions can be designed for one or more specific applications or targets. For example, a nanoparticle composition can be designed to deliver a therapeutic and/or prophylactic agent such as an RNA to a particular cell, tissue, organ, or system or group thereof in a mammal's body. Physiochemical properties of nanoparticle compositions can be altered in order to increase selectivity for particular bodily targets. For instance, particle sizes can be adjusted based on the fenestration sizes of different organs. The therapeutic and/or prophylactic agent included in a nanoparticle composition can also be selected based on the desired delivery target or targets. For example, a therapeutic and/or prophylactic agent can be selected for a particular indication, condition, disease, or disorder and/or for delivery to a particular cell, tissue, organ, or system or group thereof (e.g., localized or specific delivery). In certain embodiments, a nanoparticle composition can include an mRNA encoding a polypeptide of interest capable of being translated within a cell to produce the polypeptide of interest. Such a composition can be designed to be specifically delivered to a particular organ. In certain embodiments, a composition can be designed to be specifically delivered to a mammalian liver.

The amount of a therapeutic and/or prophylactic agent in a nanoparticle composition can depend on the size, composition, desired target and/or application, or other properties of the nanoparticle composition as well as on the properties of the therapeutic and/or prophylactic agent. For example, the amount of an RNA useful in a nanoparticle composition can depend on the size, sequence, and other characteristics of the RNA. The relative amounts of a therapeutic and/or prophylactic agent and other elements (e.g., lipids) in a nanoparticle composition can also vary. In some embodiments, the wt/wt ratio of the lipid component to a therapeutic and/or prophylactic agent in a nanoparticle composition can be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic agent can be from about 10:1 to about 40:1. In certain embodiments, the wt/wt ratio is about 20:1. The amount of a therapeutic and/or prophylactic agent in a nanoparticle composition can, for example, be measured using absorption spectroscopy (e.g., ultraviolet-visible spectroscopy).

In some embodiments, a nanoparticle composition includes one or more RNAs, and the one or more RNAs, lipids, and amounts thereof can be selected to provide a specific N:P ratio. The N:P ratio of the composition refers to the molar ratio of nitrogen atoms in one or more lipids to the number of phosphate groups in an RNA. In some embodiments, a lower N:P ratio is selected. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

The physical properties of a nanoparticle composition can depend on the components thereof. For example, a nanoparticle composition including cholesterol as a structural lipid can have different characteristics compared to a nanoparticle composition that includes a different structural lipid. Similarly, the characteristics of a nanoparticle composition can depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvem Instruments Ltd, Malvem, Worcestershire, UK) may also be used to measure multiple characteristics of a nanoparticle composition, such as particle size, polydispersity index, and zeta potential.

In various embodiments, the mean size of a nanoparticle composition can be between 10s of nm and 100s of nm. For example, the mean size can be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition can be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition can be from about 70 nm to about 100 nm. In some embodiments, the mean size can be about 80 nm. In other embodiments, the mean size can be about 100 nm.

A nanoparticle composition can be relatively homogenous. A polydispersity index can be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition can be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic agent describes the amount of therapeutic and/or prophylactic agent that is encapsulated or otherwise associated with a nanoparticle composition after preparation, relative to the initial amount provided. The encapsulation efficiency is desirably high (e.g., close to 100%). The encapsulation efficiency can be measured, for example, by comparing the amount of therapeutic and/or prophylactic agent in a solution containing the nanoparticle composition before and after breaking up the nanoparticle composition with one or more organic solvents or detergents. Fluorescence can be used to measure the amount of free therapeutic and/or prophylactic agent (e.g., RNA) in a solution. For the nanoparticle compositions described herein, the encapsulation efficiency of a therapeutic and/or prophylactic agent can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

A nanoparticle composition can optionally comprise one or more coatings. For example, a nanoparticle composition can be formulated in a capsule, film, or tablet having a coating. A capsule, film, or tablet including a composition described herein can have any useful size, tensile strength, hardness, or density.

6.6 Pharmaceutical Compositions

According to the present disclosure, nanoparticle compositions can be formulated in whole or in part as pharmaceutical compositions. Pharmaceutical compositions can include one or more nanoparticle compositions. For example, a pharmaceutical composition can include one or more nanoparticle compositions including one or more different therapeutic and/or prophylactic agents. Pharmaceutical compositions can further include one or more pharmaceutically acceptable excipients or accessory ingredients such as those described herein. General guidelines for the formulation and manufacture of pharmaceutical compositions and agents are available, for example, in Remington's The Science and Practice of Pharmacy, 21$^{st}$ Edition, A. R. Gennaro; Lippincott, Williams & Wilkins, Baltimore, Md., 2006. Conventional excipients and accessory ingredients can be used in any pharmaceutical composition, except insofar as any conventional excipient or accessory ingredient can be incompatible with one or more components of a nanoparticle composition. An excipient or accessory ingredient can be incompatible with a component of a nanoparticle composition if its combination with the component can result in any undesirable biological effect or otherwise deleterious effect.

In some embodiments, one or more excipients or accessory ingredients can make up greater than 50% of the total mass or volume of a pharmaceutical composition including a nanoparticle composition. For example, the one or more excipients or accessory ingredients can make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition can comprise between 0.1% and 100% (wt/wt) of one or more nanoparticle compositions.

In certain embodiments, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (I), (II), or (III) (and sub-formulas thereof) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the nanoparticle compositions and/or pharmaceutical compositions comprising a compound of any of Formulae (I), (II), or (III) (and sub-formulas thereof) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one embodiment, the formulation is stabilized for at least 4 weeks at about 4° C. In certain embodiments, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8, 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. "Stability," "stabilized," and "stable" in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Nanoparticle compositions and/or pharmaceutical compositions including one or more nanoparticle compositions can be administered to any patient or subject, including those patients or subjects that can benefit from a therapeutic effect provided by the delivery of a therapeutic and/or prophylactic agent to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, horses, sheep, cats, dogs, mice, and/or rats.

A pharmaceutical composition including one or more nanoparticle compositions can be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure can be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions can be prepared in a variety of forms suitable for a variety of routes and methods of administration. For example, pharmaceutical compositions can be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactic agents, additional agents such as wetting agents, emulsifying and suspending agents, sweetening, flavoring, and/or perfuming agents. In certain embodiments for parenteral administration, compositions are mixed with solubilizing agents such as Cremophor™, alcohols, oils, modified oils, glycols, polysorbates, cyclodextrins, polymers, and/or combinations thereof.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

The disclosure features methods of delivering a therapeutic and/or prophylactic agent to a mammalian cell or organ, producing a polypeptide of interest in a mammalian cell, and treating a disease or disorder in a mammal in need thereof comprising administering to a mammal and/or contacting a mammalian cell with a nanoparticle composition including a therapeutic and/or prophylactic agent.

7. EXAMPLES

The examples in this section are offered by way of illustration, and not by way of limitation.

General Methods.

General preparative HPLC method: HPLC purification is carried out on an Waters 2767 equipped with a diode array detector (DAD) on an Inertsil Pre-C8 OBD column, generally with water containing 0.1% TFA as solvent A and acetonitrile as solvent B.

General LCMS method: LCMS analysis is conducted on a Shimadzu (LC-MS2020) System. Chromatography is performed on a SunFire C18, generally with water containing 0.1% formic acid as solvent A and acetonitrile containing 0.1% formic acid as solvent B.

7.1 Example 1: Preparation of Starting Materials and Intermediates

Preparation of Compound A

A

Preparation of Compound B

B

141

Preparation of Compound C

142

Preparation of Compound E

C

Preparation of compound D

E

D

Preparation of Compound F

B

F

To a solution of compound B (446.0 mg, 1.0 mmol, 1.0 eq) and ethanolamine (180.0 mg, 3.0 mmol, 3.0 eq) dissolved in ACN (10.0 mL) was added $Cs_2CO_3$ (97.5 mg, 0.3 mmol, 0.3 eq), $K_2CO_3$ (414.0 mg, 3.0 mmol, 3.0 eq) and NaI (14.6 mg, 0.1 mmol, 0.1 eq) at RT. The mixture was stirred for 16 hours at 85° C. LCMS showed the reaction was completed. The mixture was evaporated under reduced pressure and purified by FCC (DCM/MeOH=1/0-20/1) to provide compound F (0.35 g, 82% yield) as yellow oil.

Preparation of Compound G

A

-continued

B

K$_2$CO$_3$, Cs$_2$CO$_3$, NaI

G-1

G

Step 1: Preparation of Compound G-1

To a solution of compound A (1.87 g, 12.38 mmol) in EtOH (50 mL) was added 2-(benzyloxy)ethan-1-amine (2.0 g, 8.25 mmol). The reaction was stirred at RT for 12 hours. The reaction mixture was concentrated in vacuo and purified by flash column chromatography (CH$_2$Cl$_2$: MeOH=10:1) to give the target product as yellow oil (1.4 g, yield: 43%). LCMS: Rt: 0.824 min; MS m/z (ESI): 394.3 [M+H]$^+$.

Step 2: Preparation of Compound G

To a solution of compound G-1 (1.4 g, 3.56 mmol) in CH$_3$CN (50 mL) was added K$_2$CO$_3$ (1.47 g, 10.67 mmol), Cs$_2$CO$_3$ (350 mg, 1.07 mmol), NaI (160 mg, 1.07 mmol), and compound B (2.24 g, 5.34 mmol). The reaction was stirred at 80° C. for 10 hours. The reaction mixture was concentrated in vacuo. The crude product was purified by flash column chromatography (CH$_2$Cl$_2$: MeOH=20:1) to give the target product as yellow oil (2.0 g, yield: 76%). LCMS: Rt: 1.750 min; MS m/z (ESI): 732.6 [M+H]$^+$.

Preparation of Compound H

NH(PMB)$_2$

A

EtOH

H-1

NaH, C$_{12}$H$_{25}$Br

MeOH

-continued

H-2

Pd/C, H$_2$

MeOH

H

Preparation of Compound I

I

Preparation of Compound J

H-1

NaH, DMF

-continued

J

To a solution of Compound H-1 (2.0 g, 4.0 mmol, 1.0 eq) in DMF (40 mL) was added NaH (320 mg, 8.0 mmol, 2.0 eq) at room temperature. The mixture was stirred at room temperature for 1 hour. Then 1-iodohexane (1.7 g, 8.0 mmol, 2.0 eq) and NaI (120 mg, 0.8 mmol, 0.2 eq) were added. The mixture was stirred at 70° C. for 16 hours. LCMS showed the reaction was complete. The reaction mixture was poured into water and extracted with EA. The combined organic layers were washed with brine, dried over Na$_2$SO$_4$ and concentrated. The residue was purified by column chromatography on silica gel (PE/EA=40/1) to give the title compound (1.2 g, 52% yield) as yellow oil. LCMS: Rt: 1.070 min; MS m/z (ESI): 584.4 [M+H]$^+$.

Preparation of Compound K

K

Preparation of Compound L

L

Preparation of Compound M

M-1

M-2

M-3

-continued

M-4

M

Step 1: Preparation of Compound M-2

To a solution of compound M-1 (30.0 g, 98.25 mmol) in DMF (800 mL) was added NaCN (9.63 g, 196.5 mmol). The reaction was stirred at 60° C. for 10 hours. The reaction mixture was poured into water (500 ml) and extracted with EtOAc (3×500 mL). The combined organic layers were washed with brine, dried over anhydrous Na$_2$SO$_4$ and concentrated in vacuo. The crude product was purified by flash column chromatography (EtOAc:PE=1:20) to give the target product as yellow oil (18.3 g, yield: 74%).

Step 2: Preparation of Compound M-3

To a solution of Compound M-2 (17.0 g, 67.61 mmol) in EtOH (200 mL) was added H$_2$SO$_4$ (40 mL). The reaction was stirred at 90° C. for 48 hours. The reaction mixture was poured into water (500 ml) and extracted with EtOAc (3×500 mL). The combined organic layer was washed with brine, dried over anhydrous Na$_2$SO$_4$ and concentrated in vacuo to give the target product as yellow oil (15 g, yield: 75%).

Step 3: Preparation of Compound M-4

To a solution of Compound M-3 (14 g, 46.90 mmol) in MeOH (240 mL) and H$_2$O (60 mL) was added LiOH·H2O (9.84 g, 234.5 mmol). The reaction was stirred at 50° C. for 10 hours. The reaction mixture concentrated in vacuo to give the target product. The crude product was dissolved in water. The residue was adjusted to PH=2 with 6M HCl and extracted with EtOAc (3×500 mL). The combined organic layers were washed with brine, dried over anhydrous Na$_2$SO$_4$ and concentrated in vacuo to give the target product as yellow oil (15 g, yield: 75%).

Step 4: Preparation of Compound M

To a solution of Compound M-4 (1.0 g, 4.0 mmol) in DCM (10 mL) was added SOCl$_2$ (0.9 g, 8.0 mmol). The reaction was stirred at 35° C. for 2 hours. Removal of solvent to get the compound M (1.2 g, crude) as brown oil.

Preparation of Compound N

147

-continued

N-1

$\xrightarrow{\text{LiCl}}{\text{DMF}}$

N-2

$\xrightarrow{\text{LiAlH}_4}{\text{THF}}$

N-3

$\xrightarrow{\text{MsCl, DIPEA}}{\text{DCM}}$

N-4

$\xrightarrow{\text{NaN}_3}{\text{DMF, 100° C.}}$

N-5

$\xrightarrow{\text{Pd/C}}{\text{EA}}$

N

Preparation of Compound O

N $\xrightarrow[\text{DCM}]{\text{EDCl, DMAP, DIEA}}$

O

148

Preparation of Compound P

$\xrightarrow{\text{NaCN, DMF}}$

N-4

$\xrightarrow{\text{H}_2\text{SO}_4, \text{EtOH}}$

P-1

$\xrightarrow{\text{LiOH·H}_2\text{O},}{\text{EtOH, H}_2\text{O}}$

P-2

P

Preparation of Compound Q

$\xrightarrow[\text{DMF}]{\text{NaH}}$

$\xrightarrow{\text{LiCl}}{\text{DMF}}$

Q-1

Q-2

$\xrightarrow{\text{LiAlH}_4}{\text{THF}}$

Q-3

$\xrightarrow[\text{DCM}]{\text{EDCl, DMAP, DIEA}}$

Q

Step 1: Preparation of Compound Q-1

To a mixture of NaH (3 g, 74.07 mmol, 2.5 eq) in DMF (30 mL) was added dimethyl malonate (4 g, 30 mmol, 1.0 eq) at 0° C. under $N_2$. The reaction mixture was stirred at 0° C. for 0.5 hour. The 1-iodohexane (16 g, 75 mmol, 2.5 eq) in DMF (30 ml) was added to it. The reaction mixture was stirred at RT for 16 hours. TLC showed the reaction was complete. The mixture was poured in water and washed with EA. The combined organic layers were separated and dried over $Na_2SO_4$. Removal of solvent, FCC to get the compound Q-1 (5.4 g, 59.92%) as colorless oil.

$^1H$ NMR (400 MHz, $CCl_3D$): δ: 3.70 (s, 6H), 1.88-1.84 (m, 4H), 1.63 (s, 1H), 1.27 (s, 10H), 1.13 (s, 5H), 0.88-0.86 (m, 6H).

Step 2: Preparation of Compound Q-2

To a solution of compound Q-1 (5.4 g, 17.97 mmol, 1.0 eq) in DMF (100 mL) was added LiCl (7.6 g, 179.7 mmol, 10.0 eq). The reaction mixture was stirred at 120° C. for 12 hours. TLC showed the reaction was complete. The mixture was poured in water and washed with EA. The combined organic layers were separated and dried over $Na_2SO_4$. Removal of solvent, FCC to get the compound Q-2 (3.1 g, 71.17%) as colorless oil.

$^1H$ NMR (400 MHz, $CCl_3D$): δ: 3.67 (s, 3H), 2.35-2.31 (m, 1H), 1.61-1.54 (m, 2H), 1.47-1.40 (m, 2H), 1.26 (s, 16H), 0.89-0.86 (m, 6H).

Step 3: Preparation of Compound Q-3

To a solution of compound Q-2 (3.1 g, 12.79 mmol, 1.0 eq) in THF (100 mL) was added slowly $LiAlH_4$ (972 mg, 25.58 mmol, 2.0 eq) in 0° C. The reaction mixture was stirred at reflux for 1 hour. TLC showed the reaction was complete. After being cooled to 0° C., the mixture was quenched with successive addition of water (1.3 ml), 15% aq NaOH (1.3 ml) and water (3.9 ml). The resulting mixture was diluted with EA and the precipitate was removed by titration. The filtrate was evaporated under reduced pressure and FCC to get the compound Q-3 (2.7 g, 98.46%) as yellow oil.

$^1H$ NMR (400 MHz, $CCl_3D$): δ: 3.54 (d, J=5.2 Hz, 2H), 1.47-1.43 (m, 2H), 1.28 (s, 20H), 0.90-0.87 (m, 6H).

Step 4: Preparation of Compound Q

To a solution of compound Q-3 (1 g, 4.664 mmol, 1.0 eq) in DCM (15 mL) was added 6-bromohexanoic acid (1.1 g, 5.597 mmol, 1.2 eq), EDCI (1.34 g, 6.996 mmol, 1.5 eq), DMAP (114 mg, 0.9328 mmol, 0.2 eq), DIEA (1.2 g, 9.328 mmol, 2.0 eq). The reaction mixture was stirred at 50° C. for 16 hours. TLC showed the reaction was complete. Removal of solvent, FCC to get the compound Q (650 mg, 35.61%) as yellow oil.

Preparation of Compound SM2

SM2-1

SM2-2

SM2-3

-continued

SM2

Preparation of Compound R

SM2

R-5

R-6

R

Preparation of Compound S

S-1

S-2

S-3

S

Preparation of Compound SM5

SM5-1

SM5-2
Pd/C, MeOH

SM5-3

MsCl, DIEA, DCM

SM5 silica gel (DCM/MeOH=10/1) to give the title compound (5.0 g, 56% yield) as colorless oil.

Step 2: Preparation of Compound SM5

To a solution of compound SM5-3 (500 mg, 2.67 mmol, 1.0 eq.) and DIPEA (690 mg, 5.34 mmol, 2.0 eq.) in DCM (20 mL) was added MsCl (305 mg, 2.67 mmol, 1.0 eq.). The mixture was stirred at room temperature for 2 hours. The mixture was poured into water and extracted with DCM. The combined organic layers were washed with brine, dried over $Na_2SO_4$ and concentrated to give the title compound (450 mg, 63% yield) as yellow oil. It was used in next step without further purification.

Preparation of compound SM6

$C_{11}H_{23}$—OH
SM6-1

O-2
TsOH, Toluene

SM6

7.2 Example 2: Preparation of Compound 1

$H_2N$——OBn

Ti(Oi-Pr)$_4$
MeOH, NaBH$_4$
R.T 1-1

A
EtOH R.T 1-2

NaH DMF 1-3

Pd/C,
con. HCl
MeOH

1

Step 1: Preparation of Compound SM5-3

To a solution of compound SM5-1 (5 g, 47.56 mmol, 1.0 eq.) in MeOH (200 mL) was added compound SM5-2 (9.33 g, 95.11 mmol, 2.0 eq.) and Pd/C (1.0 g). The mixture was stirred at RT for 10 hours under $H_2$. The mixture was filtered, concentrated and purified by column chromatography on Step 1: Preparation of Compound 1-1

A mixture of cyclobutanone (463 mg, 6.6 mmol, 1.0 eq), 2-(benzyloxy)ethan-1-amine (1.0 g, 6.6 mmol, 1.0 eq) and titanium tetraisopropanolate (2.3 g, 7.9 mol, 1.2 eq) in methanol (50 mL) was stirred under argon at room temperature for 16 h. Sodium borohydride (250 mg, 6.6 mmol, 1.0 eq) was then added and the resulting mixture was stirred for an additional 2 h. LCMS showed the reaction was complete. The reaction was quenched with water and then filtered through a pad of celite and washed with MeOH. The filtration was concentrated and extracted with EA. The combined organic layers were dried over Na$_2$SO$_4$ and evaporated under reduced pressured and purified by column chromatography on silica gel (DCM/MeOH=50/1) to give $^1$H NMR (400 MHz, CDCl$_3$) δ: 0.79-0.83 (m, 6H), 1.14-1.26 (m, 38H), 1.47-1.61 (m, 6H), 1.86-1.96 (m, 4H), 2.51-2.58 (m, 4H), 3.17 (s, 1H), 3.32-3.44 (m, 5H), 3.51-3.66 (m, 3H). LCMS: Rt: 0.94 min; MS m/z (ESI): 526.5 [M+H]$^+$.

7.3 Example 3: Preparation of Compound 2 the title compound (930 mg, 69% yield) as yellow oil. LCMS: Rt: 0.750 min; MS m/z (ESI): 206.2 [M+H]$^+$.

Step 2: Preparation of Compound 1-2

To a solution of compound A (915 mg, 3.77 mmol, 1.0 eq) in EtOH (40 mL) was added compound 1-1 (930 mg, 4.53 mmol, 1.2 eq). The mixture was stirred at RT for 16 hours. LCMS showed the reaction was complete. The mixture was evaporated under reduced pressured and purified by column chromatography on silica (DCM/MeOH=100/1) to give the title compound (920 mg, 54%) as yellow oil. LCMS: Rt: 0.870 min; MS m/z (ESI): 448.3 [M+H]$^+$.

Step 3: Preparation of Compound 1-3

To a stirred solution of compound 1-2 (500 mg, 1.12 mmol, 1.0 eq) in DMF (10 mL) was added NaH (58 mg, 1.46 mmol, 1.3 eq) in 0° C. The mixture was stirred at RT for 2 hours. Then 1-bromododecane 416 mg, 1.68 mmol, 1.5 e.q) was added to this mixture. The mixture was stirred at 120° C. for 16 hours. LCMS showed the reaction was complete. The mixture was poured into water (20 mL) and extracted with DCM. The combined organic layers were washed with brine, dried over Na$_2$SO$_4$ and concentrated. The residue was purified by column chromatography on silica gel (PE/EA=2/1) to give the title compound (300 mg, 43% yield) as yellow oil. LCMS: Rt: 1.360 min; MS m/z (ESI): 616.5 [M+H]$^+$.

Step 4: Preparation of Compound 1

To a solution of 1-3 (300 mg, 0.48 mmol, 1.0 eq) in MeOH (10 mL) were added Pd/C (64 mg) and concentrated HCl (4 drops). The mixture was stirred at RT under H$_2$ for 2 hours. LCMS showed the reaction was complete. The mixture was filtered through a pad of celite and washed with MeOH. The filtration was concentrated and purified by prep-HPLC to give the title compound (16 mg, 6.5% yield) as yellow oil.

Step 1: Preparation of Compound 2-1

To a stirred solution of 1-2 (300 mg, 0.67 mmol, 1.0 eq), DIPEA (260 mg, 2.01 mmol, 3.0 eq) in DCM (10 mL) were added dodecanoyl chloride (293 mg, 1.34 mmol, 2.0 eq) and DMAP (16 mg, 0.134 mmol, 0.2 eq). The mixture was stirred at RT for 16 hours. LCMS showed the reaction was complete. The mixture was poured into water (20 mL) and extracted with DCM. The combined organic layers were washed with brine, dried over Na$_2$SO$_4$ and concentrated. The residue was purified by column chromatography on silica gel (DCM/MeOH=150/1) to give the title compound (320 mg, 76% yield) as yellow oil. LCMS: Rt: 1.340 min; MS m/z (ESI): 630.5 [M+H]$^+$.

Step 2: Preparation of Compound 2

To a solution of Compound 2-1 (320 mg, 0.51 mmol, 1.0 eq) in MeOH (10 mL) were added Pd/C (64 mg) and concentrated HCl (4 drops). The mixture was stirred at RT under H$_2$ for 2 hours. LCMS showed the reaction was complete. The mixture was filtered through a pad of celite and washed with MeOH. The filtration was concentrated and purified by prep-HPLC to give the title compound (75 mg, 27% yield) as yellow oil.

$^1$H NMR (400 MHz, CDCl$_3$) δ: 0.86-0.90 (m, 6H), 1.25-1.33 (m, 35H), 1.50-1.69 (m, 7H), 1.87-1.99 (m, 1H), 2.00-2.08 (m, 2H), 2.33 (t, J=7.6 Hz, 2H), 2.56-2.81 (m, 4H), 3.17-3.27 (m, 1H), 3.38-3.48 (m, 3H), 3.50-3.65 (m, 3H), 5.08-5.14 (m, 1H). LCMS: Rt: 1.180 min; MS m/z (ESI): 540.4 [M+H]$^+$.

7.4 Example 4: Preparation of Compound 3

1-2

DIPEA, DCM 3-1

Pd/C,
con. HCl
————
MeOH

3

Compound 3-1

LCMS: Rt: 1.140 min; MS m/z (ESI): 546.4 $[M+H]^+$.

Compound 3

$^1$H NMR (400 MHz, CDCl$_3$) δ: 0.86-0.93 (m, 6H), 1.25-1.33 (m, 23H), 1.49-1.69 (m, 7H), 1.90-1.99 (m, 1H), 2.00-2.12 (m, 2H), 2.34 (t, J=7.6 Hz, 2H), 2.56-2.79 (m,

4H), 3.20-3.29 (m, 1H), 3.38-3.48 (m, 3H), 3.50-3.67 (m, 3H), 5.09-5.17 (m, 1H). LCMS: Rt: 0.890 min; MS m/z (ESI): 456.4 $[M+H]^+$.

7.5 Example 5: Preparation of Compound 4

B
DIPEA, DCM 1-2

4-1

Pd/C,
con. HCl
————
MeOH

4

Compound 4-1

LCMS: Rt: 1.380 min; MS m/z (ESI): 786.6 [M+H]$^+$.

Compound 4

$^1$H NMR (400 MHz, CDCl$_3$) δ: 0.80-0.83 (m, 13H), 1.20-1.26 (m, 58H), 1.48-1.51 (m, 2H), 1.52-1.55 (m, 7H), 2.24 (m, 1H), 3.34 (m, 1H), 3.46-3.48 (m, 2H), 3.89-3.90 (m, 1H). LCMS: Rt: 1.050 min; MS m/z (ESI): 696.6 [M+H]$^+$.

7.6 Example 6: Preparation of Compound 5

4.1 mmol, 1.5 equiv) at room temperature. After 0.5 h, 1-iodohexane (875 mg, 4.1 mmol, 1.5 equiv) was added to the mixture. The mixture was stirred overnight at 110° C. The mixture was quenched with water (10 ML), extracted over EA (3×10 ML). The combined organic layers were washed with brine (2×10 ML), dried over anhydrous sodium sulfate, and then concentrated under vacuum. The residual was purified by silica gel column chromatography (PE: EA=1:0 to 10:1) to give the desired product 9001-119-3 (340 mg, 27.6% yield) as yellow oil. LCMS: Rt: 1.080 min; MS m/z (ESI): 448.4 [M+H]$^+$.

Step 1: Preparation of Compound 5-1

A mixture of compound A (1.0 g, 4.1 mmol, 1 equiv) and N-methyl-1-phenyl-methanamine (1 g, 8.2 mmol, 2 equiv) in EtOH (15 mL) was stirred overnight at room temperature. The mixture was concentrated under vacuum and purified by silica gel column chromatography (PE:EA=1:0 to 5:3) to give the desired product (1.3 g, 86.7% yield) as yellow oil. LCMS: Rt: 0.880 min; MS m/z (ESI): 364.3 [M+H]$^+$.

Step 2: Preparation of Compound 5-2

To a stirred solution of compound 5-1 (1 g, 2.8 mmol, 1 equiv) in DMF (10 ML) was added sodium hydride (164 mg,

Step 3: Preparation of Compound 5-3

A mixture of compound 5-2 (340 mg, 0.76 mmol, 1 equiv) and Pd/C (90 mg, 10%) in MeOH (10 ML) was stirred overnight. The mixture was filtered, the filtrate was concentrated under vacuum to give the desired product (250 mg, crude) as colorless oil. LCMS: Rt: 0.997 min; MS m/z (ESI): 358.4 [M+H]$^+$.

Step 4: Preparation of Compound 5-4

A mixture of compound 5-3 (250 mg, 0.7 mmol, 1.0 equiv), 2-bromoethanol (175 mg, 1.4 mmol, 2 equiv) and DIEA (181 mg, 1.4 mmol, 2 equiv) in EtOH (16 ML) was stirred overnight at 70° C. The mixture was concentrated under vacuum to give the desired product (444 mg, crude) as colorless semi-solid. LCMS: Rt: 1.020 min; MS m/z (ESI): 402.4 [M+H]⁺.

Step 5: Preparation of Compound 5-5

A mixture of compound 5-4 (330 mg, 0.82 mmol, 1 equiv) and thionyl chloride (294 mg, 02.46 mmol, 3 equiv) in DCM (6 ML) was stirred overnight at room temperature. The mixture was concentrated under vacuum to give the desired product (331 mg, crude) as brown oil. LCMS: Rt: 1.127 min; MS m/z (ESI): 420.3 [M+H]⁺.

Step 6: Preparation of Compound 5

A mixture of 5-5 (220 mg, 0.52 mmol, 1 equiv), compound D (203 mg, 1.56 mmol, 3 equiv), DIEA (338 mg, 2.60 mmol, 5 equiv) and catalyst of NaI in THF (6 ML) was stirred overnight at 70° C. The mixture was concentrated under vacuum, the residual was purified by prep-HPLC to give the desired product (23 mg, 12.8% yield) as yellow oil.

¹H NMR (400 MHz, CDCl₃) δ: 0.84-0.93 (m, 6H), 1.13-1.40 (m, 27H), 1.48-1.61 (m, 7H), 1.66-1.77 (m, 2H), 1.80-1.94 (m, 2H), 2.48 (s, 3H), 2.67-3.05 (m, 7H), 3.35-3.51 (m, 5H), 3.54-3.81 (m, 4H). LCMS: Rt: 0.960 min; MS m/z (ESI): 513.5 [M+H]⁺.

7.7 Example 7: Preparation of Compound 6

Step 1: Preparation of Compound 6-1

To a stirred solution of 5-1 (1.4 g, 3.9 mmol, 1 equiv) in DMF (14 mL) was added sodium hydride (231 mg, 5.8 mmol, 1.5 equiv) at room temperature. After 0.5 h, 1-bromododecane (1.45 g, 5.8 mmol, 1.5 equiv) and catalyst of NaI were added to the mixture. The mixture was stirred overnight at 110° C. The mixture was quenched with water (15 mL), extracted over EA (3×15 mL). The combined organic layers were washed with brine (2×15 mL), dried over anhydrous sodium sulfate, and then concentrated under vacuum. The residual was purified by silica gel column chromatography (PE:EA=1:0 to 1:1) to give the desired product (244 mg, 11.9% yield) as brown oil. LCMS: Rt: 1.680 min; MS m/z (ESI): 532.5 [M+H]⁺.

Step 2: Preparation of Compound 6-2

A mixture of 6-1 (244 mg, 0.46 mmol, 1 equiv) and Pd/C (100 mg, 10%) in MeOH (5 mL) was stirred overnight under hydrogen atmosphere. The mixture was filtered, the filtrate was concentrated under vacuum to give the desired product (146 mg, crude) as light yellow oil. LCMS: Rt: 1.250 min; MS m/z (ESI): 442.4 [M+H]⁺.

Step 3: Preparation of Compound 6-3

A mixture of 6-2 (146 mg, 0.33 mmol, 1.0 equiv), 2-bromoethanol (83 mg, 0.66 mmol, 2 equiv) and DIEA (86 mg, 0.66 mmol, 2 equiv) in EtOH (5 mL) was stirred

6 overnight at 70° C. The mixture was concentrated under vacuum to give the desired product (438 mg, crude) as yellow oil. LCMS: Rt: 1.270 min; MS m/z (ESI): 486.5 [M+H]⁺.

Step 4: Preparation of Compound 6-4

A mixture of 6-3 (219 mg, 0.45 mmol, 1 equiv) and thionyl chloride (161 mg, 1.35 mmol, 3 equiv) in DCM (6 mL) was stirred overnight at 35° C. The mixture was concentrated under vacuum to give the desired product (133 mg, crude) as yellow oil. LCMS: Rt: 1.860 min; MS m/z (ESI): 504.4 [M+H]⁺.

Step 5: Preparation of Compound 6

A mixture of compound 6-4 (133 mg, 0.26 mmol, 1 equiv), compound E (114 mg, 0.79 mmol, 3 equiv), DIEA (170 mg, 1.32 mmol, 5 equiv) and catalyst of NaI in THF (3 ML) was stirred overnight at 70° C. The mixture was concentrated under vacuum, the residual was purified by prep-HPLC to give the desired product compound 6 (19 mg, 11.8% yield) as yellow oil.

¹H NMR (400 MHz, CDCl₃) δ: 0.81-0.93 (m, 6H), 0.99-1.14 (m, 2H), 1.26 (s, 39H), 1.49-1.59 (m, 4H), 1.61-1.70 (m, 1H), 1.76-1.87 (m, 2H), 1.90-2.19 (m, 9H), 2.53-2.95 (m, 6H), 3.35-3.53 (m, 5H), 3.54-3.75 (m, 3H). LCMS: Rt: 1.500 min; MS m/z (ESI): 611.6 [M+H]⁺.

7.8 Example 8: Preparation of Compound 7

Step 1: Preparation of Compound 7-1

To a solution of N1,N1-dimethylethane-1,2-diamine (1.2 g, 13.6 mmol, 2.0 eq) and compound B (2.8 g, 6.8 mmol, 1.0 eq) in ACN (100 mL) were added K₂CO₃ (2.8 g, 20.4 mmol, 3.0 eq), Cs₂CO₃ (665 mg, 2.04 mmol, 0.3 eq) and NaI (306 mg, 2.04 mmol, 0.3 eq). The mixture was stirred at 80° C. for 16 hours. LCMS showed the reaction was complete. The reaction mixture was poured into water and extracted with EA. The combined organic layers were washed with brine, dried over Na₂SO₄ and concentrated. The residue was purified by column chromatography on silica gel (DCM/MeOH=50/1-30/1) to give the title compound (900 mg, 31% yield) as yellow oil. LCMS: Rt: 0.780 min; MS m/z (ESI): 427.4 [M+H]⁺.

Step 2: Preparation of Compound 7

To a solution of compound A (190 mg, 0.78 mol, 1.0 eq) in EtOH (20 mL) was added 7-1 (400 mg, 0.94 mmol, 1.2 eq). The mixture was stirred at room temperature for 48 hours. LCMS showed the reaction was complete. The reaction mixture was concentrated under reduced pressure and purified by prep-HPLC to give the title compound (25 mg, 5% yield) as white solid.

¹H NMR (400 MHz, CDCl₃) δ: 0.86-0.90 (m, 9H), 1.26-1.35 (m, 45H), 1.41-1.67 (m, 7H), 2.28-2.32 (m, 3H), 2.36-2.70 (m, 11H), 2.79-2.83 (m, 2H), 3.35-3.46 (m, 4H), 3.77-3.85 (m, 1H), 3.96-3.97 (m, 2H). LCMS: Rt: 1.220 min; MS m/z (ESI): 669.6 [M+H]⁺.

7.9 Example 9: Preparation of Compound 8

8-1

8

Step 1: Preparation of Compound 8-1

To a solution of compound A (500 mg, 2.06 mol, 1.0 eq) in EtOH (20 mL) was added 2-(piperidin-1-yl)ethan-1-amine (529 mg, 4.12 mmol, 2.0 eq). The mixture was stirred at room temperature for 16 hours. LCMS showed the reaction was complete. The reaction mixture was concentrated under reduced pressure and purified by column chromatography on silica gel (DCM/MeOH=50/1-30/1) to give the title compound (480 mg, 63% yield) as yellow oil. LCMS: Rt: 0.730 min; MS m/z (ESI): 371.3 [M+H]$^+$.

Step 2: Preparation of Compound 8

To a solution of 8-1 (480 mg, 1.30 mmol, 1.0 eq) and compound B (1.1 g, 2.60 mmol, 2.0 eq) in ACN (50 mL) were added $K_2CO_3$ (539 mg, 3.90 mmol, 3.0 eq), $Cs_2CO_3$ (98 mg, 0.39 mmol, 0.3 eq) and NaI (58 mg, 0.39 mmol, 0.3 eq). The mixture was stirred at 80° C. for 16 hours. LCMS showed the reaction was complete. The reaction mixture was concentrated and purified by column chromatography on silica gel (DCM/MeOH=100/1-70/1) to give the title compound (600 mg, 65% yield) as yellow oil. Then 150 mg product was further purified by prep-HPLC to give the title compound (43 mg) as yellow oil.

$^1$H NMR (400 MHz, $CDCl_3$) δ: 0.86-0.90 (m, 9H), 1.25-1.27 (m, 47H), 1.40-1.49 (m, 4H), 1.56-1.73 (m, 8H), 2.30 (t, J=7.6 Hz, 3H), 2.40-2.82 (m, 10H), 3.32-3.38 (m, 1H), 3.43-3.46 (m, 3H), 3.70-3.80 (m, 1H), 3.92-3.97 (m, 2H). LCMS: Rt: 1.090 min; MS m/z (ESI): 709.6 [M+H]$^+$.

7.10 Example 10: Preparation of Compound 9

8

-continued

9

To a solution of 8 (120 mg, 0.17 mol, 1.0 eq) and DIPEA (66 mg, 0.51 mmol, 3.0 eq) in DCM (8 mL) at 0° C. was added acetic anhydride (35 mg, 0.34 mmol, 2.0 eq). The mixture was stirred at room temperature for 16 hours. LCMS showed the reaction was complete. The reaction mixture was concentrated under reduced pressure and purified by prep-HPLC to give the title compound (28 mg, 22% yield) as yellow oil.

$^1$H NMR (400 MHz, CDCl$_3$) δ: 0.86-0.90 (m, 9H), 1.25-1.27 (m, 47H), 1.41-1.48 (m, 4H), 1.53-1.67 (m, 8H), 2.06 (s, 3H), 2.29 (t, J=7.4 Hz, 2H), 2.45-2.75 (m, 10H), 3.35-3.52 (m, 4H), 3.95-3.97 (m, 2H), 4.98-5.00 (m, 1H). LCMS: Rt: 1.260 min; MS m/z (ESI): 751.6 [M+H]$^+$.

7.11 Example 11: Preparation of Compound 10

A 10-1

10

Compound 10-1

LCMS: Rt: 0.880 min; MS m/z (ESI): 357.3 [M+H]$^+$.

Compound 10

$^1$H NMR (400 MHz, CDCl$_3$) δ: 0.83-0.93 (m, 9H), 1.16-1.37 (m, 43H), 1.43-1.69 (m, 8H), 1.92-2.24 (m, 11H), 2.27-2.35 (m, 3H), 2.44-2.65 (m, 4H), 3.35-3.50 (m, 4H), 3.78-3.90 (m, 1H), 3.93-4.01 (m, 2H). LCMS: Rt: 1.660 min; MS m/z (ESI): 695.6 [M+H]$^+$.

7.12 Example 12: Preparation of Compound 11

Compound 11-1
    LCMS: Rt: 0.880 min; MS m/z (ESI): 359.3 [M+H]⁺.
Compound 11
    ¹H NMR (400 MHz, CDCl₃) δ: 0.86-0.90 (m, 9H), 1.05
(s, 6H), 1.25 (s, 45H), 1.45-1.65 (m, 7H), 2.28-2.32 (m, 2H),
2.43-2.70 (m, 12H), 3.43-3.44 (m, 4H), 3.75 (s, 1H), 3.96-
3.97 (m, 2H). LCMS: Rt: 1.060 min; MS m/z (ESI): 697.6
[M+H]⁺.

7.13 Example 13: Preparation of Compound 13

-continued

13

To a solution of compound F (660 mg, 1.65 mmol) in EtOH (20 mL) was added COMPOUND A (200 mg, 0.82 mmol). The reaction was stirred at RT for 10 hours. The reaction mixture was concentrated in vacuo and purified by prep-HPLC to give the target product as yellow oil (20 mg, yield: 4%).

$^1$H NMR (400 MHz, CDCl$_3$): δ: 0.87 (t, J=8 Hz, 9H), 1.35-1.68 (m, 35H), 1.43-1.91 (m, 18H), 2.29-2.33 (m, 2H), 2.51-2.71 (m, 6H), 3.35-3.47 (m, 4H), 3.58-3.63 (m, 2H), 3.83-3.86 (m, 1H), 3.96-3.97 (m, 2H). LCMS: Rt: 1.059 min; MS m/z (ESI): 642.5 [M+H]$^+$.

7.14 Example 14: Preparation of Compound 14

G 14-1

-continued

14

Step 1: Preparation of 14-1

To a solution of compound G (500 mg, 0.68 mmol) in CH$_2$Cl$_2$ (20 mL) was added DIEA (300 mg, 2.05 mmol) and hexanoyl chloride (185 mg, 1.37 mmol). The reaction was stirred at RT for 2 hours. The reaction mixture was poured into NaHCO$_3$ (aq) (50 ml) and extracted with CH$_2$Cl$_2$ (3×50 mL). The combined organic layers were washed with brine, dried over anhydrous Na$_2$SO$_4$ and concentrated in vacuo.

(50 mg). The reaction was stirred at RT for 1 hour under H$_2$. The reaction mixture was filtrated concentrated in vacuo. The crude product was purified by prep-HPLC to give the target product as yellow oil (30 mg, yield: 13%).

$^1$H NMR (400 MHz, CDCl$_3$): δ: 0.87 (t, J=8 Hz, 12H), 1.11-1.31 (m, 42H), 1.39-1.68 (m, 17H), 2.28-2.69 (m, 11H), 3.39-3.55 (m, 4H), 3.96-3.97 (m, 2H), 5.05-5.08 (m, 1H). LCMS: Rt: 1.932 min; MS m/z (ESI): 740.6 [M+H]$^+$.

7.15 Example 15: Preparation of Compound 15

DIPEA DMAP DCM

8

15

The crude product was purified by flash column chromatography (PE:EtOAc=5:1) to give the target product as yellow oil (280 mg, yield: 48%).

Step 4: Preparation of Compound 14

To a solution of compound 14-1 (250 mg, 0.3 mmol) in MeOH (10 mL) was added HCl (12N) (0.3 mL) and Pd/C Compound 15 $^1$H NMR (400 MHz, CDCl$_3$) δ: 0.86-0.91 (m, 12H), 1.25-1.39 (m, 51H), 1.40-1.47 (m, 3H), 1.50-1.66 (m, 11H), 2.27-2.31 (m, 4H), 2.45-2.65 (m, 10H), 3.35-3.51 (m, 4H), 3.95-3.97 (m, 2H), 4.99-5.04 (m, 1H). LCMS: Rt: 1.540 min; MS m/z (ESI): 807.6 [M+H]$^+$.

7.16 Example 16: Preparation of Compound 16

16-1

16-2

16-3

16

Step 1: Preparation of Compound 16-1

To a solution of compound H (400 mg, 0.94 mmol, 1.2 eq) and 1-bromohexane (165 mg, 0.78 mmol, 1.0 eq) in ACN (15 mL) were added K$_2$CO$_3$ (323 mg, 2.34 mmol, 3.0 eq), Cs$_2$CO$_3$ (76 mg, 0.23 mmol, 0.3 eq) and NaI (35 mg, 0.23 mmol, 0.3 eq). The mixture was stirred at 80° C. for 16 hours. LCMS showed the reaction was complete. The reaction mixture was concentrated and purified by column chromatography on silica gel (DCM/MeOH=70/1) to give the title compound (290 mg, 73% yield) as yellow oil. LCMS: Rt: 1.050 min; MS m/z (ESI): 512.5 [M+H]$^+$ Step 2: Preparation of Compound 16-2

To a solution of 16-1 (290 mg, 0.57 mmol, 1.0 eq) in EtOH (10 mL) were added 2-bromoethanol (143 mg, 1.14 mmol, 2.0 eq) and DIPEA (221 mg, 1.71 mmol, 3.0 eq). The mixture was stirred at 70° C. for 16 hours. LCMS showed the desired MS was detected. The reaction mixture was concentrated under reduced pressure. The residue was diluted with DCM and washed with water, brine, dried over Na$_2$SO$_4$ and concentrated give the title compound (300 mg, 95%) as yellow oil. It was used in the next step without further purification. LCMS: Rt: 1.220 min; MS m/z (ESI): 556.5 [M+H]$^+$.

Step 3: Preparation of Compound 16-3

To a solution of 16-2 (300 mg, 0.54 mmol, 1.0 eq) in DCM (10 mL) was added SOCl$_2$ (193 mg, 1.62 mmol, 3.0 eq). The mixture was stirred at 30° C. for 16 hours. LCMS showed the reaction was complete. The mixture was washed with saturated NaHCO$_3$ solution, dried over Na$_2$SO$_4$ and concentrated. The residue was purified by column chromatography on silica gel (PE/EA=10/1) to give the title compound (120 mg, 39% yield) as yellow oil. LCMS: Rt: 0.950 min; MS m/z (ESI): 538.5 [M−Cl]$^+$.

Step 4: Preparation of Compound 16

To a solution of 16-3 (120 mg, 0.21 mmol, 1.0 eq) and compound I (73 mg, 0.63 mmol, 3.0 eq) in THF (10 mL) were added DIPEA (136 mg, 1.05 mmol, 5.0 eq) and NaI (6 mg, 0.042 mmol, 0.2 eq). The mixture was stirred at 70° C. for 16 hours. LCMS showed the reaction was completed. The mixture was concentrated and purified by prep-HPLC to give the title compound (27 mg, 20% yield) as yellow oil.

¹H NMR (400 MHz, CDCl₃) δ: 0.86-0.90 (m, 9H), 1.26-1.39 (m, 44H), 1.47-1.70 (m, 8H), 1.83-2.19 (m, 6H),

176

2.41-2.74 (m, 8H), 3.40-3.62 (m, 9H). LCMS: Rt: 1.290 min; MS m/z (ESI): 653.6 [M+H]⁺.

7.17 Example 17: Preparation of Compound 17

Compound 17-1
  LCMS: Rt: 1.210 min; MS m/z (ESI): 596.6 [M+H]⁺.
Compound 17-2
  LCMS: Rt: 1.740 min; MS m/z (ESI): 640.5 [M+H]⁺.
Compound 17
  ¹H NMR (400 MHz, CCl₃D): δ: 3.61-3.41 (m, 8H), 3.19-3.14 (m, 1H), 2.63-2.45 (m, 9H), 2.03-1.84 (m, 6H), 1.66-1.41 (m, 9H), 1.26 (s, 54H), 0.90-0.86 (m, 9H). LCMS: Rt: 1.860 min; MS m/z (ESI): 737.6 [M+H]⁺.

7.18 Example 18: Preparation of Compound 18

-continued 18-1

18

Step 1: Preparation of Compound 18-1

To a solution of compound G (500 mg, 0.68 mmol) in CH₂Cl₂ (20 mL) was added DIEA (270 mg, 2.05 mmol) and AcCl (110 mg, 1.37 mmol). The reaction was stirred at RT for 2 hours. The reaction mixture was poured into NaHCO₃ (aq) (50 ml) and extracted with CH₂Cl₂ (3×100 mL). The combined organic layers were washed with brine, dried over anhydrous Na₂SO₄ and concentrated in vacuo. The crude product was purified by flash column chromatography (PE: EtOAc=5:1) to give the target product as yellow oil (300 mg, yield: 57%). LCMS: Rt: 2.360 min; MS m/z (ESI): 774.6 [M+H]⁺.

Step 2: Preparation of Compound 18

To a solution of 18-1 (300 mg, 0.39 mmol) in MeOH (10 mL) was added HCl (12N) (0.3 mL) and Pd/C (50 mg). The reaction was stirred at rt for 1 hour under H₂. The reaction mixture was filtrated concentrated in vacuo. The crude product was purified by prep-HPLC to give the target product as yellow oil (30 mg, yield: 11%).

¹H NMR (400 MHz, CDCl₃): δ: 0.87 (t, J=8 Hz, 9H), 1.11-1.31 (m, 42H), 1.39-1.68 (m, 9H), 2.04 (s, 3H), 2.28-2.32 (m, 2H), 2.48-2.73 (m, 6H), 2.89-2.91 (m, 1H), 3.39-3.55 (m, 6H), 3.96-3.97 (m, 2H), 5.05-5.08 (m, 1H). LCMS: Rt: 1.530 min; MS m/z (ESI): 684.5 [M+H]⁺.

7.19 Example 19: Preparation of Compound 19

G

-continued 19-1

19

Step 1: Preparation of Compound 19-1

A mixture of compound G (320 mg, 0.44 mmol, 1 equiv), propionic anhydride (171 mg, 1.32 mmol, 3 equiv) and DIEA (568 mg, 4.40 mmol, 10 equiv) in DCM (5 Ml) was stirred overnight at room temperature. The mixture was concentrated under vacuum. The residual was purified by silica gel column chromatography (PE:EA=60:1 to 10:1 to give the desired product (340 mg, 98.8% yield) as colorless oil. LCMS: Rt: 2.170 min; MS m/z (ESI): 788.6 [M+H]$^{+}$.

Step 2: Preparation of Compound 19

A mixture of 19-1 (340 mg, 0.43 mmol, 1.0 equiv), a drop of HCl (36.5%) and Pd/C (60 mg) in MeOH (15 mL) was stirred overnight at room temperature. The mixture was filtered through celite. The filer cake was washed with MeOH (8×10 mL). The filtrate was concentrated under vacuum. The residual was purified by prep-HPLC to give the desired product (34 mg, 11.3% yield) as light brown oil.

$^{1}$H NMR (400 MHz, CDCl$_3$): δ: 0.83-0.92 (m, 9H), 0.93-0.99 (m, 1H), 1.08-1.18 (m, 3H), 1.19-1.37 (m, 42H), 1.39-1.76 (m, 13H), 2.16-2.42 (m, 4H), 2.44-2.81 (m, 3H), 3.35-3.65 (m, 5H), 3.92-4.03 (m, 2H). LCMS: Rt: 1.480 min; MS m/z (ESI): 698.5 [M+H]$^{+}$.

7.20 Example 20: Preparation of Compound 20

18

-continued

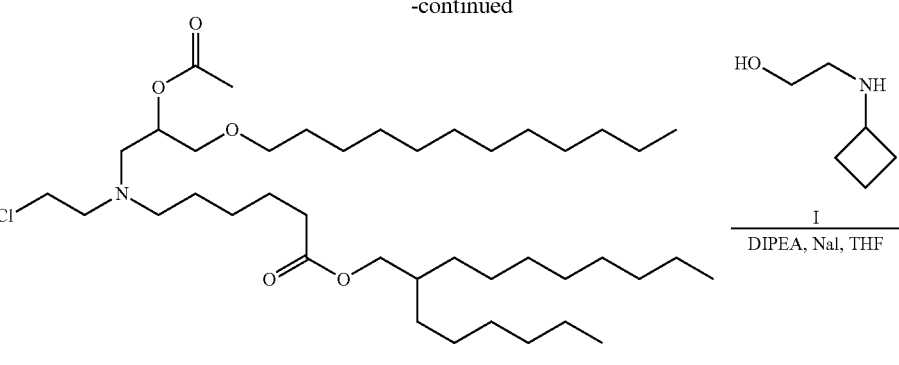

20-1

20

Step 1: Preparation of Compound 20-1

To a solution of compound 18 (1.0 g, 1.46 mmol, 1.0 eq) in DCM (30 mL) was added $SOCl_2$ (521 mg, 4.38 mmol, 3.0 eq). The mixture was stirred at 30° C. for 16 hours. LCMS showed the reaction was complete. The mixture was concentrated under reduced pressure to give the title compound (1.0 g, 97%) as brown oil. LCMS: Rt: 0.960 min; MS m/z (ESI): 666.5 $[M-Cl]^+$.

Step 2: Preparation of Compound 20

To a solution of 20-1 (250 mg, 0.36 mmol, 1.0 eq) and compound I (124 mg, 1.08 mmol, 3.0 eq) in THF (10 mL) were added DIPEA (233 mg, 1.80 mmol, 3.0 eq) and NaI (11 mg, 0.072 mmol, 0.2 eq). The mixture was stirred at 70° C. for 16 hours. LCMS showed the reaction was completed.

The mixture was concentrated and purified by prep-HPLC to give the title compound (33 mg, 12% yield) as yellow oil.

$^1H$ NMR (400 MHz, $CDCl_3$): δ: 0.86-0.90 (m, 9H), 1.26-1.40 (m, 45H), 1.48-1.68 (m, 9H), 1.81-2.07 (m, 8H), 2.31 (t, J=7.4 Hz, 2H), 2.40-2.55 (m, 5H), 2.61-2.75 (m, 3H), 3.07-3.17 (m, 2H), 3.34-3.51 (m, 4H), 3.71-3.80 (m, 1H), 3.96-3.97 (m, 2H), 4.09-4.14 (m, 2H). LCMS: Rt: 1.330 min; MS m/z (ESI): 781.6 $[M+H]^+$.

7.21 Example 21: Preparation of Compound 21

20-1

-continued

21

Compound 21 $^1$H NMR (400 MHz, CCl₃D): δ: 4.09-4.06 (m, 1H), 3.96 (d, J=6 Hz, 2H), 3.75 (s, 1H), 3.46-3.38 (m, 4H), 2.72-2.45 (m, 10H), 2.32-2.28 (m, 2H), 2.05 (s, 3H), 1.78 (d, J=9.2 Hz, 4H), 1.65-1.47 (m, 9H), 1.26 (d, J=3.2 Hz, 51H), 0.90-0.86 (m, 9H). LCMS: Rt: 1.430 min; MS m/z (ESI): 809.6 [M+H]⁺.

7.22 Example 22: Preparation of Compound 22

185 186

-continued 22-4

22

Step 1: Preparation of Compound 22-1

A mixture of compound J (1.0 g, 1.7 mmol, 1 equiv) and Pd/C (100 mg) in MeOH (100 mL) was stirred overnight at room temperature under hydrogen atmosphere. The mixture was filtered with celite; the filtrate was concentrated to give the desired product 22-1 (504 mg, 85.6% yield) as light brown oil. LCMS: Rt: 0.840 min; MS m/z (ESI): 344.3 [M+H]$^+$.

Step 2: Preparation of Compound 22-2

A mixture of compound 22-1 (504 mg, 1.47 mmol, 1 equiv), potassium carbonate (607 mg, 4.40 mmol, 3 equiv), cesium carbonate (13 mg, 0.04 mmol, 0.03 equiv), compound B (493 mg, 1.18 mmol, 0.8 equiv) and sodium iodide (50 mg, 0.33 mmol, 0.23 equiv) in ACN (35 mL) was stirred overnight at 80° C. The mixture was filtered. The filtrate was concentrated. The residual was purified by silica gel column chromatography (MeOH:DCM=0% to 2.5%) to give the desired product (500 mg, 49.9% yield) as yellow oil. LCMS: Rt: 1.140 min; MS m/z (ESI): 682.6 [M+H]$^+$.

Step 3: Preparation of Compound 22-3

A mixture of compound 22-2 (500 mg, 0.73 mmol, 1 equiv), 2-bromoethanol (138 mg, 1.10 mmol, 1.5 equiv), DIEA (283 mg, 2.19 mmol, 3 equiv) and sodium iodide (50 mg, 0.33 mmol, 0.45 mmol) in THF (10 mL) was stirred overnight at 70° C. The mixture was washed with water, extracted over EA (3×10 mL), dried and concentrated under vacuum to give the desired product (433 mg, crude) as yellow oil. LCMS: Rt: 1.550 in; MS m/z (ESI): 726.6 [M+H]$^+$.

Step 4: Preparation of Compound 22-4

A mixture of compound 22-3 (433 mg, 0.60 mmol, 1 equiv) and SOCl$_2$ (114 mg, 1.8 mmol, 3 equiv) in DCM (8 mL) was stirred overnight at 35° C. The mixture was concentrated, the residual was purified by silica gel column chromatography (MeOH:DCM=0:100 to 1:100) to give the desired product 22-4 (230 mg, 51.8% yield).

Step 5: Preparation of Compound 22

A mixture of compound 22-4 (115 mg, 0.15 mmol, 1 equiv), compound k (47 mg, 0.46 mmol, 3 equiv), sodium iodide (15 mg, 0.10 mmol, 0.6 equiv) and DIEA (100 mg, 0.78 mmol, 3 equiv) in THF (5 mL) was stirred overnight at 70° C. The mixture was concentrated under vacuum. The residual was purified by prep-HPLC to give the desired product (23 mg, 18.4% yield) as light brown oil.

$^1$H NMR (400 MHz, CDCl$_3$): δ: 0.82-0.94 (m, 12H), 1.12-1.38 (m, 53H), 1.49-1.69 (m, 8H), 1.73-2.07 (m, 10H), 2.18-2.25 (m, 1H), 2.26-2.37 (m, 2H), 2.87 (s, 1H), 3.04-3.37 (m, 4H), 3.38-3.53 (m, 4H), 3.54-3.79 (m, 2H), 3.96 (d, J=5.6 Hz, 2H). LCMS: Rt: 1.320 min; MS m/z (ESI): 809.7 [M+H]$^+$.

7.23 Example 23: Preparation of Compound 23

22-4

23

Compound 23 $^1$H NMR (400 MHz, CCl$_3$D): δ: 0.87-0.90 (m, 12H), 1.26-1.40 (m, 52H), 1.50-1.68 (m, 10H), 2.08-2.23 (m, 7H), 2.31 (t, J=7.6 Hz, 2H), 2.42-2.57 (m, 3H), 2.76-2.84 (m, 3H), 2.98-3.18 (m, 4H), 3.42-3.57 (m, 4H), 3.61-3.65 (m, 2H), 3.79-3.85 (m, 1H), 3.95-3.97 (m, 2H). LCMS: Rt: 1.480 min; MS m/z (ESI): 823.6 [M+H]$^+$.

7.24 Example 24: Preparation of Compound 24

22-4

24

Compound 24 $^1$H NMR (400 MHz, CCl$_3$D): δ: 0.82-0.94 (m, 12H), 1.19-1.40 (m, 47H), 1.41-1.69 (m, 13H), 1.73-2.14 (m, 13H), 2.18-2.36 (m, 3H), 2.43-2.84 (m, 4H), 3.01-3.25 (m, 2H), 3.35-3.65 (m, 7H), 3.96 (d, J=5.6 Hz, 2H). LCMS: Rt: 1.560 min; MS m/z (ESI): 837.7 [M+H]$^+$.

7.25 Example 25: Preparation of Compound 25

22-4

25

Compound 25 $^1$H NMR (400 MHz, CDCl$_3$): δ:0.82-0.95 (m, 12H), 1.16-1.38 (m, 50H), 1.40-1.87 (m, 26H), 1.96-2.07 (m, 2H), 2.18-2.34 (m, 2H), 2.39-2.66 (m, 6H), 3.35-3.75 (m, 6H), 3.96 (d, J=5.6 Hz, 1H). LCMS: Rt: 1.980 min; MS m/z (ESI): 851.7 [M+H]$^+$.

7.26 Example 26: Preparation of Compound 26

22-4

-continued

26

Compound 26 $^1$H NMR (400 MHz, CDCl$_3$): δ: 0.81-0.93 (m, 12H), 1.15-1.36 (m, 50H), 1.38-1.87 (m, 23H), 1.75-1.87 (m, 2H), 2.18-2.34 (m, 2H), 2.39-2.66 (m, 9H), 3.35-3.52 (m, 7H), 3.53-3.62 (m, 1H), 3.96 (d, J=5.6 Hz, 2H). LCMS: Rt: 1.860 min; MS m/z (ESI): 865.7 [M+H]$^+$.

7.27 Example 27: Preparation of Compound 27

H

B
K$_2$CO$_3$, Cs$_2$CO$_3$, NaI 27-1

Br⁀OH
DIEA, EtOH 27-2

SOCl$_2$
DCM

-continued 27-3

27

Step 1: Preparation of Compound 27-1

A mixture of compound H (2.0 g, 4.7 mmol, 1 equiv), potassium carbonate (1.9 g mg, 14.1 mmol, 3 equiv), cesium carbonate (460 mg, 1.4 mmol, 0.3 equiv), compound B (2.2 g, 5.1 mmol, 1.1 equiv) and sodium iodide (210 mg, 1.4 mmol, 0.3 equiv) in ACN (70 mL) was stirred overnight at 80° C. The mixture was filtered. The filtrate was concentrated. The residual was purified by silica gel column chromatography (MeOH:DCM=0% to 2.5%) to give the desired product (1.8 g, 50.3% yield) as yellow oil. LCMS: Rt: 1.970 min; MS m/z (ESI): 767.6 [M+H]⁺.

Step 2: Preparation of Compound 27-2

A mixture of 27-1 (1.8 g, 2.3 mmol, 1 equiv), 2-bromo-ethanol (880 mg, 7.0 mmol, 3.0 equiv), DIEA (910 mg, 7.0 mmol, 3 equiv) in ethanol (30 mL) was stirred for overnight at 80° C. The mixture was diluted with EA and washed with water and brine, concentrated. The residue was purified by a column chromatography to give product (1.6 g, 84.4% yield) as yellow oil. LCMS: Rt: 2.180 in; MS m/z (ESI): 810.7 [M+H]⁺.

Step 3: Preparation of Compound 27-3

A mixture of 27-2 (1.6 g, 2.0 mmol, 1 equiv) and SOC₂ (720 mg, 6.0 mmol, 3 equiv) in DCM (20 mL) was stirred overnight at 35° C. The mixture was concentrated, the residue was purified by column chromatography to give the desired product 27-3 (1.4 g, 84.5% yield) as yellow oil.

Step 4: Preparation of Compound 27

A mixture of 27-3 (200 mg, 0.24 mmol, 1 equiv), compound K (242 mg, 2.4 mmol, 10 equiv), sodium iodide (18 mg, 0.12 mmol, 0.5 equiv) and DIEA (100 mg, 0.72 mmol, 3 equiv) in THF (5 mL) was stirred overnight at 70° C. The mixture was concentrated under vacuum. The residual was purified by prep-HPLC to give the desired product (56 mg, 26% yield) as light brown oil.

¹H NMR (400 MHz, CDCl₃) δ: 0.43-0.47 (m, 4H), 0.86-0.90 (m, 12H), 1.26 (s, 63H), 1.43-1.67 (m, 11H), 2.28-2.32 (m, 2H), 2.44-2.62 (m, 5H), 2.72-2.79 (m, 4H), 3.40-3.50 (m, 6H), 3.56-3.58 (m, 3H), 3.97 (d, J=6.0 Hz, 2H). LCMS: Rt: 2.270 min; MS m/z (ESI): 893.7 [M+H]⁺.

7.28 Example 28: Preparation of Compound 28

27-3

-continued

28

Compound 28 $^1$H NMR (400 MHz, CDCl$_3$): δ: 0.86-0.90 (m, 12H), 1.26 (s, 59H), 1.44-1.68 (m, 15H), 1.86 (m, 2H), 1.99-2.05 (m, 2H), 2.28-2.32 (m, 2H), 2.45-2.57 (m, 10H), 3.12 (m, 1H), 3.40-3.58 (m, 9H), 3.96 (d, J=6.0 Hz, 2H). LCMS: Rt: 2.20 min; MS m/z (ESI): 907.7 [M+H]

7.29 Example 29: Preparation of Compound 29

27-3

29

Compound 29 $^1$H NMR (400 MHz, CDCl$_3$): δ: 0.86-0.90 (m, 12H), 1.26 (s, 61H), 1.39-1.75 (m, 22H), 2.28-2.32 (m, 2H), 2.47-2.61 (m, 9H), 3.08-3.12 (m, 1H), 3.40-3.60 (m, 9H), 3.96 (d, J=5.6 Hz, 2H). LCMS: Rt: 1.690 min; MS m/z (ESI): 921.7 [M+H]$^+$.

7.30 Example 30: Preparation of Compound 30

27-3

30

Compound 30 $^1$H NMR (400 MHz, CDCl$_3$): δ: 0.86-0.90 (m, 12H), 1.26 (s, 63H), 1.51-1.77 (m, 20H), 2.28-2.32 (m, 2H), 2.45-2.61 (m, 10H), 3.40-3.56 (m, 9H), 3.96 (d, J=5.6 Hz, 2H). LCMS: Rt: 1.590 min; MS m/z (ESI): 935.8 [M+H]$^+$ 7.31 Example 31: Preparation of Compound 31

27-3

31

Compound 31 $^1$H NMR (400 MHz, CDCl$_3$): δ: 0.86-0.90 (m, 12H), 1.26 (s, 61H), 1.39-1.79 (m, 24H), 2.28-2.32 (m, 2H), 2.45-2.58 (m, 10H), 3.40-3.58 (m, 9H), 3.96 (d, J=5.6 Hz, 2H). LCMS: Rt: 2.510 min; MS m/z (ESI): 949.8 [M+H]$^+$.

7.32 Example 32: Preparation of Compound 32

Step 1: Preparation of Compound 32-1

To a solution of 1-1 (1 g, 4.88 mmol, 1.0 eq) in DMF (10 mL) was added NaH (250 mg, 6.25 mmol, 1.3 eq). The mixture was stirred at 0° C. for 1 hour. 2-(bromomethyl) oxirane (868 mg, 6.25 mmol, 1.3 eq) was added in this mixture. The mixture was stirred at RT for 16 hours. LCMS showed the reaction was complete. The mixture was extracted by EA (50 ml), washed by brine (50 ml×3) and evaporated under reduced pressure, purified by column chromatography on silica (PE/EA=5/1) to give the title compound (687 mg, 54%) as yellow oil. LCMS: Rt: 0.74 min; MS m/z (ESI): 262 [M+H]$^+$.

Step 2: Preparation of Compound 32-2

To a solution of 32-1 (500 mg, 1.92 mmol, 1.0 eq) in H2O (5 mL) was added perchloric acid (0.2 ml). The mixture was stirred at 80° C. for 16 hours. LCMS showed the reaction was complete. The mixture was purified by prep-HPLC to give the title compound (220 mg, 41%) as yellow oil. LCMS: Rt: 0.735 min; MS m/z (ESI): 280.2 [M+H]$^+$.

Step 3: Preparation of Compound 32-3

To a stirred solution of 32-2 (188 mg, 0.67 mmol, 1.0 eq), DIPEA (260 mg, 2.01 mmol, 3.0 eq) in DCM (10 mL) were added compound M (578 mg, 2.01 mmol, 3.0 eq) and DMAP (16 mg, 0.134 mmol, 0.2 eq). The mixture was stirred at RT for 16 hours. LCMS showed the reaction was complete. The mixture was poured into water (20 mL) and extracted with DCM. The combined organic layers were washed with brine, dried over Na$_2$SO$_4$ and concentrated. The residue was purified by column chromatography on silica gel (PE/EA=5/1) to give the title compound (346 mg, 66% yield) as yellow oil.

Step 4: Preparation of Compound 32

To a solution of 32-3 (320 mg, 0.44 mmol, 1.0 eq) in MeOH (10 mL) were added Pd/C (64 mg) and concentrated HCl (4 drops). The mixture was stirred at RT under H$_2$ for 2 hours. LCMS showed the reaction was complete. The mixture was filtered through a pad of celite and washed with MeOH. The filtration was concentrated and purified by prep-HPLC to give the title compound (40 mg, 13.2% yield) as yellow oil.

$^1$H NMR (400 MHz, CDCl$_3$) δ: 0.86-0.90 (m, 12H), 1.31-1.41 (m, 48H), 2.05-1.61 (m, 10H), 2.19-2.28 (m, 4H), 2.64-2.78 (m, 3H), 3.18-3.21 (m, 1H), 3.22-3.59 (m, 2H), 4.01-4.35 (m, 2H), 5.18-5.22 (m, 1H). LCMS: Rt: 1.240 min; MS m/z (ESI): 694.4 [M+H]$^+$.

7.33 Example 33: Preparation of Compound 33

-continued 33-2

B
K₂CO₃, Cs₂CO₃, NaI 33-3

Br⌢OH
DIPEA
EtOH 33-4

SOCl2
DCM 33-5

HO⌢NH

I
DIPEA, NaI, THF

33

Step 1: Preparation of Compound 33-1

To a solution of J-1 (5.5 g, 11.0 mmol, 1.0 eq) in DMF (110 mL) was added NaH (880 mg, 22.0 mmol, 2.0 eq) at room temperature. The mixture was stirred at room tem-perature for 1 hour. Then 1-bromooctane (4.2 g, 22.0 mmol, 2.0 eq) and NaI (330 mg, 2.2 mmol, 0.2 eq) were added. The mixture was stirred at 70° C. for 16 hours. LCMS showed the reaction was complete. The reaction mixture was poured into water and extracted with EA. The combined organic layers were washed with brine, dried over $Na_2SO_4$ and concentrated. The residue was purified by column chromatography on silica gel (PE/EA=40/1) to give the title compound (3.5 g, 52% yield) as yellow oil. LCMS: Rt: 1.040 min; MS m/z (ESI): 612.4 [M+H]$^+$.

Step 2: Preparation of Compound 33-2

To a solution of 33-1 (3.5 g, 5.72 mmol, 1.0 eq) in MeOH (60 mL) was added Pd/C (350 mg). The mixture was stirred at RT under $H_2$ for 16 hours. LCMS showed the reaction was complete. The mixture was filtered through a pad of celite and washed with MeOH. The filtrate was concentrated and purified by column chromatography on silica gel (DCM/MeOH=30/1-20/1) give the title compound (1.8 g, 86% yield) as light yellow oil. LCMS: Rt: 1.080 min; MS m/z (ESI): 372.3 [M+H]$^+$.

Step 3: Preparation of Compound 33-3

To a solution of 33-2 (1.8 g, 4.8 mmol, 1.2 eq) and compound B (1.7 g, 4.0 mmol, 1.0 eq) in ACN (50 mL) were added $K_2CO_3$ (1.6 g, 12.0 mmol, 3.0 eq), $Cs_2CO_3$ (391 mg, 1.2 mmol, 0.3 eq) and NaI (180 mg, 1.2 mmol, 0.3 eq). The mixture was stirred at 80° C. for 16 hours. LCMS showed the reaction was complete. The reaction mixture was concentrated and purified by column chromatography on silica gel (DCM/MeOH=50/1) to give the title compound (1.7 g, 61% yield) as yellow oil. LCMS: Rt: 1.420 min; MS m/z (ESI): 710.6 [M+H]$^+$.

Step 4: Preparation of Compound 33-4

To a solution of 33-3 (1.7 g, 2.4 mmol, 1.0 eq) in EtOH (25 mL) were added 2-bromoethanol (600 mg, 4.8 mmol, 2.0 eq) and DIPEA (930 mg, 7.2 mmol, 3.0 eq). The mixture was stirred at 70° C. for 16 hours. LCMS showed the desired MS was detected. The reaction mixture was concentrated under reduced pressure. The residue was diluted with DCM and washed with water, brine, dried over $Na_2SO_4$ and concentrated give the title compound (1.8 g, 100%) as yellow oil. It was used in the next step without further purification. LCMS: Rt: 1.980 min; MS m/z (ESI): 754.6 [M+H]$^+$.

Step 5: Preparation of Compound 33-5

To a solution of 33-4 (1.8 g, 2.39 mmol, 1.0 eq) in DCM (30 mL) was added $SOCl_2$ (853 mg, 7.17 mmol, 3.0 eq). The mixture was stirred at 30° C. for 16 hours. LCMS showed the reaction was complete. The mixture was washed with saturated $NaHCO_3$ solution, dried over $Na_2SO_4$ and concentrated. The residue was purified by column chromatography on silica gel (PE/EA=10/1) to give the title compound (750 mg, 42% yield) as yellow oil. LCMS: Rt: 1.230 min; MS m/z (ESI): 736.6 [M–Cl]$^+$.

Step 6: Preparation of Compound 33

To a solution of 33-5 (150 mg, 0.19 mmol, 1.0 eq) and compound I (66 mg, 0.57 mmol, 3.0 eq) in THF (10 mL) were added DIPEA (123 mg, 0.95 mmol, 5.0 eq) and NaI (6 mg, 0.038 mmol, 0.2 eq). The mixture was stirred at 70° C. for 16 hours. LCMS showed the reaction was completed. The mixture was concentrated and purified by prep-HPLC to give the title compound (65 mg, 40% yield) as yellow oil. $^1$H NMR (400 MHz, CDCl$_3$) δ: 0.86-0.90 (m, 12H), 1.26-1.40 (m, 56H), 1.46-1.67 (m, 11H), 1.80-1.92 (m, 1H), 1.96-2.08 (m, 2H), 2.30 (t, J=7.6 Hz, 2H), 2.41-2.73 (m, 10H), 3.15-3.25 (m, 1H), 3.40-3.61 (m, 9H), 3.95-3.97 (m, 2H). LCMS: Rt: 2.250 min; MS m/z (ESI): 851.7 [M+H]$^+$.

7.34 Example 34: Preparation of Compound 34

33-5

34

Compound 34 $^1$H NMR (400 MHz, CDCl$_3$) δ: 0.40-0.52 (m, 4H), 0.86-0.90 (m, 12H), 1.26-1.40 (m, 56H), 1.44-1.65 (m, 9H), 1.84-1.92 (m, 1H), 2.30 (t, J=7.6 Hz, 2H), 2.40-2.82 (m, 9H), 3.38-3.63 (m, 9H), 3.95-3.97 (m, 2H). LCMS: Rt: 2.090 min; MS m/z (ESI): 837.7 [M+H]$^+$.

7.35 Example 35: Preparation of Compound 35
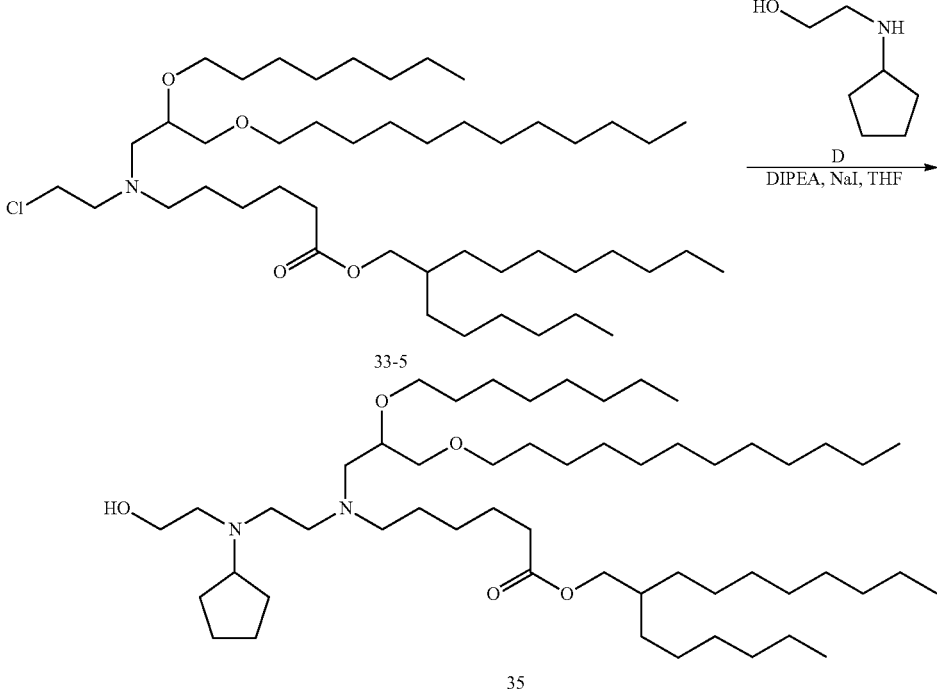
33-5
35
Compound 35 $^1$H NMR (400 MHz, CDCl$_3$) δ: 0.86-0.90 (m, 12H), 1.26-1.42 (m, 56H), 1.44-1.55 (m, 9H), 1.56-1.73 (m, 5H), 1.76-1.82 (m, 1H), 2.30 (t, J=7.4 Hz, 2H), 2.47-2.68 (m, 9H), 3.40-3.60 (m, 9H), 3.95-3.97 (m, 2H). LCMS: Rt: 2.520 min; MS m/z (ESI): 865.7 [M+H]$^+$.
7.36 Example 36: Preparation of Compound 36
33-5

-continued

36

Compound 36 $^1$H NMR (400 MHz, CDCl$_3$) δ: 0.86-0.90 (m, 12H), 1.26-1.40 (m, 58H), 1.41-1.63 (m, 11H), 1.70-1.85 (m, 4H), 2.05-2.07 (m, 1H), 2.30 (t, J=7.4 Hz, 2H), 2.39-2.65 (m, 9H), 2.85-3.03 (m, 1H), 3.40-3.61 (m, 9H), 3.95-3.97 (m, 2H). LCMS: Rt: 2.480 min; MS m/z (ESI): 879.7 [M+H]$^+$.

7.37 Example 37: Preparation of Compound 37

33-5

37

Compound 37 $^1$H NMR (400 MHz, CDCl$_3$) δ: 0.86-0.90 (m, 12H), 1.26-1.40 (m, 56H), 1.41-1.69 (m, 16H), 1.75-1.84 (m, 2H), 2.07-2.24 (m, 4H), 2.30 (t, J=7.6 Hz, 2H), 2.40-2.61 (m, 5H), 2.74-2.80 (m, 2H), 3.00-3.06 (m, 1H), 3.16-3.23 (m, 1H), 3.40-3.61 (m, 7H), 3.84-3.89 (m, 1H), 3.95-3.97 (m, 2H). LCMS: Rt: 2.520 min; MS m/z (ESI): 893.7 [M+H]$^+$.

7.38 Example 38: Preparation of Compound 38

5-5

I / DIEA, THF

38

Compound 38 $^1$H NMR (400 MHz, CDCl$_3$) δ: 0.86-0.90 (m, 6H), 1.26-1.54 (m, 25H), 1.56-1.70 (m, 6H), 1.91-2.02 (m, 4H), 2.32 (s, 3H), 2.48-2.58 (m, 8H), 3.11-3.23 (m, 1H), 3.41-3.60 (m, 9H). LCMS: Rt: 0.909 min; MS m/z (ESI): 499.4 [M+H]$^+$.

7.39 Example 39: Preparation of Compound 39

6-4

I / DIEA, THF

39

Compound 39 $^1$H NMR (400 MHz, CDCl$_3$) δ: 0.86-0.90 (m, 12H), 1.26-1.54 (m, 36H), 1.52-1.67 (m, 6H), 1.91-2.02 (m, 4H), 2.32 (s, 3H), 2.50-2.58 (m, 8H), 3.17-3.21 (m, 1H), 3.43-3.62 (m, 9H). LCMS: Rt: 1.030 min; MS m/z (ESI): 583.5 [M+H]$^+$.

7.40 Example 40: Preparation of Compound 40

40-1          40-2

-continued 40-3

A
EtOH 40-4

DIPEA, DMAP, DCM 40-5

Pd/C, H₂
con. HCl(cat.)

40-6

MsCl, DIPEA
DCM 40-7

I
K₂CO₃
ACN, 70° C.

40

Step 1: Preparation of Compound 40-1

To a solution of 2-(methylamino)ethan-1-ol (7.5 g, 0.10 mol, 1.0 eq) in DCM (300 mL) at 0° C. was added di-tert-butyl dicarbonate (24.0 g, 0.11 mmol, 1.1 eq). The mixture was stirred at room temperature for 1 hour. LCMS showed the reaction was completed. The mixture was washed with water, brine, dried over $Na_2SO_4$ and concentrated to give the title compound (17.5 g, 100% yield) as colorless oil. LCMS: Rt: 0.820 min; MS m/z (ESI): 120.2 $[M-56]^+$.

Step 2: Preparation of Compound 40-2

To a stirred solution of 40-1 (12.5 g, 71.2 mol, 1.0 eq) and Benzyl bromide (14.6 g, 85.4 mmol, 1.2 eq) in THF (140 mL) at 0° C. under $N_2$ was added NaH (3.4 g, 85.4 mmol, 1.2 eq) portionwise. The resulting mixture was stirred at room temperature for 16 hours. TLC showed the reaction was completed. The mixture was poured into water and extracted with EA. The combined organic layers were washed with brine, dried over $Na_2SO_4$ and concentrated.

The residue was purified by column chromatography on silica gel (PE/EA=15/1) to give the title compound (12.5 g, 60% yield) as colorless oil.

Step 3: Preparation of Compound 40-3

To a solution of 40-2 (12.5 g, 47.1 mol, 1.0 eq) in DCM (100 mL) under $N_2$ was added a solution of HCl in 1,4-dioxane (23.6 mL, 94.2 mmol, 2.0 eq, 4.0 M). The resulting mixture was stirred at room temperature for 2 hours. LCMS showed the reaction was completed. The mixture was basified to pH=9 with saturated $NaHCO_3$ aqueous solution. The mixture was extracted with DCM. The combined organic layers were washed with brine, dried over $Na_2SO_4$ and concentrated to give the title compound (5.1 g, 65% yield) as yellow oil. LCMS: Rt: 0.650 min; MS m/z (ESI): 166.2 $[M+H]^+$.

Step 4: Preparation of Compound 40-4

To a solution of compound A (6.0 g, 25.0 mmol, 1.0 eq) in EtOH (100 mL) was added 40-3 (5.0 g, 30.0 mmol, 1.2 eq). The mixture was stirred at RT for 16 hours. LCMS showed the reaction was complete. The mixture was evaporated under reduced pressure and purified by column chromatography on silica (DCM/MeOH=100/1-40/1) to give the title compound (6.1 g, 61%) as yellow oil. LCMS: Rt: 0.890 min; MS m/z (ESI): 408.3 [M+H]⁺.

Step 5: Preparation of Compound 40-5

To a stirred solution of 40-4 (300 mg, 0.74 mmol, 1.0 eq), DIPEA (289 mg, 2.22 mmol, 3.0 eq) in DCM (10 mL) were added valeryl chloride (178 mg, 1.48 mmol, 2.0 eq) and DMAP (18 mg, 0.15 mmol, 0.2 eq). The mixture was stirred at RT for 16 hours. LCMS showed the reaction was complete. The mixture was poured into water (20 mL) and extracted with DCM. The combined organic layers were washed with brine, dried over Na₂SO₄ and concentrated.

and purified by prep-HPLC to give the title compound (200 mg, 83% yield) as yellow oil.

$^1$H NMR (400 MHz, CDCl₃) δ: 0.86-0.94 (m, 6H), 1.25-1.38 (m, 21H), 1.54-1.62 (m, 6H), 1.87-1.94 (m, 2H), 1.97-2.04 (m, 2H), 2.31 (t, J=7.4 Hz, 3H), 2.39-2.48 (m, 3H), 2.52-2.66 (m, 4H), 2.72-2.76 (m, 3H), 3.13-3.21 (m, 1H), 3.42-3.47 (m, 4H), 3.90-3.97 (m, 1H), 4.11-4.15 (m, 2H). LCMS: Rt: 0.910 min; MS m/z (ESI): 499.4 [M+H]⁺.

7.41 Example 41: Preparation of Compound 41

40-4

DIPEA, DMAP, DCM 41-1

Pd/C, H₂
con. HCl(cat.)

41

The residue was purified by column chromatography on silica gel (DCM/MeOH=100/1) to give the title compound (320 mg, 88% yield) as yellow oil. LCMS: Rt: 0.940 min; MS m/z (ESI): 492.4 [M+H]⁺.

Step 6: Preparation of Compound 40-6

To a solution of 40-5 (320 mg, 0.65 mmol, 1.0 eq) in MeOH (15 mL) were added Pd/C (64 mg) and concentrated HCl (4 drops). The mixture was stirred at RT under H₂ for 2 hours. LCMS showed the reaction was complete. The mixture was filtered through a pad of celite and washed with MeOH. The filtration was concentrated and purified by column chromatography on silica gel (DCM/MeOH=75/1) to give the title compound (200 mg, 77% yield) as yellow oil. LCMS: Rt: 0.920 min; MS m/z (ESI): 402.3 [M+H]⁺.

Step 7: Preparation of Compound 40-7

To a stirred solution of 40-6 (200 mg, 0.50 mmol, 1.0 eq) and DIPEA (129 mg, 1.0 mmol, 2.0 eq) in DCM (10 mL) at 0° C. was added methane sulfonyl chloride (69 mg, 0.60 mmol, 1.2 eq). The mixture was stirred at RT for 2 hours. LCMS showed the reaction was complete. The mixture was poured into water (20 mL) and extracted with DCM. The combined organic layers were washed with brine, dried over Na₂SO₄ and concentrated to give the title compound (200 mg, 83% yield) as yellow oil. LCMS: Rt: 1.480 min; MS m/z (ESI): 480.3 [M+H]⁺.

Step 8: Preparation of Compound 40

To a solution of 40-7 (200 mg, 0.42 mmol, 1.0 eq) in ACN (10 mL) were added compound I (97 mg, 0.84 mmol, 2.0 eq) and potassium carbonate (174 mg, 1.26 mmol, 3.0 eq). The mixture was stirred at 70° C. for 16 hours. LCMS showed the reaction was complete. The mixture was concentrated Step 1: Preparation of Compound 41-1

To a stirred solution of 40-4 (600 mg, 1.47 mmol, 1.0 eq), DIPEA (570 mg, 4.41 mmol, 3.0 eq) in DCM (20 mL) were added dodecanoyl chloride (643 mg, 2.94 mmol, 2.0 eq) and DMAP (35 mg, 0.29 mmol, 0.2 eq). The mixture was stirred at RT for 16 hours. LCMS showed the reaction was complete. The mixture was poured into water (20 mL) and extracted with DCM. The combined organic layers were washed with brine, dried over Na₂SO₄ and concentrated. The residue was purified by column chromatography on silica gel (DCM/MeOH=100/1) to give the title compound (750 mg, 75% yield) as yellow oil. LCMS: Rt: 0.940 min; MS m/z (ESI): 590.4 [M+H]⁺.

Step 2: Preparation of Compound 41

To a solution of 41-1 (700 mg, 1.19 mmol, 1.0 eq) in MeOH (15 mL) were added Pd/C (140 mg) and concentrated HCl (4 drops). The mixture was stirred at RT under H₂ for 2 hours. LCMS showed the reaction was complete. The mixture was filtered through a pad of celite and washed with MeOH. The filtration was concentrated and purified by column chromatography on silica gel (DCM/MeOH=75/1) to give the title compound (550 mg, 93% yield) as yellow oil. 250 mg product was then further purified by prep-HPLC to give the title compound (62 mg, 10% yield) as colorless oil.

$^1$H NMR (400 MHz, CDCl₃) δ: 0.88 (t, J=6.8 Hz, 6H), 1.26-1.29 (m, 35H), 1.53-1.64 (m, 4H), 2.35 (t, J=7.6 Hz, 2H), 2.44 (s, 3H), 2.66-2.80 (m, 4H), 3.40-3.45 (m, 2H), 3.46-3.59 (m, 2H), 3.64-3.66 (m, 2H), 5.16-5.20 (m, 1H). LCMS: Rt: 1.190 min; MS m/z (ESI): 500.4 [M+H]⁺.

7.42 Example 42: Preparation of Compound 42

Compound 42-1

LCMS: Rt: 0.920 min; MS m/z (ESI): 482.5 [M−OMs]⁺.

Compound 42

$^1$H NMR (400 MHz, CDCl$_3$) δ: 0.86-0.90 (m, 6H), 1.25-1.38 (m, 35H), 1.56-1.67 (m, 6H), 1.87-1.96 (m, 2H), 1.97-2.04 (m, 2H), 2.05-2.28 (m, 2H), 2.30-2.32 (m, 3H), 2.42-2.53 (m, 3H), 2.60-2.79 (m, 5H), 3.16-3.21 (m, 1H), 3.40-3.47 (m, 4H), 3.93-4.00 (m, 1H), 4.12-4.14 (m, 2H). LCMS: Rt: 1.080 min; MS m/z (ESI): 597.5 [M+H]⁺.

7.43 Example 43: Preparation of Compound 43

-continued 43-5

43-6

43

Step 1: Preparation of Compound 43-1

A mixture of 3-(methylamino)propane-1,2-diol (5.0 g, 47.6 mmol, 1.0 eq), ((2-bromoethoxy)methyl)benzene (12.3 g, 57.1 mmol, 1.2 eq) and DIPEA (18.5 g, 142.8 mmol, 3.0 eq) in THF (100 mL) was stirred at 70° C. for 16 hours. LCMS showed the reaction was completed. The mixture was poured into water (100 mL) and extracted with EA (50 mL×3). The combined organic layers were washed with brine, dried over $Na_2SO_4$ and concentrated. The residue was purified by column chromatography on silica gel (DCM/MeOH=50/1-20/1) to give the title compound (3.7 g, 32% yield) as yellow oil. LCMS: Rt: 0.630 min; MS m/z (ESI): 240.2 [M+H]$^+$.

Step 2: Preparation of Compound 43-2

To a mixture of 43-1 (2.0 g, 8.36 mmol, 1.0 eq) in methyl acrylate (12 mL) was added NaOH (66 mg, 1.67 mmol, 0.2 eq). The resulting mixture was stirred at 50° C. for 16 hours. TLC showed the reaction was completed. The mixture was poured into water (40 mL) and extracted with EA. The combined organic layers were washed with brine, dried over $Na_2SO_4$ and concentrated. The residue was purified by prep-HPLC to give the title compound (800 mg, 24% yield) as colorless oil. LCMS: Rt: 0.730 min; MS m/z (ESI): 412.2 [M+H]$^+$.

Step 3: Preparation of Compound 43-3

To a solution of 43-2 (800 mg, 1.94 mol, 1.0 eq) in THF/H2O (8 mL/8 mL) was added Lithium hydroxide monohydrate (326 mg, 7.76 mmol, 4.0 eq). The reaction mixture was stirred at room temperature for 16 hours. LCMS showed the reaction worked completely. The reaction mixture was concentrated under reduced pressure to remove the organic solvent. The aqueous layer was acidified to pH=5 with 2 N HCl and then purified by prep-HPLC to give the title compound (280 mg, 38% yield) as colorless oil. LCMS: Rt: 0.740 min; MS m/z (ESI): 384.2 [M+H]$^+$.

Step 4: Preparation of Compound 43-4

A mixture of 43-3 (280 mg, 0.73 mmol, 1.0 eq), nonan-1-ol (316 mg, 2.19 mmol, 3.0 eq), EDCI (420 mg, 2.19 mmol, 3.0 eq), DMAP (178 mg, 1.46 mmol, 2.0 eq) and DIPEA (472 mg, 3.65 mmol, 5.0 eq) in DCM (30 mL) was stirred at reflux for 16 hours. LCMS showed the reaction worked completely. The reaction mixture was poured into water and extracted with DCM. The combined organic layers were washed with brine, dried over $Na_2SO_4$ and concentrated. The residue was purified by prep-HPLC to give the title compound (150 mg, 32% yield) as colorless oil. LCMS: Rt: 0.890 min; MS m/z (ESI): 636.4 [M+H]$^+$.

Step 5: Preparation of Compound 43-5

To a solution of 43-4 (150 mg, 0.24 mmol, 1.0 eq) in MeOH (10 mL) were added Pd/C (30 mg) and concentrated HCl (5 drops). The mixture was stirred at RT under $H_2$ for 2 hours. LCMS showed the reaction was complete. The mixture was filtered through a pad of celite and washed with MeOH. The filtration was concentrated and the residue was diluted with DCM washed with saturated $NaHCO_3$ aqueous solution. The combined organic layers were dried $Na_2SO_4$ and concentrated to give the title compound (100 mg, 77% yield) as yellow oil. LCMS: Rt: 0.860 min; MS m/z (ESI): 546.4 [M+H]$^+$.

Step 6: Preparation of Compound 43-6

To a solution of 43-5 (100 mg, 0.18 mmol, 1.0 eq) in DCM (10 mL) was added $SOC_2$ (65 mg, 0.54 mmol, 3.0 eq) at RT. The mixture was stirred at 30° C. for 16 hours. LCMS showed the reaction was completed. The mixture was evaporated under reduced pressure to give the title compound (100 mg, 99% yield) as yellow oil. LCMS: Rt: 0.950 min; MS m/z (ESI): 564.3 [M+H]$^+$.

Step 7: Preparation of Compound 43

To a solution of 43-6 (100 mg, 0.18 mmol, 1.0 eq) and compound B (62 mg, 0.54 mmol, 3.0 eq) in THF (10 mL) were added DIPEA (116 mg, 0.90 mmol, 5.0 eq) and NaI (5 mg, 0.036 mmol, 0.2 eq). The mixture was stirred at 70° C. for 16 hours. LCMS showed the reaction was complete. The mixture was concentrated and purified by prep-HPLC to give the title compound (11 mg, 10% yield) as yellow oil.

$^1$H NMR (400 MHz, CDCl$_3$) δ: 0.86-0.90 (m, 6H), 1.27-1.30 (m, 25H), 1.60-1.70 (m, 6H), 1.90-2.06 (m, 4H), 2.28-2.35 (m, 3H), 2.44-2.67 (m, 12H), 3.18-3.26 (m, 1H), 3.47-3.55 (m, 5H), 3.61-3.65 (m, 2H), 3.71-3.77 (m, 1H), 3.80-3.90 (m, 1H), 4.05-4.09 (m, 4H). LCMS: Rt: 0.910 min; MS m/z (ESI): 643.4 [M+H]$^+$.

7.44 Example 44: Preparation of Compound 44

Compound 44-1
LCMS: Rt: 0.940 min; MS m/z (ESI): 506.3 [M+H]$^+$.
Compound 44-2
LCMS: Rt: 1.010 min; MS m/z (ESI): 416.3 [M+H]$^+$.
Compound 44-3
LCMS: Rt: 1.630 min; MS m/z (ESI): 398.1 [M−OMs]$^+$.
Compound 44
$^1$H NMR (400 MHz, CDCl$_3$) δ: 0.86-0.94 (m, 6H), 1.25-1.32 (m, 24H), 1.54-1.64 (m, 6H), 1.87-1.93 (m, 2H), 1.97-2.05 (m, 2H), 2.30 (t, J=7.6 Hz, 3H), 2.36-2.39 (m, 3H), 2.46-2.65 (m, 4H), 2.72-2.76 (m, 2H), 3.12-3.20 (m, 1H), 3.40-3.50 (m, 4H), 3.87-3.90 (m, 1H), 4.12-4.16 (m, 2H). LCMS: Rt: 0.890 min; MS m/z (ESI): 513.4 [M+H]$^+$.

7.45 Example 45: Preparation of Compound 45

5-5

45

Compound 45 $^1$H NMR (400 MHz, CDCl$_3$) δ: 0.81-0.93 (m, 6H), 1.01-1.14 (m, 1H), 1.16-1.38 (m, 29H), 1.47-1.60 (m, 4H), 1.61-1.70 (m, 1H), 1.76-1.91 (m, 3H), 1.98-2.35 (m, 7H), 2.55-2.97 (m, 6H), 3.35-3.53 (m, 5H), 3.54-3.75 (m, 3H). LCMS: Rt: 1.050 min; MS m/z (ESI): 527.5 [M+H]$^+$.

7.46 Example 46: Preparation of Compound 46

-continued 46-6

46-7

46

Step 1: Preparation of Compound 46-1

To a solution of 2-(bromomethyl)oxirane (5.4 g, 20 mmol, 1.0 eq) in THF (50 ml) was added NaH (1.6 g, 40 mmol, 2.0 eq) and stirred for 2 h at RT. Then $C_{18}H_{37}Br$ (5.4 g, 40 mmol, 2.0 eq) was added and stirred for 16 h at 70° C. LCMS showed the reaction was completed. H2O was added, exacted with EA, and concentrated and purified by FCC (PE/EA=10/1) to get the 46-1 (1.0 g, 20% yield) as colorless oil.

$^1$H NMR (400 MHz, CDCl$_3$) δ: 0.84-0.89 (s, 3H), 1.30 (s, 32H), 1.50-1.60 (m, 4H), 2.60-2.62 (m, 1H), 2.79-2.80 (m, 1H), 3.14-3.16 (m, 1H), 3.36-3.52 (m, 3H), 3.68-3.73 (m, 1H).

Step 2: Preparation of Compound 46-2

To a solution of 46-1 (1.0 g, 3.07 mmol, 1.0 eq) and bis (4-methoxybenzyl)amine (617 mg, 3.98 mmol, 1.3 eq) in EtOH (10.0 ml) was stirred for 16 h at RT. LCMS showed the reaction was completed, concentrated and purified by FCC (PE/EA=10/1) to get the 46-2 (1.2 g, 68% yield) as white solid. LCMS: Rt: 1.421 min; MS m/z (ESI): 584.4 [M+H]$^+$.

Step 3: Preparation of Compound 46-3

To a solution of 46-2 (1.5 g, 2.57 mmol, 1.0 eq) in THF (20 ml) was added NaH (308 mg, 7.72 mmol, 3.0 eq) and stirred for 2 h at RT, then $C_6H_{13}Br$ (1.26 g, 7.72 mmol, 3.0 eq) was added and stirred for 16 h at 70° C. LCMS showed the reaction was completed, H2O was added, exacted with EA, concentrated and purified by FCC (PE/EA=10/1) to get 46-3 (1.2 g, 70% yield) as yellow oil. LCMS: Rt: 1.585 min; MS m/z (ESI): 669.1 [M+H]$^+$.

Step 4: Preparation of Compound 46-4

To a solution of 46-3 (1.2 g, 1.8 mmol, 1.0) in EtOH (10 ml) was added Pd/C (120.0 mg) and then was stirred for 16 h at RT under H$_2$. LCMS showed the reaction was completed, filtered and concentrated to get 46-4 (750.0 mg, 97% yield) as yellow oil. LCMS: Rt: 1.422 min; MS m/z (ESI): 428.4 [M+H]$^+$.

Step 5: Preparation of Compound 46-5

To a solution of 46-4 (750.0 mg, 1.75 mmol, 1.0 eq) and compound C (469.0 mg, 1.4 mmol, 0.8 eq) in ACN (10 ml) was added K$_2$CO$_3$ (724.5 mg, 5.25 mmol, 3.0 eq), Cs$_2$CO$_3$ (170 mg, 0.525 mmol, 0.3 eq) and NaI (25 mg, 0.175 mmol, 0.1 eq) was stirred for 16 h at 85° C. LCMS showed the reaction was completed, concentrated and purified by FCC (DCM/MeOH=20/1) to get 46-5 (320 mg, 33% yield) as brown oil. LCMS: Rt: 1.770 min; MS m/z (ESI): 682.6 [M+H]$^+$.

Step 6: Preparation of Compound 46-6

To a solution of 46-5 (300 mg, 0.44 mmol, 1.0 eq) and 2-Bromoethanol (110 mg, 0.88 mmol, 4.0 eq) in EtOH (5 ml) was added DIEA (170 mg, 1.32 mmol, 3.0 eq) and NaI (25 mg, 0.0176 mmol, 0.1 eq). The mixture was stirred for 48 h at 70° C. LCMS showed the reaction was completed, concentrated to get 46-6 (350 mg, crude) as brown oil. LCMS: Rt: 2.010 min; MS m/z (ESI): 726.6 [M+H]$^+$.

Step 7: Preparation of Compound 46-7

A mixture of 46-6 (100 mg, 0.137 mmol, 1.0 eq) and SOCl$_2$ (48 mg, 0.413 mmol, 3.0 eq) in DCM (5 ml) was stirred at 35° C. for 16 h. The reaction was filtered and the filtrate was concentrated. The residue was purified by column chromatography on silica (PE/EA=10/1) to give 46-7 (80 mg, 74% yield) as a colorless oil. LCMS: Rt: 1.030 min; MS m/z (ESI): 708.6 [M–Cl]$^+$.

Step 8: Preparation of Compound 46

A mixture of 46-7 (100 mg, 0.134 mmol, 1.0 eq), compound I (46 mg, 0.4 mmol, 3.0 eq), DIEA (87 mg, 0.67 mmol, 5.0 eq) in THF (5 ml) was stirred at 70° C. for 16 h. LCMS showed the reaction was complete. After removal of solvent, the residue was purified by prep-HPLC to provide 46 (16.0 mg, 14% yield) as colorless oil.

$^1$H NMR (400 MHz, CDCl$_3$) δ: 0.84-0.89 (s, 9H), 1.14-1.31 (s, 59H), 1.50-1.65 (m, 10H), 1.98-2.09 (m, 2H), 2.28-2.31 (m, 2H), 2.48-2.63 (m, 8H), 3.40-3.61 (m, 10H), 4.03-4.07 (m, 2H). LCMS: Rt: 1.670 min; MS m/z (ESI): 823.7[M+H]$^+$.

7.47 Example 47: Preparation of Compound 47

47

Step 1: Preparation of Compound 47-1

To a mixture of NaH (800 mg, 20.01 mmol, 5.0 eq) in THF (50 mL) was added J-1 (2 g, 4.002 mmol, 1.0 eq) at RT under $N_2$. The reaction mixture was stirred at RT for 4 hours. The $C_{14}H_{29}Br$ (1.66 g, 6.004 mmol, 1.5 eq) was added to it. The reaction mixture was stirred at 70° C. for 16 hours. LCMS showed the reaction was complete. The mixture was poured in water and washed with EA. The combined organic layers were separated and dried over $Na_2SO_4$. Removal of solvent, FCC to get the compound 47-1 (1.6 g, 57.43%) as yellow oil. LCMS: Rt: 1.660 min; MS m/z (ESI): 696.5 $[M+H]^+$.

Step 2: Preparation of Compound 47-2

To a solution of 47-1 (1.6 g, 2.299 mmol) in EA (100 mL) was added Pd/C (300 mg). The reaction mixture was stirred at RT for 40 hours under hydrogen. LCMS showed the reaction was complete. The mixture was filtered through diatomite. Removal of solvent to get the compound 47-2 (1.1 g, crude) as yellow oil. LCMS: Rt: 1.100 min; MS m/z (ESI): 456.4 $[M+H]^+$.

Step 3: Preparation of Compound 47-3

To a solution of compound 47-2 (1.1 g, 2.299 mmol, 1.2 eq) in ACN (30 mL) was added compound C (642 mg, 1.916 mmol, 1.0 eq), $K_2CO_3$ (794 mg, 5.748 mmol, 3.0 eq), $Cs_2CO_3$ (187 mg, 0.5748 mmol, 0.3 eq), NaI (29 mg, 0.1916 mmol, 0.1 eq). The reaction mixture was stirred at 80° C. for 88 hours. LCMS showed the reaction was complete. Removal of solvent, FCC to get the compound 47-3 (500 mg, 36.74%) as yellow oil. LCMS: Rt: 1.540 min; MS m/z (ESI): 710.7 $[M+H]^+$.

Step 4: Preparation of Compound 47-4

To a mixture of compound 47-3 (500 mg, 0.7040 mmol, 1.0 eq), DIEA (455 mg, 3.520 mmol, 5.0 eq) in EtOH (20 mL) was added 2-bromoethan-1-ol (352 mg, 2.816 mmol, 4.0 eq), NaI (10 mg). The reaction mixture was stirred at 70° C. for 16 hours. LCMS showed the reaction was complete. Removal of solvent to get the compound (500 mg, crude) as yellow oil. LCMS: Rt: 2.150 min; MS m/z (ESI): 754.7 $[M+H]^+$.

Step 5: Preparation of Compound 47-5

To a solution of compound 47-4 (500 mg, 0.6629 mmol, 1.0 eq) in DCM (15 mL) was added $SOCl_2$ (237 mg, 1.989 mmol, 3.0 eq). The reaction mixture was stirred at 35° C. for 16 hours. LCMS showed the reaction was complete. Removal of solvent, FCC to get the compound 47-5 (200 mg, 39.05%) as yellow oil. LCMS: Rt: 1.380 min; MS m/z (ESI): 736.7 $[M–Cl]^+$.

Step 6: Preparation of Compound 47

To a mixture of compound 47-5 (180 mg, 0.2329 mmol, 1.0 eq), DIEA (150 mg, 1.65 mmol, 5.0 eq) in THF (15 mL) was added compound I (81 mg, 0.6988 mmol, 3.0 eq), NaI (20 mg). The reaction mixture was stirred at 70° C. for 16 hours. LCMS showed the reaction was complete. After removal of solvent, the residue was purified by prep-HPLC to give the title compound (60 mg, 30.26% yield) as yellow oil.

$^1H$ NMR (400 MHz, $CDCl_3$) δ: 4.07-4.03 (m, 2H), 3.60-3.40 (m, 9H), 3.18-3.14 (m, 1H), 2.57-2.45 (m, 10H), 2.31-2.27 (m, 2H), 2.01-1.84 (m, 5H), 1.65-1.48 (m, 15H), 1.26 (s, 53H), 0.90-0.86 (m, 9H). LCMS: Rt: 2.230 min; MS m/z (ESI): 851.8 $[M+H]^+$.

7.48 Example 48: Preparation of Compound 48

-continued 48-5

48

Compound 48-1
LCMS: Rt: 1.040 min; MS m/z (ESI): 612.4 [M+H]⁺.
Compound 48-2
LCMS: Rt: 0.930 min; MS m/z (ESI): 372.3 [M+H]⁺.
Compound 48-3
LCMS: Rt: 1.010 min; MS m/z (ESI): 626.5 [M+H]⁺.
Compound 48-4
LCMS: Rt: 1.270 min; MS m/z (ESI): 670.6 [M+H]⁺.
Compound 48-5
LCMS: Rt: 1.030 min; MS m/z (ESI): 652.6 [M−Cl]⁺.

Compound 48
$^1$H NMR (400 MHz, CDCl$_3$) δ: 4.07-4.03 (m, 2H), 3.61-3.40 (m, 9H), 3.19 (s, 1H), 2.58-2.49 (m, 9H) 2.31-2.27 (m, 2H), 2.01 (s, 2H), 1.89 (s, 1H), 1.65-1.45 (m, 12H), 1.26 (s, 47H), 0.90-0.86 (m, 9H). LCMS: Rt: 1.150 min; MS m/z (ESI): 767.7 [M+H]⁺.

7.49 Example 49: Preparation of Compound 49

49-1

49-2

-continued 49-3

49

Step 1: Preparation of Compound 49-1

To a solution of compound 22-1 (800 mg, 2.328 mmol, 1.2 eq) in ACN (20 mL) was added compound C (650 mg, 1.940 mmol, 1.0 eq), $K_2CO_3$ (804 mg, 5.821 mmol, 3.0 eq), $Cs_2CO_3$ (190 mg, 0.5821 mmol, 0.3 eq), NaI (29 mg, 0.1940 mmol, 0.1 eq). The reaction mixture was stirred at 80° C. for 16 hours. LCMS showed the reaction was complete. Removal of solvent, FCC to get the compound 49-1 (240 mg, 18.39%) as yellow oil. LCMS: Rt: 1.040 min; MS m/z (ESI): 598.5 [M+H]$^+$.

Step 2: Preparation of Compound 49-2

To a mixture of compound 49-1 (220 mg, 0.3679 mmol, 1.0 eq), DIEA (238 mg, 1.840 mmol, 5.0 eq) in EtOH (15 mL) was added 2-bromoethan-1-ol (184 mg, 1.472 mmol, 4.0 eq). The reaction mixture was stirred at 70° C. for 30 hours. LCMS showed the reaction was complete. Removal of solvent to get the compound (260 mg, crude) as yellow oil. LCMS: Rt: 1.160 min; MS m/z (ESI): 642.5 [M+H]$^+$.

Step 3: Preparation of Compound 49-3

To a solution of compound 49-2 (260 mg, 0.3582 mmol, 1.0 eq) in DCM (10 mL) was added $SOCl_2$ (128 mg, 1.675 mmol, 3.0 eq). The reaction mixture was stirred at 35° C. for 16 hours. LCMS showed the reaction was complete. Removal of solvent to get the compound 49-3 (240 mg, crude) as yellow oil. LCMS: Rt: 2.170 min; MS m/z (ESI): 660.5 [M+H]$^+$.

Step 4: Preparation of Compound 49

To a mixture of compound 49-3 (220 mg, 0.3331 mmol, 1.0 eq), DIEA (215 mg, 1.666 mmol, 5.0 eq) in THF (20 mL) was added compound I (115 mg, 0.9993 mmol, 3.0 eq), NaI (20 mg). The reaction mixture was stirred at 70° C. for 16 hours. LCMS showed the reaction was complete. After removal of solvent, the residue was purified by prep-HPLC to give the title compound (100 mg, 40.6% yield) as yellow oil.

$^1$H NMR (400 MHz, CDCl$_3$) δ: 4.07-4.03 (m, 2H), 3.61-3.19 (m, 10H), 2.55 (s, 9H), 2.31-2.27 (m, 2H), 2.04-1.87 (m, 3H), 1.65-1.52 (m, 12H), 1.26 (s, 43H), 0.90-0.86 (m, 9H). LCMS: Rt: 1.220 min; MS m/z (ESI): 739.6 [M+H]$^+$.

7.50 Example 50: Preparation of Compound 50

43-3

-continued 50-1

50

Step 1: Preparation of Compound 50-1

To a solution of 43-3 (300 mg, 0.78 mmol, 1.0 eq) and compound N (462 mg, 1.72 mmol, 2.2 eq) in DCM (15 mL) were added HATU (742 mg, 2.19 mmol, 2.5 eq) and DIPEA (504 mg, 3.90 mmol, 3.0 eq). The mixture was stirred at room temperature for 16 hours. LCMS showed the reaction worked completely. The reaction mixture was poured into water and extracted with DCM. The combined organic layers were washed with brine, dried over $Na_2SO_4$ and concentrated. The residue was purified by column chromatography on silica gel (DCM/MeOH=50/1) to give the title compound (550 mg, 79% yield) as yellow oil. LCMS: Rt: 1.460 min; MS m/z (ESI): 886.7 [M+H]$^+$.

Step 2: Preparation of Compound 50

To a solution of 50-1 (100 mg, 0.10 mmol, 1.0 eq) in MeOH (10 mL) were added Pd/C (10 mg) and concentrated HCl (3 drops). The mixture was stirred at RT under $H_2$ for 2 hours. LCMS showed the reaction was complete. The mixture was filtered through a pad of celite and washed with MeOH. The filtration was concentrated and purified by prep-HPLC to give the title compound (34 mg, 38% yield) as colorless oil.

$^1$H NMR (400 MHz, CDCl$_3$) δ: 0.86-0.90 (m, 12H), 1.26-1.34 (m, 58H), 1.43-1.53 (m, 2H), 2.38-2.52 (m, 7H), 2.58-2.88 (m, 3H), 3.10-3.18 (m, 4H), 3.54-3.56 (m, 2H), 3.64-3.89 (m, 6H), 3.91-3.95 (m, 1H), 6.13-6.18 (m, 1H), 6.38-6.44 (m, 1H). LCMS: Rt: 1.280 min; MS m/z (ESI): 796.7 [M+H]$^+$.

7.51 Example 51: Preparation of Compound 51

50

235 236

-continued 51-1

51

Compound 51-1

LCMS: Rt: 1.610 min; MS m/z (ESI): 814.7 [M+H]$^+$.

Compound 51

$^1$H NMR (400 MHz, CDCl$_3$) δ: 0.86-0.90 (m, 12H), 1.26-1.35 (m, 62H), 1.45-1.48 (m, 2H), 1.54-1.66 (m, 2H), 1.98-2.10 (m, 2H), 2.33-2.83 (m, 12H), 3.11-3.23 (m, 5H), 3.46-3.86 (m, 8H), 3.91-3.95 (m, 1H), 6.31-6.37 (m, 1H), 6.64-6.74 (m, 1H). LCMS: Rt: 1.460 min; MS m/z (ESI): 893.7 [M+H]$^+$.

7.52 Example 52: Preparation of Compound 52

51-1

52

Compound 52 $^1$H NMR (400 MHz, CDCl$_3$) δ: 0.86-0.90 (m, 12H), 1.26-1.31 (m, 64H), 1.44-1.48 (m, 2H), 1.54-1.60 (m, 2H), 1.76-1.88 (m, 2H), 2.18-2.80 (m, 16H), 3.09-3.17 (m, 4H), 3.44-3.59 (m, 3H), 3.72-3.86 (m, 4H), 3.89-3.93 (m, 1H), 6.36-6.45 (m, 1H), 6.72-6.78 (m, 1H). LCMS: Rt: 1.410 min; MS m/z (ESI): 921.8 [M+H]$^+$.

7.53 Example 53: Preparation of Compound 53

-continued

53

Step 1: Preparation of Compound 53-1

To a mixture of NaH (3.5 g, 87.61 mmol) in THF (200 mL) was added C$_{16}$H$_{33}$OH (14.16 g, 58.40 mmol) at RT under N$_2$. The reaction mixture was stirred at RT for 3 hours. 2-(bromomethyl)oxirane (4.0 g, 29.2 mmol) was added to it. The reaction mixture was stirred at RT for 10 hours. TLC showed the reaction was complete. The mixture was poured in water and washed with EA. The combined organic layers were separated and dried over Na$_2$SO$_4$. Removal of solvent, FCC to get the compound 53-1 (4.0 g, 46% yield) as colorless oil.

Step 2: Preparation of Compound 53-2

To a mixture of compound 53-1 (4.0 g, 13.40 mmol), bis(4-methoxybenzyl)amine (6.9 g, 26.8 mmol) in EtOH (200 mL) was stirred at RT for 10 hours. LCMS showed the reaction was complete. Removal of solvent, FCC to get the compound 53-2 (4.5 g, 67% yield) as colorless oil. LCMS: Rt: 1.088 min; MS m/z (ESI): 556.4 [M+H]$^+$.

Step 3: Preparation of Compound 53-3

To a mixture of NaH (450 mg, 7.2 mmol) in THF (50 mL) was added 53-3 (1 g, 1.8 mmol,) at RT under N$_2$. The reaction mixture was stirred at RT for 2 hours. The C$_6$H$_{13}$Br (1.04 g, 6.3 mmol) was added to it. The reaction mixture was stirred at 70° C. for 10 hours. LCMS showed the reaction was complete. The mixture was poured in water and washed with EA. The organic layers were separated and dried over Na$_2$SO$_4$. Removal of solvent, FCC to get the compound 53-3 (1.0 g, 87% yield) as colorless oil. LCMS: Rt: 1.960 min; MS m/z (ESI): 640.4 [M+H]$^+$.

Step 4: Preparation of Compound 53-4

To a solution of 53-3 (1.0 g, 1.56 mmol) in EA (100 mL) was added Pd/C (1.0 g). The reaction mixture was stirred at RT for 40 hours under H$_2$. LCMS showed the reaction was complete. The mixture was filtered through diatomite. Removal of solvent to get the compound 53-4 (0.5 g, 80% yield) as colorless oil. LCMS: Rt: 0.920 min; MS m/z (ESI): 400.3 [M+H]$^+$.

Step 5: Preparation of Compound 53-5

To a solution of compound 53-5 (0.5 g, 1.25 mmol) in ACN (30 mL) was added C (420 mg, 1.25 mmol), K$_2$CO$_3$ (550 mg, 3.75 mmol), Cs$_2$CO$_3$ (130 mg, 0.37 mmol), NaI (60 mg, 0.37 mmol). The reaction mixture was stirred at 80° C. for 10 hours. LCMS showed the reaction was complete. Removal of solvent, FCC to get the compound 53-5 (200 mg, 23% yield) as yellow oil. LCMS: Rt: 1.310 min; MS m/z (ESI): 654.6 [M+H]$^+$.

Step 6: Preparation of Compound 53-6

To a mixture of 53-5 (200 mg, 0.3 mmol), DIEA (240 mg, 1.83 mmol) in EtOH (20 mL) was added 2-bromoethan-1-ol (150 mg, 1.22 mmol), NaI (45 mg). The reaction mixture was stirred at 70° C. for 20 hours. LCMS showed the reaction was complete. Removal of solvent to get the compound (150 mg, 70% yield) as yellow oil. LCMS: Rt: 1.30 min; MS m/z (ESI): 698.6 [M+H]$^+$.

Step 7: Preparation of Compound 53-7

To a solution of compound 53-6 (150 mg, 0.21 mmol) in DCM (10 mL) was added SOCl$_2$ (80 mg, 0.64 mmol). The reaction mixture was stirred at 35° C. for 10 hours. LCMS showed the reaction was complete. Removal of solvent, FCC to get the compound 53-7 (154 mg, 100% yield) as yellow oil. LCMS: Rt: 0.640 min; MS m/z (ESI): 716.5 [M+H]$^+$.

Step 8: Preparation of Compound 53

To a mixture of compound 53-7 (150 mg, 0.21 mmol, 1.0 eq), DIEA (80 mg, 0.63 mmol) in THF (10 mL) was added Compound I (50 mg, 0.42 mmol), NaI (30 mg). The reaction mixture was stirred at 70° C. for 10 hours. LCMS showed the reaction was complete. After removal of solvent, the residue was purified by prep-HPLC to give the title compound (20 mg, 12% yield) as yellow oil.

$^1$H NMR (400 MHz, CDCl$_3$) δ: 0.87 (t, J=8 Hz, 9H), 1.20-1.41 (m, 50H), 1.45-2.09 (m, 15H), 2.27-2.55 (m, 12H), 3.21-3.57 (m, 10H), 4.03-4.07 (m, 2H). LCMS: Rt: 1.800 min; MS m/z (ESI): 795.7 [M+H]$^+$.

7.54 Example 54: Preparation of Compound 55

43-3

55-1

55-2

55-3

55

Step 1: Preparation of Compound 55-1

To a solution of 43-3 (135 mg, 0.35 mmol, 1.0 eq) and 2-octyldecan-w-ol (284 mg, 1.05 mmol, 3.0 eq) in DCM (10 mL) were added EDCI (201 mg, 1.05 mmol, 3.0 eq), DMAP (22 mg, 0.18 mmol, 0.5 eq) and DIPEA (226 mg, 1.75 mol, 5.0 eq). The mixture was stirred under reflux for 16 hours. LCMS showed the reaction worked completely. The reaction mixture was concentrated and purified by by column chromatography on silica gel (DCM/MeOH=50/1) to give the title compound (150 mg, 489 yield) as colorless oil. LCMS: Rt: 1.510 mmi; MS m/z (ESI): 888.7 [M+H].

Step 2: Preparation of Compound 55-2

To a solution of 55-1 (150 mg, 0.17 mmol, 1.0 eq) in MeOH (8 mL) were added Pd/C (15 mg) and concentrated HCl (3 drops). The mixture was stirred at RT under $H_2$ for 2 hours. LCMS showed the reaction was complete. The mixture was filtered through a pad of celite and washed with MeOH. The filtration was concentrated The residue was diluted with DCM and washed with saturated $NaHCO_3$ aqueous solution. The organic layers were dried over $Na_2SO_4$ and concentrated to give the title compound (128 mg, 95 yield) as yellow oil. LCMS: Rt: 1.627 mmi; MS m/z (ESI): 798.5 [M+H]$^+$.

Step 3: Preparation of Compound 55-3

To a solution of 55-2 (128 mg, 0.16 mmol, 1.0 eq) in DCM (10 mL) was added $SOC_2$ (57 mg, 0.48 mmol, 3.0 eq) at RT. The mixture was stirred at 30° C. for 16 hours. LCMS showed the reaction was completed. The mixture was evaporated under reduced pressure to give the title compound (128 mg, 98% yield) as yellow oil. LCMS: Rt: 1.660 min; MS m/z (ESI): 817.6 [M+H]$^+$.

Step 4: Preparation of Compound 55

To a solution of 55-3 (128 mg, 0.16 mmol, 1.0 eq) and Compound I (55 mg, 0.48 mmol, 3.0 eq) in THF (10 mL) were added DIPEA (103 mg, 0.80 mmol, 5.0 eq) and NaI (7 mg, 0.048 mmol, 0.3 eq). The mixture was stirred at 70° C. for 16 hours. LCMS showed the reaction was complete. The mixture was concentrated and purified by prep-HPLC to give the title compound (26 mg, 18% yield) as yellow oil.

$^1$H NMR (400 MHz, CDCl$_3$) δ: 0.86-0.90 (m, 12H), 1.26-1.32 (m, 58H), 1.55-1.70 (m, 4H), 1.78-2.08 (m, 4H), 2.25-2.33 (m, 3H), 2.40-2.62 (m, 11H), 3.11-3.21 (m, 1H), 3.48-3.63 (m, 5H), 3.71-3.74 (m, 2H), 3.77-3.80 (m, 1H), 3.81-3.90 (m, 1H), 3.96-3.99 (m, 4H). LCMS: Rt: 1.730 min; MS m/z (ESI): 895.7 [M+H]$^+$.

7.55 Example 55: Preparation of Compound 56

56-1

56-2

56-3

-continued 56-4

HCl/dioxane →

56-5

MsCl, DIEA, DCM →

56-6

I →

56

Step 1: Preparation of Compound 56-1

To a mixture of compound 4-bromobutan-1-ol (10 g, 65.79 mmol, 1.0 eq), TsOH (500 mg) in EA (300 mL) was added DHP (6.63 g, 78.94 mmol, 1.2 eq). The reaction mixture was stirred at 24° C. for 3 hours. TLC showed the reaction was complete. The mixture was quenched with water, extracted over EA, concentrated and purified by silica gel column chromatography (PE:EA=50:1) to give the desired product 56-1 (11 g, 70.9% yield) as colorless oil.

Step 2: Preparation of Compound 56-2

To a mixture of NaH (2 g, 50 mmol, 1.2 eq) in DMF (80 ml) was added dimethyl malonate (6.6 g, 50 mmol 1.2 eq) dropwise. The mixture was stirred at 0° C. for 2 hours. Then compound 56-1 (10 g, 42.37 mmol, 1.0 eq) was added. The reaction mixture was stirred at 90° C. for 4 hours. TLC showed the reaction was complete. The mixture was quenched with water, extracted over EA, concentrated and purified by silica gel column chromatography (PE:EA=4:1) to give the desired product 56-2 (7.9 g, 64.7% yield) as colorless oil.

Step 3: Preparation of Compound 56-3

To a mixture of LiAlH$_4$ (2.13 g, 56.15 mmol, 2.1 eq) in THF (150 ml) was added 56-2 (7.7 g, 26.73 mmol 1.0 eq) dropwise in 0° C. The mixture was stirred at RT for 16 hours. TLC showed the reaction was complete. The mixture was quenched with water, extracted over EA, concentrated and purified by silica gel column chromatography (PE:EA=1:1) to give the desired product 56-3 (2.4 g, 39.1% yield) as colorless oil.

Step 4: Preparation of Compound 56-4

To a mixture of Compound P (1.4 g, 4.74 mmol, 2.2 eq) in DCM (40 ml) was added EDCl (1.03 g, 5.37 mmol, 2.5 eq), DIEA (1.39 g, 10.75 mmol, 5 eq). The mixture was stirred at RT for 1 hour. Then 56-3 (500 mg, 2.15 mmol 1.0 eq) and DMAP (100 mg) was added in it. The mixture was stirred at RT for 16 hours. TLC showed the reaction was complete. The mixture was quenched with water, extracted over EA, concentrated and purified by silica gel column chromatography (PE:EA=20:1) to give the desired product 56-4 (860 mg, 50.5% yield) as colorless oil.

Step 5: Preparation of Compound 56-5

To a mixture of 56-4 (860 mg, 1.09 mmol, 1.0 eq) was added HCl/dioxane (4 M, 5 ml). The mixture was stirred at RT for 16 hours. TLC showed the reaction was complete. The mixture was quenched with NaHCO₃ solution (50 ml), extracted over EA, concentrated in vacuo. The crude product was used for next step without further purification 56-5 (700 mg, crude).

Step 6: Preparation of Compound 56-6

To a mixture of 56-5 (650 mg, 0.92 mmol, 1.0 eq) in 20 ml DCM was added DIEA (356 mg, 2.76 mmol, 3.0 eq), MsCl (125 mg, 1.1 mmol, 1.2 eq). The mixture was stirred at RT for 2 hours. TLC showed the reaction was complete. The mixture was quenched with water (50 ml), extracted over EA, concentrated in vacuo. The crude product was used for next step without further purification 56-6 (700 mg, crude).

Step 7: Preparation of Compound 56

To a mixture of 56-6 (200 mg, 0.25 mmol, 1.0 eq) in 10 ml ACN was added $K_2CO_3$ (103 mg, 0.75 mmol, 3.0 eq), $Cs_2CO_3$ (98 mg, 0.08 mmol, 0.3 eq), NaI (20 mg). Then compound I (86.25 mg, 0.75 mmol, 3.0 eq) was added. The mixture was stirred at 80° C. for 16 hours. LCMS showed the reaction was complete. The mixture was quenched with water (50 ml), extracted over EA, concentrated in vacuo. The mixture was concentrated and purified by prep-HPLC to give the title compound (70 mg, 34.7% yield) as yellow oil.

$^1$H NMR (400 MHz, CDCl₃) δ: 4.09-4.00 (m, 4H), 3.52-3.51 (m, 2H), 3.15-3.11 (m, 1H), 2.54-2.39 (m, 4H), 2.24-2.23 (m, 4H), 2.02-1.95 (m, 3H), 1.86-1.82 (m, 4H), 1.67-1.58 (m, 2H), 1.42-1.38 (m, 3H), 1.33-1.26 (m. 60H), 0.89-0.86 (m, 12H). LCMS: Rt: 2.21 min; MS m/z (ESI): 806.7 [M+H]⁺.

7.56 Example 56: Preparation of Compound 57

51-1

57

Compound 57 $^1$H NMR (400 MHz, CDCl₃) δ: 0.86-0.90 (m, 12H), 1.26-1.33 (m, 58H), 1.37-1.59 (m, 6H), 1.72-1.84 (m, 4H), 2.20-2.46 (m, 10H), 2.54-2.79 (m, 4H), 3.07-3.20 (m, 5H), 3.43-3.58 (m, 5H), 3.63-3.78 (m, 3H), 3.86-3.93 (m, 1H), 6.34-6.41 (m, 1H), 6.70-6.76 (m, 1H). LCMS: Rt: 1.390 min; MS m/z (ESI): 907.8 [M+H]⁺.

7.57 Example 57: Preparation of Compound 58

51-1

58

Compound 58

$^{1}$H NMR (400 MHz, CDCl$_3$) δ: 0.86-0.90 (m, 12H), 1.26-1.32 (m, 58H), 1.35-1.60 (m, 10H), 1.64-1.88 (m, 4H), 2.20-2.29 (m, 3H), 2.35-2.66 (m, 12H), 3.09-3.21 (m, 4H), 3.41-3.62 (m, 5H), 3.71-3.74 (m, 3H), 3.84-3.90 (m, 1H), 6.38-6.42 (m, 1H), 6.71-6.76 (m, 1H). LCMS: Rt: 1.580 min; MS m/z (ESI): 935.8 [M+H]$^+$.

7.58 Example 58: Preparation of Compound 59

Q 59-1

59-2

-continued 59-3

Pd/C →

59-4

SOCl₂ →

59-5

-continued

59

Step 1: Preparation of Compound 59-1

To a solution of compound Q (2.0 g, 5.11 mmol) in ACN (100 mL) was added 2-(benzyloxy)ethan-1-amine (1.55 g, 10.22 mmol), K₂CO₃ (2.12 g, 15.33 mmol), Cs₂CO₃ (500 mg, 1.53 mmol), NaI (250 mg, 1.53 mmol). The reaction mixture was stirred at 80° C. for 10 hours. LCMS showed the reaction was complete. Removal of solvent, FCC to get the compound 59-1 (1.8 g, 76% yield) as yellow oil. LCMS: Rt: 0.930 min; MS m/z (ESI): 462.3 [M+H]⁺.

Step 2: Preparation of Compound 59-2

To a mixture of compound 59-1 (1.6 g, 3.47 mmol), oxiran-2-ylmethanol (0.4 g, 5.2 mmol) in EtOH (50 mL) was added DIEA (1.34 g, 10.4 mmol). The reaction mixture was stirred at 80° C. for 10 hours. LCMS showed the reaction was complete. Removal of solvent, FCC to get the compound 59-2 (1.1 g, 59% yield) as yellow oil. LCMS: Rt: 0.86 min; MS m/z (ESI): 536.4 [M+H]⁺.

Step 3: Preparation of Compound 59-3

To a mixture of 59-2 (500 mg, 0.93 mmol), DIEA (750 mg, 5.6 mmol) in CH₂Cl₂ (20 mL) was added hexanoyl chloride (500 mg, 3.73 mmol). The reaction mixture was stirred at 70° C. for 20 hours. LCMS showed the reaction was complete. Removal of solvent to get the compound 59-3 (500 mg, 73% yield) as yellow oil. LCMS: Rt: 0.60 min; MS m/z (ESI): 732.4 [M+H]⁺.

Step 4: Preparation of Compound 59-4

To a solution of 59-3 (500 mg, 0.68 mmol) in EA (50 mL) was added Pd/C (1.0 g). The reaction mixture was stirred at RT for 10 hours under H₂. LCMS showed the reaction was complete. The mixture was filtered through diatomite. Removal of solvent to get the compound 59-4 (400 mg, 91% yield) as yellow oil. LCMS: Rt: 0.480 min; MS m/z (ESI): 642.4 [M+H]⁺.

Step 5: Preparation of Compound 59-5

To a solution of 59-4 (200 mg, 0.31 mmol) in DCM (10 mL) was added SOCl₂ (110 mg, 0.93 mmol). The reaction mixture was stirred at 35° C. for 10 hours. LCMS showed the reaction was complete. Removal of solvent to get the compound 59-5 (205 mg, 100% yield) as yellow oil. LCMS: Rt: 0.653 min; MS m/z (ESI): 660.4 [M+H]⁺.

Step 6: Preparation of Compound 59

To a mixture of compound 59-5 (200 mg, 0.3 mmol), DIEA (120 mg, 0.9 mmol) in THF (10 mL) was added pyrrolidin-3-ol (53 mg, 0.6 mmol), NaI (45 mg). The reaction mixture was stirred at 70° C. for 10 hours. LCMS showed the reaction was complete. After removal of solvent, the residue was purified by prep-HPLC to give the title compound (70 mg, 32% yield) as yellow oil.

¹H NMR (400 MHz, CDCl₃) δ: 0.87 (t, J=8 Hz, 12H), 1.20-1.79 (m, 40H), 2.16-2.99 (m, 20H), 3.96-4.11 (m, 3H), 4.34-4.41 (m, 2H), 5.12-5.14 (m, 1H). LCMS: Rt: 1.020 min; MS m/z (ESI): 711.5 [M+H]⁺.

7.59 Example 59: Preparation of Compound 60

56-3

60-1

-continued 60-2

HCl/dioxane →

60-3

MsCl, DIEA, DCM →

60-4

I →

60

Step 1: Preparation of Compound 60-1

To a mixture of compound P (298 mg, 1.0 mmol, 1.0 eq) in DCM (10 ml) was added EDCl (229 mg, 1.2 mmol, 1.2 eq), DIEA (387 mg, 3.0 mmol, 3 eq). The mixture was stirred at RT for 1 hour. Then 56-3 (232 mg, 1.0 mmol 1.0 eq) and DMAP (10 mg) was added in. The mixture was stirred at RT for 16 hours. TLC showed the reaction was complete. The mixture was quenched with water, extracted over EA, concentrated and purified by silica gel column chromatography (PE:EA=10:1) to give the desired product 60-1 (330 mg, 64.4% yield) as colorless oil.

Step 2: Preparation of Compound 60-2

To a mixture of 60-1 (512 mg, 1.0 mmol, 1.0 eq) in 10 ml DCM was added DIEA (387 mg, 3.0 mmol, 3 eq), hexanoyl chloride (160 mg, 1.2 mmol, 1.2 eq). The mixture was stirred at RT for 16 hours. TLC showed the reaction was complete. The mixture was quenched with water (30 ml), extracted over DCM, concentrated in vacuo, and purified by silica gel column chromatography (PE:EA=10:1) to give the desired product 60-2 (420 mg, 68%).

Step 3: Preparation of Compound 60-3

To a mixture of 60-2 (610 mg, 1.0 mmol, 1.0 eq) was added HCl/dioxane (4 M, 5 ml). The mixture was stirred at RT for 16 hours. TLC showed the reaction was complete. The mixture was quenched with NaHCO$_3$ solution (50 ml), extracted over EA, concentrated in vacuo. The crude product was used for next step without further purification 60-3 (700 mg, crude).

Step 4: Preparation of Compound 60-4

To a mixture of 60-3 (526 mg, 1.0 mmol, 1.0 eq) in 10 ml DCM was added DIEA (387 mg, 3.0 mmol, 3.0 eq), MsCl (137 mg, 1.2 mmol, 1.2 eq). The mixture was stirred at RT for 2 hours. TLC showed the reaction was complete. The mixture was quenched with water (50 ml), extracted over EA, concentrated in vacuo. The crude product was used for next step without further purification 60-4 (490 mg, crude).

Step 5: Preparation of Compound 60

To a mixture of 60-4 (151 mg, 0.25 mmol, 1.0 eq) in 10 ml ACN was added K$_2$CO$_3$ (103 mg, 0.75 mmol, 3.0 eq), Cs$_2$CO$_3$ (98 mg, 0.08 mmol, 0.3 eq), NaI (20 mg). Then compound I (86.25 mg, 0.75 mmol, 3.0 eq) was added. The mixture was stirred at 80° C. for 16 hours. LCMS showed the reaction was complete. The mixture was quenched with water (50 ml), extracted over EA, concentrated in vacuo. The mixture was concentrated and purified by prep-HPLC to give the title compound (33 mg, 21.2% yield) as yellow oil.

$^1$H NMR (400 MHz, CDCl$_3$) δ: 4.09-4.00 (m, 4H), 3.52-3.49 (m, 2H), 3.17-3.09 (m, 1H), 2.56-2.54 (m, 4H), 2.43-2.23 (m, 6H), 2.04-1.80 (m, 6H), 1.67-1.58 (m, 4H), 1.46-1.43 (m, 3H), 1.33-1.26 (m. 36H), 0.89-0.86 (m, 9H). LCMS: Rt: 0.97 min; MS m/z (ESI): 624.5 [M+H]$^+$.

7.60 Example 60: Preparation of Compound 64

16 hours. The mixture was poured into water and extracted with EA. The combined organic layers were washed with brine, dried over Na$_2$SO$_4$ and concentrated. The residue was purified by column chromotography on silica gel (PE/EA=100/1) to give the title compound (2.6 g, 68% yield) as colorless oil.

Step 2: Preparation of Compound 64-3

To a solution of compound 64-2 (995 mg, 4.16 mmol, 0.8 eq.) and compound I (600 mg, 5.20 mmol, 1.0 eq.) in ACN (30 mL) was added K$_2$CO$_3$ (2.2 g, 15.6 mmol, 3.0 eq.), Cs$_2$CO$_3$ (508 mg, 1.56 mmol, 0.3 eq.) and NaI (234 mg, 1.56 mmol, 0.3 eq.). The mixture was stirred at 80° C. for 16

Step 1: Preparation of Compound 64-2

To a solution of compound 64-1 (2.0 g, 16.0 mmol, 1.0 eq.) in DMF (32 mL) was added imidazole (2.2 g, 32.0 mmol, 2.0 eq.) and then TBSCl (3.6 g, 24.0 mmol, 1.5 eq.) dropwise. The mixture was stirred at room temperature for hours. LCMS showed the reaction was complete. The reaction mixture was concentrated and purified by column chromatography on silica gel (DCM/MeOH=40/1) to give the title compound (670 mg, 61% yield) as yellow oil. LCMS: Rt: 0.770 min; MS m/z (ESI): 274.2 [M+H]$^+$.

Step 3: Preparation of Compound 64-4

To a solution of compound 64-3 (670 mg, 2.45 mmol, 1.0 eq.) and DIPEA (633 mg, 4.90 mmol, 2.0 eq.) in DCM (25 mL) was added MsCl (337 mg, 2.94 mmol, 1.2 eq.) at 0° C. The mixture was stirred at room temperature for 2 hours. LCMS showed the reaction was completed. The mixture was poured into water and extracted with DCM. The combined organic layers were washed with brine, dried over $Na_2SO_4$ and concentrated to give the title compound (715 mg, 83% yield) as yellow oil. It was used in the next step without further purification. LCMS: Rt: 0.810 min; MS m/z (ESI): 292.2 [M−OMs+Cl]$^+$.

Step 4: Preparation of Compound 64-5

To a solution of compound 64-4 (715 mg, 2.04 mmol, 1.0 eq.) and compound W (257 mg, 2.45 mmol, 1.2 eq.) in THF (20 mL) was added DIPEA (791 mg, 6.12 mmol, 3.0 eq.) and NaI (92 mg, 0.612 mmol, 0.3 eq.). The mixture was stirred at at 70° C. for 16 hours. LCMS showed the reaction was completed. The mixture was poured into water and extracted with EA. The combined organic layers were washed with brine, dried over $Na_2SO_4$ and concentrated. The residue was purified by column chromatography on silica gel (DCM/MeOH=20/1) to give the title compound (340 mg, 46% yield) as colorless oil. LCMS: Rt: 0.710 min; MS m/z (ESI): 361.2 [M+H]$^+$.

Step 5: Preparation of Compound 64-6

To a solution of compound 64-5 (340 mg, 0.94 mmol, 1.0 eq.) in DCM (10 mL) was added compound X (659 mg, 2.35 mmol, 2.5 eq.), EDCI (541 mg, 2.82 mmol, 3.0 eq.), DMAP (57 mg, 0.47 mmol, 0.5 eq.) and DIPEA (607 mg, 4.70 mmol, 5.0 eq.). The mixture was stirred under reflux for 16 hours. LCMS showed the reaction worked completely. The reaction mixture was poured into water and extracted with DCM. The combined organic layers were washed with brine, dried over $Na_2SO_4$ and concentrated. The residue was purified by column chromatography on silica gel (DCM/MeOH=40/1) to give the title compound (360 mg, 43% yield) as colorless oil. LCMS: Rt: 1.387 min; MS m/z (ESI): 885.5 [M+H]$^+$.

Step 6: Preparation of Compound 64

To a solution of compound 64-6 (310 mg, 0.35 mmol, 1.0 eq.) in MeOH (5 mL) was added HCl in Dioxane (0.5 mL, 4.0 M). The mixture was stirred at room temperature for 2 hours. The reaction mixture was diluted with DCM and washed with saturated $NaHCO_3$ aqueous solution. The mixture was extracted with DCM. The combined organic layers were washed with brine, dried over $Na_2SO_4$ and concentrated. The residue was purified by prep-HPLC to give the title compound (65 mg, 24% yield) as colorless oil.

$^1$H NMR (400 MHz, CDCl$_3$) δ: 0.87-0.91 (m, 6H), 1.30-1.37 (m, 30H), 1.63-1.86 (m, 6H), 1.95-2.07 (m, 12H), 2.30-2.38 (m, 6H), 2.39-2.54 (m, 6H), 2.75-2.79 (m, 6H), 3.10-3.26 (m, 1H), 3.90-4.09 (m, 2H), 4.14-4.20 (m, 3H), 5.29-5.42 (m, 8H). LCMS: Rt: 1.140 min; MS m/z (ESI): 771.5 [M+H]$^+$.

7.61 Example 61: Preparation of Compound 65

56

MsCl, DIEA, DCM 65-1

-continued

65

Step 1: Preparation of Compound 65-1

To a mixture of compound 56 (402 mg, 0.5 mmol, 1.0 eq.) in DCM (8 mL) was added DIEA (193.5 mg, 1.5 mmol, 3.0 eq.), MsCl (68 mg, 0.6 mmol, 1.2 eq.). The mixture was stirred at RT for 2 hours. TLC showed the reaction was complete. The mixture was quenched with water (50 mL), extracted over EA, concentrated in vacuo. The crude product was used for next step without further purification (380 mg, crude).

Step 2: Preparation of Compound 65

To a mixture of compound 65-1 (200 mg, 0.23 mmol, 1.0 eq.) in ACN (10 mL) were added K$_2$CO$_3$ (95.2 mg, 0.69 mmol, 3.0 eq.), Cs$_2$CO$_3$ (22.9 mg, 0.07 mmol, 0.3 eq.), NaI (10 mg). Then compound Y (51.75 mg, 0.69 mmol, 3.0 eq.) was added. The mixture was stirred at 80° C. for 16 hours.

LCMS showed the reaction was complete. The mixture was quenched with wather (50 mL), extracted over EA, concentrated in vacuo. The mixture was concentrated and purified by prep-HPLC to give the title compound (15 mg, 7.5% yield) as yellow oil.

$^1$H NMR (400 MHz, CCl$_3$D): δ:0.79-0.83 (m, 12H), 1.23-1.27 (m, 62H), 1.29-1.37 (m, 2H), 1.51-1.61 (m, 2H), 1.76-1.93 (m, 7H), 2.13-2.16 (m, 4H), 2.17-2.25 (m, 3H), 2.41-2.51 (m, 7H), 3.05-3.06 (m, 1H), 3.52-3.54 (m. 2H), 3.92-4.03 (m, 4H). LCMS: Rt: 0.588 min; MS m/z (ESI): 863.6 [M+H]$^+$.

The following compounds were prepared in analogous fashion as Compound 65, using corresponding starting material.

| Compound | Characterization |
|---|---|
| Compound 66 | $^1$H NMR (400 MHz, CCl$_3$D): δ: 0.86-0.89 (m, 12H), 1.26-1.32(m, 58H), 1.33-1.51 (m, 8H), 1.82-2.02 (m, 7H), 2.22-2.25(m, 7H), 2.40-2.57 (m, 7H), 3.04-3.20 (m, 1H), 3.55-3.57 (m, 2H), 3.99-4.09 (m, 4H). LCMS: Rt: 0.588 min; MS m/z (ESI): 863.6 [M + H]$^+$. |
| Compound 67 | $^1$H NMR (400 MHz, CCl$_3$D): δ: 0.86-0.89 (m, 12H), 1.25-1.29(m, 62H), 1.39-1.42 (m, 4H), 1.57-1.69(m, 3H), 1.77-1.85 (m, 2H), 1.96-2.10(m, 4H), 2.23-2.24(m, 4H), 2.50-3.18 (m, 11H), 3.61-3.75 (m, 2H), 4.02-4.07 (m, 4H). LCMS: Rt: 0.903 min; MS m/z (ESI): 877.6 [M + H]$^+$. |

7.62 Example 62: Preparation of Compound 68

SM2

EDCl, DMAP, DIEA, DCM 68-1

Pd/C, MeOH, H2

68-2

MsCl, DIEA, DCM 68-3

K₂CO₃, Cs₂CO₃, ACN

68

Step 1: Preparation of Compound 68-1

To a solution of compound SM2 (14.0 g, 16.8 mmol, 1.0 eq.) and compound S (13.6 g, 50.4 mmol, 3.0 eq.) in DCM (100 mL) were added DIEA (10.8 g, 83.9 mmol, 5.0 eq.), EDCI (9.7 g, 50.4 mmol, 3.0 eq.) and DMAP (1.0 g, 8.4 mmol, 0.5 eq.). The mixture was stirred at 40° C. for 16 hours. TLC showed the reaction was completed. The reaction mixture was concentrated and purified by column chromatography on silica gel (PE/EA=50:1) to give the title compound 68-1 (10.1 g, crude) as yellow oil.

Step 2: Preparation of Compound 68-2

To a mixture of compound 68-1 (10.1 g, 13.6 mmol, 1.0 eq.) and Pd/C (1 g, 10%) in the MeOH (50 mL) and THF (50 mL) was added compound T (199 mg, 14.9 mmol, 1.1 eq.) at room temperature. The mixture was stirred for 24 h at room temperature under hydrogen atmosphere. TLC showed the reaction was completed. The mixture was filtered, the filtrate was concentrated and then purified by column chromatography on silica gel (PE/EA=10:1) to give the title compound 68-2 (9.1 g, crude) as colorless oil. $^1$H NMR (400 MHz, CDCl$_3$) δ: 0.86-0.90 (m, 12H), 1.26-1.46 (m, 53H), 1.56-1.62 (m, 2H), 1.83 (s, 2H), 1.96-2.02 (m, 1H), 2.23-2.24 (m, 4H), 3.64 (s, 2H), 4.02-4.11 (m, 4H).

Step 3: Preparation of Compound 68-3

A mixture of compound 68-2 (150 mg, 0.23 mmol, 1.0 eq.), MsCl (32 mg, 0.28 mmol, 1.2 eq.), DIEA (89 mg, 0.69 mmol, 3.0 eq.) in DCM (5 mL) was stirred for an hour at ambient temperature. The mixture was quenched with water, extracted over EA, dried and concentrated to give the desired product 68-3 (212 mg, crude) as yellow oil.

Step 4: Preparation of Compound 68

A mixture of compound 68-3 (212 mg, 0.29 mmol, 1.0 eq.), compound E (50 mg, 0.35 mmol, 1.2 eq.), K$_2$CO$_3$ (120 mg, 0.87 mmol, 3.0 eq.) and Cs$_2$CO$_3$ (3 mg, 0.01 mmol, 0.03 eq.) in ACN (3 mL) was stirred overnight at 80° C. The mixture was concentrated, purified by Prep-HPLC to give the desired product 68 (18 mg, 7.98% yield) as light yellow oil.

$^1$H NMR (400 MHz, CDCl$_3$) δ: 0.83-0.92 (m, 12H), 1.17-1.37 (m, 56H), 1.38-1.45 (m, 2H), 1.64-1.67 (m, 2H), 1.70-1.86 (m, 6H), 1.92-2.04 (m, 2H), 2.19-2.26 (m, 4H), 2.40-2.49 (m, 3H), 2.57-2.65 (m, 2H), 3.41-3.51 (m, 2H), 3.97-4.12 (m, 4H). LCMS: Rt: 0.080 min; MS m/z (ESI): 778.5 [M+H]$^+$.

7.63 Example 63: Preparation of Compound 69

68-3

69-1

69-2

69

Step 1: Preparation of Compound 69-1

A mixture of compound 68-3 (361 mg, 0.49 mmol, 1.0 eq.), compound I (68 mg, 0.59 mmol, 1.2 eq.), $K_2CO_3$ (204 mg, 1.48 mmol, 3.0 eq.) and $Cs_2CO_3$ (5 mg, 0.01 mmol, 0.03 eq.) in ACN (7 mL) was stirred overnight at 80° C. The mixture was concentrated, purified by FCC to give the desired product 69-1 (78 mg, 21.06% yield) as colorless oil. LCMS: Rt: 1.290 min; MS m/z (ESI): 750.7 [M+H]$^+$.

Step 2: Preparation of Compound 69-2

A mixture of compound 69-1 (78 mg, 0.10 mmol, 1.0 eq.), MsCl (14 mg, 0.12 mmol, 1.2 eq.), DIEA (40 mg, 0.31 mmol, 3.0 eq.) in DCM (2 mL) was stirred for an hour at ambient temperature. The mixture was quenched with water, extracted over EA, dried and concentrated to give the desired product 69-2 (98 mg, crude) as yellow oil.

Step 3: Preparation of Compound 69

A mixture of compound 69-2 (78 mg, 0.09 mmol, 1.0 eq.), compound U (10 mg, 0.11 mmol, 1.2 eq.), $K_2CO_3$ (39 mg, 0.28 mmol, 3.0 eq.) and $Cs_2CO_3$ (1 mg, 0.003 mmol, 0.03 eq.) in ACN (3 mL) was stirred overnight at 80° C. The mixture was concentrated, purified by Prep-HPLC to give the desired product 69 (23 mg, 8.75% yield) as light yellow oil.

$^1$H NMR (400 MHz, CDCl$_3$) δ: 0.83-0.92 (m, 12H), 0.98-1.06 (m, 3H), 1.17-1.47 (m, 52H), 1.54-1.72 (m, 5H), 1.78-2.06 (m, 8H), 2.20-2.27 (m, 4H), 2.37-2.46 (m, 4H), 2.49-2.66 (m, 5H), 3.01-3.12 (m, 1H), 3.52-3.59 (m, 2H), 3.98-4.11 (m, 4H). LCMS: Rt: 0.093 min; MS m/z (ESI): 821.6 [M+H]$^+$.

The following compounds were prepared in analogous fashion as Compound 69, using corresponding starting material.

| Compound | Characterizaton |
|---|---|
| Compound 76 | $^1$H NMR (400 MHz, CDCl$_3$) δ: 0.86-0.95 (m, 15H), 1.26-1.38 (m, 56H), 1.63-1.66 (m, 4H), 1.80-1.86 (m, 2H), 1.96-2.09 (m, 4H), 2.23-2.24 (m, 4H), 2.64 (s, 4H), 2.85-2.92 (m, 6H), 3.09 (s, 1H), 3.32-3.38 (m, 1H), 3.72-3.78 (m, 1H), 3.99-4.11 (m, 4H). LCMS: Rt: 1.950 min; MS m/z (ESI): 835.7 [M + H]$^+$. |
| Compound 78 | $^1$H NMR (400 MHz, CDCl$_3$) δ: 0.86-0.89 (m, 12H), 1.25-1.38 (m, 52H), 1.71-1.80 (m, 12H), 2.06-2.24 (m, 4H), 2.82-2.93 (m, 6H), 3.11-4.00 (m, 12H), 4.01-4.05 (m, 4H), 5.18-5.34 (m, 2H). LCMS: Rt: 1.575 min; MS m/z (ESI): 861.7 [M + H]$^+$. |
| Compound 79 | $^1$H NMR (400 MHz, CDCl$_3$) δ: 0.86-0.90 (m, 12H), 1.26-1.47 (m, 55H), 1.58-1.70 (m, 4H), 1.82-2.01 (m, 11H), 2.22-2.24 (m, 4H), 2.43-2.58 (m, 8H), 3.13-3.26 (m, 2H), 3.58 (s, 2H), 3.99-4.11 (m, 4H). LCMS: Rt: 1.870 min; MS m/z (ESI): 847.7 [M + H]$^+$. |

-continued
| Compound | Characterizaton |
|---|---|
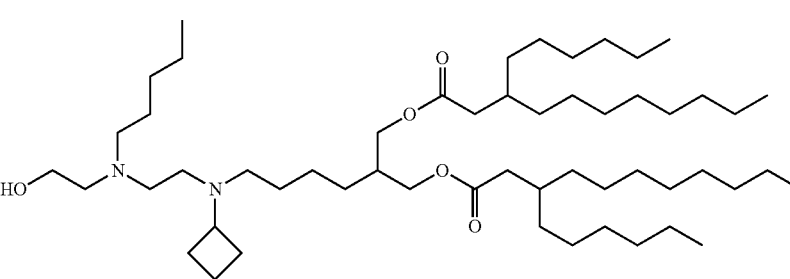
Compound 80
¹H NMR (400 MHz, CDCl₃) δ: 0.86-0.91 (m, 15H), 1.26-1.48 (m, 60H), 1.82-2.02 (m, 8H), 2.22-2.24 (m, 4H), 2.49-2.65 (m, 8H), 3.10-3.15 (m, 1H), 3.60 (s, 2H), 3.99-4.11 (m, 4H). LCSM: Rt: 1.850 min; MS m/z (ESI): 835.7 [M + H]⁺.
Compound 83
¹H NMR (400 MHz, CDCl₃) δ: 4.14-3.98 (m, 4H), 3.58 (s, 2H), 3.21 (s, 1H), 2.72-2.36 (m, 8H), 2.23 (d, J = 6.9 Hz, 4H), 2.10-2.93 (m, 4H), 1.83 (s, 2H), 1.74-1.00 (m, 64H), 0.97-0.86 (m, 15H). LCMS: Rt: 1.970 min; MS m/z (ESI): 849.8 [M + H]⁺.
Compound 109
¹H NMR (400 MHz, CDCl₃) δ: 0.86-0.93 (m, 15H), 1.26-1.35 (m, 56H), 1.54-1.65 (m, 3H), 1.72-2.04 (m, 9H), 2.23 (d, J = 6.8 Hz, 4H), 2.37-2.63 (m, 10H), 3.00-3.12 (m, 1H), 3.52-3.58 (m, 2H), 3.99-4.13 (m, 4H). LCMS: Rt: 2.207 min; MS m/z (ESI): 849.9 [M + H]⁺.
Compound 110
¹H NMR (400 MHz, CDCl₃) δ: 0.86-0.91 (m, 15H), 1.26-1.68 (m, 63H), 1.83-1.99 (m, 7H), 2.22-2.24 (m, 4H), 2.39-2.61 (m, 10H), 3.05-3.09 (m, 1H), 3.53-3.55 (m, 2H), 3.99-4.09 (m, 4H). LCMS: Rt: 2.127 min; MS m/z (ESI): 863.9 [M + H]⁺.

-continued
| Compound | Characterizaton |
|---|---|
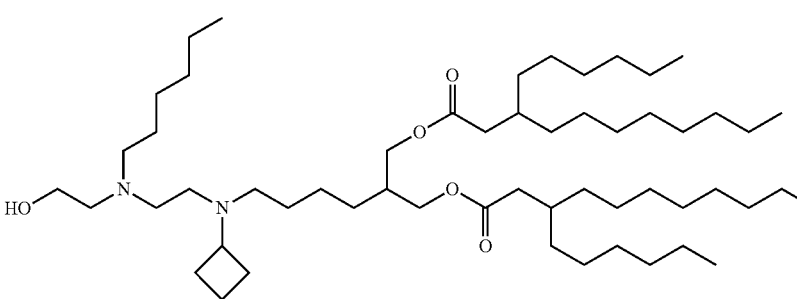
Compound 111
¹H NMR (400 MHz, CDCl₃) δ: 0.86-0.90 (m, 15H), 1.26-1.44 (m, 63H), 1.54-1.68 (m, 2H), 1.79-2.01 (m, 7H), 2.23-2.24 (m, 4H), 2.36-2.63 (m, 10H), 3.01-3.12 (m, 1H), 3.51-3.58 (m, 2H), 3.99-4.11 (m, 4 H). LCMS: Rt: 2.397 min; MS m/z (ESI): 877.9 [M + H]⁺.
Compound 112
¹H NMR (400 MHz, CDCl₃) δ: 0.86-0.90 (m, 12H), 1.26-2.03 (m, 72H), 2.22-2.24 (m, 4H), 2.37-2.46 (m, 4H), 2.56-2.66 (m, 4H), 3.02-3.14 (m, 2H), 3.52-3.59 (m, 2H), 3.99-4.09 (m, 4H). LCMS: Rt: 2.187 min; MS m/z (ESI): 861.9 [M + H]⁺.
Compound 113
¹H NMR (400 MHz, CDCl₃) δ: 0.86-0.90 (m, 12H), 1.07-1.43 (m, 58H), 1.56-1.97 (m, 15H), 2.22-2.63 (m, 13H), 3.03-3.10 (m, 1H), 3.50-3.57 (m, 2H), 3.99-4.09 (m, 4H), 5.09-5.30 (m, 1H). LCMS: Rt: 2.217 min; MS m/z (ESI): 875.9 [M + H]⁺.
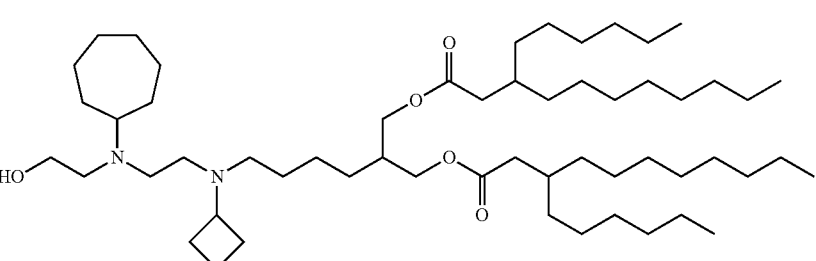
Compound 114
¹H NMR (400 MHz, CDCl₃) δ: 0.86-0.90 (m, 12H), 1.26-1.48 (m, 60H), 1.56-1.61 (m, 3H), 1.68-1.73 (m, 3H), 1.81-2.02 (m, 10H), 2.23 (d, J = 6.8 Hz, 4H), 2.34-2.42 (m, 4H), 2.49-2.61 (m, 5H), 3.02-3.13 (m, 1H), 3.47-3.54 (m, 2H), 3.98-4.11 (m, 4H). LCMS: Rt: 2.367 min; MS m/z (ESI): 890.0 [M + H]⁺.

43-3

Z
TsOH•H₂O 70-1

Pd/C
con. HCl 70-2

SOCl₂,
DCM 70-3

K
DIPEA
NaI, THF

70

Step 1: Preparation of Compound 70-1

A mixture of compound 43-3 (410 mg, 1.06 mmol, 1.0 eq.), compound Z (720 mg, 2.66 mmol, 2.5 eq.), TsOH (20 mg) in toluene (50 mL) was stirred for 2 h at 180° C. TLC showed the reaction was completed. The mixture was concentrated and purified by column chromatography silica gel (EA:PE=0% to 5%) to give the compound 70-1 (700 mg, 78% yield) as colorless oil. LCMS: Rt: 1.750 min; MS m/z (ESI): 888.7 [M+H]⁺.

Step 2: Preparation of Compound 70-2

A mixture of compound 70-1 (500 mg, 0.56 mmol, 1.0 eq.) and Pd/C (110 mg, 0.56 mmol, 1.0 eq.) in solution of MeOH (10 mL) and concentrated HCl (5 drops) was stirred for 16 h under H₂ at RT. TLC showed the reaction was completed. The mixture was concentrated to give the desired product 70-2 (310 mg, 70% yield) as colorless oil. LCMS: Rt: 1.490 min; MS m/z (ESI): 798.7 [M+H]⁺.

Step 3: Preparation of Compound 70-3

To a solution of compound 70-2 (150 mg, 0.19 mmol, 1.0 eq.) was dissolved in DCM (10 mL) was added SOCl₂ (113 mg, 0.95 mmol, 5.0 eq.) at RT. The mixture was stirred for 16 hours at 35° C. TLC showed the reaction was completed, the mixture was evaporated under reduced pressure to provide 70-3 (150 mg, crude) as yellow oil.

Step 4: Preparation of Compound 70

A mixture of compound K (93 mg, 0.92 mmol, 1.2 eq.), compound 70-3 (150 mg, 0.38 mmol, 1.0 eq.), DIEA (70 mg, 0.54 mmol, 3.0 eq.), NaI (7 mg, 0.05 mmol, 0.3 eq.) in THF (10 mL) was stirred overnight at 75° C. The mixture was concentrated under vacuum. The residual was purified by Prep-HPLC to give the desired product 70 (16 mg, 10% yield) as yellow oil.

¹H NMR (400 MHz, CDCl₃) δ: 0.37-0.55 (m, 2H), 0.56-0.77 (m, 1H), 0.78-0.96 (m, 12H), 1.13-1.33 (m, 54H), 1.51-1.70 (m, 2H), 1.84-2.34 (m, 10H), 2.50-2.65 (m, 5H), 2.75-2.93 (m, 4H), 2.94-3.07 (m, 1H), 3.19-3.43 (m, 1H), 3.44-3.67 (m, 3H), 3.68-3.82 (m, 4H), 3.83-3.93 (m, 1H), 3.94-4.05 (m, 4H). LCMS: Rt: 1.540 min; MS m/z (ESI): 881.8 [M+H]⁺.

The following compounds were prepared in analogous fashion as Compound 70, using corresponding starting material.

| Compound | Characterization |
|---|---|
| 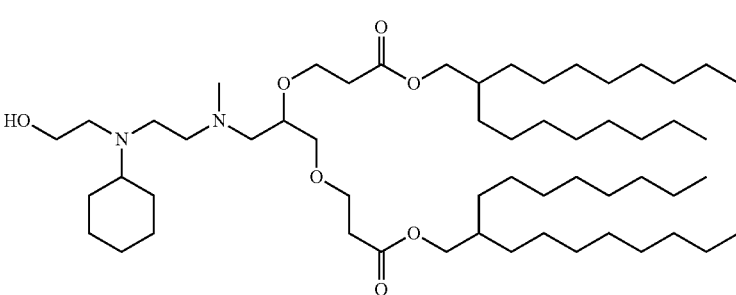<br>Compound 71 | ¹H NMR (400 MHz, CDCl₃) δ: 0.73-0.95 (m, 12H), 1.05-1.35 (m, 56H), 1.36-1.47 (m, 1H), 1.48-1.69 (m, 6H), 1.70-1.88 (m, 3H), 1.89-2.19 (m, 3H), 2.20-2.36 (m, 3H), 2.37-2.56 (m, 3H), 2.57-2.71 (m ,7H), 2.96-3.22 (m, 2H), 3.42-3.65 (m, 3H), 3.66-3.75 (m, 1H), 3.76-3.82 (m, 2H), 3.83-3.89 (m, 1H), 3.90-3.91 (m, 1H), 3.92-4.04 (m, 4H). LCMS: Rt: 2.100 min; MS m/z (ESI): 909.8 [M + H]⁺. |
| Compound 72 | ¹H NMR (400 MHz, CDCl₃) δ: 0.86-0.90 (m, 12H), 1.26-1.30 (m, 66H), 1.53-1.87 (m ,6H), 2.49-2.56 (m, 6H), 2.57-2.60 (m, 8H), 3.46-3.60 (m, 4H), 3.72-3.91 (m, 4H), 3.96-3.98 (m, 4H). LCMS: Rt: 0.617 min; MS m/z (ESI): 923.8 [M + H]⁺. |
| Compound 73 | ¹H NMR (400 MHz, CDCl₃) δ: 0.72-0.97 (m, 12H), 1.10-1.35 (m, 55H), 1.36-1.48 (m, 6H), 1.50-1.65 (m, 5H), 1.66-1.77 (m, 2H), 1.78-1.90 (m, 2H), 1.91-2.16 (m, 5H), 2.17-2.34 (m, 3H), 2.35-2.71 (m, 10H), 3.37-3.64 (m, 3H), 3.65-3.91 (m, 5H), 3.92-4.09 (m, 4H). LCMS: Rt: 1.050 min; MS m/z (ESI): 937.8 [M + H]⁺. |

-continued

| Compound | Characterization |
|---|---|
| <br>Compound 74 | $^1$H NMR (400 MHz, CDCl$_3$) δ: 0.72-0.96 (m, 12H), 1.02-1.31 (m, 55H), 1.32-1.53 (m, 6H), 1.54-1.69 (m, 8H), 1.70-1.85 (m, 3H), 1.86-2.21 (m, 9H), 2.22-2.35 (m, 1H), 2.36-2.67 (m, 8H), 2.90-3.16 (m, 2H), 3.44-3.58 (m, 2H), 3.64-3.90 (m, 5H), 3.91-4.05 (m, 3H). LCMS: Rt: 2.070 min; MS m/z (ESI): 951.8 [M + H]$^+$. |

7.65 Example 66: Preparation of Compound 77

Compound 77

$^1$H NMR (400 MHz, CDCl$_3$) δ: 0.86-0.89 (m, 12H), 1.18-1.55 (m, 40H), 1.73-1.79 (m, 14H), 1.86-1.96 (m, 10H), 2.23-2.25 (m, 4H), 2.96-2.99 (m, 4H), 3.74-3.94 (m, 2H), 3.95-3.98 (m, 5H), 4.01-4.03 (m, 1H), 4.06-4.09 (m, 1H). LCMS: Rt: 1.345 min; MS m/z (ESI): 764.6 [M+H]$^+$.

7.66 Example 67: Preparation of Compound 81

81-1

81-2

81-3

81-4

81

Step 1: Preparation of Compound 81-1

To a solution of compound S (5.2 g, 19.2 mmol, 1.0 eq.) and compound SM2 (5.5 g, 23.0 mmol, 1.2 eq.) in DCM (100 mL) were added EDCI (11.0 g, 57.6 mmol, 3.0 eq.), DMAP (1.2 g, 9.6 mmol, 0.3 eq.) and DIPEA (12.4 g, 9.6 mmol, 0.3 eq.). The mixture was stirred under 50° C. for 16 hours. After which the TLC showed complete disappearance of starting compound S, the reaction mixture was poured into water and extracted with DCM. The combined organic layers were washed with brine, dried over Na$_2$SO$_4$ and concentrated. The crude product was purified by column chromatography silica gel (PE/EA=20/1) to give the title compound 81-1 (3.8 g, 40.43% yield) as yellow oil. $^1$H NMR (400 MHz, CDCl$_3$) δ: 0.86-0.96 (m, 6H), 1.26-1.49 (m, 28H), 1.59-1.66 (m, 2H), 1.73-2.84 (m, 2H), 1.99-2.08 (m, 1H), 2.20-2.31 (m, 2H), 3.42-3.64 (m, 4H), 4.02-4.24 (m, 2H), 4.46-4.57 (m, 2H), 7.26-7.37 (m, 5H).

Step 2: Preparation of Compound 81-2

To a solution of compound 81-1 (900 mg, 1.83 mmol, 1.0 eq.) and compound V (682 mg, 3.66 mmol, 2.0 eq.) in DCM (20 mL) were added EDCI (1.05 g, 5.49 mmol, 3.0 eq.), DMAP (67 mg, 0.55 mmol, 0.3 eq.) and DIPEA (71 mg, 0.55 mmol, 0.3 eq.). The mixture was stirred at 50° C. for 16 hours. TLC showed the reaction was completed. The reaction mixture was poured into water and extracted with DCM. The combined organic layers were washed with brine dried over Na$_2$SO$_4$ and concentrated. The residue was purified by column chromatography silica gel (0-1% EA in PE) to give the title compound 81-2 (1.15 mg, 94.96% yield) as colorless oil. $^1$H NMR (400 MHz, CDCl$_3$) δ: 0.86-0.89 (m, 9H), 1.25-1.40 (m, 42H), 1.59-1.62 (m, 4H), 1.77-1.83 (m, 1H), 1.97-2.03 (m, 1H), 2.20-2.33 (m, 4H), 3.45-3.48 (m, 2H), 4.00-4.10 (m, 4H), 4.47-4.53 (m, 2H), 7.26-7.40 (m, 5H).

Step 3: Preparation of Compound 81-3

To a solution of compound 81-2 (1.15 g, 1.74 mmol, 1.0 eq.) in MeOH (20 mL) were added Pd/C (288 mg) and CHCl$_2$CH$_2$Cl (279 mg, 2.09 mmol, 1.2 eq.). The mixture was stirred at room temperature under H$_2$ for 2 hours. TLC showed the reaction was completed. The reaction mixture was filtrated by a pad of Celite and washed with MeOH. The filtrate was concentrated and purified by column chromatography silica gel (PE/EA=10/1) to give the title compound 81-3 (859 mg, 86.8% yield) as colorless oil. $^1$H NMR (400 MHz, CDCl$_3$) δ: 0.86-0.90 (m, 9H), 1.26-1.36 (m, 38H), 1.37-1.44 (m, 4H), 1.54-1.64 (m, 5H), 1.64-1.95 (m, 1H), 1.99-2.06 (m, 1H), 2.20-2.34 (m, 4H), 3.63-3.69 (m, 2H), 4.02-4.13 (m, 4H).

Step 4: Preparation of Compound 81-4

To a solution of compound 81-3 (850 mg, 1.49 mmol, 1.0 eq.) in DCM (15 mL) were added SOCl$_2$ (532 mg, 4.47 mol, 3.0 eq.) and pyridine (236 mg, 2.98 mmol, 2.0 eq.). The mixture was stirred at room temperature for 2 hours. TLC showed the reaction was completed. The reaction mixture was extracted with DCM and water. The combined organic layers were washed with brine dried over Na$_2$SO$_4$ and concentrated to give the title compound 81-4 (850 mg, 97.14% yield) as yellow oil.

Step 5: Preparation of Compound 81

To a solution of compound 81-4 (850 mg, 1.45 mmol, 1.0 eq.) in THF (10 mL) were added compound I (334 mg, 2.9 mmol, 2.0 eq.), DIPEA (562 mg, 4.35 mmol, 3.0 eq.) and NaI (66 mg, 0.44 mmol, 0.3 eq.). The reaction mixture was stirred at 70° C. for 16 hours. LCMS showed the reaction was completed. The reaction mixture was poured into water and extracted with EA. The organic layer was washed with brine, dried over Na$_2$SO$_4$ and concentrated. The residue was purified by column chromatography silica gel (DCM/MeOH=70/1-50/1) to give crude title compound 81 (418 mg, 43.27% yield). Crude compound 81 (100 mg) was purified by prep-HPLC to give the title compound (28 mg, 28.0% yield) as colorless oil.

$^1$H NMR (400 MHz, CDCl$_3$) δ: 0.86-0.90 (m, 9H), 1.16-1.39 (m, 45H), 1.55-1.66 (m, 5H), 1.75-1.87 (m, 2H), 1.94-2.11 (m, 4H), 2.23-2.32 (m, 4H), 2.48-2.69 (m, 3H), 3.09-3.26 (m, 1H), 3.46-3.68 (m, 2H), 4.01-4.11 (m, 4H). LCMS: Rt: 1.185 min; MS m/z (ESI): 666.5 [M+H]$^+$.

The following compounds were prepared in analogous fashion as Compound 81, using corresponding starting material.

| Compound | Characterization |
|---|---|
| 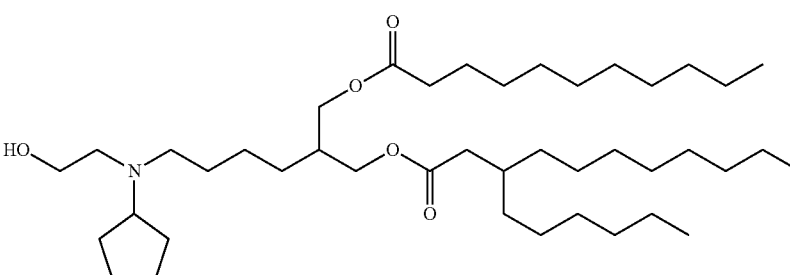<br>Compound 84 | $^1$H NMR (400 MHz, CDCl$_3$) δ: 4.12-3.94 (m, 4H), 2.36-2.19 (m, 4H), 1.98 (s, 2H), 1.83 (s, 3H), 1.59-1.51 (m, 6H), 1.45-1.26 (m, 53H), 0.88 (t, J = 6.8 Hz, 9H). LCMS: Rt: 1.205 min; MS m/z (ESI): 680.6 [M + H]$^+$. |

-continued

| Compound | Characterization |
|---|---|

Compound 85

$^1$H NMR (400 MHz, CDCl$_3$) δ: 4.11-3.92 (m, 5H), 2.33-2.19 (m, 5H), 2.03-1.92 (m, 2H), 1.88-1.88 (m, 3H), 1.60-1.51 (d, 5H), 1.45-1.26 (m, 54H), 0.88 (t, J = 6.8 Hz, 9H). LCMS: Rt: 22.575 min; MS m/z (ESI): 694.6 [M + H]$^+$.

Compound 86

$^1$H NMR (400 MHz, CDCl$_3$) δ: 0.86-0.89 (m, 9H), 1.25-1.73 (m, 55H), 1.75-1.82 (m, 6H), 1.93-1.97 (m, 4H), 1.98-2.04 (m, 4H), 2.28-2.29 (m, 5H), 2.30-2.70 (m, 3H), 2.51-4.00 (m, 2H), 4.04-4.09 (m, 5H). LCMS: Rt: 1.600 min; MS m/z (ESI): 764.8 [M + H]$^+$.

Compound 87

$^1$H NMR (400 MHz, CDCl$_3$) δ: 0.86-0.89 (m, 9H), 1.25-1.68 (m, 51H), 1.69-1.86 (m, 13H), 1.95-2.04 (m, 4H), 2.23-2.30 (m, 2H), 2.31-2.41 (m, 6H), 2.85-3.28 (m, 3H), 3.31-3.47 (m, 2H), 4.03-4.09 (m, 5H). LCMS: Rt: 1.900 min; MS m/z (ESI): 778.8 [M + H]$^+$.

Compound 88

$^1$H NMR (400 MHz, CDCl$_3$) δ: 0.82-0.90 (m, 9H), 1.15-1.47 (m, 62H), 1.55-1.87 (m, 12H), 1.93-2.01 (m, 1H), 2.19-2.30 (m, 4H), 2.35-2.40 (m, 1H), 2.43-2.58 (m, 1H), 2.69-2.82 (m, 1H), 3.36-3.57 (m, 2H), 4.03-4.11 (m, 4H). LCMS: Rt: 1.325 min; MS m/z (ESI): 792.7 [M + H]$^+$.

-continued

| Compound | Characterization |
|---|---|

Compound 92

<sup></sup>¹H NMR (400 MHz, CDCl₃) δ: 0.86-0.90 (m, 9H), 1.26-1.44 (m, 48H), 1.53-1.83 (m, 12H), 1.95-1.99 (m, 1H), 2.23-2.32 (m, 4H), 2.39-2.43 (m, 2H), 2.56-2.63 (m, 3H), 3.46-3.48 (m, 2H), 4.00-4.10 (m, 4H). LCMS: Rt: 0.093 min; MS m/z (ESI): 708.5 [M + H]⁺.

Compound 93

¹H NMR (400 MHz, CDCl₃) δ: 0.86-0.90 (m, 9H), 1.26 (s, 39H), 1.35-1.48 (m, 11H), 1.59-1.83 (m, 12H), 1.95-2.01 (m, 1H), 2.23-2.32 (m, 4H), 2.37-2.41 (m, 2H), 2.54-2.56 (m, 2H), 2.75 (s, 1H), 3.46-3.48 (m, 2H), 4.00-4.10 (m, 4H). LCMS: Rt: 0.080 min; MS m/z (ESI): 722.5 [M + H]⁺.

Compound 94

¹H NMR (400 MHz, CDCl₃) δ: 0.86-0.90 (m, 9H), 1.26-1.38 (m, 43H), 1.51-1.63 (m, 7H), 1.77-1.86 (m, 4H), 1.95-2.00 (m, 1H), 2.23-2.32 (m, 4H), 2.52-2.77 (m, 4H), 3.18-3.32 (m, 2H), 3.60-3.71 (m, 2H), 4.00-4.10 (m, 4H), 5.22-5.30 (m, 1H). LCMS: Rt: 1.370 min; MS m/z (ESI): 680.8 [M + H]⁺.

Compound 98

¹H NMR (400 MHz, CDCl₃) δ: 4.11-3.99 (m, 4H), 3.59-3.54 (m, 2H), 3.21-3.10 (m, 1H), 2.57 (s, 2H), 2.46 (s, 2H), 2.30 (t, J = 7.6 Hz, 2H), 2.24 (d, J = 6.9 Hz, 2H), 2.10-1.80 (m, 6H), 1.70-1.56 (m, 4H), 1.45 (s, 2H), 1.34-1.26 (m, 53H), 0.88 (t, J = 6.8 Hz, 9H). LCMS: Rt: 2.320 min; MS m/z (ESI): 758.7 [M + Na]⁺.

-continued

| Compound | Characterization |
|---|---|
|

Compound 99 | $^1$H NMR (400 MHz, CDCl$_3$) δ: 4.10-4.00 (m, 4H), 3.74-3.59 (m, 1H), 2.91-2.63 (m, 2H), 2.30-2.23 (m, 4H), 2.03-1.59 (m 14H), 1.37-1.26 (m, 57H), 0.87 (d, J = 6.8 Hz, 9H). LCMS: Rt: 1.680 min; MS m/z (ESI): 750.8 [M + H]$^+$. |

7.67 Example 68: Preparation of Compound 82

Compound 82-1
    LCMS: Rt: 1.487 min; MS m/z (ESI): 684.5 [M+H]$^+$.
Compound 82
    $^1$H NMR (400 MHz, CDCl$_3$) δ:0.86-0.90 (i, 9H), 1.26-1.39 (m, 45H), 1.56-1.75 (m, 6H), 1.78-2.09 (in, 10H), 2.23-2.36 (m, 5H), 2.46-2.68 (m, 7H), 3.08-3.26 (m, 2H), 3.53-3.65 (m, 2H), 4.00-4.11 (m, 4H). LCMS: Rt: 1.275 min; MS m/z (ESI): 763.5 [M+H]$^+$.

The following compounds were prepared in analogous fashion as Compound 82, using corresponding starting material.

| Compound | Characterization |
|---|---|
| Compound 115 | ¹H NMR (400 MHz, CDCl₃) δ: 0.86-0.93 (m, 12H), 1.26-1.99 (m, 59H), 2.22-2.61 (m, 14H), 3.03-3.10 (m, 1H), 3.53-3.56 (m, 2H), 4.02-4.07 (m, 4H). LCMS: Rt: 1.227 min; MS m/z (ESI): 765.8 [M + H]⁺. |
| Compound 116 | ¹H NMR (400 MHz, CDCl₃) δ: 0.86-0.91 (m, 12H), 1.26-2.00 (m, 61H), 2.22-2.61 (m, 14H), 3.04-3.09 (m, 1H), 3.53-3.56 (m, 2H), 4.01-4.07 (m, 4H). LCMS: Rt: 1.227 min; MS m/z (ESI): 779.8 [M + H]⁺. |

-continued

| Compound | Characterization |
|---|---|
| Compound 117 | ¹H NMR (400 MHz, CDCl₃) δ: 0.86-0.90 (m, 12H), 1.26-1.44 (m, 53H), 1.51-1.66 (m, 4H), 1.70-2.03 (m, 6H), 2.22-2.24 (m, 2H), 2.28-2.30 (m, 2H), 2.35-2.66 (m, 10H), 3.02-3.12 (m, 1H), 3.51-3.59 (m, 2H), 3.99-4.10 (m, 4H). LCMS: Rt: 1.177 min; MS m/z (ESI): 793.9 [M + H]⁺. |
| Compound 118 | ¹H NMR (400 MHz, CDCl₃) δ: 4.10-3.99 (m, 4H), 3.59-3.525 (m, 2H), 3.15-3.01 (m, 2H), 2.66-2.62 (m, 4H), 2.52 (s, 4H), 2.31-2.23 (m, 2H), 2.24-2.22 (m, 2H), 2.01-1.95 (m, 5H), 1.63-1.30 (m, 58H), 0.88 (t, J = 6.8 Hz, 9H). LCMS: Rt: 2.075 min; MS m/z (ESI): 777.7 [M + H]⁺. |

-continued

| Compound | Characterization |
|---|---|

Compound 119

¹H NMR (400 MHz, CDCl₃) δ: 0.89-1.18 (m, 9H), 1.20-1.41 (m, 51H), 1.42-1.57 (m, 5H), 1.43-1.60 (m, 4H), 1.89-1.94 (m, 4H), 2.22-2.36 (m, 10H), 2.27-2.53 (m, 4H), 2.61-3.06 (m, 1H), 3.06-3.99 (m, 2H), 4.02-4.06 (m, 4H). LCMS: Rt: 1.377 min; MS m/z (ESI): 791.9 [M + H]⁺.

Compound 120

¹H NMR (400 MHz, CDCl₃) δ: 0.89-1.18 (m, 9H), 1.20-1.41 (m, 51H), 1.42-1.57 (m, 8H), 1.43-1.60 (m, 8H), 1.89-1.94 (m, 8H), 2.22-2.36 (m, 5H), 2.27-2.57 (m, 1H), 3.06-3.99 (m, 2H), 4.02-4.06 (m, 4H). LCMS: Rt: 1.297 min; MS m/z (ESI): 805.8 [M + H]⁺.

Compound 121

¹H NMR (400 MHz, CDCl₃) δ: 0.89-0.92 (m, 12H), 1.35-1.45 (m, 59H), 1.42-1.45 (m, 4H), 1.58-1.62 (m, 6H), 1.99-2.24 (m, 4H), 2.27-2.31 (m, 10H), 2.51-2.53 (m, 1H), 2.55-4.01 (m, 2H), 4.03-4.06 (m, 4H). LCMS: Rt: 2.257 min; MS m/z (ESI): 835.9 [M + H]⁺.

-continued

| Compound | Characterization |
|---|---|
| Compound 122 | ¹H NMR (400 MHz, CDCl₃) δ: 0.86-0.92 (m, 12H), 1.25-1.35 (m, 60H), 1.38-1.47 (m, 4H), 1.56-1.69 (m, 6H), 1.82-2.00 (m, 4H), 2.22-2.32 (m, 10H), 2.59-3.08 (m, 1H), 3.53-3.57 (m, 2H), 3.98-4.10 (m, 4H). LCMS: Rt: 1.827 min; MS m/z (ESI): 849.7 [M + H]⁺. |
| Compound 123 | ¹H NMR (400 MHz, CDCl₃) δ: 0.86-0.90 (m, 12H), 1.25-1.44 (m, 62H), 1.58-1.66 (m, 4H), 1.88-2.00 (m, 6H), 2.22-2.32 (m, 4H), 2.39-2.62 (m, 10H), 3.06-3.56 (m, 1H), 3.99-4.02 (m, 2H), 4.01-4.10 (m, 4H). LCMS: Rt: 0.493 min; MS m/z (ESI): 863.7 [M + H]⁺. |

-continued

| Compound | Characterization |
| --- | --- |
| Compound 124 | $^1$H NMR (400 MHz, CDCl$_3$) δ: 0.89-1.31 (m, 9H), 1.35-1.45 (m, 58H), 1.46-1.53 (m, 8H), 1.55-1.63 (m, 7H), 1.96-1.97 (m, 4H), 1.98-1.99 (m, 4H), 2.22-2.27 (m, 4H), 12.59-2.63 (m, 2H), 3.54-3.57 (m, 2H), 4.01-4.03 (m, 4H). LCMS: Rt: 2.377 min; MS m/z (ESI): 847.9 [M + H]$^+$. |
| Compound 125 | $^1$H NMR (400 MHz, CDCl$_3$) δ: 0.88-1.05 (m, 9H), 1.07-1.43 (m, 60H), 1.45-1.68 (m, 10H), 1.75-1.80 (m, 5H), 1.90-2.32 (m, 9H), 2.37-2.63 (m, 4H), 3.05-3.10 (m, 1H), 3.49-4.00 (m, 2H), 4.01-4.10 (m, 4H). LCMS: Rt: 0.480 min; MS m/z (ESI): 861.8 [M + H]$^+$. |
| Compound 126 | $^1$H NMR (400 MHz, CDCl$_3$) δ: 0.86-0.90 (m, 9H), 1.25-1.70 (m, 68H), 1.78-1.99 (m, 9H), 2.22-2.51 (m, 8H), 2.52-2.60 (m, 5H), 3.00-3.15 (m, 2H), 3.49-3.52 (m, 2H), 4.01-4.09 (m, 4H). LCMS: Rt: 0.480 min; MS m/z (ESI): 875.8 [M + H]$^+$. |

-continued

| Compound | Characterization |
|---|---|
| <br>Compound 127 | $^1$H NMR (400 MHz, CDCl$_3$) δ: 4.12-3.99 (m, 4H), 3.57-3.53 (m, 2H), 2.63 (m, 2H), 2.60-2.54 (m, 4H), 2.49 (s, 3H), 2.31-2.27 (m, 2H), 2.24-2.22 (m, 2H), 1.99-1.95 (m, 3H), 1.89-1.29 (m, 72H), 0.91-0.86 (m, 12H), LCMS: Rt: 1.165 min; MS m/z (ESI): 863.7 [M + H]$^+$. |
| <br>Compound 128 | $^1$H NMR (400 MHz, CDCl$_3$) δ: 4.12-3.98 (m, 4H), 3.58-3.51 (m, 2H), 3.13-3.03 (m, 1H), 2.64-2.37 (m, 10H), 2.33-2.20 (m, 4H), 1.83-1.25 (m, 75H), 0.90-0.86 (m, 12H), LCMS: Rt: 1.445 min; MS m/z (ESI): 877.8 [M + H]$^+$. |

-continued

| Compound | Characterization |
|---|---|

Compound 129

¹H NMR (400 MHz, CDCl₃) δ: 4.13-3.96 (m, 4H), 3.60-3.49 (m, 2H), 3.11-3.01 (m, 1H), 2.64-2.39 (m, 10H), 2.35-2.20 (m, 4H), 1.76-1.13 (m, 77H), 0.90-0.86 (m, 12H), LCMS: Rt: 1.555 min; MS m/z (ESI): 891.8 [M + H]⁺.

Compound 130

¹H NMR (400 MHz, CDCl₃) δ: 4.06-4.01 (m, 4H), 3.55 (s, 2H), 3.12-3.00 (s, 2H), 2.67-2.52 (m, 4H), 2.45-2.41 (m, 3H), 2.36-2.22 (m, 4H), 2.02-1.97 (m, 5H), 1.62-1.33 (m, 73H), 0.89-0.86 (m, 9H), LCMS: Rt: 1.575 min; MS m/z (ESI): 875.8 [M + H]⁺.

-continued

| Compound | Characterization |
| --- | --- |
| Compound 131 | ¹H NMR (400 MHz, CDCl₃) δ: 4.13-3.97 (m, 4H), 3.55-3.46 (m, 2H), 2.66-2.51 (m, 4H), 2.42-2.36 (m, 4H), 2.31-2.18 (m, 4H), 2.01-1.89 (m, 4H), 1.77-1.20 (m, 77 H), 0.89-0.86 (m, 9H). LCMS: Rt: 1.795 min; MS m/z (ESI): 889.8 [M + H]⁺. |
| Compound 132 | ¹H NMR (400 MHz, CDCl₃) δ: 4.10-3.99 (m, 4H), 3.52-3.49 (m, 2H), 3.11-3.02 (m, 1H), 2.59-2.56 (m, 2H), 2.53-2.51 (m, 2H), 2.41-2.37 (m, 4H), 2.29-2.24 (m, 2H), 2.24-2.22 (m, 2H), 2.01-1.88 (m, 6H), 1.82-1.67 (m, 3H), 1.62-1.33 (m, 73H), 0.89-0.86 (m, 9H). LCMS: Rt: 2.315 min; MS m/z (ESI): 903.9 [M + H]⁺. |

7.68 Example 69: Preparation of Compound 89

81-1

89-1

89-2

89-3

89

Step 1: Preparation of Compound 89-1

To a solution of compound 81-1 (3.8 g, 7.7 mmol, 1.0 eq.) and compound X (4.3 g, 15.4 mmol, 2.0 eq.) in DCM (30 mL) were added EDCI (4.4 g, 23.1 mmol, 3.0 eq.), DMAP (470 mg, 3.9 mmol, 0.5 eq.) and DIPEA (5.0 g, 38.5 mmol, 5.0 eq.). The mixture was stirred under 50° C. for 16 hours. After which the TLC showed complete disappearance of starting compound 81-1, the reaction mixture was poured into water and extracted with DCM. The combined organic layers were washed with brine, dried over $Na_2SO_4$ and concentrated. The crude product was purified by column chromatography silica gel (PE/EA=50/1) to give the title compound 89-1 (5.1 g, 87.9% yield) as yellow oil. $^1$H NMR (400 MHz, $CDCl_3$) δ: 0.86-0.90 (m, 9H), 1.17-1.47 (m, 42H), 1.55-1.60 (m, 4H), 1.62-1.79 (m, 1H), 1.96-2.10 (m, 5H), 2.22-2.32 (m, 4H), 2.70-2.82 (m, 2H), 3.39-3.50 (m, 2H), 3.94-3.12 (m, 4H), 4.44-4.54 (m, 2H), 5.24-5.46 (m, 4H), 7.26-7.37 (m, 5H).

Step 2: Preparation of Compound 89-2

To a stirred solution of compound 89-1 (5.0 g, 6.6 mmol, 1.0 eq.) in DCM (60 mL) were added $BCl_3$ (9.3 g, 79.2 mmol, 12.0 eq.) at −78° C. The mixture was stirred at −78° C. for 2 hours. After which the TLC showed complete disappearance of starting compound 89-1, the reaction mixture was poured into $NaHCO_3$ and extracted with DCM. The organic layer was washed with brine and dried over $Na_2SO_4$ and concentrated. The crude product was purified by column chromatography on silica gel (PE/EA=20/1) to give the title compound 89-2 (2.5 g, 56.8% yield) as yellow solid. $^1$H NMR (400 MHz, CDCl$_3$) δ: 0.86-0.90 (m, 9H), 1.17-1.48 (m, 44H), 1.49-1.59 (m, 5H), 1.63-1.74 (m, 2H), 1.89-2.07 (m, 4H), 2.20-2.32 (m, 4H), 2.73-2.79 (m, 1H), 3.56-3.71 (m, 2H), 4.00-4.17 (m, 4H), 5.31-5.47 (m, 3H).

Step 3: Preparation of Compound 89-3

To a solution of compound 89-2 (400 mg, 0.6 mmol, 1.0 eq.) and DIPEA (155 mg, 1.2 mmol, 2.0 eq.) in DCM (20 mL) was added MsCl (83 mg, 0.7 mmol, 1.2 eq.) at 0° C. The mixture was stirred at room temperature for 2 hours. TLC showed the reaction was completed. The reaction mixture was poured into water and extracted with DCM. The combined organic layers were washed with brine dried over Na$_2$SO$_4$ and concentrated to give the title compound 89-3 (440 g, 98.9% yield) as yellow oil.

Step 4: Preparation of Compound 89

To a solution of compound 89-3 (440 mg, 0.6 mmol, 1.0 eq.) and compound I (115 mg, 1.2 mmol, 2.0 eq.) in ACN (10 mL) were added K$_2$CO$_3$ (111 mg, 1.8 mmol, 3.0 eq.), Cs$_2$CO$_3$ (65 mg, 0.2 mmol, 0.3 eq.) and NaI (30 mg, 0.2 mmol, 0.3 eq.). The reaction mixture was stirred at 80° C. for 16 hours. LCMS showed the reaction was completed. The reaction mixture was poured into water and extracted with EA. The organic layer was washed with brine, dried over Na$_2$SO$_4$ and concentrated. The residue was purified by prep-HPLC to give the title compound (107 mg, 23.8% yield) as colorless oil.

$^1$H NMR (400 MHz, CDCl$_3$) δ: 0.86-0.90 (m, 9H), 1.19-1.53 (m, 46H), 1.58-1.84 (m, 7H), 1.86-2.10 (m, 7H), 2.14-2.34 (m, 5H), 2.38-2.71 (m, 4H), 2.75-2.81 (m, 1H), 3.09-3.27 (m, 1H), 3.33-3.73 (m, 2H), 4.00-4.13 (m, 4H), 5.24-5.59 (m, 3H). LCMS: Rt: 1.395 min; MS m/z (ESI): 760.6 [M+H]$^+$.

The following compounds were prepared in analogous fashion as Compound 89, using corresponding starting material.

| Compound | Characterization |
|---|---|
|  Compound 90 | $^1$H NMR (400 MHz, CDCl$_3$) δ: 0.86-0.91 (m, 9H), 1.26-1.53 (m, 47H), 1.59-1.64 (m, 5H), 1.74-1.77 (m, 4H), 2.02-2.08 (m, 5H), 2.22-2.25 (m, 2H), 2.28-2.32 (m, 2H), 2.47-2.51 (m, 2H), 2.60-2.63 (m, 2H), 2.75-2.79 (m, 2H), 3.01-3.25 (m, 1H), 3.50-3.53 (m, 2H), 4.01-4.07 (m, 4H), 5.32-5.38 (m, 4H). LCMS: Rt: 1.480 min; MS m/z (ESI): 774.7 [M + H]$^+$. |
|  Compound 91 | $^1$H NMR (400 MHz, CDCl$_3$) δ: 0.86-0.90 (m, 9H), 1.21-1.41 (m, 48H), 1.54-1.67 (m, 10H), 1.75-1.82 (m, 3H), 1.96-1.99 (m, 1H), 2.02-2.10 (m, 4H), 2.20-2.30 (m, 4H), 2.38-2.40 (m, 2H), 2.44-2.47 (m, 2H), 2.54-2.61 (m, 2H), 2.64-2.80 (m, 2H), 3.43-3.52 (m, 4H), 5.28-5.44 (m, 4H). LCMS: Rt: 1.155 min; MS m/z (ESI): 802.7 [M + H]$^+$. |
|  Compound 100 | $^1$H NMR (400 MHz, CDCl$_3$) δ: 5.52-5.31 (m, 4H), 4.10-4.03 (m, 5H), 3.86-3.47 (m, 2H), 2.77-2.42 (m, 7H), 2.32-2.30 (m, 2H), 2.28-2.23 (m, 2H), 2.06-1.96 (m, 6H), 1.82-1.72 (m, 6H), 1.36-1.26 (m, 50H), 0.91-0.87 (m, 9H). LCMS: Rt: 1.370 min; MS m/z (ESI): 788.7 [M + H]$^+$. |

-continued

| Compound | Characterization |
|---|---|
|

Compound 101 | $^1$H NMR (400 MHz, CDCl$_3$) δ: 0.83-0.89 (m, 9H), 1.06-1.90 (m, 65H), 1.96-2.07 (m, 5H), 2.18-2.65 (m, 7H), 2.73-2.81 (m, 2H), 3.43-3.55 (m, 1H), 4.01-4.10 (m, 4H), 5.27-5.43 (m, 4H). LCMS: Rt: 1.445 min; MS m/z (ESI): 816.8 [M + H]$^+$. |

7.69 Example 70: Preparation of Compound 95

-continued 95-6

DIEA, MsCl 95-7

$K_2CO_3$, $Cs_2CO_3$, NaI

108

$SOCl_2$ 95-9

DIEA, NaI

-continued

95

Step 1: Preparation of Compound 95-2

To a solution of compound 95-1 (12.1 g, 66.4 mmol, 1.0 eq.) and compound SM3 (17.6 g, 662 mmol, 5.0 eq.) in DCM (330 mL) at 0° C. was added TRITON B (2.2 g, 13.3 mmol, 0.2 eq.) dropwise. The mixture was stirred at RT for 16 hours. TLC showed the reaction was completed. The mixture was concentrated and purified by column chromatography on silica gel (PE/EA=10/1-4/1) to give the title compound (16.7 g, 87% yield) as colorless oil.

Step 2: Preparation of Compound 95-3

To a solution of compound 95-2 (15.8 g, 54.8 mmol, 1.0 eq.) in EtOH (250 mL) was added concentrated $H_2SO_4$ (30 mL). The mixture was stirred at 90° C. for 16 hours. TLC showed the reaction was completed. The mixture was poured into water and extracted with EA. The combined organic layers were washed with brine, dried over $Na_2SO_4$ and concentrated. The residue was purified by column chromatography on silica gel concentrated and purified by column chromatography on silica gel (PE/EA=10/1-5/1) to give the title compound (8.9 g, 43% yield) as colorless oil.

Step 3: Preparation of Compound 95-4

To a solution of compound 95-3 (8.9 g, 23.3 mol, 1.0 eq.) in $THF/H_2O$ (120 mL/40 mL) was added lithium hydroxide monohydrate (7.8 g, 186.4 mmol, 8.0 eq.). The reaction mixture was stirred at room temperature for 16 hours. TLC showed the reaction worked completely. The reaction mixture was concentrated under reduced pressure to remove the organic solvent. The aqueous layer was acidified to pH=3-4 with 2 N HCl and then extracted with EA. The combined organic layers were washed with brine, dried over $Na_2SO_4$ and concentrated to give the title compound (6.7 g, 88% yield) as colorless oil.

Step 4: Preparation of Compound 95-5

A mixture of compound 95-4 (3.26 g, 10 mmol, 1.0 eq.), compound SM4 (7.3 g, 30 mmol, 3.0 eq.), EDCI (5.8 g, 30 mmol, 3.0 eq.), DMAP (611 mg, 5 mmol, 0.5 eq.) and DIPEA (6.5 g, 50 mmol, 5.0 eq.) in DCM (100 mL) was stirred at reflux overnight. TLC showed the reaction worked completely. The reaction mixture was concentrated and purified by column chromatography on silica gel (PE/EA=100/1-50/1-20/1) to give the title compound (5.7 g, 73% yield) as colorless oil.

Step 5: Preparation of Compound 95-6

To a solution of compound 95-5 (5.7 g, 7.4 mmol, 1.0 eq.) in MeOH (100 mL) were added Pd/C (570 mg) and trichloroethane (1.1 g, 8.1 mmol, 1.1 eq.). The mixture was stirred at RT under $H_2$ for 2 hours. TLC showed the reaction was complete. The mixture was filtered through a pad of Celite and washed with EA. The filtration was concentrated and concentrated and by column chromatography on silica gel (PE/EA=10/1-4/1) to give the title compound (3.8 g, 76% yield) as colorless oil. $^1$H NMR (400 MHz, CDCl$_3$) δ: 0.86-0.90 (m, 12H), 1.27-1.30 (m, 48H), 1.59-1.68 (m, 2H), 2.51-2.67 (m, 4H), 2.79-2.84 (m, 1H), 3.48-3.58 (m, 4H), 3.69-3.74 (m, 3H), 3.82-3.89 (m, 2H), 3.98-4.01 (m, 4H).

Step 6: Preparation of Compound 95-7

To a solution of compound 95-6 (1.5 g, 2.2 mmol, 1.0 eq.) and TEA (445 mg, 4.4 mmol, 2.0 eq.) in DCM (22 mL) was added MsCl (302 mg, 2.64 mmol, 1.2 eq.). The mixture was stirred at room temperature for 2 hours. TLC showed the reaction was complete. The mixture was poured into water and extracted with DCM. The combined organic layers were washed with brine, dried over $Na_2SO_4$ and concentrated to give the title compound (1.6 g, 96% yield) as yellow oil. It was used in the next step without further purification.

Step 7: Preparation of Compound 108

To a solution of compound 95-7 (300 mg, 0.39 mmol, 1.0 eq.) and compound I (91 mg, 0.79 mmol, 2.0 eq.) in ACN (10 mL) were added $K_2CO_3$ (163 mg, 1.18 mmol, 3.0 eq.), $Cs_2CO_3$ (39 mg, 0.12 mmol, 0.3 eq.) and NaI (18 mg, 0.12 mmol, 0.3 eq.). The mixture was stirred at 80° C. for 10 hours. LCMS showed the reaction was completed. The mixture was concentrated and purified by prep-HPLC to give the title compound (18 mg, 6% yield) as colorless oil. $^1$H NMR (400 MHz, CDCl$_3$) δ: 0.80-0.83 (m, 12H), 1.19-1.31 (m, 50H), 1.51-1.94 (m, 8H), 2.41-2.52 (m, 6H), 2.96-2.98 (m, 1H), 3.06-3.16 (m, 1H), 3.39-3.92 (m, 13H). LCMS: Rt: 1.607 min; MS m/z (ESI): 782.7 [M+H]$^+$.

Step 8: Preparation of Compound 95-9

To a solution of compound 108 (110 mg, 0.14 mmol, 1.0 eq.) in DCM (10 mL) were added SOCl$_2$ (50 mg, 0.42 mmol, 3.0 eq.). The mixture was stirred at 35° C. for 10 hours. TLC showed the reaction mixture was complete. The reaction mixture was concentrated to give the title compound (112 mg, 100% yield) as yellow oil.

Step 9: Preparation of Compound 95

To a solution of compound 95-9 (110 mg, 0.14 mmol, 1.0 eq.) and compound I (32 mg, 0.27 mmol, 2.0 eq.) in THF (10 mL) were added DIEA (54 mg, 0.42 mmol, 3.0 eq.) and NaI (21 mg, 0.14 mmol, 1.0 eq.). The mixture was stirred at 70° C. for 10 hours. LCMS showed the reaction was completed. The mixture was concentrated and purified by prep-HPLC to give the title compound (25 mg, 20% yield) as colorless oil.

$^1$H NMR (400 MHz, CDCl$_3$) δ: 0.85-0.90 (m, 12H), 1.26-1.43 (m, 52H), 1.56-1.99 (m, 14H), 2.51-2.59 (m, 10H), 3.13-3.15 (m, 2H), 3.46-3.56 (m, 4H), 3.70-3.99 (m, 8H). LCMS: Rt: 1.477 min; MS m/z (ESI): 879.9 [M+H]$^+$.

The following compounds were prepared in analogous fashion as Compound 95, using

| Compound | Characterization |
|---|---|
|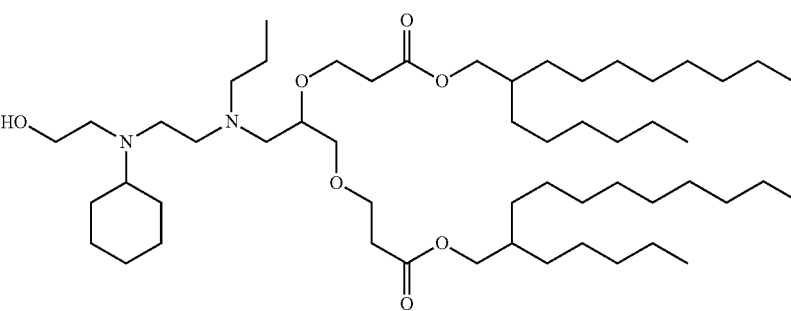
Compound 96 | ¹H NMR (400 MHz, CDCl₃) δ: 0.87-0.90 (m, 12H), 0.99-1.03 (m, 3H), 1.19-1.26 (m, 55H), 1.61-1.77 (m, 6H), 2.47-2.62 (m, 15H), 3.46-3.56 (m, 5H), 3.71-3.98 (m, 8H). LCMS: Rt: 1.057 min; MS m/z (ESI): 881.9 [M + H]⁺. |
|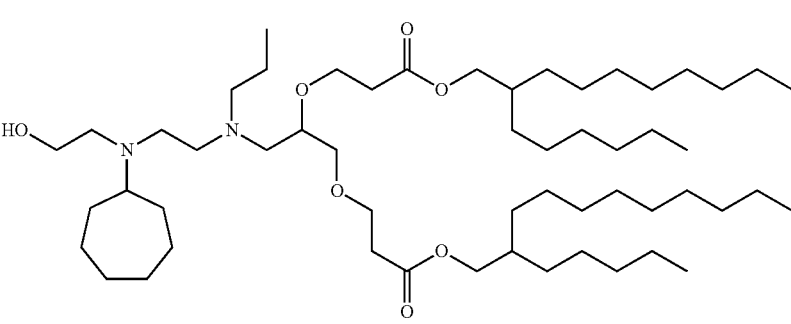 [SMILES: CCCCCCCCC(CCCCCCCC)CNC(=O)CCOCC(CN(C)CCN(CCO)C1CCCCCC1)OCCC(=O)NCC(CCCCCCCC)CCCCCCCC]
Compound 97 | ¹H NMR (400 MHz, CDCl₃) δ: 4.01-3.96 (m, 4H), 3.88-3.76 (m, 5H), 3.68-3.43 (m, 4H), 2.62-2.56 (m, 8H), 2.39-2.37 (m, 3H), 1.83-1.78 (m, 4H), 1.72 (s, 3H), 1.35-1.15 (m, 60H), 0.89-0.86 (m, 15H). LCMS: Rt: 1.985 min; MS m/z (ESI): 895.8 [M + H]⁺. |
|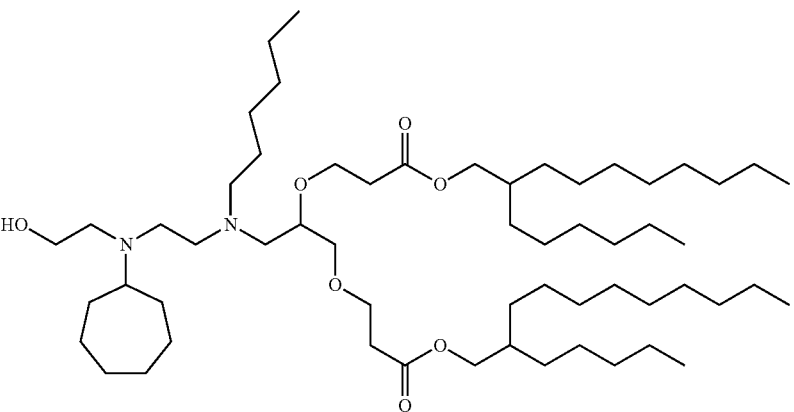
Compound 106 | ¹H NMR (400 MHz, CDCl₃) δ: 3.98-3.96 (m, 4H), 3.84-3.79 (m, 5H), 3.54-3.46 (m, 5H), 2.61-2.54 (m, 7H), 2.52-2.50 (m, 3H), 2.40 (s, 2H), 1.61-1.60 (m, 2H), 1.55-1.53 (m, 4H), 1.48-1.42 (m, 7H), 1.35-1.15 (m, 54H), 0.89-0.84 (m, 15H). LCMS: Rt: 1.875 min; MS m/z (ESI): 909.8 [M + H]⁺. |
| Compound 107 | ¹H NMR (400 MHz, CDCl₃) δ: 0.86-0.90 (m, 15H), 1.27-1.32 (m, 56H), 1.38-1.58 (m, 14H), 1.71-1.83 (m, 2H), 2.39-2.59 (m, 14H), 3.43-3.56 (m, 5H), 3.70-3.83 (m, 4H), 3.89-3.99 (m, 4H). LCMS: Rt: 1.997 min; MS m/z (ESI): 952.0 [M + H]⁺. |

7.70 Example 71: Preparation of Compound 104

104-1

104-2

104-3

104-4

104-5

-continued 104-6

104

Step 1: Preparation of Compound 104-2

To a solution of compound 104-1 (2.4 g, 7.4 mmol, 1.0 eq.) and compound compound X (4.3 g, 16.3 mmol, 2.2 eq.) in DCM (40 mL) were added EDCI (4.3 g, 22.2 mmol, 3.0 eq.), DMAP (452 mg, 3.7 mmol, 0.5 eq.) and DIPEA (4.8 g, 37 mmol, 5.0 eq.). The mixture was stirred under reflux for 16 hours. TLC showed the reaction was complete. The reaction mixture was concentrated and purified by column chromatography silica gel (PE/EA=20/1) to give the title compound 104-2 (3.8 g, 62% yield) as colorless oil. (MC22-163-118)

Step 2: Preparation of Compound 104-3

To a stirred solution of compound 104-2 (3.7 g, 4.4 mmol, 1.0 eq.) in DCM (30 mL) were added $BCl_3$ (44 mL, 44 mmol, 10.0 eq.) at −78° C. The mixture was stirred at −78° C. for 1 hours. TLC showed the reaction was complete. The reaction was quenched with $NaHCO_{3(aq)}$ and extracted with DCM. The organic layer was washed with brine and dried over $Na_2SO_4$ and concentrated. The residue was purified by column chromatography on silica gel (PE/EA=10/1-4/1) to give the title compound 104-3 (2.0 g, 61% yield) as colorless oil. (MC22-163-119)

Step 3: Preparation of Compound 104-4

To a solution of compound 104-3 (2.0 g, 2.7 mmol, 1.0 eq.) and DIPEA (698 mg, 5.4 mmol, 2.0 eq.) in DCM (25 mL) was added MsCl (371 mg, 3.2 mmol, 1.2 eq.). The mixture was stirred at room temperature for 2 hours. TLC showed the reaction was complete. The mixture was poured into water and extracted with DCM. The combined organic layers were washed with brine, dried over $Na_2SO_4$ and concentrated to give the title compound (2.2 g, 100% yield) as yellow oil. It was used in the next step without further purification. (MC22-163-120)

Step 4: Preparation of Compound 104-5

To a solution of compound 104-4 (2.0 g, 2.5 mmol, 1.0 eq.) and compound Y (376 mg, 5.0 mmol, 2.0 eq.) in ACN (30 mL) were added $K_2CO_3$ (1.0 g, 7.5 mmol, 3.0 eq.), $Cs_2CO_3$ (244 mg, 0.75 mmol, 0.3 eq.) and NaI (112 mg, 0.75 mmol, 0.3 eq.). The mixture was stirred at 80° C. for 16 hours. LCMS showed the reaction was complete. The mixture was poured into water and extracted with EA. The combined organic layers were washed with brine, dried over $Na_2SO_4$ and concentrated. The residue was purified by column chromatography on silica gel (DCM/MeOH=50/1) to give the title compound (1.1 g, 58% yield) as colorless oil. (MC22-163-123) LCMS: Rt: 1.247 min; MS m/z (ESI): 790.6 $[M+H]^+$.

Step 5: Preparation of Compound 104-6

To a solution of compound 104-5 (1.1 g, 1.4 mmol, 1.0 eq.) and DIPEA (362 mg, 2.8 mmol, 2.0 eq.) in DCM (15 mL) was added MsCl (192 mg, 1.68 mmol, 1.2 eq.). The mixture was stirred at room temperature for 2 hours. TLC showed the reaction was complete. The mixture was poured into water and extracted with DCM. The combined organic layers were washed with brine, dried over $Na_2SO_4$ and concentrated to give the title compound (1.1 g, 91% yield) as yellow oil. It was used in the next step without further purification. (MC22-163-125)

Step 6: Preparation of Compound 104

To a solution of compound 104-6 (300 mg, 0.34 mmol, 1.0 eq.) and compound K (69 mg, 0.68 mmol, 2.0 eq.) in ACN (10 mL) were added $K_2CO_3$ (141 mg, 1.02 mmol, 3.0 eq.), $Cs_2CO_3$ (33 mg, 0.102 mmol, 0.3 eq.) and NaI (15 mg, 0.102 mmol, 0.3 eq.). The mixture was stirred at 80° C. for 16 hours. LCMS showed the reaction was completed. The mixture was poured into water and extracted with EA. The combined organic layers were washed with brine, dried over $Na_2SO_4$ and concentrated. The residue was purified by prep HPLC to give the title compound (15 mg, 5% yield) as colorless oil. (MC22-163-126)

$^1H$ NMR (400 MHz, $CDCl_3$) δ: 0.40-0.69 (m, 4H), 0.87-0.90 (m, 6H), 1.26-1.34 (m, 36H), 1.56-1.78 (m, 6H), 1.99-2.04 (m, 6H), 2.06-2.19 (m, 4H), 2.28-2.58 (m, 8H), 2.70-2.81 (m, 6H), 3.45-3.60 (m, 4H), 3.71-3.92 (m, 4H), 4.04-4.09 (m, 4H), 5.30-5.55 (m, 8H). LCMS: Rt: 0.093 min; MS m/z (ESI): 873.7 $[M+H]^+$.

The following compounds were prepared in analogous fashion as Compound 104, using corresponding starting material.

| Compound | Characterization |
|---|---|
| <br>Compound 105 | $^1$H NMR (400 MHz, CDCl3) δ: 0.87-0.90 (m, 6 H), 1.26-1.83 (m, 55 H), 2.02-2.06(m, 6 H), 2.19-2.26 (m, 3 H), 2.38-2.59 (m, 12 H), 2.76-2.79 (m, 2 H), 3.43-3.61(m, 4 H), 3.72-3.92 (m, 4 H), 4.05-4.08(m, 4 H), 5.31-5.56(m, 8H). LCMS: Rt: 0.093 min; MS m/z (ESI): 929.8 [M + H]$^+$. |

7.71 Example 72: Preparation of Compound 108

95-7

108

Compound 108 $^1$H NMR (400 MHz, CDCl$_3$) δ:0.80-0.83 (m, 12H), 1.19-1.31 (m, 50H), 1.51-1.94 (m, 8H), 2.41-2.52 (m, 6H), 2.96-2.98 (m, 1H), 3.06-3.16 (m, 1H), 3.39-3.92 (m, 13H). LCMS: Rt: 1.607 min; MS m/z (ESI): 782.7 [M+H]$^+$.

7.72 Example 73: Preparation of Compound 133

89

133-1

133

Step 1: Preparation of Compound 133-1

To a solution of compound 89 (2.0 g, 2.6 mmol, 1.0 eq.) and DIPEA (672 mg, 5.2 mmol, 2.0 eq.) in DCM (20 mL) was added MsCl (357 mg, 3.1 mmol, 1.2 eq.). The mixture was stirred at room temperature for 2 hours. TLC showed the reaction was complete. The mixture was poured into water and extracted with DCM. The combined organic layers were washed with brine, dried over $Na_2SO_4$ and concentrated to give the title compound (2.2 g, 10000 yield) as yellow oil. It was used in the next step without further purification. (MC22-163-115)

Step 2: Preparation of Compound 133

To a solution of compound 133-1 (300 mg, 0.36 mmol, 1.0 eq.) and compound SM8 (84 mg, 0.72 mmol, 2.0 eq.) in ACN (10 mL) were added $K_2C_3$ (149 mg, 1.08 mmol, 3.0 eq.), $Cs_4CO_3$ (35 mg, 0.108 mmol, 0.3 eq.) and NaI (16 mg, 0.108 mmol, 0.3 eq.). The mixture was stirred at 80° C. for 16 hours. LCMS showed the reaction was completed. The mixture was poured into water and extracted with EA. The combined organic layers were washed with brine, dried over $Na_2SO_4$ and concentrated. The residue was purified by prep HPLC to give the title compound (115 mg, 37% yield) as colorless oil. (MC22-163-116)

$^1$H NMR (400 MHz, $CDCl_3$) δ: 0.86-0.90 (m, 12H), 1.26-1.47 (m, 51H), 1.53-1.77 (m, 4H), 1.89-2.07 (i, 8H), 2.22-2.32 (m, 4H), 2.37-2.64 (1, 10H), 2.75-2.79 (m, 2H), 3.02-3.14 (m, 1H), 3.54-3.59 (m, 2H), 3.99-4.10 (i, 4H), 5.29-5.43 (m, 4H). LCMS: Rt: 0.107 min; MS m/z (ESI): 859.7 [M+H]$^+$.

The following compounds were prepared in analogous fashion as Compound 133, using corresponding starting material.

| Compound | Characterization |
|---|---|
| Compound 134 | ¹H NMR (400 MHz, CDCl3) δ: 0.88-0.91 (m, 12H), 1.26-2.07 (m, 63H), 2.22-2.79 (m, 18H), 3.02-3.14 (m, 1H), 3.48-3.60 (m, 2H), 4.01-4.07 (m, 4H), 5.32-5.38 (m, 4H). LCMS: Rt: 0.507 min; MS m/z (ESI): 873.8 [M + H]⁺. |
| Compound 135 | ¹H NMR (400 MHz, CDCl3) δ: 0.86-0.90 (m, 12 H), 1.26-1.37 (m, 54 H), 1.59-1.76 (m, 4 H), 1.75-2.06 (m, 8 H), 2.22-2.32 (m, 4 H), 2.37-2.61 (m, 10 H), 2.75-2.80 (m, 2 H), 3.03-3.14 (m, 2 H), 3.54-3.58 (m, 2 H), 3.99-4.07 (m, 4 H), 5.30-5.42 (m, 4 H). LCMS: Rt: 0.093 min; MS m/z (ESI): 887.7 [M + H]⁺. |

-continued

| Compound | Characterization |
|---|---|
| Compound 136 | ¹H NMR (400 MHz, CDCl3) δ: 5.35-5.34 (m, 4H), 4.03-4.02 (m, 4H), 3.61-3.51 (m, 2H), 3.16-3.08 (m, 2H), 2.98-2.77 (m, 6H), 2.05-1.28 (m, 75H), 0.90-0.88 (m, 9H). LCMS: Rt: 0.427 min; MS m/z (ESI): 871.8 [M + H]⁺. |
| Compound 137 | ¹H NMR (400 MHz, CDCl3) δ: 5.36-5.34 (m, 4H), 4.06-4.02 (m, 5H), 3.54-3.46 (m, 2H), 2.77-2.64 (m, 2H), 2.64-2.55 (m, 4H), 2.41-2.22 (m, 10H), 2.05-1.96 (m, 5H), 1.79-1.75 (m, 8H), 1.62-1.61 (m, 4H), 1.37-1.18 (m, 51H), 0.89-0.88 (m, 9H). LCMS: Rt: 0.107 min; MS m/z (ESI): 885.7 [M + H]⁺. |
| Compound 139 | ¹H NMR (400 MHz, CDCl3) δ: 0.86-0.93 (m, 12H), 1.26-2.02 (m, 69H), 2.22-2.63 (m, 14H), 3.04-3.17 (m, 1H), 3.52-3.59 (m, 2H), 4.01-4.09 (m, 4H), 5.33-5.36 (m, 2H). LCMS: Rt: 0.453 min; MS m/z (ESI): 861.7 [M + H]⁺. |

-continued

| Compound | Characterization |
|---|---|

Compound 140

¹H NMR (400 MHz, CDCl3) δ: 0.77-0.84 (m, 12H), 1.19-1.95 (m, 71H), 2.16-2.60 (m, 14H), 2.97-3.07 (m, 1H), 3.47-3.55 (m, 2H), 3.92-4.03 (m, 4H), 5.26-5.29 (m, 2H). LCMS: Rt: 0.480 min; MS m/z (ESI): 875.8 [M + H]⁺.

Compound 141

¹H NMR (400 MHz, CDCl3) δ: 0.86-0.90 (m, 12 H), 1.26-1.44 (m, 59 H), 1.59-1.70 (m, 4 H), 1.82-2.02 (m, 10 H), 2.22-2.32 (m, 4 H), 2.36-2.65 (m, 10 H), 3.01-3.13 (m, 1 H), 3.49-3.62 (m, 2 H), 3.99-4.10 (m, 4 H), 5.32-5.39 (m, 2 H). LCMS: Rt: 0.093 min; MS m/z (ESI): 889.8 [M + H]⁺.

-continued

| Compound | Characterization |
|---|---|

Compound 142

1H NMR (400 MHz, CDCl3) δ: 5.36-5.34 (m, 2H), 4.06-4.01 (m, 4H), 3.66-3.55 (m, 1H), 3.18-3.04 (m, 2H), 2.74-2.22 (m, 16H), 1.66-1.25 (m, 70H), 0.89-0.86 (m, 9H). LCMS: Rt: 0.107 min; MS m/z (ESI): 873.8 [M + H]+.

Compound 143

1H NMR (400 MHz, CDCl3) δ: 5.36-5.34 (m, 2H), 4.06-4.02 (m, 4H), 3.59-3.25 (m, 2H), 3.13-2.98 (m, 1H), 2.68-2.22 (m, 12H), 2.01-1.21 (m, 76H), 0.89-0.86 (m, 9H). LCMS: Rt: 0.107 min; MS m/z (ESI): 887.8 [M + H]+.

Compound 144

1H NMR (400 MHz, CDCl3) δ: 0.06-1.03 (m, 9H), 1.19-1.56 (m, 64H), 1.57-1.67 (m, 12H), 1.78-1.92 (m, 9H), 1.94-2.27 (m, 5H), 2.42-2.53 (m, 1H), 3.50-3.52 (m, 2H), 3.99-4.07 (m, 4H), 5.34-5.35 (m, 2H). LCMS: Rt: 0.107 min; MS m/z (ESI): 901.8 [M + H]+.

7.73 Example 74: Preparation of Compound 145

SM2

SM7

TsOH, Toluene, reflux 145-1

Pd/C 145-2

MsCl, DCM 145-3

K $K_2CO_3$, ACN 80°C.

145

Step 1: Preparation of Compound 145-1

To a solution of compound SM2 (800 mg, 3.36 mmol, 1.0 eq.) and compound SM7 (144 mg, 8.40 mmol, 2.5 eq.) in toluene (50 mL) was added TsOH (20 mg). The mixture was stirred at 180° C. for 16 hours. TLC showed the reaction was completed. The mixture was diluted with EA and washed with Saturated $NaHCO_3$ aqueous solution. The organic layer was washed with brine, dried over $Na_2SO_4$ and concentrated. The residue was purified by column chromatography on silica gel (PE/EA=100/1) to give 145-1 (850 mg, 49% yield) as colorless oil. (MC21-151-081)

Step 2: Preparation of Compound 145-2

To a solution of compound 145-1 (850 mg, 1.73 mmol, 1.0 eq.) in MeOH (10 mL) was added Pd/C (20 mg). The mixture was stirred at RT under $H_2$ for 16 hours. TLC showed the reaction was completed. The mixture was filtered through a pad of Celite and washed with EA. The filtration was concentrated and purified by column chromatography on silica gel (PE/EA=5/1) to give 145-2 (610 mg, 63% yield) as colorless oil. (MC21-151-082)

Step 3: Preparation of Compound 145-3

To a solution of compound 145-2 (400 mg, 1.00 mmol, 1.0 eq.) and DIPEA (129 mg, 1.00 mmol, 1.0 eq.) in DCM (10 mL) at 0° C. was added MsCl (114 mg, 1.00 mmol, 1.0 eq.). The mixture was stirred at room temperature for 1 hour. The mixture was poured into water and extracted with DCM. The combined organic layers were washed with brine, dried over $Na_2SO_4$ and concentrated to give 145-3 (478 mg) as yellow oil. It was used in the next step without further purification. (MC21-151-086) LCMS: Rt: 0.900 min; MS m/z (ESI): 428.4 [M+H]$^+$.

Step 4: Preparation of Compound 145

To a solution of compound 145-3 (478 mg, 1.0 mmol, 1.0 eq) and compound K (121 mg, 1.2 mmol, 1.2 eq.) in ACN (10 mL) were added K$_2$CO$_3$ (414 mg, 3.0 mmol, 3.0 eq), Cs$_2$CO$_3$ (98 mg, 0.3 mmol, 0.3 eq) and NaI (14 mg, 0.1 mmol, 0.1 eq). The mixture was stirred at 80° C. for 16 hours. LCMS showed the reaction was complete. The mixture was poured into water and extracted with EA. The combined organic layers were washed with brine, dried over Na$_2$SO$_4$ and concentrated. The residue was purified by column chromatography on silica gel (DCM/MeOH=10/1) to give 145 (300 mg, 62% yield) as yellow oil. (MC21-151-087) LCMS: Rt: 0.810 min; MS m/z (ESI): 484.4 [M+H]$^+$.

The following compounds were prepared in analogous fashion as Compound 145, using corresponding starting material.

| Compound | Characterization |
|---|---|
|  Compound 146 | LCMS: Rt: 0.830 min; MS m/z (ESI): 498.4 [M + H]$^+$. |
|  Compound 147 | LCMS: Rt: 0.800 min; MS m/z (ESI): 512.4 [M + H]$^+$. |
|  Compound 148 | LCMS: Rt: 0.850 min; MS m/z (ESI): 526.5 [M + H]$^+$. |

-continued

| Compound | Characterization |
|---|---|

LCMS: Rt: 0.847 min; MS m/z (ESI): 540.5 [M + H]+.

Compound 149

LCMS: Rt: 0.840 min; MS m/z (ESI): 554.4 [M + H]+.

Compound 150

LCMS: Rt: 0.870 min; MS m/z (ESI): 512.3 [M + H]+.

Compound 151

LCMS: Rt: 0.770 min; MS m/z (ESI): 414.2 [M + H]+.

Compound 152

-continued

| Compound | Characterization |
| --- | --- |
| | LCMS: Rt: 0.770 min; MS m/z (ESI): 442.3 [M + H]+. |

Compound 153

| | LCMS: Rt: 0.773 min; MS m/z (ESI): 470.3 [M + H]+. |

Compound 154

| | LCMS: Rt: 0.820 min; MS m/z (ESI): 526.4 [M + H]+. |

Compound 155

| | LCMS: Rt: 1.160 min; MS m/z (ESI): 554.4 [M + H]+. |

Compound 156

-continued

| Compound | Characterization |
|---|---|
| <br><br>Compound 157 | LCMS: Rt: 1.220 min; MS m/z (ESI): 582.4 [M + H]$^+$. |
| <br><br>Compound 158 | LCMS: Rt: 1.460 min; MS m/z (ESI): 610.4 [M + H]$^+$. |
| <br><br>Compound 159 | LCMS: Rt: 1.380 min; MS m/z (ESI): 798.6 [M + H]$^+$. |
| <br><br>Compound 160 | LCMS: Rt: 1.050 min; MS m/z (ESI): 593.5 [M + H]$^+$. |

-continued

| Compound | Characterization |
|---|---|
| <br>Compound 161 | LCMS: Rt: 0.870 min; MS m/z (ESI): 606.6 [M + H]+. |
| <br>Compound 162 | LCMS: Rt: 1.135 min; MS m/z (ESI): 794.7 [M + H]+. |
| <br>Compound 163 | LCMS: Rt: 0.850 min; MS m/z (ESI): 498.6 [M + H]+. |
| <br>Compound 164 | LCMS: Rt: 0.900 min; MS m/z (ESI): 554.5 [M + H]+. |

7.74 Example 75: Preparation and Characterization of Lipid Nanoparticles

Briefly, a cationic lipid provided herein, DSPC, cholesterol, and PEG-lipid were solubilized in ethanol at a molar ratio of 50:10:38.5:1.5, and mRNA were diluted in 10 to 50 mM citrate buffer, pH=4. The LNPs were prepared at a total lipid to mRNA weight ratio of approximately 10:1 to 30:1 by mixing the ethanolic lipid solution with the aqueous mRNA solution at a volume ratio of 1:3 using a microfluidic apparatus, total flow rate ranging from 9-30 mL/min. Ethanol were thereby removed and replaced by DPBS using dialysis. Finally, the lipid nanoparticles were filtered through a 0.2 m sterile filter.

Lipid nanoparticle size were determined by dynamic light scattering using a Malvern Zetasizer Nano ZS (Malvern UK) using a 1730 backscatter detection mode. The encapsulation efficiency of lipid nanoparticles were determined using a Quant-it Ribogreen RNA quantification assay kit (Thermo Fisher Scientific, UK) according to the manufacturer's instructions.

As reported in literature, the apparent pKa of LNP formulations correlates with the delivery efficiency of LNPs for nucleic acids in vivo. The apparent pKa of each formulation was determined using an assay based on fluorescence of 2-(p-toluidino)-6-napthalene sulfonic acid (TNS). LNP formulations comprising of cationic lipid/DSPC/cholesterol/DMG-PEG (50/10/38.5/1.5 mol %) in PBS were prepared as described above. TNS was prepared as a 300 uM stock solution in distilled water. LNP formulations were diluted to 0.1 mg/ml total lipid in 3 mL of buffered solutions containing 50 mM sodium citrate, 50 mM sodium phosphate, 50 mM sodium borate, and 30 mM sodium chloride where the pH ranged from 3 to 9. An aliquot of the TNS solution was added to give a final concentration of 0.1 mg/ml and following vortex mixing fluorescence intensity was measured at room temperature in a Molecular Devices Spectramax iD3 spectrometer using excitation and mission wavelengths of 325 nm and 435 nm. A sigmoidal best fit analysis was applied to the fluorescence data and the pKa value was measured as the pH giving rise to half-maximal fluorescent intensity.

7.75 Example 61: Animal Study

Lipid nanoparticles comprising compounds in the following table encapsulating human erythropoietin (hEPO) mRNA were systemically administered to 6-8 week old female ICR mice (Xipuer-Bikai, Shanghai) at 0.5 mg/kg dose by tail vein injection and mice blood were sampled at specific time points (e.g., 6 hours) post administration. In addition to the aforementioned tested groups, lipid nanoparticles comprising dilinoleylmethyl-4-dimethylaminobutyrate (DLin-MC3-DMA, usually abbreviated to MC3) encapsulating hEPO mRNA were similarly administered at the same dose to age and gender comparative groups of mice as a positive control.

Mice were euthanized by $CO_2$ overdoses after the last sampling time point. Serum were separated from total blood by centrifugation at 5000 g for 10 minutes at 4° C., snap-frozen and stored at −80° C. for analysis. ELSA assay were carried out using a commercial kit (DEP00, R&D systems) according to manufacturer's instructions.

Characteristics of tested lipid nanoparticles, including expression levels over MC3 measured from the tested group are listed the table below.

TABLE 4

| Lipid | size (nm) | polydispersity | Encapsulation Efficiency | Expression over MC3 | Apparant Pka |
|---|---|---|---|---|---|
| 1 | 72.4 | 0.12 | 96.3% | D | 5.902 |
| 2 | 69.05 | 0.094 | 94.5% | D | 5.177 |
| 3 | 105.6 | 0.124 | 92.8% | D | |
| 4 | 54.52 | 0.2 | 94.6% | D | 5.083 |
| 5 | 78.36 | 0.384 | 92.4% | D | 7.315 |
| 6 | 126.4 | 0.241 | 93.4% | D | 7.035 |
| 7 | 85.46 | 0.063 | 96.7% | D | 8.7 |
| 8 | 102.9 | 0.156 | 88.2% | D | 7.327 |
| 9 | 70.97 | 0.144 | 90.8% | C | |
| 10 | 84.22 | 0.356 | 94.8% | D | |
| 11 | 77.98 | 0.196 | 82.2% | D | 7.701 |

TABLE 4-continued

| Lipid | size (nm) | polydispersity | Encapsulation Efficiency | Expression over MC3 | Apparant Pka |
|---|---|---|---|---|---|
| 13 | 61.3 | 0.128 | 94.2% | D | 7.089 |
| 14 | 56.31 | 0.4 | 86.1% | D | 4.536 |
| 15 | 62.11 | 0.139 | 93.5% | C | 5.875 |
| 16 | 74.31 | 0.060 | 89.8% | C | |
| 17 | 79.43 | 0.186 | 92.8% | C | 5.835 |
| 18 | 65.06 | 0.17 | 90.6% | D | 4.916 |
| 19 | 117.5 | 0.156 | 88.5% | D | 4.957 |
| 20 | 67.7 | 0.145 | 90.7% | D | 5.96 |
| 21 | 74.88 | 0.221 | 85.5% | D | 5.49 |
| 22 | 68.67 | 0.206 | 83.5% | D | 5.457 |
| 23 | 74.73 | 0.076 | 88.5% | B | 5.993 |
| 24 | 56.39 | 0.094 | 93.0% | C | 6.005 |
| 25 | 58.01 | 0.112 | 94.70% | C | |
| 26 | 55.8 | 0.153 | 93.30% | C | 5.696 |
| 27 | 65.62 | 0.139 | 73.3% | D | 5.351 |
| 28 | 54.96 | 0.2 | 86.9% | D | 5.905 |
| 29 | 53.73 | 0.110 | 80.1% | C | 5.699 |
| 30 | 49.64 | 0.107 | 92.7% | D | 5.409 |
| 31 | 51.35 | 0.127 | 80.1% | D | 5.704 |
| 32 | 59.1 | 0.232 | 44.6% | D | 3.519 |
| 33 | 63.54 | 0.06 | 94.30% | C | 5.943 |
| 34 | 58.33 | 0.103 | 89.60% | D | 5.482 |
| 35 | 56.71 | 0.1 | 96.80% | C | 5.940 |
| 36 | 59.91 | 0.078 | 94.20% | C | 5.774 |
| 37 | 51.77 | 0.156 | 92.70% | C | 5.726 |
| 38 | 97.62 | 0.194 | 76.2% | D | 6.971 |
| 39 | 111.2 | 0.162 | 94.7% | D | 6.712 |
| 40 | 230 | 0.326 | 36.4% | D | |
| 41 | 82.81 | 0.136 | 83.5% | D | 5.746 |
| 42 | 82.81 | 0.155 | 94.4% | D | 6.283 |
| 43 | 138.6 | 0.362 | 78.4% | D | 7.227 |
| 44 | 112.8 | 0.178 | 85.2% | D | 6.65 |
| 45 | 68.33 | 0.289 | 86.8% | D | 7.466 |
| 46 | 103.3 | 0.039 | 95.9% | C | 6.047 |
| 47 | 82.89 | 0.082 | 91.3% | C | 6.120 |
| 48 | 79.39 | 0.113 | 91.7% | C | 6.263 |
| 49 | 99.66 | 0.031 | 83.7% | A | 6.221 |
| 50 | 58.14 | 0.099 | 90.4% | C | 8.298 |
| 51 | 75.11 | 0.057 | 94.7% | C | 7.727 |
| 52 | 66.03 | 0.14 | 96.5% | D | |
| 53 | 90.06 | 0.014 | 89.79% | C | 6.069 |
| 55 | 75.43 | 0.034 | 89.5% | C | 6.851 |
| 56 | 53.32 | 0.107 | 91.0% | B | 6.403 |
| 57 | 70.05 | 0.055 | 97.0% | C | 7.73 |
| 58 | 56.37 | 0.032 | 97.3% | D | |
| 59 | 94.89 | 0.049 | 96.1% | D | |
| 60 | 73.31 | 0.068 | 92.6% | C | 6.985 |
| 61 | 70.83 | 0.055 | 96.2% | C | 7.219 |
| 62 | 58.44 | 0.075 | 94.1% | D | 7.062 |
| 63 | 150.2 | 0.076 | 95.9% | C | 6.928 |
| 64 | 73.8 | 0.075 | 91.6% | D | |
| 65 | 73.61 | 0.082 | 97.0% | C | 6.428 |
| 66 | 72.85 | 0.044 | 96.6% | B | 6.749 |
| 67 | 130.6 | 0.116 | 91.83% | D | 6.444 |
| 68 | 55.01 | 0.084 | 89.42% | C | 6.22 |
| 69 | 110.30 | 0.013 | 91.81% | C | 6.789 |
| 70 | 78.45 | 0.049 | 93.32% | A | 6.351 |
| 71 | 76.45 | 0.077 | 94.62% | B | 6.727 |
| 72 | 81.89 | 0.055 | 95.22% | A | |
| 73 | 76.26 | 0.088 | 94.69% | A | 6.616 |
| 74 | 101.00 | 0.031 | 93.97% | A | 6.539 |
| 77 | 56.88 | 0.046 | 89.92% | B | 6.439 |
| 78 | 159.72 | 0.017 | 93.77% | C | 6.166 |
| 79 | 103.64 | 0.01 | 91.29% | A | 5.927 |
| 80 | 98.95 | 0.027 | 92.20% | A | 6.063 |
| 81 | 72.78 | 0.023 | 88.28% | B | 6.79 |
| 82 | 84.46 | 0.079 | 92.38% | A | 6.621 |
| 83 | 94.04 | 0.019 | 92.39% | A | 6.182 |
| 84 | 83.05 | 0.01 | 93.44% | B | 6.785 |
| 85 | 74.14 | 0.066 | 92.17% | B | 6.438 |
| 86 | 73.58 | 0.03 | 92.81% | A | |
| 87 | 64.08 | 0.044 | 92.47% | B | 6.372 |
| 88 | 59.54 | 0.063 | 92.91% | B | 6.309 |
| 89 | 69.36 | 0.04 | 92.56% | B | 6.926 |
| 90 | 70.38 | 0.043 | 93.02% | C | 7.024 |
| 91 | 63.89 | 0.111 | 92.11% | B | 6.608 |
| 92 | 70.85 | 0.051 | 90.25% | A | |

TABLE 4-continued

| Lipid | size (nm) | polydispersity | Encapsulation Efficiency | Expression over MC3 | Apparant Pka |
|---|---|---|---|---|---|
| 93 | 63.32 | 0.111 | 85.30% | C | 6.377 |
| 94 | 77.15 | 0.04 | 93.93% | A | 6.793 |
| 98 | 77.16 | 0.01 | 93.58% | B | 6.997 |
| 99 | 77.25 | 0.025 | 94.14% | B | 7.059 |
| 100 | 64.54 | 0.055 | 91.24% | B | 6.666 |
| 101 | 59.51 | 0.111 | 92.79% | B | 6.488 |
| 106 | 65.31 | 0.046 | 93.17% | A | 6.035 |
| 107 | 61.18 | 0.067 | 93.66% | B | |
| 108 | 47.87 | 0.097 | 92.04% | D | |
| 109 | 74 | 0.011 | 92.59% | A | 6.204 |
| 110 | 75.71 | 0.038 | 92.71% | A | 6.147 |
| 111 | 62.77 | 0.048 | 92.54% | B | 6.072 |

A: ≥2
B: ≥1 and <2
C: ≥0.1 and <1
D: <0.1

---

---

What is claimed is:

1. A compound of Formula (III):

(III)

or a pharmaceutically acceptable salt, prodrug or stereoisomer thereof, wherein:

$R^1$ and $R^2$ are each independently $C_5$-$C_{32}$ alkyl or $C_5$-$C_{32}$ alkenyl;

$R^0$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

$G^3$ is $C_2$-$C_{12}$ alkylene or $C_2$-$C_{12}$ alkenylene;

$G^4$ is $C_2$-$C_{12}$ alkylene or $C_2$-$C_{12}$ alkenylene;

$R^3$ is-N($R^4$) $R^5$ or —O$R^6$;

$R^4$ is $C_1$-$C_{12}$ alkyl, $C_2$-$C_{12}$ alkenyl, $C_3$-$C_8$ cycloalkyl, $C_3$-$C_8$ cycloalkenyl, $C_6$-$C_{10}$ aryl, or 4- to 8-membered heterocycloalkyl;

---

346

$R^5$ is $C_1$-$C_{12}$ alkyl, $C_3$-$C_8$ cycloalkyl, $C_3$-$C_8$ cycloalkenyl, $C_6$-$C_{10}$ aryl, 4- to 8-membered heterocycloalkyl, —$(CH_2)_n$Q, —$(CH_2)_n$CHQR, -CHQR, or -CQ$(R)_2$, wherein Q is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, 5- to 10-membered heteroaryl, —OR, —O$(CH_2)_p$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S(O)$_2$R, —N(R)C(O)N$(R)_2$, —N(R)C(S)N$(R)_2$, —N(R) $R^{22}$, —O$(CH_2)_p$OR, —N(R)C($=NR^{23}$)N$(R)_2$, —N(R)C($=CHR^{23}$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C($=NR^{23}$)N$(R)_2$, —N(OR)C($=CHR^{23}$)N$(R)_2$, —C($=NR^{23}$)N$(R)_2$, —C($=NR^{23}$)R, —C(O)N(R)OR, or —C(R)N$(R)_2$C(O)OR, and each p is independently 1, 2, 3, 4, or 5;

$R^{22}$ is $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered heteroaryl;

$R^{23}$ is H, —CN, —$NO_2$, $C_1$-$C_6$ alkyl, —OR, —S(O)$_2$R, —S(O)$_2$N$(R)_2$, $C_2$-$C_6$ alkenyl, $C_3$-$C_8$ cycloalkyl, $C_3$-$C_8$ cycloalkenyl, $C_3$-$C_8$ cycloalkynyl, 4- to 8-membered heterocyclyl, $C_6$-$C_{10}$ aryl, or 5- to 10-membered heteroaryl;

each R is independently H, $C_1$-$C_3$ alkyl, or $C_2$-$C_3$ alkenyl; or two R in a N$(R)_2$ moiety together with the nitrogen to which they are attached form a cyclic moiety; and each X is independently F, Cl, Br, or I;

or $R^4$, $R^5$, together with the nitrogen to which they are attached form a cyclic moiety;

$R^6$ is hydrogen, $C_1$-$C_{12}$ alkyl, $C_3$-$C_8$ cycloalkyl, $C_3$-$C_8$ cycloalkenyl, or $C_6$-$C_{10}$ aryl; and wherein, unless otherwise specified, each alkyl, alkenyl, cycloalkyl, cycloalkenyl, cycloalkynyl, heterocyclyl, heterocycloalkyl, aryl, heteroaryl, alkylene, alkenylene, and cyclic moiety is unsubstituted.

2. The compound of claim 1, wherein $R^3$ is —OH.

3. The compound of claim 1, wherein $R^3$ is —N($R^4$) $R^5$.

4. The compound of claim 1, wherein $G^3$ is $C_2$-$C_4$ alkylene and $G^4$ is $C_2$-$C_4$ alkylene.

5. The compound of claim 1, which is a compound of Formula (VII):

347

(VII)

wherein t is an integer from 2 to 12, u is an integer from 2 to 12, or a pharmaceutically acceptable salt, prodrug or stereoisomer thereof.

6. The compound of claim 5, wherein t is 2 and u is 4.

7. The compound of claim 1, wherein $R^0$ is $C_1$-$C_6$ alkyl, $C_2$-$C_6$ alkenyl, or $C_3$-$C_8$ cycloalkyl.

8. The compound of claim 1, wherein $R^4$ is $C_1$-$C_6$ alkyl or $C_3$-$C_8$ cycloalkyl.

9. The compound of claim 1, wherein $R^5$ is —CH$_2$CH$_2$OH.

10. The compound of claim 1, wherein $R^1$ and $R^2$ are each independently branched $C_6$-$C_{24}$ alkyl or branched $C_6$-$C_{24}$ alkenyl.

11. The compound of claim 10, wherein $R^1$ and $R^2$ are each independently —$R^7$—CH($R^8$)($R^9$), wherein $R^7$ is $C_1$-$C_5$ alkylene, and $R^8$ and $R^9$ are independently $C_2$-$C_{10}$ alkyl or $C_2$-$C_{10}$ alkenyl.

12. The compound of claim 1, wherein $R^1$ is straight $C_6$-$C_{24}$ alkyl and $R^2$ is branched $C_6$-$C_{24}$ alkyl.

13. The compound of claim 12, wherein $R^1$ is straight $C_6$-$C_{24}$ alkyl and $R^2$ is —$R^7$—CH($R^8$)($R^9$), wherein $R^7$ is $C_1$-$C_5$ alkylene, and $R^8$ and $R^9$ are independently $C_2$-$C_{10}$ alkyl.

14. A compound, which is:

Compound 56

Compound 60

Compound 65

Compound 66

-continued

Compound 67

Compound 68

Compound 69

Compound 76

Compound 77

-continued

Compound 78

Compound 79

Compound 80

Compound 81

Compound 82

-continued

Compound 83

Compound 84

Compound 85

Compound 86

Compound 87

-continued

Compound 88

Compound 89

Compound 90

Compound 91

Compound 92

-continued

Compound 93

Compound 94

Compound 98

Compound 99

Compound 100

-continued

Compound 101

Compound 109

Compound 110

Compound 111

Compound 112

-continued

Compound 113

Compound 114

Compound 115

Compound 116

Compound 117

-continued

Compound 118

Compound 119

Compound 120

Compound 121

Compound 122

-continued

Compound 123

Compound 124

Compound 125

Compound 126

Compound 127

-continued

Compound 128

Compound 129

Compound 130

Compound 131

Compound 132

-continued

Compound 133

Compound 134

Compound 135

Compound 136

Compound 137

-continued

Compound 138

Compound 139

Compound 140

Compound 141

-continued

Compound 142

Compound 143

, or

Compound 144

, or a pharmaceutically acceptable salt thereof.

15. A composition comprising the compound of claim 1, and a therapeutic or prophylactic agent.

16. A lipid nanoparticle comprising the compound of claim 1.

17. A pharmaceutical composition comprising the compound of claim 1, and a pharmaceutically acceptable excipient or diluent.

18. A method of delivering a therapeutic or prophylactic agent to a mammalian cell or organ, comprising contacting the mammalian cell or organ with the composition of claim 15.

19. The compound of claim 1, which is:

Compound 86

, or a pharmaceutically acceptable salt thereof.

20. The compound of claim 1, which is:

Compound 92 or a pharmaceutically acceptable salt thereof.

\* \* \* \* \*

SEQUENCE LISTING

```
Sequence total quantity: 2
SEQ ID NO: 1              moltype = DNA  length = 24
FEATURE                   Location/Qualifiers
source                    1..24
                          mol_type = other DNA
                          note = stem-loop sequence
                          organism = synthetic construct
SEQUENCE: 1
caaaggctct tttcagagcc acca                                          24

SEQ ID NO: 2              moltype = RNA  length = 24
FEATURE                   Location/Qualifiers
source                    1..24
                          mol_type = other RNA
                          note = stem-loop sequence
                          organism = synthetic construct
SEQUENCE: 2
caaaggctct tttcagagcc acca                                          24
```